United States Patent [19]

Ikegami et al.

[11] Patent Number: 6,140,274
[45] Date of Patent: Oct. 31, 2000

[54] DIHALOPROPENE COMPOUNDS, THEIR USE AS INSECTICIDES/ACARICIDES AND INTERMEDIATES FOR THEIR PRODUCTION

[75] Inventors: Hiroshi Ikegami, Takarazuka; Keiichi Izumi, Toyonaka; Masaya Suzuki, Takarazuka; Noriyasu Sakamoto, Toyonaka; Hirotaka Takano, Sanda, all of Japan

[73] Assignee: Sumitomo Chemical Company, Limited, Osaka, Japan

[21] Appl. No.: 09/091,082

[22] PCT Filed: Jan. 1, 1997

[86] PCT No.: PCT/JP97/00141

§ 371 Date: Jun. 12, 1998

§ 102(e) Date: Jun. 12, 1998

[87] PCT Pub. No.: WO97/28112

PCT Pub. Date: Aug. 7, 1997

[30] Foreign Application Priority Data

Jan. 30, 1996 [JP] Japan .................................. 8-014120
Nov. 25, 1996 [JP] Japan .................................. 8-330443

[51] Int. Cl.[7] .......................... A01N 35/00; A01N 43/40; C07C 39/24
[52] U.S. Cl. .......................... 504/348; 504/351; 504/354; 514/345; 568/442; 568/630; 568/648; 568/774
[58] Field of Search ...................... 568/630, 648, 568/649, 650, 656, 657, 663, 425, 442, 716, 774; 514/345; 504/348, 351, 354

[56] References Cited

U.S. PATENT DOCUMENTS 5,530,015 6/1996 Sakamoto et al. ...................... 514/345

FOREIGN PATENT DOCUMENTS

| 06 48729 A1 | 4/1995 | European Pat. Off. . |
| 07330651 | 12/1995 | Japan . |
| WO 9604228 A1 | 2/1996 | WIPO . |
| WO 9611909 | 4/1996 | WIPO . |
| WO 9633160 | 10/1996 | WIPO . |

*Primary Examiner*—Sreeni Padmanabhan
*Attorney, Agent, or Firm*—Birch, Stewart, Kolasch & Birch, LLP

[57] ABSTRACT

Dihalopropene compounds of the general formula:

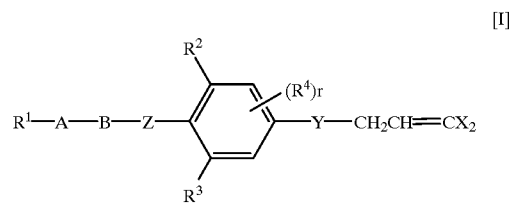

wherein $R^1$ is substituted alkyl; $R^2$, $R^3$ and $R^4$ are each independently halogen, alkyl, haloalkyl, alkoxy, haloalkoxy, nitro or cyano; A is O, $S(O)_t$ or $NR^{14}$ in which $R^{14}$ is H or alkyl and t is 0 to 2; B is substituted alkylene, alkenylene or alkynylene; r is 0 to 2; X's are each independently halogen; Y is O, S or NH; Z is O, S or $NR^{25}$ in which $R^{25}$ is H, acetyl or alkyl, which are useful as active ingredients of insecticidal/acaricidal agents.

23 Claims, No Drawings

DIHALOPROPENE COMPOUNDS, THEIR USE AS INSECTICIDES/ACARICIDES AND INTERMEDIATES FOR THEIR PRODUCTION

This application is the national phase under 35 U.S.C. §371 of prior PCT International Application No. PCT/JP97/00141 which has an International filing date of Jan. 1, 1997 which designated the United States of America, the entire contents of which are hereby incorporated by reference.

TECHNICAL FIELD

The present invention relates to dihalopropene compounds, their use and intermediates for their production.

BACKGROUND ART

As disclosed in JP-A 49-1526/1974, for example, it is well known that some kinds of propene compounds can be used as active ingredients of insecticides.

In view of their insecticidal/acaricidal activity, however, it cannot always be said that these compounds are satisfactorily effective for the control of noxious insects, mites and ticks.

DISCLOSURE OF INVENTION

The present inventors have intensively studied to find a compound having excellent insecticidal/acaricidal activity. As a result, they have found that particular dihalopropene compounds have satisfactory insecticidal/acaricidal activity for the control of noxious insects, mites and ticks, thereby completing the present invention.

That is, the present invention provides dihalopropene compounds of the general formula:

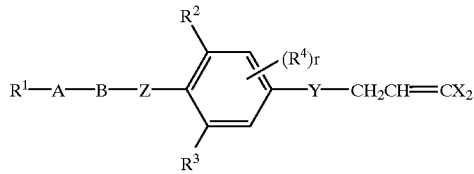

[I]

(hereinafter referred to as the present compound(s)) and insecticidal/acaricidal agents containing them active ingredients,
wherein $R^1$ is $C_1$–$C_8$ alkyl substituted with at least one atom or group selected from the class consisting of:
  halogen; $C_1$–$C_6$ alkoxy; $C_2$–$C_6$ haloalkoxy; $C_3$–$C_6$ alkenyloxy; $C_3$–$C_6$ haloalkenyloxy; $C_3$–$C_6$ alkynyloxy; $C_3$–$C_6$ haloalkynyloxy; $C_1$–$C_6$ alkylthio; $C_2$–$C_6$ haloalkylthio; $C_3$–$C_6$ alkenylthio; $C_3$–$C_6$ haloalkenylthio; $C_3$–$C_6$ alkynylthio; $C_3$–$C_6$ haloalkynylthio; $C_2$–$C_6$ alkanoyloxy optionally substituted with halogen; $C_2$–$C_6$ alkanoylamino optionally substituted with halogen; ($C_1$–$C_6$ alkoxy)carbonyl; ($C_2$–$C_6$ haloalkoxy)-carbonyl; ($C_3$–$C_6$ alkenyloxy)carbonyl; ($C_3$–$C_6$ haloalkenyloxy)carbonyl; ($C_3$–$C_6$ alkynyloxy) carbonyl; ($C_3$–$C_6$ haloalkynyloxy)carbonyl; cyano; nitro; hydroxyl; amino substituted with $C_1$–$C_6$ alkyl, $C_2$–$C_6$ haloalkyl, $C_3$–$C_6$ alkenyl, $C_3$–$C_6$ haloalkenyl, $C_3$–$C_6$ alkynyl or $C_3$–$C_6$ haloalkynyl; and carbamoyl substituted with $C_1$–$C_6$ alkyl, $C_2$–$C_6$ haloalkyl, $C_3$–$C_6$ alkenyl, $C_3$–$C_6$ haloalkenyl, $C_3$–$C_6$ alkynyl or $C_3$–$C_6$ haloalkynyl;

or $R^1$ is $Q^1$, $Q^2$ or $Q^3$ of the general formula:

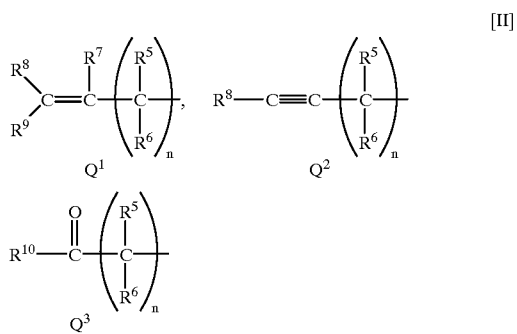

[II]

wherein $R^5$ and $R^6$ are each independently hydrogen, halogen, $C_1$–$C_3$ alkyl or $C_1$–$C_3$ haloalkyl,
  $R^7$ is hydrogen, halogen, $C_1$–$C_6$ alkyl or $C_1$–$C_6$ haloalkyl,
  $R^8$ and $R^9$ are each independently hydrogen, halogen, $C_1$–$C_6$ alkyl, $C_1$–$C_6$ haloalkyl, $C_2$–$C_6$ alkanoyl optionally substituted with halogen, ($C_1$–$C_6$ alkoxy)carbonyl, ($C_2$–$C_6$ haloalkoxy)carbonyl, ($C_3$–$C_6$ alkenyloxy) carbonyl, ($C_3$–$C_6$ haloalkenyloxy)carbonyl, ($C_3$–$C_6$ alkynyloxy)carbonyl, ($C_3$–$C_6$ haloalkynyloxy) carbonyl, cyano, nitro, or carbamoyl substituted with $C_1$–$C_6$ alkyl, $C_2$–$C_6$ haloalkyl, $C_3$–$C_6$ alkenyl, $C_3$–$C_6$ haloalkenyl, $C_3$–$C_6$ alkynyl or $C_3$–$C_6$ haloalkynyl,
  $R^{10}$ is $C_1$–$C_6$ alkyl or $C_1$–$C_6$ haloalkyl, and
  n ia an integer of 1 to 5;
  $R^2$, $R^3$ and $R^4$ are each independently halogen, $C_1$–$C_3$ alkyl, $C_1$–$C_3$ haloalkyl, $C_1$–$C_3$ alkoxy, $C_1$–$C_3$ haloalkoxy, nitro or cyano;
  A is oxygen, $S(O)_t$ or $NR^{14}$ in which $R^{14}$ is hydrogen or $C_1$–$C_3$ alkyl and t is an integer of 0 to 2;
  B is $B^5$, $B^2$ or $B^3$ of the general formula:

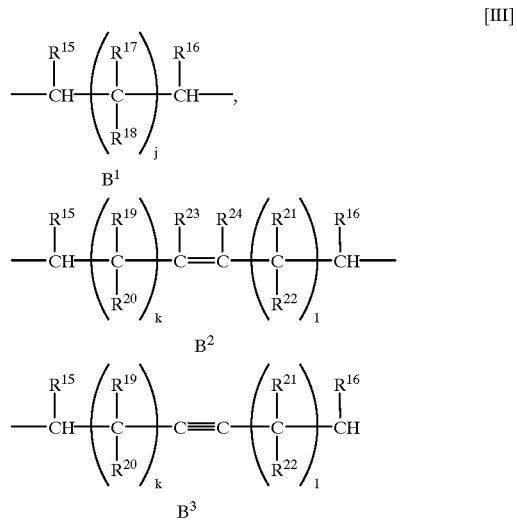

[III]

wherein $R^{15}$, $R^{16}$, $R^{17}$, $R^{18}$, $R^{19}$, $R^{20}$, $R^{21}$, $R^{22}$, $R^{23}$ and $R^{24}$ are each independently hydrogen, $C_1$–$C_3$ alkyl or trifluoromethyl, j is an integer of 0 to 5, and k and l are each independently an integer of 0 to 2;
  r is an integer of 0 to 2;
  X's are each independently halogen;
  Y is oxygen, sulfur or NH; and Z is oxygen, sulfur or $NR^{25}$ in which $R^{25}$ is hydrogen, acetyl or $C_1$–$C_3$ alkyl.

The present invention further provides compounds of the general formula:

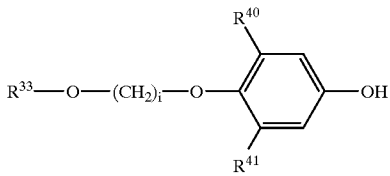

[IV]

which are useful as intermediates for the production of some of the present compounds, wherein $R^{33}$ is $P^1$ or $P^2$ of the general formula:

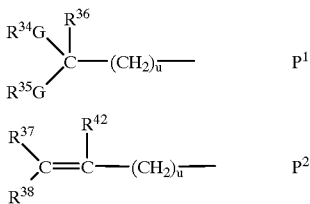

[V]

in which $R^{34}$ and $R^{35}$ are each independently $C_1$–$C_6$ alkyl or $C_2$–$C_3$ haloalkyl, $R^{37}$ and $R^{38}$ are each independently hydrogen, halogen, $C_1$–$C_6$ alkyl, $C_1$–$C_3$ haloalkyl, ($C_1$–$C_6$ alkoxy)carbonyl or cyano, $R^{36}$ is hydrogen, $C_1$–$C_6$ alkyl or $C_1$–$C_3$ haloalkyl, $R^{42}$ is hydrogen, halogen, $C_1$–$C_6$ alkyl or $C_1$–$C_3$ haloalkyl, G is oxygen or sulfur, and u is an integer of 1 to 3;

$R^{40}$ and $R^{41}$ are each independently halogen or $C_1$–$C_3$ alkyl; and i is an integer of 2 to 7.

The present invention further provides compounds of the general formula:

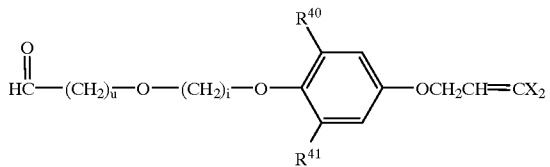

[VI]

which are useful as intermediates for the production of some of the present compounds, wherein $R^{40}$ and $R^{41}$ are each independently halogen or $C_1$–$C_3$ alkyl;

X's are each independently halogen;

u is an integer of 1 to 3; and i is an integer of 2 to 7.

DETAILED DESCRIPTION OF THE INVENTION

The variables in the above formulas for the present compounds and/or the compounds of the general formula [IV] or [VI] can take the following specific examples.

Examples of the halogen atom represented by $R^2$, $R^3$, $R^4$, $R^5$, $R^6$, $R^7$, $R^8$, $R^9$, $R^{37}$, $R^{38}$, $R^{40}$, $R^{41}$, $R^{42}$ or X, or present in $R^1$ may include fluorine, chlorine, bromine and iodine.

Examples of the $C_1$–$C_3$ alkyl group represented by $R^2$, $R^3$, $R^4$, $R^5$, $R^6$, $R^{14}$, $R^{15}$, $R^{16}$, $R^{17}$, $R^8$, $R^{19}$, $R^{20}$, $R^{21}$, $R^{22}$, $R^{23}$, $R^{24}$, $R^{25}$, $R^{40}$ or $R^{41}$ may include methyl, ethyl, n-propyl and isopropyl.

Examples of the $C_1$–$C_6$ alkyl group represented by $R^7$, $R^8$, $R^9$, $R^{10}$, $R^{34}$, $R^{35}$, $R^{36}$, $R^{37}$, $R^{38}$ or $R^{42}$ may include methyl, ethyl, n-propyl, isopropyl, n-butyl, isobutyl, sec-butyl, tert-butyl, n-pentyl, isopentyl, neopentyl, tert-pentyl, 1-ethylpropyl, n-hexyl, isohexyl, 2-ethylbutyl, 1-methylpentyl, 1-ethylbutyl, 3-methylpentyl and 1,3-dimethylbutyl.

Examples of the $C_1$–$C_8$ alkyl group present in $R^1$ may include methyl, ethyl, n-propyl, isopropyl, n-butyl, isobutyl, sec-butyl, tert-butyl, n-pentyl, isopentyl, neopentyl, tert-pentyl, 1-ethylpropyl, n-hexyl, isohexyl, 2-ethylbutyl, 1-methylpentyl, 1-ethylbutyl, 3-methylpentyl, 1,3-dimethylbutyl, n-heptyl, n-octyl and 1-methylheptyl.

Examples of the $C_1$–$C_3$ haloalkyl group represented by $R^2$, $R^3$, $R^4$, $R^5$, $R^6$, $R^{37}$, $R^{38}$ or $R^{42}$ may include trifluoromethyl, difluoromethyl, bromodifluoromethyl, 2,2,2-trifluoroethyl, 2-fluoroethyl, 2-chloroethyl, 2-bromoethyl, 1-fluoroethyl, 1-chloroethyl, 1-bromoethyl, 2,2,3,3,3-pentafluoropropyl, 3,3,3-trifluoropropyl, 1-fluoropropyl, 2-chloropropyl and 3-bromopropyl.

Examples of the $C_2$–$C_3$ haloalkyl group represented by $R^{34}$ or $R^{35}$ may include 2,2,2-trifluoroethyl, perfluoroethyl, 2-fluoroethyl, 2-chloroethyl, 2-bromoethyl, 2-iodoethyl, 2,2-dichloroethyl, 2-bromo-1,1,2,2-tetrafluoroethyl, 1,1,2,2-tetrafluoroethyl, 2-chloro-1,1,2-trifluoroethyl, 2-bromo-1,1,2-trifluoroethyl, 2,2,2-trifluoroethyl, 2,2,2-tribromoethyl, 3-chloropropyl, 3-bromopropyl, 3-fluoropropyl, 3-iodopropyl, 3,3,3-trifluoropropyl, 2,2,3,3,3-pentafluoropropyl, 1,1,2,3,3,3-hexafluoropropyl, 2-chloropropyl, 1-chloro-1-methylethyl, 1-bromo-1-methylethyl, 2-fluoro-1-(fluoromethyl)ethyl, 2-chloro-1-(chloromethyl)ethyl, 2-bromo-1-bromomethyl-ethyl, 2,2,2-trifluoro-1-(trifluoromethyl)ethyl and 2,3-dibromopropyl.

Examples of the $C_1$–$C_6$ haloalkyl group represented by $R^7$, $R^8$, $R^9$ or $R^{10}$ may include trifluoromethyl, difluoromethyl, bromodifluoromethyl, 2,2,2-trifluoroethyl, perfluoroethyl, 2-fluoroethyl, 2-chloroethyl, 2-bromoethyl, 2-iodoethyl, 2,2-dichloroethyl, 2-bromo-1,1,2,2-tetrafluoroethyl, 1,1,2,2-tetrafluoroethyl, 2-chloro-1,1,2-trifluoroethyl, 2-bromo-1,1,2-trifluoroethyl, 2,2,2-trichloroethyl, 2,2,2-tribromoethyl, 3-chloropropyl, 3-bromopropyl, 3-fluoropropyl, 3-iodopropyl, 3,3,3-trifluoropropyl, 2,2,3,3,3-pentafluoropropyl, 1,1,2,3,3,3-hexafluoropropyl, 2-chloropropyl, 1-chloro-1-methylethyl, 1-bromo-1-methylethyl, 2-fluoro-1-(fluoromethyl)ethyl, 2-chloro-1-(chloromethyl)ethyl, 2-bromo-1-bromomethylethyl, 2,2,2-trifluoro-1-(trifluoromethyl)ethyl, 2,3-dibromopropyl, 4-fluorobutyl, 4-bromobutyl, 4-chlorobutyl, 4-iodobutyl, 4-bromomethylpropyl, 3-chloro-2-dimethyl-n-propyl, 3-bromo-2,2-dimethylpropyl, 2,2,3,4,4,4-hexafluorobutyl, 3-bromo-1-bromomethylpropyl, 2,2,3,3,4,4,5,5-octafluoropentyl, 6-chlorohexyl and 6-bromohexyl.

Examples of the $C_1$–$C_3$ alkoxy group represented by $R^2$, $R^3$ or $R^4$ may include methoxy, ethoxy, n-propyloxy and isopropyloxy.

Examples of the $C_2$–$C_6$ haloalkoxy group present in $R^1$ may include 2,2,2-trifluoroethoxy, 2-fluoroethoxy, 2-chloroethoxy, 2-bromoethoxy, 2-iodoethoxy, 2,2- dichloroethoxy, 2,2,2-trichloroethoxy, 2,2,2-tribromoethoxy, 3-chloropropyloxy, 3-bromopropyloxy, 3-fluoropropyloxy, 3-iodopropyloxy, 3,3,3-trifluoropropyloxy, 2,2,3,3,3-pentafluoropropyloxy, 2-chloropropyloxy, 2-chloro-1-(chloromethyl)ethoxy, 2-bromo-1-bromomethyl-ethoxy, 2,2,2-trifluoro-1-(trifluoromethyl)ethoxy, 2,3-dibromopropyloxy, 4-fluorobutyloxy, 4-bromobutyloxy, 4-chlorobutyloxy, 4-iodobutyloxy, 4-bromomethylpropyloxy, 3-chloro-2-dimethyl-n-propyloxy, 3-bromo-2,2-dimethylpropyloxy, 2,2,3,4,4,4-hexafluorobutyl, 3-bromo-1-bromomethylpropyloxy, 2,2,3,3,4,4,5,5-octafluoropentyloxy, 6-chlorohexyloxy and 6-bromohexyloxy.

Examples of the $C_1$–$C_3$ haloalkoxy group represented by $R^2$, $R^3$ or $R^4$ may include trifluoromethoxy, difluoromethoxy, 2,2,2-trifluoroethoxy, 2,2,2,1,1-pentafluoroethoxy, 2-chloro-1,1,2-trifluoroethoxy, 2-bromo-1,1,2-trifluoroethoxy, 1,1,2,2-tetrafluoroethoxy and 3,3,3,2,2,1-hexafluoropropoxy.

Examples of the $C_3$–$C_6$ alkenyloxy group present in $R^5$ may include allyloxy, homoallyloxy, 2-butenyloxy, 1-methyl-2-propenyloxy, prenyloxy, 3-methyl-3-butenyloxy, 1-ethyl-2-propenyloxy, 2-ethyl-2-propenyloxy, 2-pentenyloxy, 2-methyl-2-butenyloxy, 1-methyl-2-butenyloxy, 2-methyl-3-butenyloxy, 4-pentenyloxy, 1-methyl-3-butenyloxy, 1-ethyl-2-propenyloxy, 1-propyl-2-propenyloxy, 3-hexenyloxy, 2-isopropyl-2-propenyloxy, 2-ethyl-2-butenyloxy, 2-methyl-2-pentenyloxy, 1-ethyl-2-butenyloxy, 1-methyl-4-pentenyloxy, 1,3-dimethyl-2-butenyloxy, 2-hexenyloxy, 4-hexenyloxy, 5-hexenyloxy and 1-n-propyl-2-propenyloxy.

Examples of the $C_3$–$C_6$ haloalkenyloxy group present in $R^1$ may include 3-chloro-2-propenyloxy, 3-bromo-2-propenyloxy, 2-chloro-2-propenyloxy, 2-bromo-2-propenyloxy, 3,3-dichloro-2-propenyloxy, 3,3-dibromo-2-propenyloxy, 3,3-difluoro-2-propenyloxy, 2-chloromethyl-2-propenyloxy, 4-chloro-2-butenyloxy, 4-chloro-2-butenyloxy, 3-chloro-4,4,4-trifluoro-2-butenyloxy, 4-bromo-3-fluoro-4,4-difluoro-2-butenyloxy, 3,4,4,4-tetrafluoro-2-butenyloxy, 4,4-dichloro-3-butenyloxy, 4,4-dibromo-3-butenyloxy, 3-chloro-2-butenyloxy and 6,6-dichloro-5-hexenyloxy.

Examples of the $C_3$–$C_6$ alkynyloxy group present in $R^1$ may include 2-propynyloxy, 1-methyl-2-propynyloxy, 2-butynyloxy, 3-butynyloxy, 2-methyl-3-butynyloxy, 1-methyl-3-butynyloxy, 2-pentynyloxy, 4-pentynyloxy, 3-pentynyloxy, 1-ethyl-2-propynyloxy, 2-hexynyloxy, 3-hexynyloxy and 5-hexynyloxy.

Examples of the $C_3$–$C_6$ haloalkynyloxy group present in $R^1$ may include 3-chloro-2-propynyloxy, 3-bromo-2-propynyloxy, 4-chloro-2-butynyloxy, 3-chloro-1-methyl-2-propynyloxy, 3-bromo-1-methyl-2-propynyloxy, 4-chloro-3-butynyloxy, 4-bromo-3-butynyloxy, 4-chloro-2-methyl-3-butynyloxy, 4-bromo-2-methyl-3-butynyloxy, 1-methyl-4-chloro-3-butynyloxy, 1-methyl-4-bromo-3-butynyloxy, 5-chloro-4-pentynyloxy, 5-bromo-4-pentynyloxy, 1-ethyl-3-chloro-2-propenyloxy, 1-ethyl-3-bromo-2-propynyloxy, 6-chloro-5-hexynyloxy and 6-bromo-5-hexynyloxy.

Examples of the $C_1$–$C_6$ alkylthio group present in $R^1$ may include methylthio, ethylthio, n-propylthio, isopropylthio, n-butylthio, isobutylthio, sec-butylthio, tert-butylthio, n-pentylthio, isopentylthio, neopentylthio, tert-pentylthio, 1-ethylpropylthio, n-hexylthio, isohexylthio, 2-ethylabutylthio, 1-methylpentylthio, 1-ethylbutylthio, 3-methylpentylthio and 1,3-dimethylbutylthio.

Examples of the $C_2$–$C_6$ haloalkylthio group present in $R^1$ may include 2,2,2-trifluoroethylthio, 2-fluoroethylthio, 2-chloroethylthio, 2-bromoethylthio, 2-iodoethylthio, 2,2-dichloroethylthio, 2,2,2-trichloroethylthio, 2,2,2-tribromoethylthio, 3-chloropropylthio, 3-bromopropylthio, 3-fluoropropylthio, 3-iodopropylthio, 3,3,3-trifluoropropylthio, 2,2,3,3,3-pentafluoropropylthio, 2-chloro-1-(chloromethyl)ethylthio, 2-bromo-1-bromomethyl-ethylthio, 2,2,2-trifluoro-1-(trifluoromethyl)ethylthio, 2,3-dibromopropylthio, 4-fluorobutylthio, 4-bromobutylthio, 4-chlorobutylthio, 4-iodobutylthio, 4-bromomethylpropylthio, 3-chloro-2-dimethyl-n-propylthio, 3-bromo-2,2-diemthylpropylthio, 2,2,3,4,4,4-hexafluorobutylthio, 3-bromo-1-bromomethylpropylthio, 2,2,3,3,4,4,5,5-octafluoropentylthio, 6-chlorohexylthio and 6-bromohexylthio.

Examples of the $C_3$–$C_6$ alkenylthio group present in $R^1$ may include allylthio, homoallylthio, 2-butenylthio, 1-methyl-2-propenylthio, prenylthio, 3-methyl-3-butenylthio, 1-methyl-2-propenylthio, 2-ethyl-2-propenylthio, 2-pentenylthio, 2-methyl-2-butenylthio, 1-methyl-2-butenylthio, 2-methyl-3-butenylthio, 4-pentenylthio, 1-methyl-3-butenylthio, 1-ethyl-2-propenylthio, 1-propyl-2-propenylthio, 3-hexenylthio, 2-isopropyl-2-propenylthio, 2-ethyl-2-butenylthio, 2-methyl-2-pentenylthio, 1-ethyl-2-butenylthio, 1-methyl-4-pentenylthio, 1,3-dimethyl-2-butenylthio, 2-hexenylthio, 4-hexenylthio, 5-hexenylthio and 1-n-propyl-2-propenylthio.

Examples of the $C_3$–$C_6$ haloalkenylthio group present in $R^1$ may include 3-chloro-2-propenylthio, 3-bromo-2-propenylthio, 2-chloro-2-propenylthio, 2-bromo-2-propenylthio, 3,3-dichloro-2-propenylthio, 3,3-dibromo-2-propenylthio, 3,3-difluoro-2-propenylthio, 2-chloromethyl-2-propenylthio, 4-chloro-2-butenylthio, 4-chloro-2-butenylthio, 3-chloro-4,4,4-trifluoro-2-butenylthio, 4-bromo-3-fluoro-4,4-difluoro-2-butenylthio, 3,4,4,4-tetrafluoro-2-butenylthio, 4,4-dichloro-2-butenylthio, 4,4-dibromo-3-butenylthio, 3-chloro-2-butenylthio and 6,6-dichloro-5-hexenylthio.

Examples of the $C_3$–$C_6$ alkynylthio group present in $R^1$ may include 2-propynylthio, 1-methyl-2-propynylthio, 2-butynylthio, 3-butynylthio, 2-methyl-3-butynylthio, 1-methyl-3-butynylthio, 2-pentynylthio, 4-pentynylthio, 3-pentynylthio, 1-ethyl-2-propynylthio, 2-hexynylthio, 3-hexynylthio and 5-hexynylthio.

Examples of the $C_3$–$C_6$ haloalkynylthio group present in $R^1$ may include 3-chloro-2-propynylthio, 3-bromo-2-propynylthio, 4-chloro-2-butynylthio, 3-chloro-1-methyl-2-propynylthio, 3-bromo-1-methyl-2-propynylthio, 4-chloro-3-butynylthio, 4-bromo-3-butynylthio, 4-chloro-2-methyl-3-butynylthio, 4-bromo-2-methyl-3-butynylthio, 1-methyl-4-chloro-3-butynylthio, 1-methyl-4-bromo-3-butynylthio, 5-chloro-4-pentynylthio, 5-bromo-4-pentynylthio, 1-ethyl-3-chloro-2-propynylthio, 1-ethyl-3-bromo-2-propynylthio, 6-chloro-5-hexynylthio and 6-bromo-5-hexynylthio.

Examples of the $C_2$–$C_6$ alkanoyl group optionally substituted with halogen, which is represented by $R^8$ or $R^9$, may include acetyl, trifluoroacetyl, trichloroacetyl, fluoroacetyl, chloroacetyl, propionyl, pentafluoropropionyl, 2-chloropropionyl, butyryl, isobutyryl, valeryl, pivaloyl and hexanoyl.

Examples of the $C_2$–$C_6$ alkanoyloxy group optionally substituted with halogen, which is present in $R^1$, may include acetyloxy, trifluoroacetyloxy, trichloroacetyloxy, fluoroacetyloxy, chloroacetyl, propionyloxy, pentafluoropropionyloxy, 2-chloropropionyloxy, butyryloxy, isobutyryloxy, valeryloxy, pivaloyloxy and hexanoyloxy.

Examples of the $C_2$–$C_6$ alkanoylamino group optionally substituted with halogen, which is present in $R^1$, may include acetylamino, trifluoroacetylamino, trichloroacetylamino, fluoroacetylamino, chloroacetylamino, propionylamino, tetrafluoropropionylamino, 2-chloropropionyloxy, butyrylamino, isobutyrylamino, valerylamino, pivaloylamino and hexanoylamino.

Examples of the ($C_1$–$C_6$ alkoxy)carbonyl group represented by $R^8$, $R^9$, $R^{37}$ or $R^{38}$, or present in $R^1$, may include methoxycarbonyl, ethoxycarbonyl, n-propyloxycarbonyl, isopropyloxycarbonyl, n-butyloxycarbonyl, isobutyloxycarbonyl, sec-butyloxycarbonyl, tert-butyloxycarbonyl, n-pentyloxycarbonyl, isopentyloxycarbonyl, neopentyloxycarbonyl, tert-pentyloxycarbonyl, 1-ethylpropyloxycarbonyl, n-hexyloxycarbonyl, isohexyloxycarbonyl, 2-ethylbutyloxycarbonyl, 1-methylpentyloxycarbonyl, 1-ethylbutyloxycarbonyl, 3-methylpentyloxycarbonyl and 1,3-dimethylbutyloxycarbonyl.

Examples of the ($C_2$–$C_6$ haloalkoxy)carbonyl group represented by $R^8$ or $R^9$, or present in $R^1$, may include 2,2,2-trifluoroethoxycarbonyl, 2-fluoroethoxycarbonyl, 2-chloroethoxycarbonyl, 2-bromoethoxycarbonyl, 2-iodoethoxycarbonyl, 2,2-dichloroethoxycarbonyl, 2,2,2-trichloroethoxycarbonyl, 2,2,2-tribromoethoxycarbonyl, 3-chloropropyloxycarbonyl, 3-bromopropyloxycarbonyl, 3-fluoropropyloxycarbonyl, 3-iodopropyloxycarbonyl, 3,3,3-trifluoropropyloxycarbonyl, 2,2,3,3,3-pentafluoropropyloxycarbonyl, 2-chloro-1-(chloromethyl)ethoxycarbonyl, 2-bromo-1-bromomethylethoxycarbonyl, 2,2,2-trifluoro-1-(trifluoromethyl)ethoxycarbonyl, 2,3-dibromopropyloxycarbonyl, 4-fluorobutyloxycarbonyl 4-bromobutyloxycarbonyl, 4-chlorobutyloxycarbonyl, 4-iodobutyloxycarbonyl, 4-bromomethylpropyloxycarbonyl, 3-chloro-2-dimethyl-n-propyloxycarbonyl, 3-bromo-2,2-dimethylpropyloxycarbonyl, 2,2,3,4,4,4-hexafluorobutyloxycarbonyl, 3-bromo-1-bromomethylpropyloxycarbonyl, 2,2,3,3,4,4,5,5-octafluoropentyloxycarbonyl, 6-chlorohexyloxycarbonyl and 6-bromohexyloxycarbonyl.

Examples of the ($C_3$–$C_6$ alkenyloxy)carbonyl group represented by $R^8$ or $R^9$, or present in $R^1$, may include allyloxycarbonyl, homoallyloxycarbonyl, 2-butenyloxycarbonyl, 1-methyl-2-propenyloxycarbonyl, prenyloxycarbonyl, 3-methyl-3-butenyloxycarbonyl, 1-ethyl-2-propenyloxycarbonyl, 2-ethyl-2-propenyloxycarbonyl, 2-pentenyloxycarbonyl, 2-methyl-2-butenyloxycarbonyl, 1-methyl-2-butenyloxycarbonyl, 2-methyl-3-butenyloxycarbonyl, 4-pentenyloxycarbonyl, 1-methyl-3-butenyloxycarbonyl, 1-ethyl-2-propenyloxycarbonyl, 1-propyl-2-propenyloxycarbonyl, 3-hexnyloxycarbonyl, 2-isopropyl-2-propenyloxycarbonyl, 2-ethyl-2-butenyloxycarbonyl, 2-methyl-2-pentenyloxycarbonyl, 1-ethyl-2-butenyloxycarbonyl, 1-methyl-4-pentenyloxycarbonyl, 1,3-dimethyl-2-butenyloxycarbonyl, 2-hexenyloxycarbonyl, 4-hexenyloxycarbonyl, 5-hexenyloxycarbonyl and 1-n-propyl-2-propenyloxycarbonyl.

Examples of the ($C_3$–$C_6$ haloalkenyloxy)carbonyl group represented by $R^8$ or $R^9$, or present in $R^1$, may include 3-chloro-2-propenyloxycarbonyl, 3-bromo-2-propenyloxycarbonyl, 2-chloro-2-propenyloxycarbonyl, 2-bromo-2-propenyloxycarbonyl, 3,3-dichloro-2-propenyloxycarbonyl, 3,3-dibromo-2-propenyloxycarbonyl, 3,3-difluoro-2-propenyloxycarbonyl, 2-chloromethyl-2-propenyloxycarbonyl, 4-chloro-2-butenyloxycarbonyl, 4-chloro-2-butenyloxycarbonyl, 3-chloro-4,4,4-trifluoro-2-butenyloxycarbonyl, 4-bromo-3-fluoro-4,4-difluoro-2-butenyloxycarbonyl, 3,4,4,4-tetrafluoro-2-butenyloxycarbonyl, 4,4-dichloro-3-butenyloxycarbonyl, 4,4-dibromo-3-butenyloxycarbonyl, 3-chloro-2-butenyloxycarbonyl and 6,6-dichloro-5-hexenyloxycarbonyl.

Examples of the ($C_3$–$C_6$ alkynyloxy)carbonyl group represented by $R^8$ or $R^9$, or present in $R^1$, may include 2-propynyloxycarbonyl, 1-methyl-2-propynyloxycarbonyl, 2-butynyloxycarbonyl, 3-butynyloxycarbonyl, 2-methyl-3-butynyloxycarbonyl, 1-methyl-3-butynyloxycarbonyl, 2-pentynyloxycarbonyl, 4-pentynyloxycarbonyl, 3-pentynyloxycarbonyl, 1-ethyl-2-propynyloxycarbonyl, 2-hexynyloxycarbonyl, 3-hexynyloxycarbonyl and 5-hexynyloxycarbonyl.

Examples of the ($C_3$–$C_6$ haloalkynyloxy)carbonyl group represented by $R^8$ or $R^9$, or present in $R^1$, may include 3-chloro-2-propynyloxycarbonyl, 3-bromo-2-propynyloxycarbonyl, 4-chloro-2-butynyloxycarbonyl, 3-chloro-5-methyl-2-propynyloxycarbonyl, 3-bromo-1-methyl-2-propynyloxycarbonyl, 4-chloro-3-butynyloxycarbonyl, 4-bromo-3-butynyloxycarbonyl, 4-chloro-2-methyl-3-butynyloxycarbonyl, 4-bromo-2-methyl-3-butynyloxycarbonyl, 1-methyl-4-chloro-3-butynyloxycarbonyl, 1-methyl-4-bromo-3-butynyloxycarbonyl, 5-chloro-4-pentynyloxycarbonyl, 5-bromo-4-pentynyloxycarbonyl, 1-ethyl-3-chloro-2-propynyloxycarbonyl, 1-ethyl-3-bromo-2-propynyloxycarbonyl, 6-chloro-5-hexynyloxycarbonyl and 6-bromo-5-hexynyloxycarbonyl.

Examples of the amino group substituted with $C_1$–$C_6$ alkyl, $C_2$–$C_6$ haloalkyl, $C_3$–$C_6$ alkenyl, $C_3$–$C_6$ haloalkenyl, $C_3$–$C_6$ alkynyl or $C_3$–$C_6$ haloalkynyl, which is present in $R^5$, may include methylamino, ethylamino, n-propylamino, (2,2,2-trifluoroethyl)-amino, allylamino, 3-chloro-2-propenylamino, 3,3-dichloro-2-propenylamino, 2-propynylamino, 3-chloro-2-propynylamino, N,N-dimethylamino, N-ethyl-N-methylamino, diallylamino, N-allyl-N-methylamino, N-(3,3-dichloro-2-propenyl)-N-methylamino and N,N-dipropargylamino.

Examples of the carbamoyl group substituted with $C_1$–$C_6$ alkyl, $C_2$–$C_6$ haloalkyl, $C_3$–$C_6$ alkenyl, $C_3$–$C_6$ haloalkenyl, $C_3$–$C_6$ alkynyl or $C_3$–$C_6$ haloalkynyl, which is represented by $R^8$ or $R^9$, or present in $R^1$, may include methylcarbamoyl, ethylcarbamoyl, n-propylcarbamoyl, 2,2,2-trifluoroethylcarbamoyl, allylcarbamoyl, 3-chloro-2-propenylcarbamoyl, 3,3-dichloro-2-propenylcarbamoyl, 2-propynylcarbamoyl, 3-chloro-2-propynylcarbamoyl, N,N-dimethylcarbamoyl, N-ethyl-N-methylcarbamoyl, diallylcarbamoyl, N-allyl-N-methylcarbamoyl, N-3,3-dichloro-2-propenyl-N-methylcarbamoyl and N,N-dipropargylcarbamoyl.

The following are preferred examples of the present compounds:

dihalopropene compounds wherein Y and Z are both oxygen;

dihalopropene compounds wherein $R^2$, $R^3$ and $R^4$ are each independently halogen, $C_1$–$C_3$ alkyl or $C_1$–$C_3$ haloalkyl;

dihalopropene compounds wherein $R^2$ and $R^3$ are each independently halogen, $C_1$–$C_3$ alkyl or $C_1$–$C_3$ haloalkyl, and r is 0;

dihalopropene compounds wherein $R^2$ and $R^3$ are each independently halogen or $C_1$–$C_3$ alkyl, and r is 0;

dihalopropene compounds wherein A is oxygen;

dihalopropene compounds wherein B is $B^1$, and X is chlorine or bromine;

dihalopropene compounds wherein B is $B^1$ in which $R^{15}$, $R^{16}$, $R^{17}$ and $R^{18}$ are all hydrogen, and X is chlorine or bromine;

dihalopropene compounds wherein $R^1$ is $C_1$–$C_8$ alkyl substituted with 1 to 3 groups selected from the class consisting of:

$C_1$–$C_6$ alkoxy; $C_2$–$C_6$ haloalkoxy; $C_3$–$C_6$ alkenyloxy; $C_3$–$C_6$ haloalkenyloxy; $C_3$–$C_6$ alkynyloxy; $C_3$–$C_6$ haloalkynyloxy; $C_1$–$C_6$ alkylthio; $C_2$–$C_6$ haloalkylthio; $C_3$–$C_6$ alkenylthio; $C_3$–$C_6$ haloalkenylthio; $C_3$–$C_6$ alkynylthio; $C_3$–$C_6$ haloalkynylthio; $C_2$–$C_6$ alkanoyloxy optionally substituted with halogen; $C_2$–$C_6$ alkanoylamino optionally substituted with halogen; and amino substituted with $C_1$–$C_6$ alkyl, $C_2$–$C_6$ haloalkyl, $C_3$–$C_6$ alkenyl, $C_3$–$C_6$ haloalkenyl, $C_3$–$C_6$ alkynyl or $C_3$–$C_6$ haloalkynyl.

dihalopropene compounds wherein $R^1$ is $C_1$–$C_8$ alkyl substituted with 1 to 3 groups selected from the class consisting of $C_1$–$C_6$ alkoxy and $C_2$–$C_6$ haloalkoxy;

dihalopropene compounds wherein $R^1$ is $Q^1$;

dihalopropene compounds wherein $R^1$ is $Q^1$, $Q^2$ or $Q^3$ in which $R^5$ and $R^6$ are both hydrogen; and dihalopropene compounds wherein Y and Z are both oxygen, $R^2$ and $R^3$ are each independently halogen, $C_1$–$C_3$ alkyl or $C_1$–$C_3$ haloalkyl, A is oxygen, B is $B^1$ in which $R^{15}$, $R^{16}$, $R^{17}$ and $R^{18}$ are all hydrogen, and $R^1$ is $Q^1$ in which $R^5$ and $R^6$ are both hydrogen, n is 1, and $R^7$, $R^8$ and $R^9$ are each independently hydrogen, halogen, $C_1$–$C_6$ alkyl or $C_1$–$C_3$ haloalkyl.

The present compounds can be produced, for example, by the following production processes A to S.

(Production process A)

In this process, a compound of the general formula:

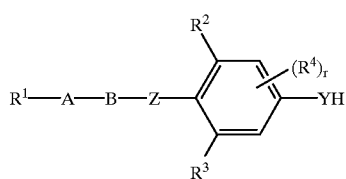

[VII]

wherein $R^1$, $R^2$, $R^3$, $R^4$, A, B, r, Y and Z are as defined above, is reacted with a halide compound of the general formula:

L—CH$_2$CH=CX$_2$  [VIII]

wherein X is as defined above and L is halogen (e.g., chlorine, bromine, iodine), mesyloxy or tosyloxy.

The reaction is preferably effected in the presence of a suitable base in an inert solvent.

Examples of the solvent which can be used may include ketones such as acetone, methyl ethyl ketone and cyclohexanone; ethers such as 1,2-dimethoxyethane, tetrahydrofuran, dioxane and dialkyl (e.g., $C_1$–$C_4$) ether (e.g., diethyl ether, diisopropyl ether); N,N-dimethylformamide, dimethylsulfoxide, hexamethylphosphoric triamide, sulforane, acetonitrile, nitromethane; halogenated hydrocarbons such as dichloromethane, chloroform, 1,2-dichloroethane and chlorobenzene; hydrocarbons such as toluene, benzene and xylene; and water. If necessary, a mixture of these solvents can be used.

Examples of the base which can be used may include hydroxides of alkali metals or alkaline earth metals, such as lithium hydroxide, sodium hydroxide, potassium hydroxide and calcium hydroxide; carbonates of alkali metals or alkaline earth metals, such as lithium carbonate, potassium carbonate, sodium carbonate and calcium carbonate; hydrides of alkali metals or alkaline earth metals, such as lithium hydride, sodium hydride, potassium hydride and calcium hydride; alkali metal alkoxides (e.g., $C_1$–$C_4$), such as sodium methoxide, sodium ethoxide and potassium tert-butoxide; and organic bases such as triethylamine and pyridine. If necessary, catalysts such as ammonium salts (e.g., benzyltriethylammonium chloride) may be added to the reaction system at a ratio of 0.01 to 1 mole per mole of the compound of the general formula [VII].

The reaction temperature is usually set within the range of –20° C. to +150° C. or the boiling point of a solvent used in the reaction, preferably –5° C. to +100° C. or the boiling point of a solvent used in the reaction.

The molar ratio of the starting materials and bases to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Furthermore, purification may be carried out, if necessary, by an ordinary technique such as chromatography, distillation or recrystallization.

(Production process B for the present compounds wherein Y is oxygen)

In this process, a compound of the general formula [VII] is reacted with an alcohol compound of the general formula:

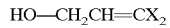

HO—CH$_2$CH=CX$_2$  [IX]

wherein X is as defined above.

The reaction is preferably effected in the presence of a suitable dehydrating agent in an inert solvent, if necessary.

Examples of the dehydrating agent which can be used may include dicyclohexylcarbodiimide, and dialkyl (e.g., $C_1$–$C_4$) azodicarboxylates (e.g., diethyl azodicarboxylate, diisopropyl azodicarboxylate)-trialkyl (e.g., $C_1$–$C_{20}$) phosphine or triarylphosphine (e.g., triphenylphosphine, trioctylphosphine, tributylphosphine).

Examples of the solvent which can be used may include hydrocarbons such as benzene, xylene and toluene; ethers such as diethyl ether, diisopropyl ether, tetrahydrofuran and dioxane; and halogenated hydrocarbons such as carbon tetrachloride, dichloromethane, chlorobenzene and dichlorobenzene.

The reaction temperature is usually set within the range of –20° C. to +200° C. or the boiling point of a solvent used in the reaction.

The molar ratio of the starting materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Furthermore, purification may be carried out, if necessary, by an ordinary technique such as chromatography, distillation or recrystallization.

(Production process C for the present compounds wherein Y is oxygen and $R^1$ is not $Q^3$)

In this process, an aldehyde compound of the general formula:

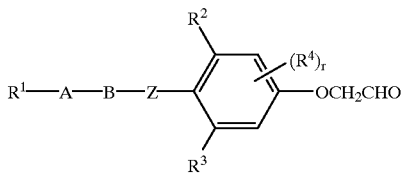

[X]

wherein $R^1$, $R^2$, $R^3$, $R^4$, A, B, r and Z are as defined above, is reacted with a halogenated compound of the general formula:

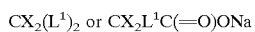

[XI]

wherein X is as defined above and $L^1$ is chlorine or bromine.

The reaction is preferably effected in the presence of a suitable trialkylphosphine or triarylphosphine, and if necessary, in the presence of metal zinc, in an inert solvent.

Examples of the solvent which can be used may include hydrocarbons such as benzene, xylene and toluene; ethers such as diethyl ether, diisopropyl ether, tetrahydrofuran, dioxane and diglyme; and halogenated hydrocarbons (exclusive of carbon tetrabromide and carbon tetrachloride) such as dichloromethane, 1,2-dichloroethane and chlorobenzene.

The reaction temperature is usually set within the range of $-30°$ C. to $+200°$ C. or the boiling point of a solvent used in the reaction.

Examples of the trialkyl (e.g., $C_1$–$C_{20}$) phosphine or triarylphosphine, which can be used in the reaction, may include triphenylphosphine and trioctylphosphine. The metal zinc which is used, if necessary, is preferably in dust form.

The molar ratio of the starting materials and reagents to be used in the reaction can be freely determined, but the ratio is preferably such that the halogenated compound of the general formula [XI], trialkylphosphine or triarylphosphine, and zinc when used, are 1 to 5 moles, 2 to 10 moles, and 1 to 5 moles, respectively, per mole of the aldehyde compound of the general formula [X], or it is favorable to effect the reaction at a ratio closer thereto.

After completion of the reaction, the reaction mixture is subjected to ordinary post-treatments such as organic solvent extraction and concentration, and the desired compound of the present invention can be isolated. Furthermore, purification may be carried out, if necessary, by an ordinary technique such as chromatography, distillation or recrystallization.

(Production process D for the present compounds wherein Y and Z are both oxygen)

In this process, a compound of the general formula:

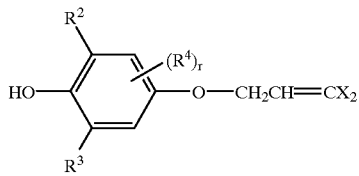

[XII]

wherein $R^2$, $R^3$, $R^4$, r, X, Y and Z are as defined above, is reacted with a compound of the general formula:

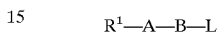

[XIII]

wherein $R^1$, A, B and L are as defined above.

The reaction is preferably effected in the presence of a suitable base in an inert solvent.

Examples of the solvent which can be used may include ketones such as acetone, methyl ethyl ketone and cyclohexanone; ethers such as 1,2-dimethoxyethane, tetrahydrofuran, dioxane and dialkyl (e.g., $C_1$–$C_4$) ethers (e.g., diethyl ether, diisopropyl ether); N,N-dimethylformamide, dimethylsulfoxide, hexamethylphosphoric triamide, sulforane, acetonitrile, nitromethane; halogenated hydrocarbons such as dichloromethane, chloroform, 1,2-dichloroethane and chlorobenzene; hydrocarbons such as toluene, benzene and xylene; and water. If necessary, a mixture of these solvents can be used.

Examples of the base which can be used may include hydroxides of alkali metals or alkaline earth metals, such as lithium hydroxide, sodium hydroxide, potassium hydroxide and calcium hydroxide; carbonates of alkali metals or alkaline earth metals, such as lithium carbonate, potassium carbonate, sodium carbonate and calcium carbonate; hydrides of alkali metals or alkaline earth metals, such as lithium hydride, sodium hydride, potassium hydride and calcium hydride; alkali metal alkoxides (e.g., $C_1$–$C_4$) such as sodium methoxide, sodium ethoxide and potassium tert-butoxide; organic bases such as triethylamnine and pyridine. If necessary, catalysts such as ammonium salts (e.g., benzyltriethylammonium chloride) may be added to the reaction system at a ratio of 0.01 to 1 mole per mole of the compound of the general formula [XII].

The reaction temperature is usually set within the range of $-20°$ C. to $+150°$ C. or the boiling point of a solvent used in the reaction, preferably $-5°$ C. to $+100°$ C. or the boiling point of a solvent used in the reaction.

The molar ratio of the starting materials and bases to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Furthermore, purification may be carried out, if necessary, by an ordinary technique such as chromatography, distillation or recrystallization.

(Production process E for the present compounds wherein Y and Z are both oxygen)

In this process, a compound of the general formula [XII] is reacted with a compound of the general formula:

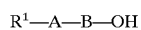

[XIV]

wherein $R^1$ is as defined above.

The reaction is preferably effected in the presence of a suitable dehydrating agent in an inert solvent, if necessary.

Examples of the dehydrating agent which can be used may include dicyclohexylcarbodiimide, and dialkyl (e.g., $C_1$–$C_4$) azodicarboxylates (e.g., diethyl azodicarboxylate, diisopropyl azodicarboxylate)-trialkyl (e.g., $C_1$–$C_{20}$) phosphine or triarylphosphine (e.g., triphenylphosphine, trioctylphosphine, tributylphosphine).

Examples of the solvent which can be used may include hydrocarbons such as benzene, xylene and toluene; ethers such as diethyl ether, diisopropyl ether, tetrahydrofuran and dioxane; and halogenated hydrocarbons such as carbon tetrachloride, dichloromethane, chlorobenzene and dichlorobenzene.

The reaction temperature is usually set within the range of –20° C. to +200° C. or the boiling point of a solvent used in the reaction.

The molar ratio of the materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Furthermore, purification may be carried out, if necessary, by an ordinary technique such as chromatography, distillation or recrystallization.

(Production process F for the present compounds wherein Y and Z are both oxygen and A is $A^1$ in which $A^1$ is A other than SO and $SO_2$, and A is as defined above)

In this process, a compound of the general formula:

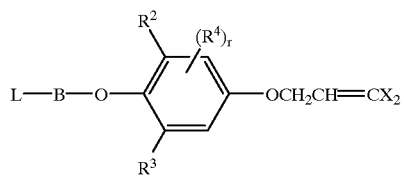

[XV]

wherein $R^2$, $R^3$, $R^4$, B, X, L and r are as defined above, is reacted with a compound of the general formula:

$R^1$—$A^1$H [XVI]

wherein $R^1$ and $A^1$ are as defined above.

The reaction is preferably effected in the presence of a suitable base in an inert solvent.

Examples of the solvent which can be used may include ethers such as 1,2-dimethoxyethane, tetrahydrofuran, dioxane and dialkyl (e.g., $C_1$–$C_4$) ethers (e.g., diethyl ether, diisopropyl ether); N,N-dimethylformamide, dimethylsulfoxide, hexamethylphosphoric triamide, sulforane, acetonitrile, nitromethane; halogenated hydrocarbons such as dichloromethane, chloroform, 1,2-dichloroethane and chlorobenzene; hydrocarbons such as toluene, benzene and xylene; and water. If necessary, a mixture of these solvents can be used.

Examples of the base which can be used may include hydroxides of alkali metals or alkaline earth metals, such as lithium hydroxide, sodium hydroxide, potassium hydroxide and calcium hydroxide; carbonates of alkali metals or alkaline earth metals, such as lithium carbonate, potassium carbonate, sodium carbonate and calcium carbonate; hydrides of alkali metals or alkaline earth metals, such as lithium hydride, sodium hydride, potassium hydride and calcium hydride; alkali metal alkoxides (e.g., $C_1$–$C_4$) such as sodium methoxide, sodium ethoxide and potassium tert-butoxide; organic bases such as triethylamine and pyridine. If necessary, catalysts such as ammonium salts (e.g., benzyltriethylammonium chloride) may be added to the reaction system at a ratio of 0.01 to 1 mole per mole of the compound of the general formula [XV].

The reaction temperature is usually set within the range of –20° C. to +150° C. or the boiling point of a solvent used in the reaction, preferably –5° C. to +100° C. or the boiling point of a solvent used in the reaction.

The molar ratio of the starting materials and bases to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Furthermore, purification may be carried out, if necessary, by an ordinary technique such as chromatography, distillation or recrystallization.

(Production process G for the present compounds wherein Y and Z are both oxygen and A is $A^1$ in which $A^1$ is as defined above)

In this process, a compound of the general formula:

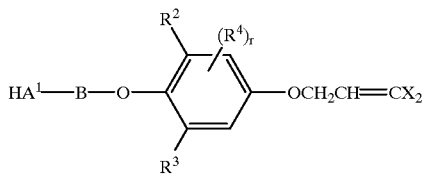

[XVII]

wherein $R^2$, $R^3$, $R^4$, $A^1$, B, X and r are as defined above, is reacted with a compound of the general formula:

$R^1$—L [XVIII]

wherein $R^1$ and L are as defined above.

The reaction is preferably effected in the presence of a suitable base in an inert solvent.

Examples of the solvent which can be used may include ethers such as 1,2-dimethoxyethane, tetrahydrofuran, dioxane and dialkyl (e.g., $C_1$–$C_4$) ether (e.g., diethyl ether, diisopropyl ether); N,N-dimethylformamide, dimethylsulfoxide, hexamethylphosphoric triamide, sulforane, acetonitrile, nitromethane; halogenated hydrocarbons such as dichloromethane, chloroform, 1,2-dichloroethane and chlorobenzene; hydrocarbons such as toluene, benzene and xylene; and water. If necessary, a mixture of these solvents can be used.

Examples of the base which can be used may include hydroxides of alkali metals or alkaline earth metals, such as lithium hydroxide, sodium hydroxide, potassium hydroxide and calcium hydroxide; carbonates of alkali metals or alkaline earth metals, such as lithium carbonate, potassium carbonate, sodium carbonate and calcium carbonate; hydrides of alkali metals or alkaline earth metals, such as lithium hydride, sodium hydride, potassium hydride and calcium hydride; alkali metal alkoxides (e.g., $C_1$–$C_4$) such as sodium methoxide, sodium ethoxide and potassium tert-butoxide; organic bases such as triethylamine and pyridine.

If necessary, catalysts such as ammonium salts (e.g., benzyltriethylammonium chloride) may be added to the reaction system at a ratio of 0.01 to 1 mole per mole of the compound of the general formula [XVII].

The reaction temperature is usually set within the range of −20° C. to +150° C. or the boiling point of a solvent used in the reaction, preferably −5° C. to +100° C. or the boiling point of a solvent used in the reaction The molar ratio of the materials and dehydrating agents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Furthermore, purification may be carried out, if necessary, by an ordinary technique such as chromatography, distillation or recrystallization.

(Production process H for the present compounds wherein Y and Z are both oxygen and $R^1$ is of the general formula:

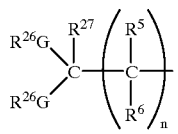

[XIX]

wherein $R^{26}$ is $C_1$–$C_6$ alkyl, $C_2$–$C_6$ haloalkyl, $C_2$–$C_6$ alkenyl, $C_3$–$C_6$ haloalkenyl, $C_3$–$C_6$ alkynyl or $C_3$–$C_6$ haloalkynyl, $R^{27}$ is hydrogen, $C_1$–$C_6$ alkyl or $C_3$–$C_6$ haloalkyl, G, $R^5$, $R^6$ and n are as defined above)

In this process, a compound of the general formula:

$R^{26}GH$                               [XX]

wherein $R^{26}$ and G are as defined above, is reacted with a carbonyl compound of the general formula:

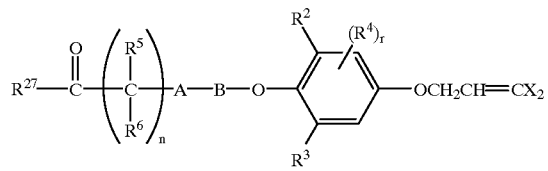

[XXI]

wherein $R^2$, $R^3$, $R^4$, $R^5$, $R^6$, $R^{27}$, A, B, X, r and n are as defined above.

The reaction is preferably effected in a suitable acid catalyst in an inert solvent.

Examples of the acid catalyst which can be used may include hydrochloric acid, sulfuric acid, hydrogen chloride, hydrogen bromide, calcium chloride, ammonium chloride, p-toluenesulfonic acid, pyridinium p-toluenesulfonate, trimethylsilyl chloride, aluminum chloride and alumina.

Examples of the solvent which can be used may include hydrocarbons such as benzene, toluene, xylene, hexane and cyclohexane; and halogenated hydrocarbons such as carbon tetrachloride, chloroform, dichloromethane, chlorobenzene and dichlorobenzene. If necessary, a mixture of these solvents can be used.

Alternatively, the reaction can also be effected with a large excess of the compound of the general formula [XX] to the carbonyl compound of the general formula [XXI].

If necessary, water formed as a by-product can be removed as an azeotropic mixture with benzene or the like, or using a dehydrating agent (e.g., calcium sulfate, aluminum oxide, copper sulfate, molecular sieves).

The reaction temperature is usually set within the range of −20° C. to +200° C. or the boiling point of a solvent used in the reaction.

The molar ratio of the starting materials and reagents to be used in the reaction can be freely determined.

After completion of the reaction, the reaction mixture is subjected to ordinary post-treatments such as organic solvent extraction and concentration, and the desired compound of the present invention can be isolated. Furthermore, purification may be carried out, if necessary, by an ordinary technique such as chromatography, distillation or recrystallization.

(Production process J for the present compounds wherein Y and Z are both oxygen and $R^1$ is of the general formula:

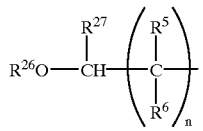

[XXII]

wherein $R^{26}$, $R^{27}$, $R^5$, $R^6$ and n are as defined above)

In this process, a compound of the general formula:

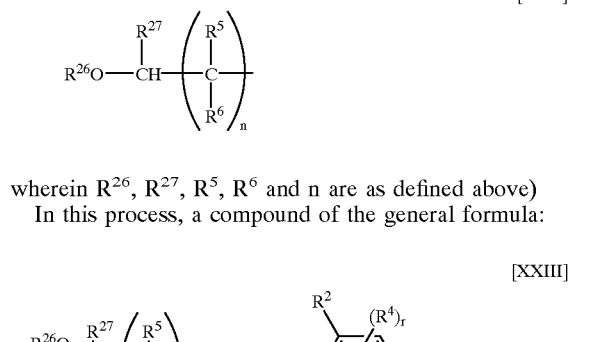

[XXIII]

wherein $R^2$, $R^3$, $R^4$, $R^5$, $R^6$, $R^{26}$, $R^{27}$, A, B, X, r and n are as defined above, is reduced.

Examples of the reducing agent which can be used may include aluminum lithium hydride, diisobutyl aluminum hydride, sodium borohydride and triethylsilane. If necessary, catalysts such as Lewis acids (e.g., aluminum chloride, titanium tetrachloride, boron trifluoride) may be added to the reaction system at a ratio of 0.1 to 10 moles per mole of the compound of the general formula [XXIII].

The reaction is usually effected in an inert solvent. Examples of the solvent which can be used may include ethers such as diethyl ether, diisopropyl ether, tetrahydrofuran and dioxane; hydrocarbons such as hexane, benzene, xylene and toluene; and halogenated hydrocarbons such as carbon tetrachloride, chloroform, dichloromethane, chlorobenzene and dichlorobenzene.

The reaction temperature is usually set within the range of −20° C. to +150° C. or the boiling point of a solvent used in the reaction.

The molar ratio of the starting materials to be used in the reaction can be freely determined.

After completion of the reaction, the reaction mixture is subjected to ordinary post-treatments such as organic solvent extraction and concentration, and the desired compound of the present invention can be isolated. Furthermore, purification may be carried out, if necessary, by an ordinary technique such as chromatography, distillation or recrystallization.

(Production process K for the present compounds wherein Y and Z are both oxygen and $R^1$ is of the general formula:

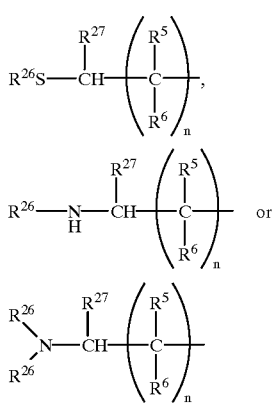

[XXIV]

wherein $R^{26}$, $R^{27}$, $R^5$, $R^6$ and n are as defined above)

In this process, a compound of the general formula:

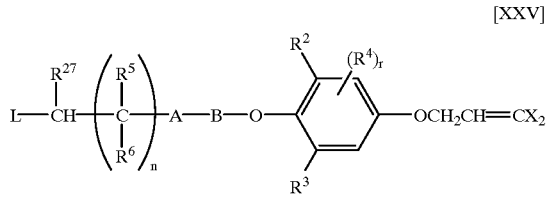

[XXV]

wherein $R^2$, $R^3$, $R^4$, $R^5$, $R^6$, $R^{27}$, X, A, B, L, r and n are as defined above, is reacted with a thiol compound of the general formula:

 [XXVI]

wherein $R^{26}$ is as defined above, or an amine compound of the general formula:

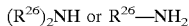 [XXVII]

wherein $R^{26}$ is as defined above.

The reaction is preferably effected in the presence of a suitable base in an inert solvent.

Examples of the solvent which can be used may include ethers such as 1,2-dimethoxyethane, tetrahydrofuran, dioxane, dialkyl (e.g., $C_1$–$C_4$) ether (e.g., diethyl ether, diisopropyl ether); N,N-dimethylformamide, dimethylsulfoxide, hexamethylphosphoric triamide, sulforane, acetonitrile, nitromethane; halogenated hydrocarbons such as dichloromethane, chloroform, 1,2-dichloroethane and chlorobenzene; hydrocarbons such as toluene, benzene and xylene; and water. If necessary, a mixture of these solvents or a mixture of these solvents and water can be used.

Examples of the base which can be used may include hydroxides of alkali metals or alkaline earth metals, such as lithium hydroxide, sodium hydroxide, potassium hydroxide and calcium hydroxide; carbonates of alkali metals or alkaline earth metals, such as potassium carbonate, potassium carbonate, sodium carbonate and calcium carbonate; hydrides of alkali metals or alkaline earth metals, such as lithium hydride, sodium hydride, potassium hydride and calcium hydride; alkoxide (e.g., $C_1$–$C_4$) of alkali metals, such as sodium methoxide, sodium ethoxide and potassium tert-butoxide; and organic bases such as triethylamnine and pyridine. If necessary, catalysts such as ammonium salts (e.g., benzyltriethylammonium chloride) may be added to the reaction system at a ratio of 0.01 to 1 mole per mole of the compound of the-general formula [XXV].

The reaction temperature is usually set within the range of −20° C. to +150° C. or the boiling point of a solvent used in the reaction, preferably −5° C. to +500° C. or the boiling point of a solvent used in the reaction.

The molar ratio of the materials to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Furthermore, purification may be carried out, if necessary, by an ordinary technique such as chromatography, distillation or recrystallization.

(Production process L for the present compounds wherein Y and Z are both oxygen and $R^1$ is of the general formula:

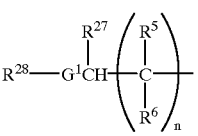

[XXVIII]

wherein $R^5$, $R^6$, $R^{27}$ and n are as defined above, $G^1$ is oxygen or NH, and $R^{28}$ is $C_2$–$C_6$ alkanoyl optionally substituted with halogen)

In this process, an acid anhydride of the general formula:

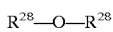   [XXIX]

wherein $R^{28}$ is as defined above, is reacted with a compound of the general formula:

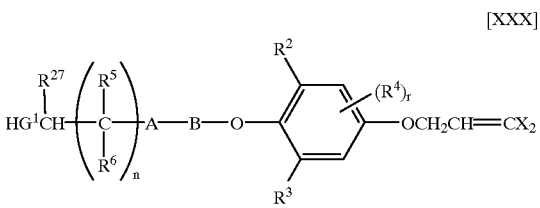

[XXX]

wherein all the symbols are as defined above.

The reaction is preferably effected in the presence of a suitable base in an inert solvent.

Examples of the reaction solvent which can be used may include ethers such as diethyl ether, tetrahydrofuran and dioxane; aromatic hydrocarbons such as benzene, toluene, xylene, chlorobenzene and pyridine; hydrocarbons such as n-hexane, n-heptane and cyclohexane; halogenated hydrocarbons such as methylene chloride, chloroform, carbon tetrachloride and 1,2-dichloroethane; esters such as ethyl acetate and methyl acetate; water; nitriles such as acetonitrile; polar solvents such as N,N-dimethylformamide, N,N-dimethylacetamide, N-methylpyrrolidone and dimethylsulfoxide; and mixtures thereof.

The reaction temperature is usually set within the range of −20° C. to +150° C. or the boiling point of a solvent used in the reaction, preferably 0° C. to +50° C.

The reaction is usually effected in the presence of a base such as sodium hydroxide, potassium hydroxide, sodium carbonate, potassium carbonate, triethylamine or pyridine at a ratio of 1 to 10 moles per mole of the compounds of the general formula [XXX].

If necessary, 4-(N,N-dimethylamino)pyridine may be added as a catalyst at a ratio of 0.001 to 1 mole per mole of the acid anhydride of the general formula [XXIX].

The molar ratio of the acid anhydride of the general formula [XXIX] and the compound of the general formula [XXX] to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Furthermore, purification may be carried out, if necessary, by an ordinary technique such as chromatography, distillation or recrystallization.

(Production process M for the present compounds wherein Y and Z are both oxygen and $R^1$ is of the general formula:

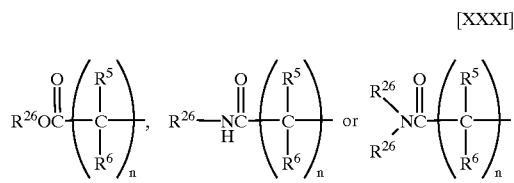

[XXXI]

wherein $R^{26}$, $R^5$, $R^6$ and n are as defined above)

In this process, an acid anhydride of the general formula:

[XXXII]

wherein $R^{26}$ is as defined above, or an amine compound of the general formula [XXVII] as depicted above, is reacted with a carboxylic acid compound of the general formula:

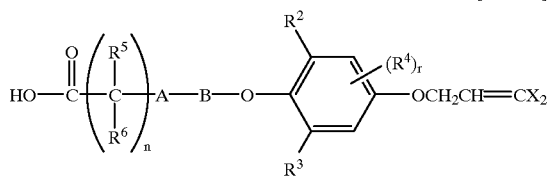

[XXXIII]

wherein $R^2$, $R^3$, $R^4$, $R^5$, $R^6$, A, B, X, r and n are as defined above.

The reaction is preferably effected in the presence of a suitable dehydrating agent in an inert solvent.

Examples of the dehydrating agent which can be used may include carbodiimides such as dicyclohexylcarbodiimide and 1-ethyl-3-(3-dimethylaminopropyl)carbodiimide; and inorganic dehydrating agents such as silicon tetrachloride.

Examples of the solvent which can be used may include non-aromatic hydrocarbons such as n-pentane, n-hexane, n-heptane and cyclohexane; aromatic hydrocarbons such as benzene, toluene and xylene; halogenated hydrocarbons such as methylene chloride, chloroform, carbon tetrachloride, 1,2-dichloroethane, chlorobenzene and dichlorobenzene; esters such as ethyl acetate and methyl acetate; amides such as N,N-dimethylformamide, N,N-dimethylacetamide and N-methylpyrrolidone; nitrites such as acetonitrile; ethers such as diethyl ether, tetrahydrofuran and dioxane; and pyridine.

The reaction temperature is usually set within the range of −20° C. to +150° C. or the boiling point of a solvent used in the reaction.

The molar ratio of the starting materials and the dehydrating agent to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Furthermore, purification may be carried out, if necessary, by an ordinary technique such as chromatography, distillation or recrystallization.

(Production process N for the present compounds wherein Y and Z are both oxygen and $R^1$ is $Q^1$; $R^7$ is $R^{27}$, $R^8$ and $R^9$ are both X in which $Q^1$, X and $R^{27}$ are as defined above)

In this process, a halogenated compound of the general formula [XI] is reacted with a carbonyl compound of the general formula [XXI].

The reaction is preferably effected in the presence of a suitable trialkylphosphine or triarylphosphine, and if necessary, in the presence of metal zinc, in an inert solvent.

Examples of the solvent which can be used may include hydrocarbons such as benzene, xylene and toluene; ethers such as diethyl ether, diisopropyl ether, tetrahydrofuran, dioxane and diglyme; and halogenated hydrocarbons (exclusive of carbon tetrabromide and carbon tetrachloride) such as dichloroethane, 1,2-dichloroethane and chlorobenzene.

The reaction temperature is usually set within the range of −30° C. to +200° C. or the boiling point of a solvent used in the reaction.

Examples of the trialkyl (e.g., $C_1$–$C_{20}$) phosphine or triarylphosphine which can be used in the reaction may include triphenylphosphine and trioctylphosphine. The metal zinc which is used, if necessary, is preferably in dust form.

The molar ratio of the starting materials and reagents to be used in the reaction can be freely determined, but the ratio is preferably such that the halogenated compound of the general formula [XI], trialkylphosphine or triarylphosphine, and zinc when used, are 1 to 5 moles, 2 to 10 moles, and 1 to 5 moles, respectively, per mole of the carbonyl compound of the general formula [XXI], or it is favorable to effect the reaction at a ratio closer thereto.

After completion of the reaction, the reaction mixture is subjected to ordinary post-treatments such as organic solvent extraction and concentration, and the desired compound of the present invention can be isolated. Furthermore, purification may be carried out, if necessary, by an ordinary technique such as chromatography, distillation or recrystallization.

(Production process O)
This production process is according to the following scheme 1:

SCHEME 1

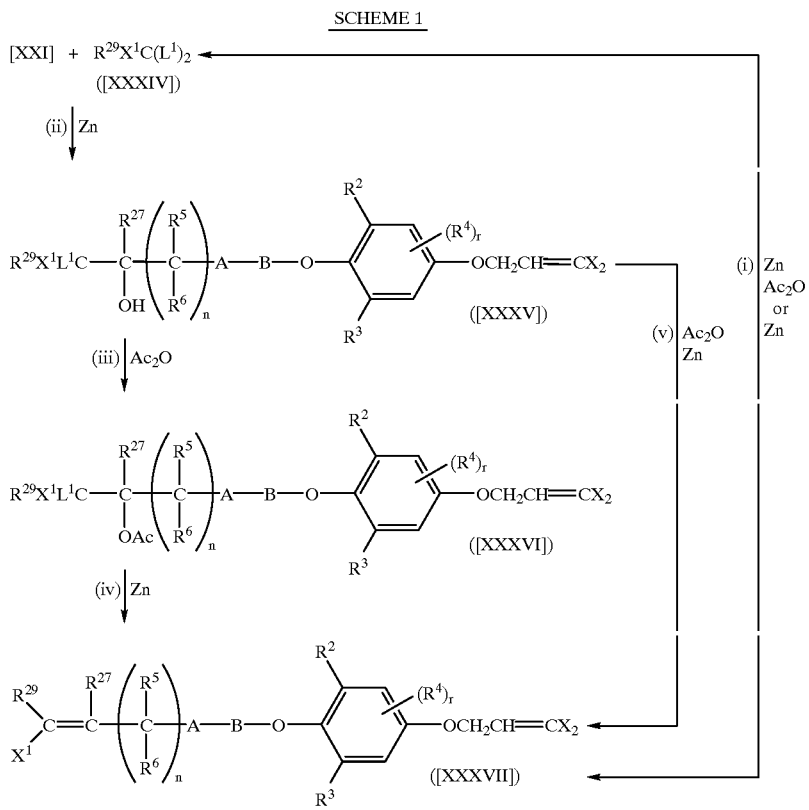

wherein $X^1$ is chlorine or bromine, $R^{29}$ is trifluoromethyl, cyano or $COOR^{30}$ in which $R^{30}$ is $C_1$–$C_3$ alkyl, and the other symbols are as defined above. In the compound of the general formula [XXXVII], geometrical isomerism on the double bond to which $R^{29}$ is attached may be E or Z form, or a mixture thereof.

The respective steps (i) to (v) are explained in detail below.

(i) The reaction is effected in an inert solvent using metal zinc and acetic anhydride, or using metal zinc.

Examples of the solvent which can be used may include amides such as N,N-dimethylformamide, N,N-dimethylacetamide and N-methylpyrrolidone; and ethers such as diethyl ether, tetrahydrofuran and dioxane. The metal zinc is preferably used in dust form. If necessary, catalysts (e.g., cuprous chloride (CuCl), aluminum chloride) may be added to the reaction system at a ratio of 0.01 to 1 mole per mole of the compound of the general formula [XXXIV].

The reaction temperature is usually set within the range of –30° C. to +150° C. or the boiling point of a solvent used in the reaction.

The molar ratio of the starting materials and reagents to be used in the reaction can be freely determined, but it is favorable to effect the reaction at a ratio such that the compound of the general formula [XXXIV], acetic anhydride used if necessary, and metal zinc, are 1 to 1.5 moles, 1 to 1.5 moles, and 2 to 3 moles, respectively, per mole of the carbonyl compound of the general formula [XXI].

(ii) The present compounds of the general formula [XXXV] can be obtained by reacting a compound of the general formula [XXXIV] with a carbonyl compound of the general formula [XXI] as depicted above using metal zinc.

Examples of the solvent which can be used may include amides such as N,N-dimethylformamide, N,N-dimethylacetamide and N-methylpyrrolidone; and ethers such as diethyl ether, tetrahydrofuran and dioxane. The metal zinc is preferably used in dust form. If necessary, catalysts (e.g., cuprous chloride (CuCl), aluminum chloride) may be added to the reaction system at a ratio of 0.01 to 1 mole per mole of the compound of the general formula [XXXIV].

The reaction temperature is usually set within the range of –30° C. to +150° C. or the boiling point of a solvent used in the reaction.

The molar ratio of the starting materials and reagents to be used in the reaction can be freely determined, but it is favorable to effect the reaction at a ratio such that the compound of the general formula [XXXIV] and metal zinc, are 1 to 1.5 moles and 1 to 1.5 moles, respectively, per mole of the carbonyl compound of the general formula [XXI].

(iii) The present compounds of the general formula [XXXVI] can be obtained by reacting the present compounds of the general formula [XXXV] with acetic anhydride according to the process as described in the above production process L.

(iv) The present compounds of the general formula [XXXVII] can be obtained-by treating the present compounds of the general formula [XXXVI] with metal zinc.

Examples of the solvent which can be used may include amides such as N,N-dimethylformamide, N,N- dimethylacetamide and N-methylpyrrolidone; ethers such as diethyl ether, tetrahydrofuran and dioxane; and alcohols such as methanol, ethanol and isopropanol. The metal zinc is preferably used in dust form.

The reaction temperature is usually set within the range of −30° C. to +150° C. or the boiling point of a solvent used in the reaction.

The molar ratio of the starting materials to be used in the reaction can be freely determined, but the ratio is preferably such that metal zinc is 1 to 1.5 moles per mole of the present compounds of the general formula [XXXVI].

(v) The present compounds of the general formula [XXXVII] can be obtained by reacting the present compounds of the general formula [XXXV] in an inert solvent using acetic anhydride and metal zinc.

Examples of the solvent which can be used may include amides such as N,N-dimethylformamide, N,N-dimethylacetamide and N-methylpyrrolidone; ethers such as diethyl ether, tetrahydrofuran and dioxane; and alcohols such as methanol, ethanol and isopropanol. The metal zinc is preferably used in dust form.

The reaction temperature is usually set within the range of −30° C. to +150° C. or the-boiling point of a solvent used in the reaction.

If necessary, 4-(N,N-dimethylamino)pyridine may be added as a catalyst to the reaction system at a ratio of 0.001 to 1 mole per mole of acetic anhydride.

The molar ratio of the starting materials and reagents to be used in the reaction can be freely determined, but it is favorable to effect the reaction at the ratio such that acetic anhydride and metal zinc are 1 to 1.5 moles and 1 to 1.5 moles, respectively, per mole of the present compounds of the general formula [XXXV].

After completion of the reaction in each of the steps (i) to (v), the reaction mixture is subjected to ordinary post-treatments such as organic solvent extraction and concentration, and the desired compound of the present invention can be isolated. Furthermore, purification may be carried out, if necessary, by an ordinary technique such as chromatography, distillation or recrystallization.

(Production process R for the present compounds wherein Y and Z are both oxygen and $R^1$ is $Q^1$ in which $R^7$ is $R^{27}$, $R^8$ is $X^1$ and $R^9$ is $CF_2X^2$ in which $X^2$ is fluorine, chlorine or bromine and $R^{27}$ is as defined above)

In this process, an allyl alcohol compound of the general formula:

chloroform and dichloromethane; ethers such as diglyme; and hydrocarbons such as isooctane.

The reaction temperature is usually set within the range of −100° C. to +50° C., but the temperature is slowly raised from −80° C. to 0° C.

The molar ratio of the starting materials and reagents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated:, Furthermore, purification may be carried out, if necessary, by an ordinary technique such as chromatography, distillation or recrystallization.

(ii) In the case where $X^2$ is chlorine or bromine:

The reaction can be effected with thionyl chloride or thionyl bromide as the halogenating agent in the presence of pyridine.

Examples of the solvent which can be used may include halogenated hydrocarbons such as carbon tetrachloride, chloroform and dichloromethane; ethers such as diglyme, diethyl ether and THF; and hydrocarbons such as benzene, toluene and xylene.

The reaction temperature is usually set within the range of 0° C. to +100° C. or the boiling point of a solvent used in the reaction.

The molar ratio of the starting materials and reagents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Furthermore, purification may be carried out, if necessary, by an ordinary technique such as chromatography, distillation or recrystallization.

(Production process S for the present compounds wherein Y and Z are both oxygen and $R^1$ is of the general formula:

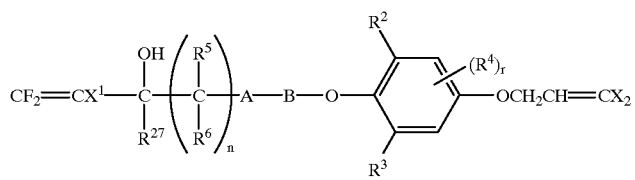

[XXXVIII]

wherein $R^2$, $R^3$, $R^4$, $R^5$, $R^6$, $R^{27}$, A, B, X, $X^1$, n and r are as defined above, is reacted with a halogenating agent as defined below.

The reaction can be effected in the following method (i) or (ii).

(i) In the case where $X^2$ is fluorine:

The reaction can be effected with diethylaminosulfur trifluoride (DAST) as the halogenating agent.

Examples of the solvent which can be used may include halogenated hydrocarbons such as carbon tetrachloride,

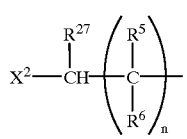

[XXXIX]

wherein $R^5$, $R^6$, $R^{27}$, $X^2$ and n are as defined above)

In this process, an alcohol compound of the general formula:

[XXXX]

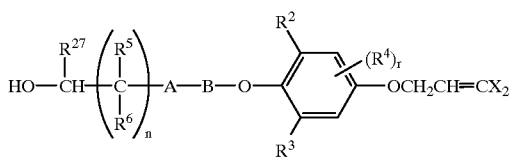

wherein all the symbols are as defined above, is reacted with a halogenating agent as defined below.

The reaction can be effected in the following method (i) or (ii).

(i) In the case where $X^2$ is fluorine:

The reaction can be effected with diethylaminosulfur trifluoride (DAST) as the halogenating agent.

Examples of the solvent which can be used may include halogenated hydrocarbons such as carbon tetrachloride, chloroform and dichloromethane; ethers such as diglyme; and hydrocarbons such as isooctane.

The reaction temperature is usually set within the range of −100° C. to +50° C., but the temperature is slowly raised from −80° C. to 0° C.

The molar ratio of the starting materials and reagents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Furthermore, purification may be carried out, if necessary, by an ordinary technique such as chromatography, distillation or recrystallization.

(ii) In the case where $X^2$ is chlorine or bromine:

The reaction can be effected with thionyl chloride, thionyl bromide, phosphorus trichloride, phosphorus tribromide, phosphorus pentachloride or the like as the halogenating agent.

Alternatively, the reaction can also be effected with carbon tetrachloride or carbon tetrabromide in the presence of triphenylphosphine.

Examples of the solvent which can be used may include halogenated hydrocarbons such as chloroform and dichloromethane, ethers such as diglyme, diethyl ether and THF; and hydrocarbons such as benzene, toluene and xylene.

The reaction temperature is usually set within the range of 0° C. to +100° C. or the boiling point of a solvent used in the reaction.

The molar ratio of the starting materials and reagents to be used in the reaction can be freely determined, but it is favorable to effect the reaction at an equimolar ratio or a ratio closer thereto.

After completion of the reaction, the reaction mixture is subjected to ordinary post-treatments such as organic solvent extraction and concentration, and the desired compound of the present invention can be isolated. Furthermore, purification may be carried out, if necessary, by an ordinary technique such as chromatography, distillation or recrystallization.

When any one of the present compounds has an asymmetric carbon atom, it is to be construed to include its optically active isomers (i.e., (+)-form and (−)-form) having biological activity and their mixtures at any ratio. When any one of the present compounds exhibits geometrical isomerism, it is to be construed to include its geometrical isomers (i.e., cis-form and trans-form) and their mixtures at any ratio.

The following are specific examples of the present compounds; however, the present invention is not limited to these examples.

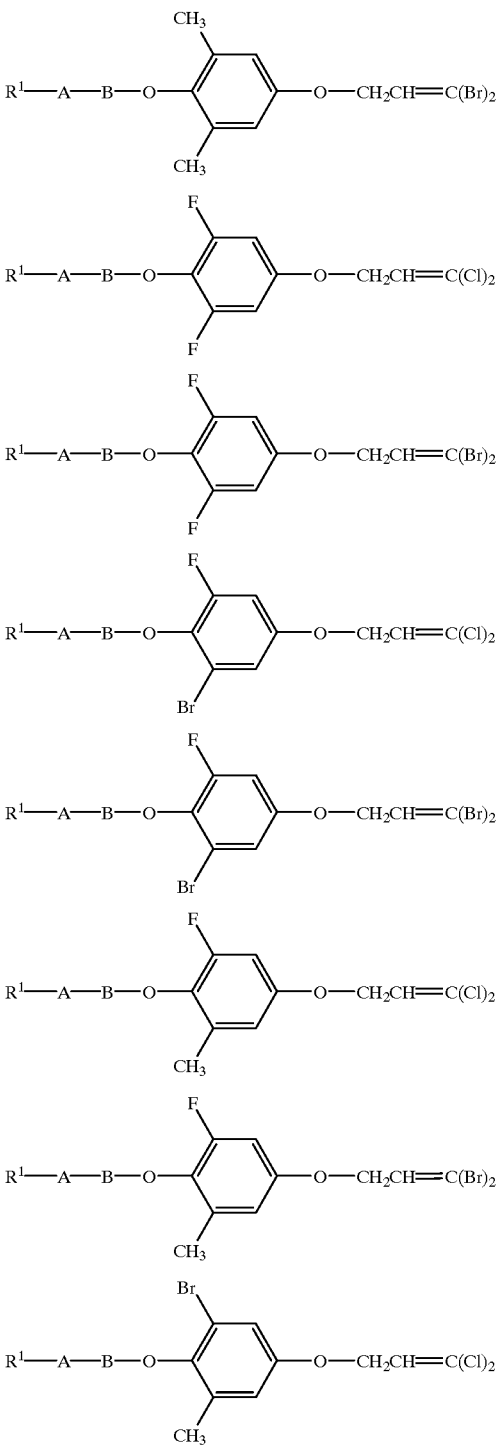

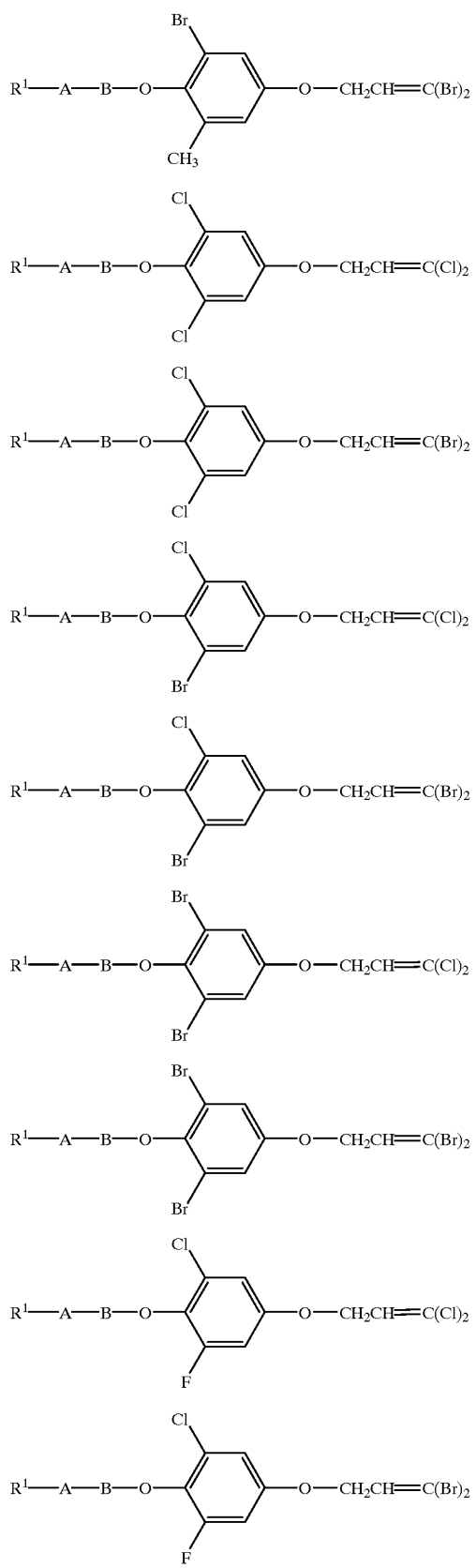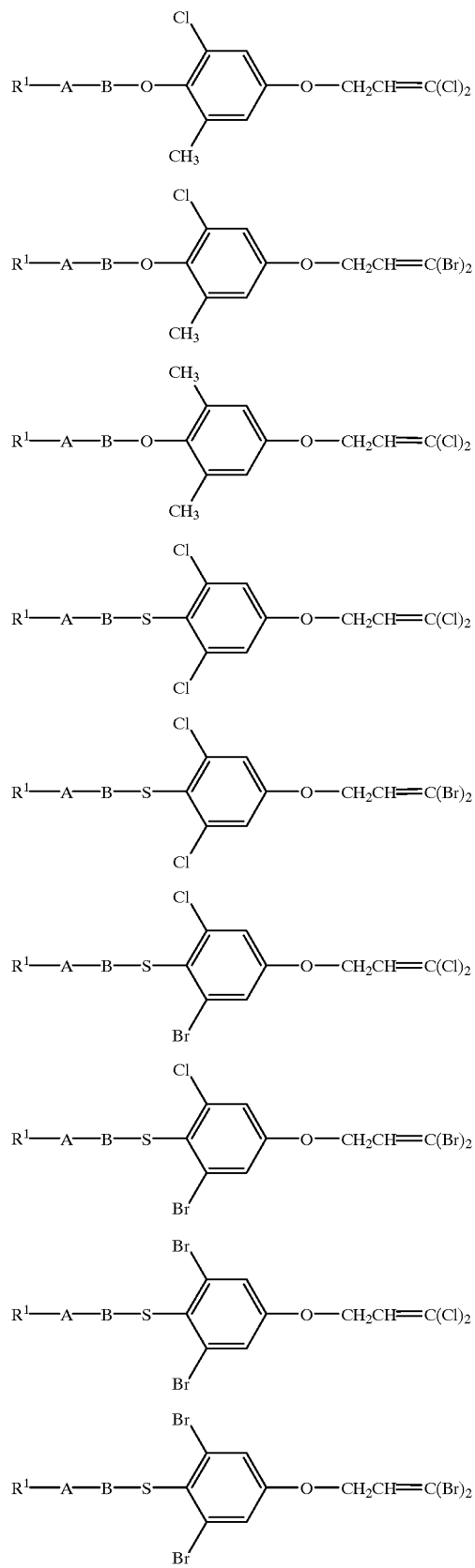

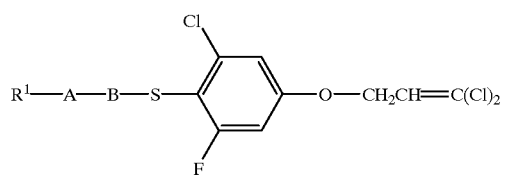
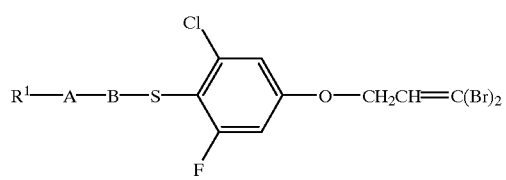
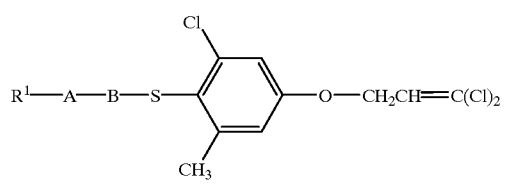
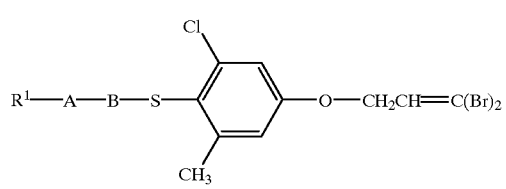
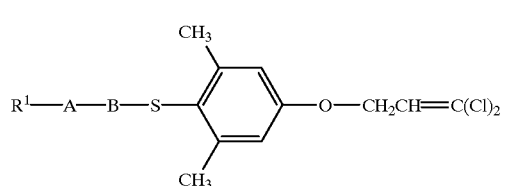
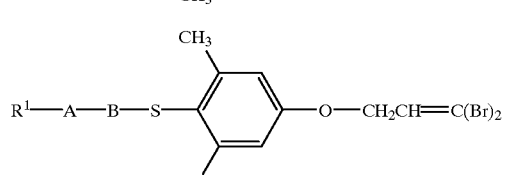
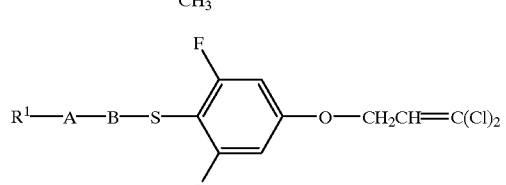
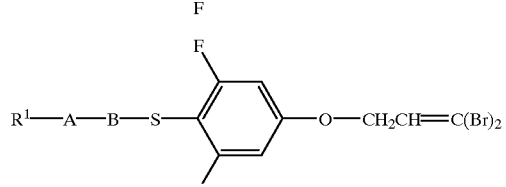
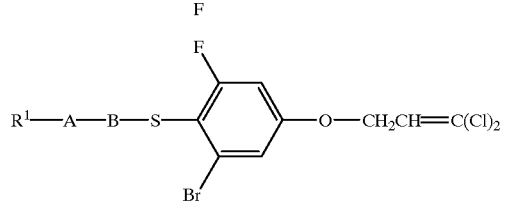
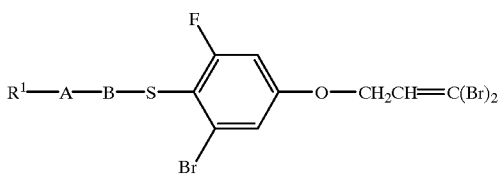
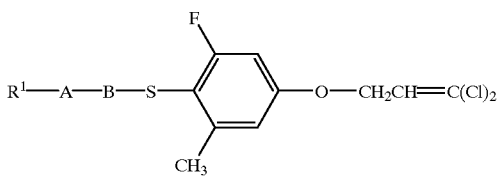
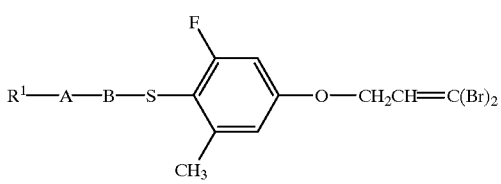
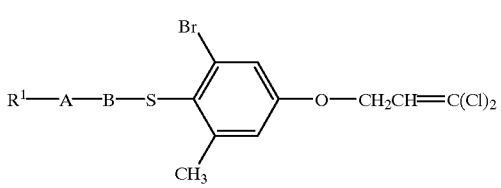
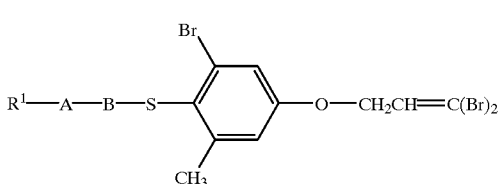
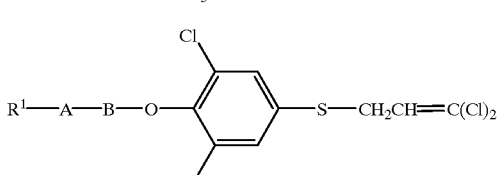
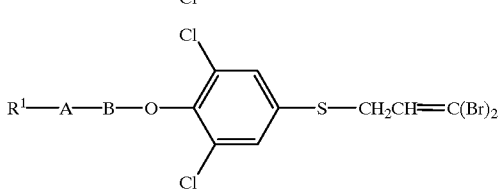
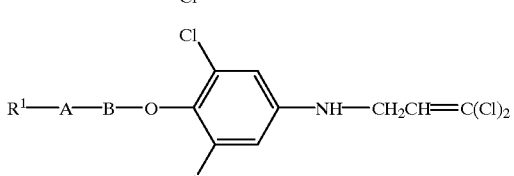
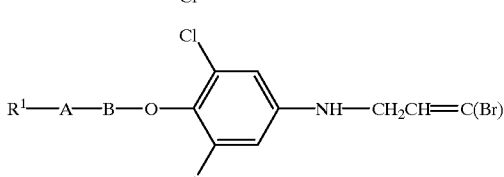

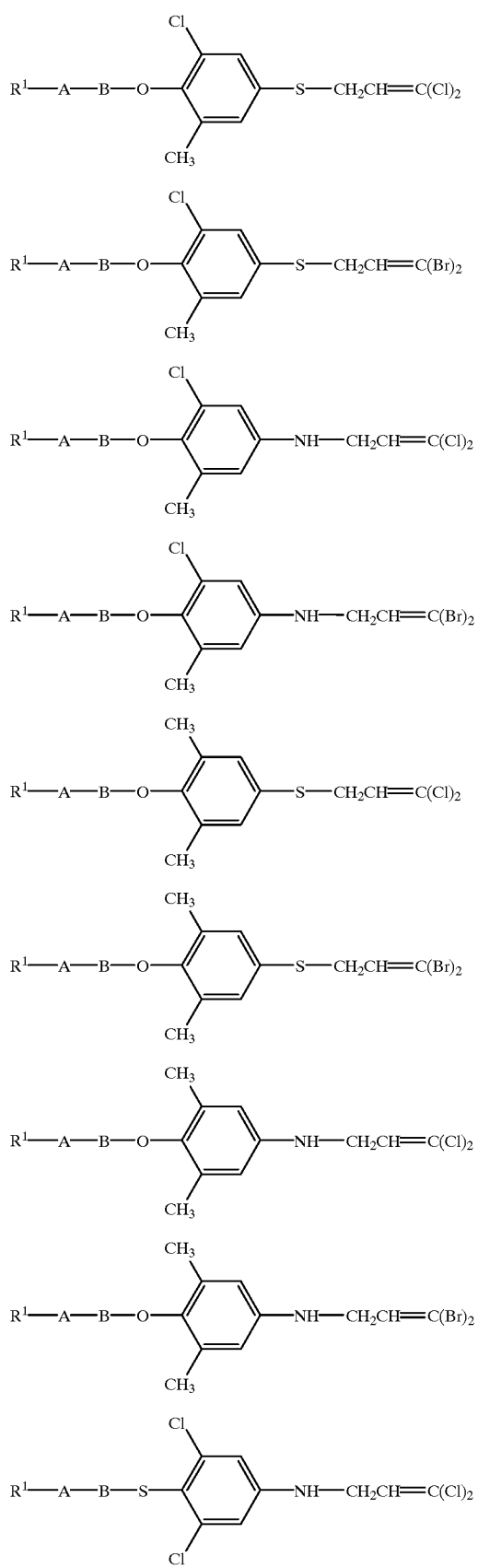
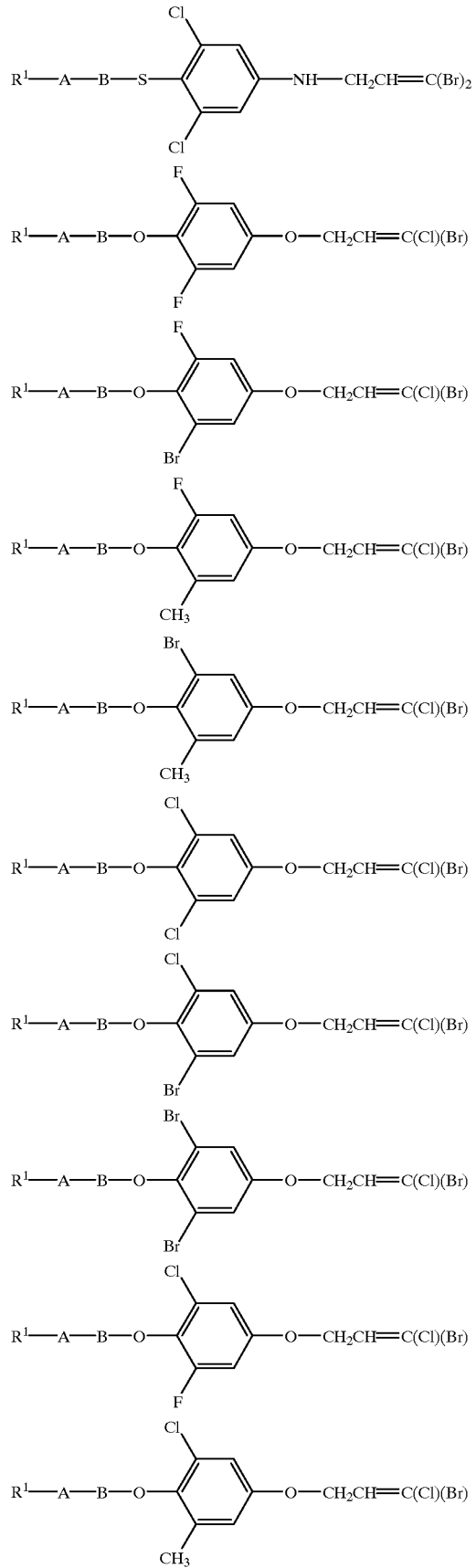

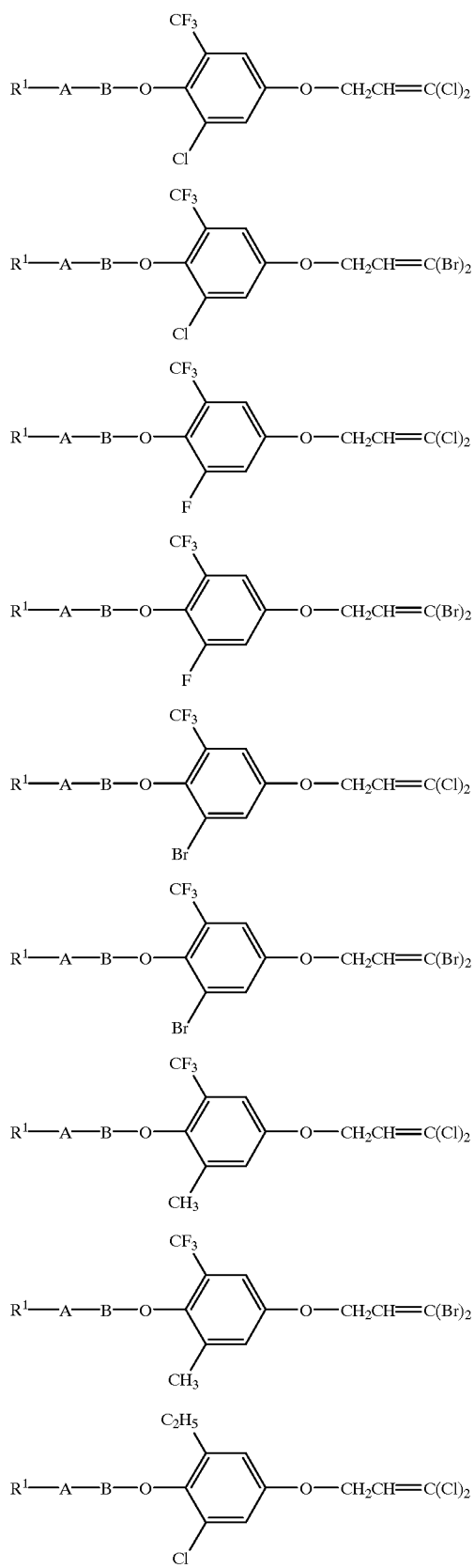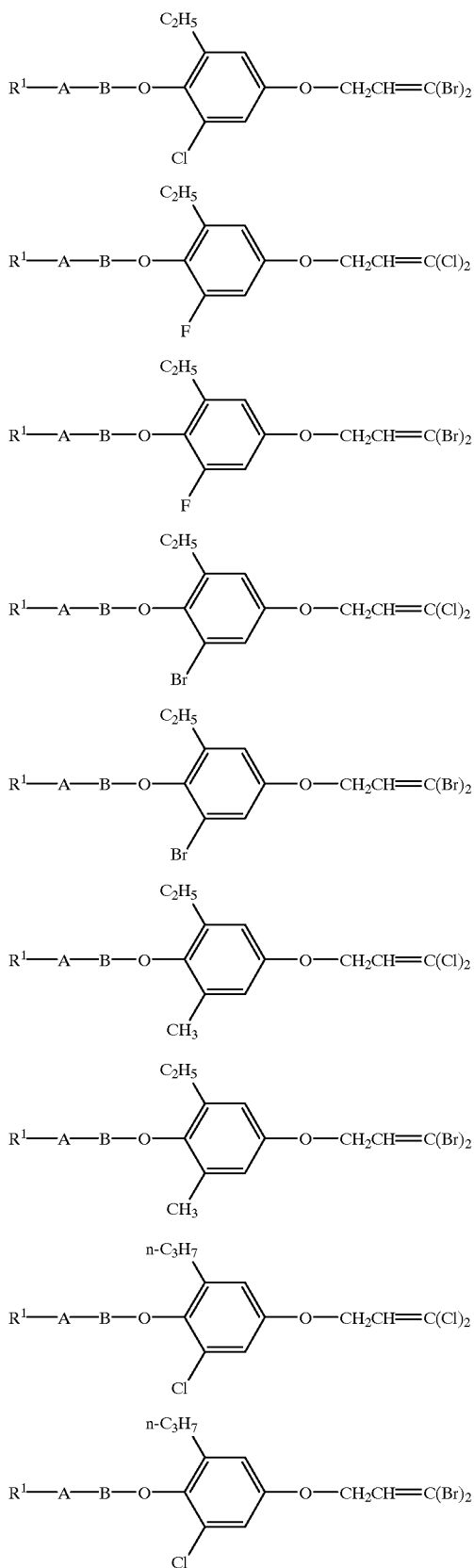

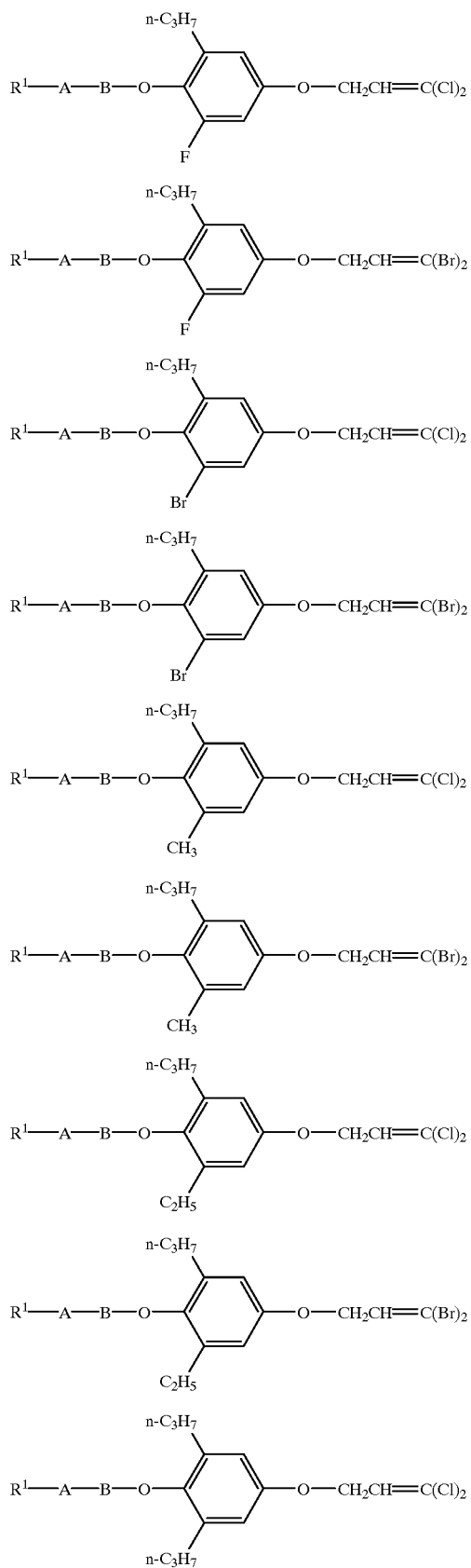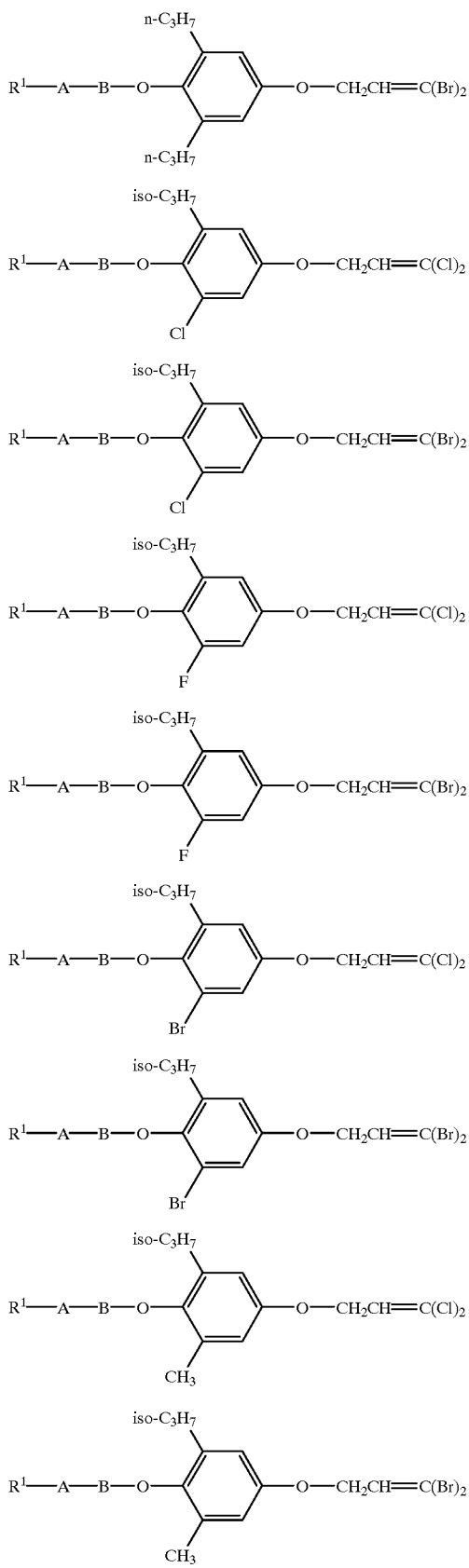

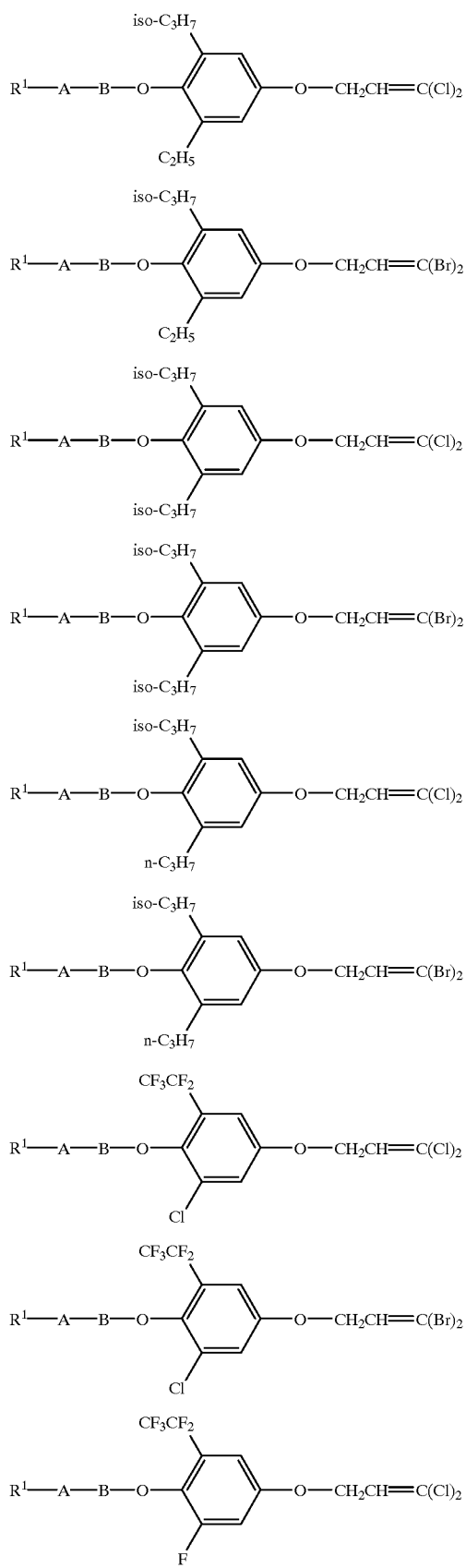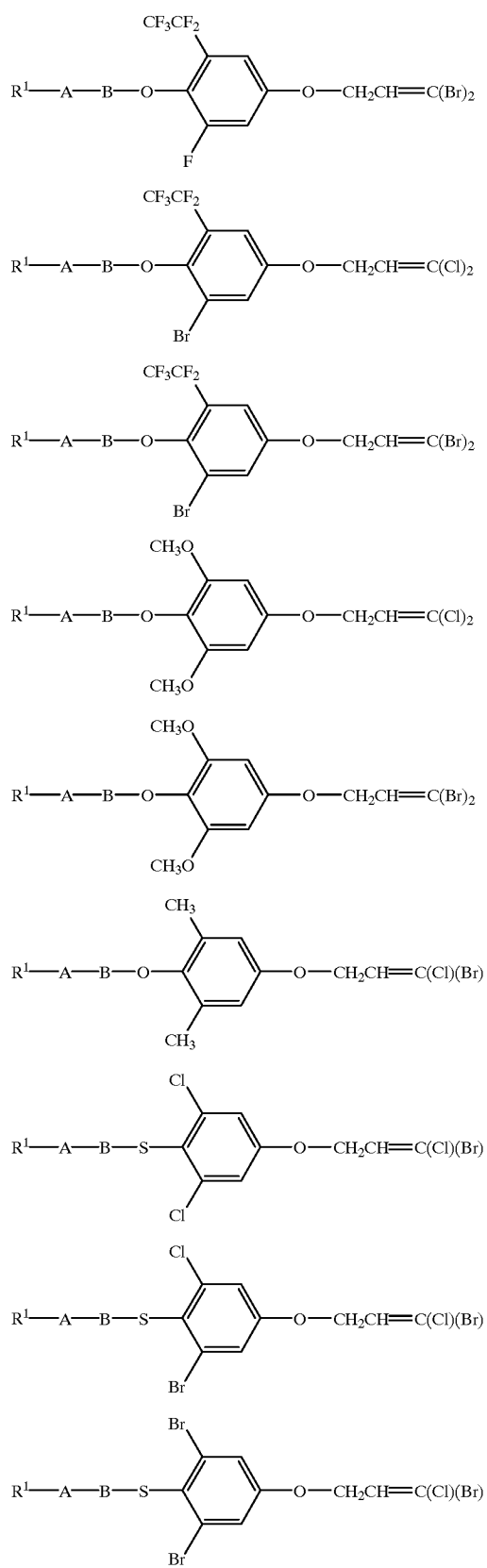

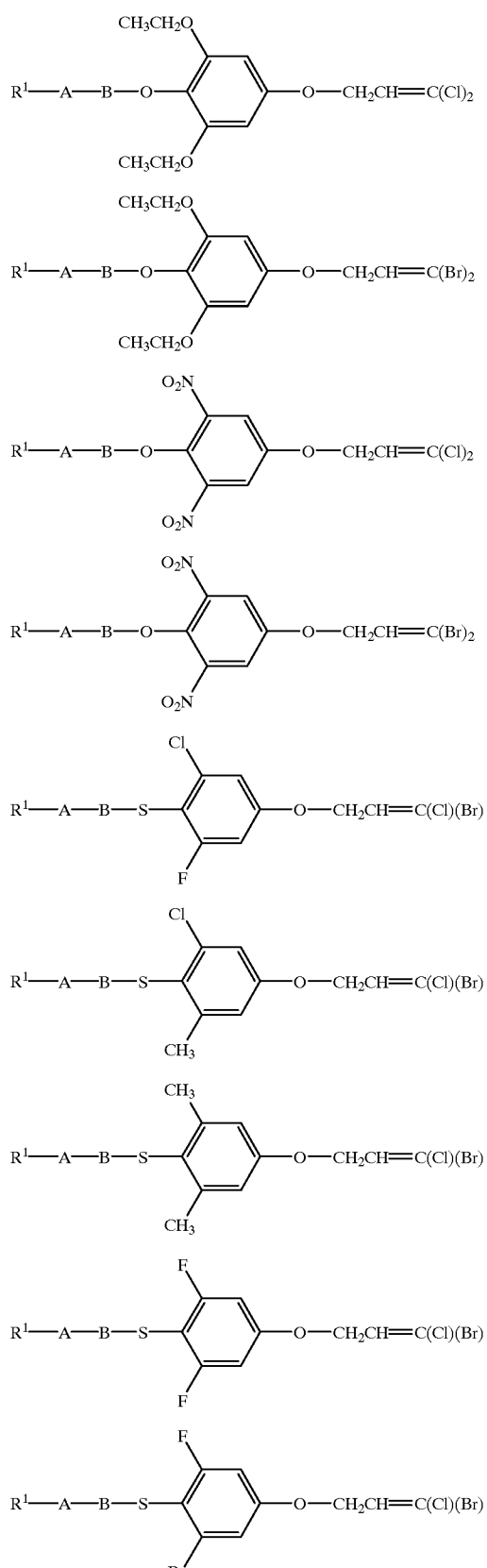
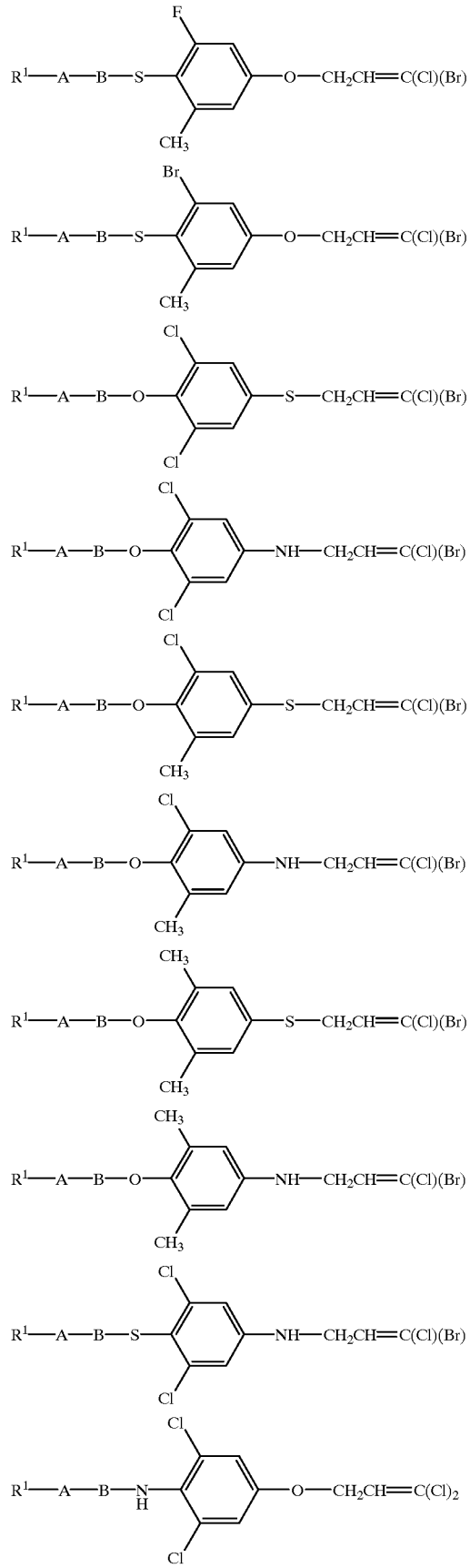

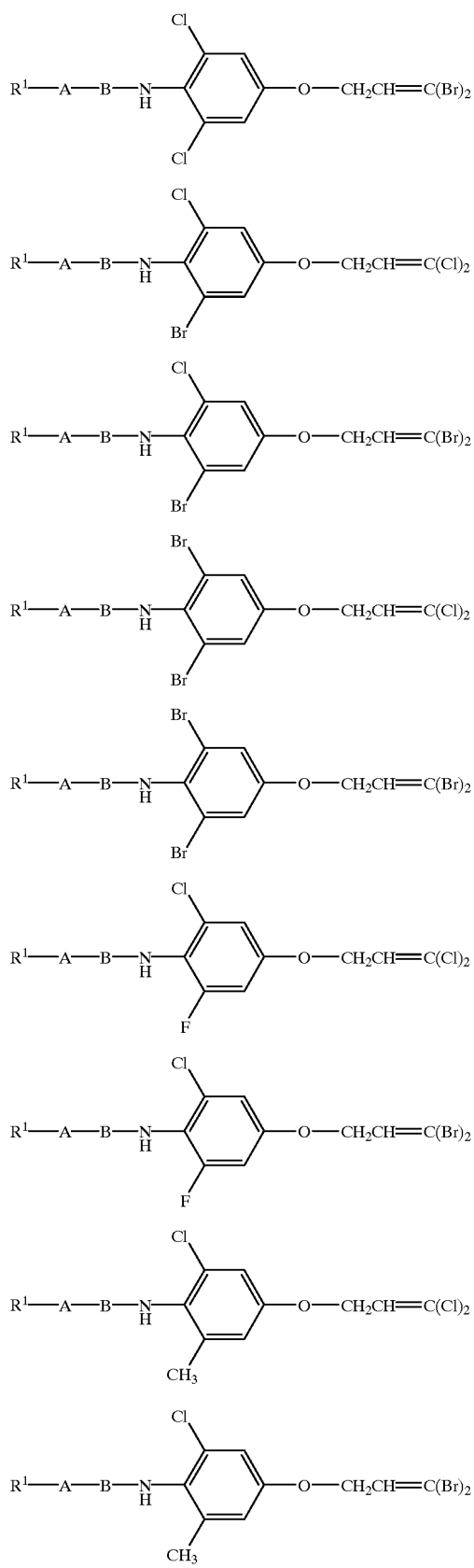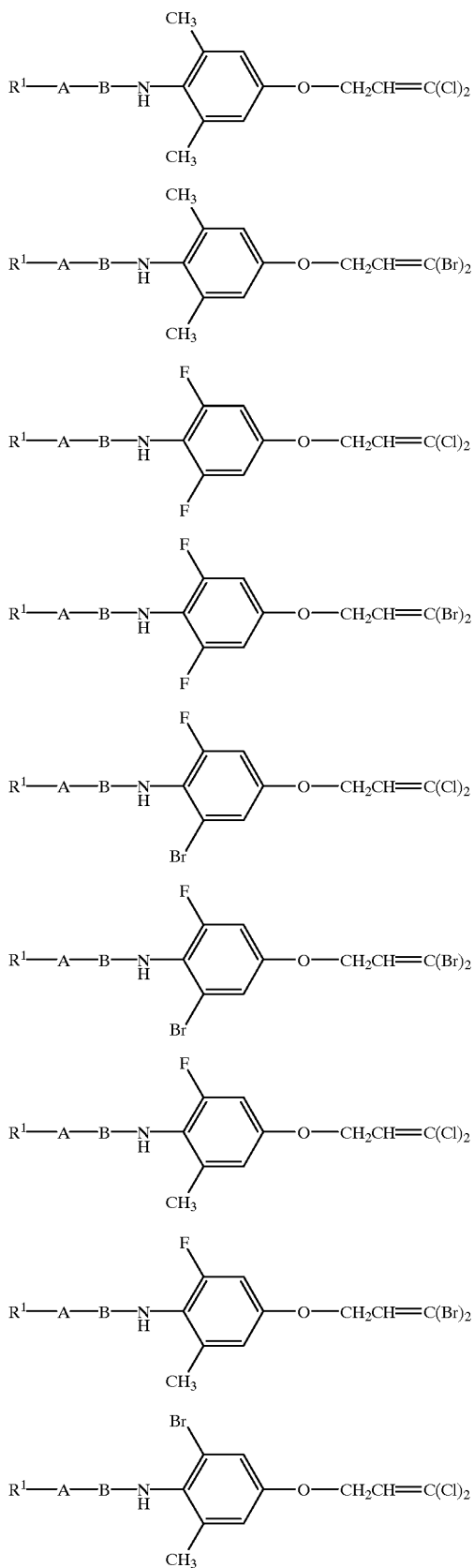

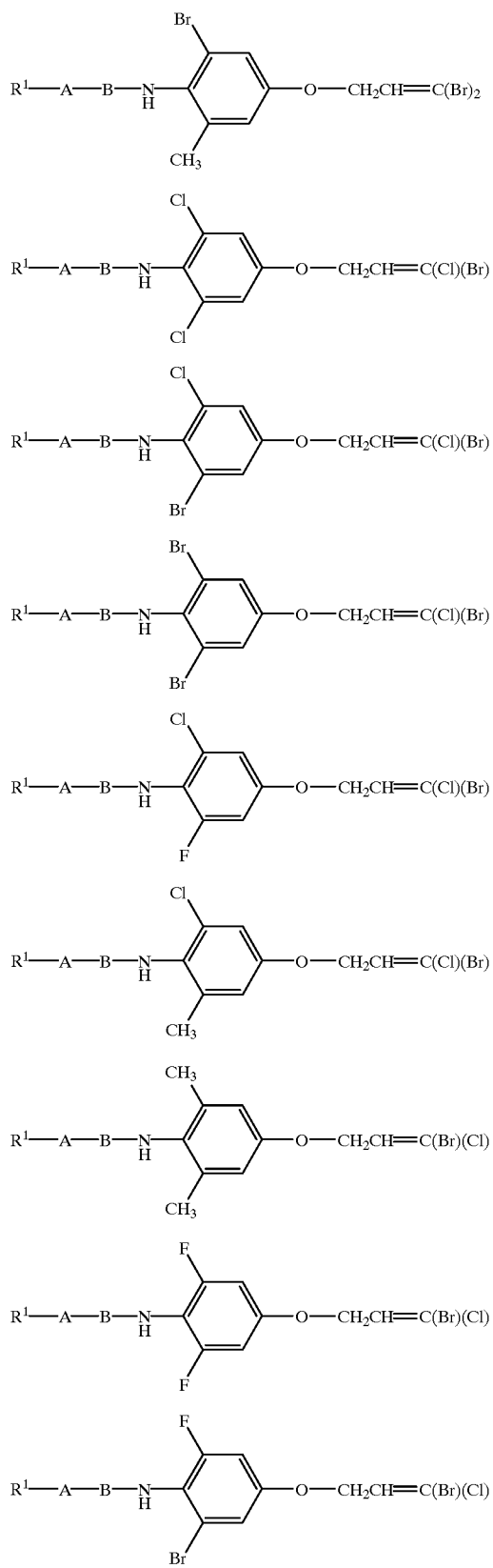
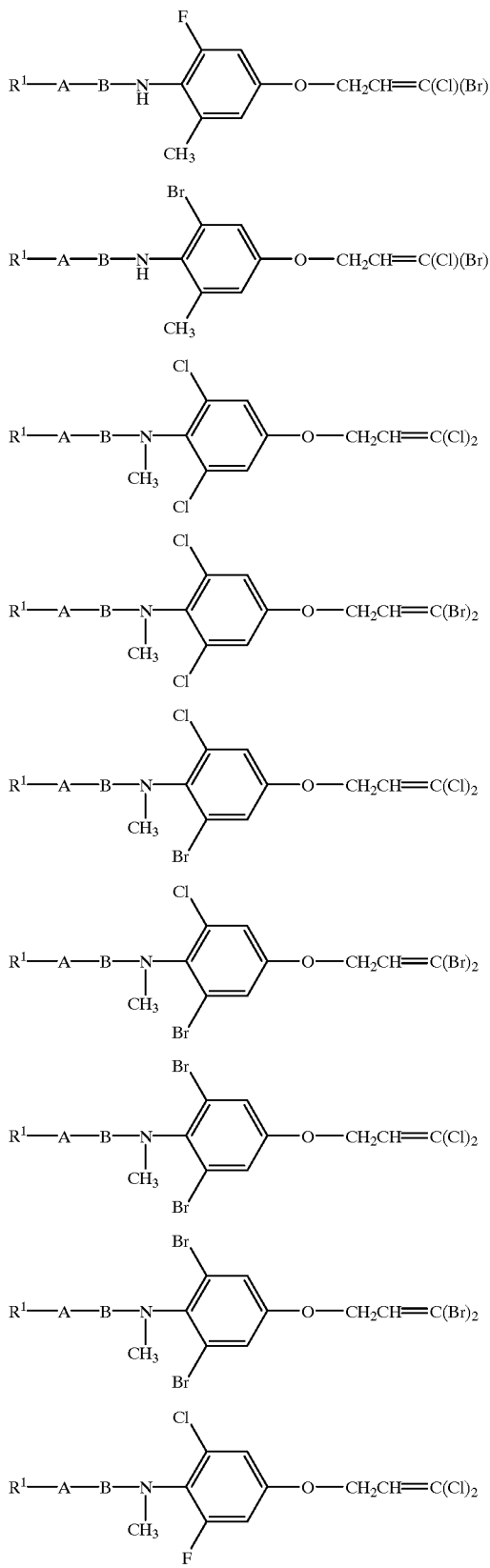

-continued
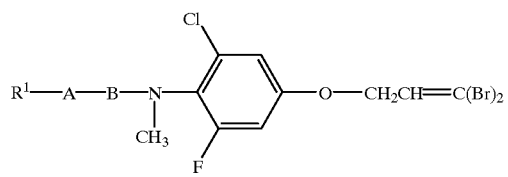
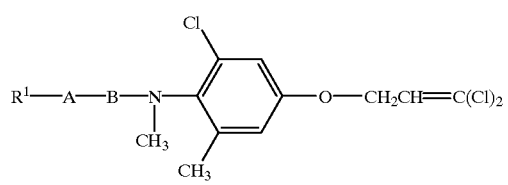
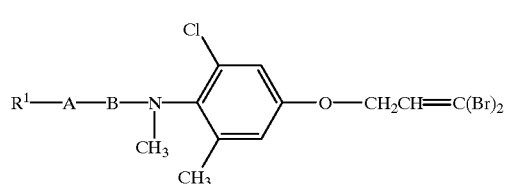
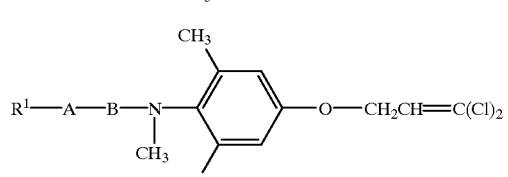
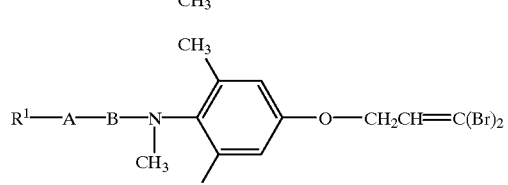
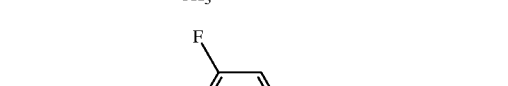
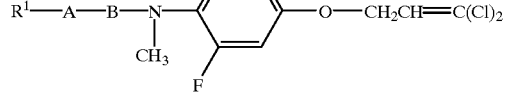
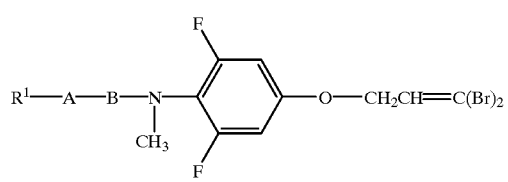
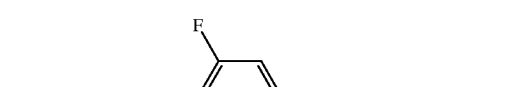
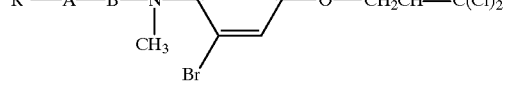
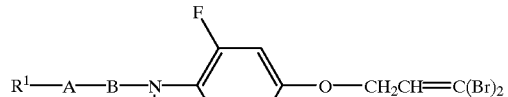
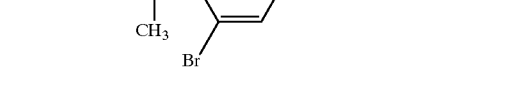
-continued
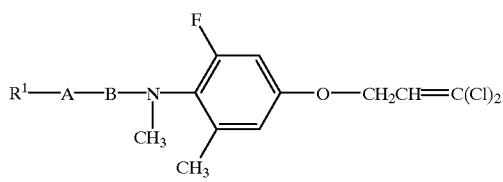
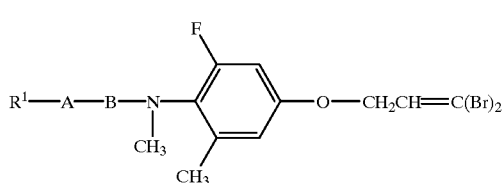
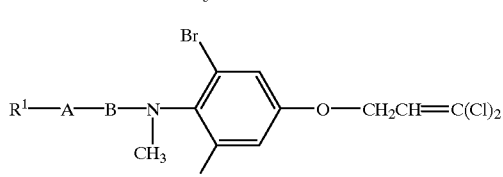
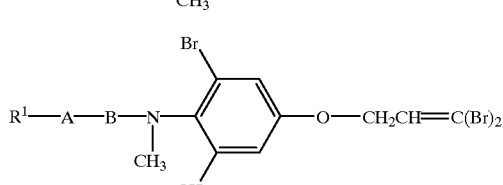
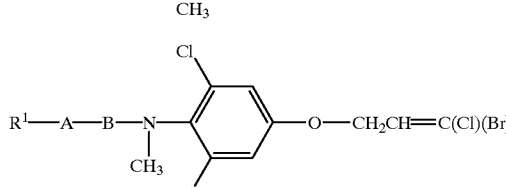
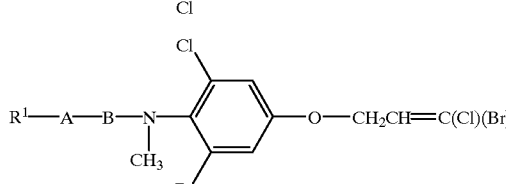
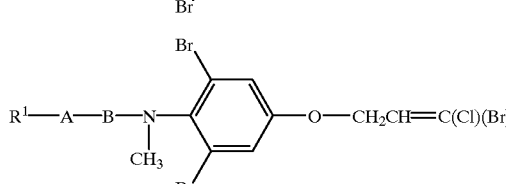
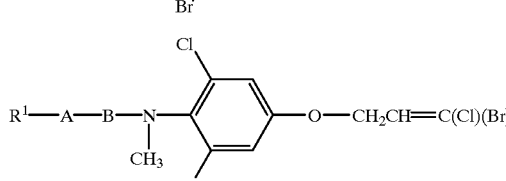
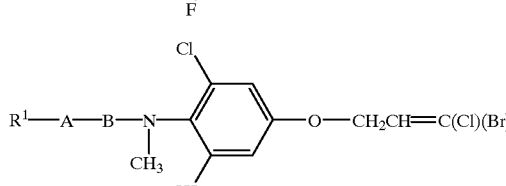

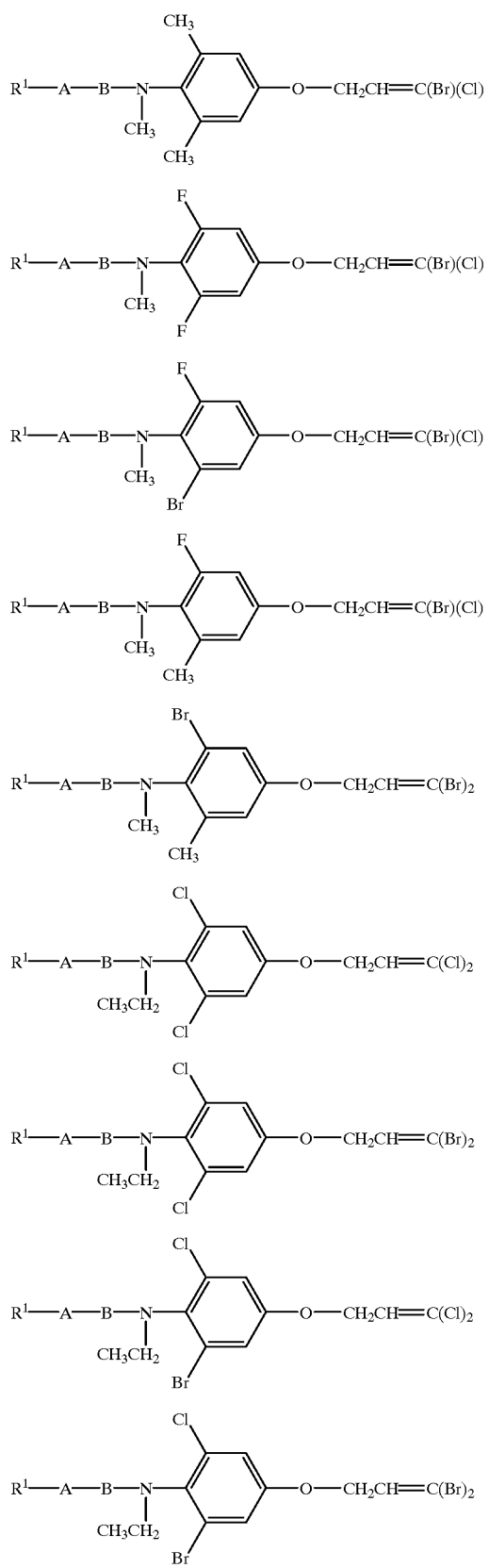
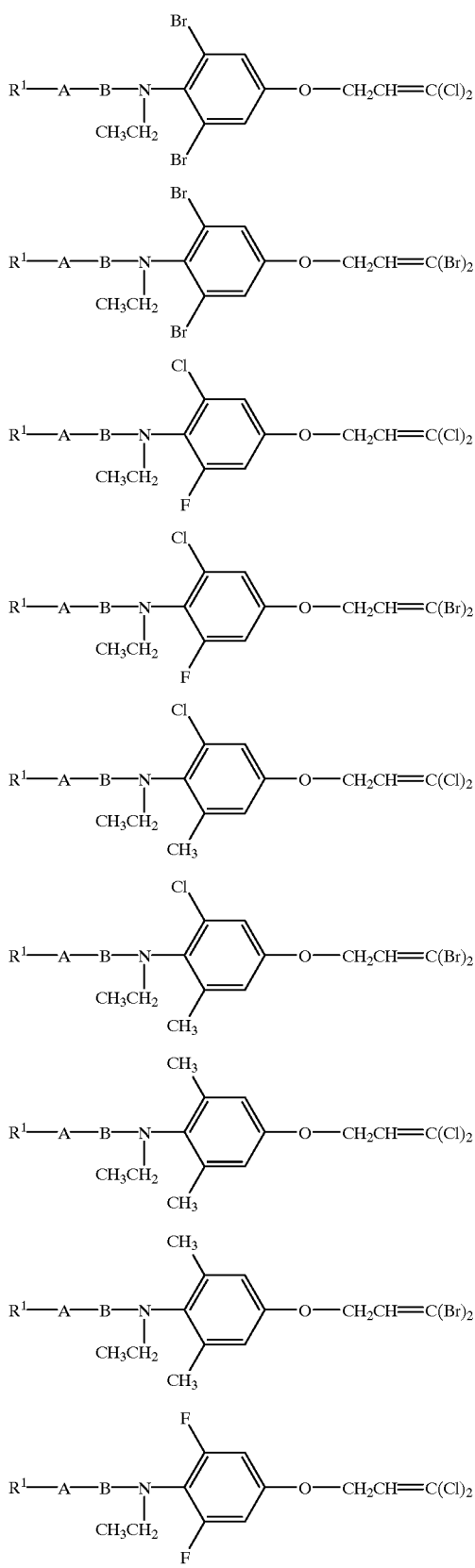

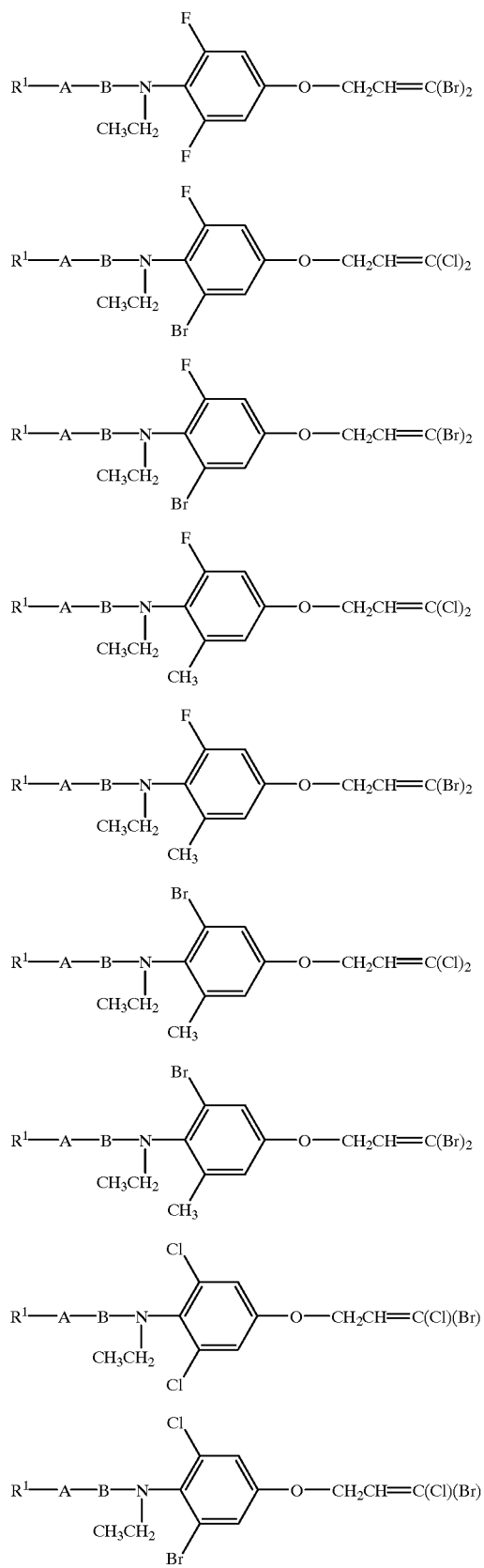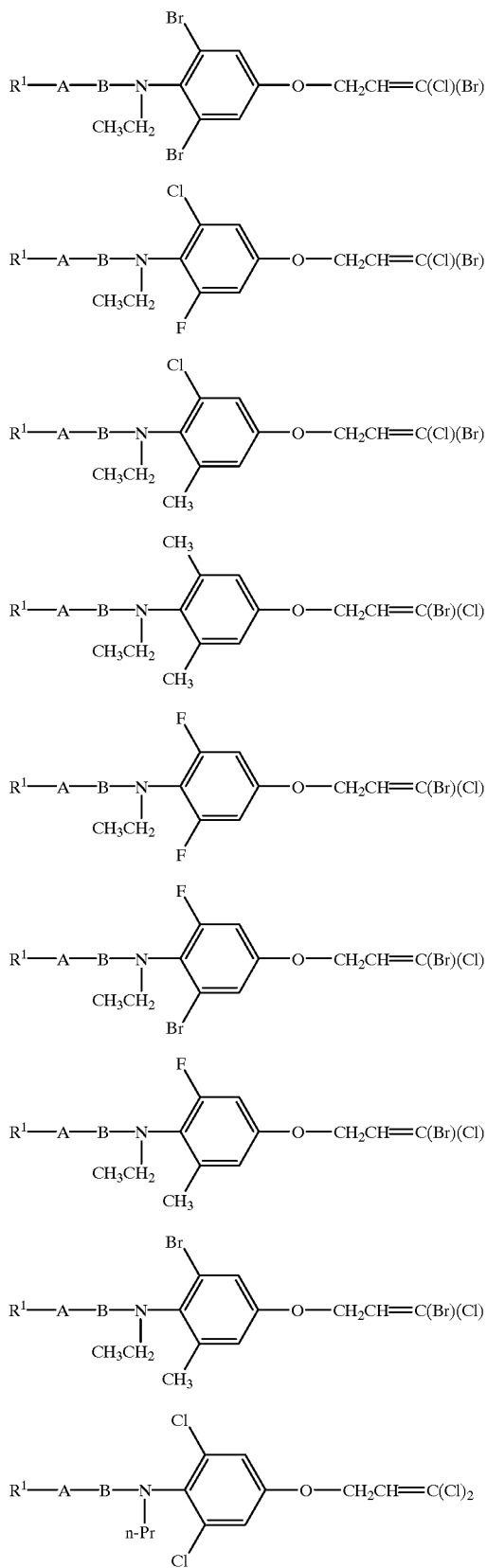

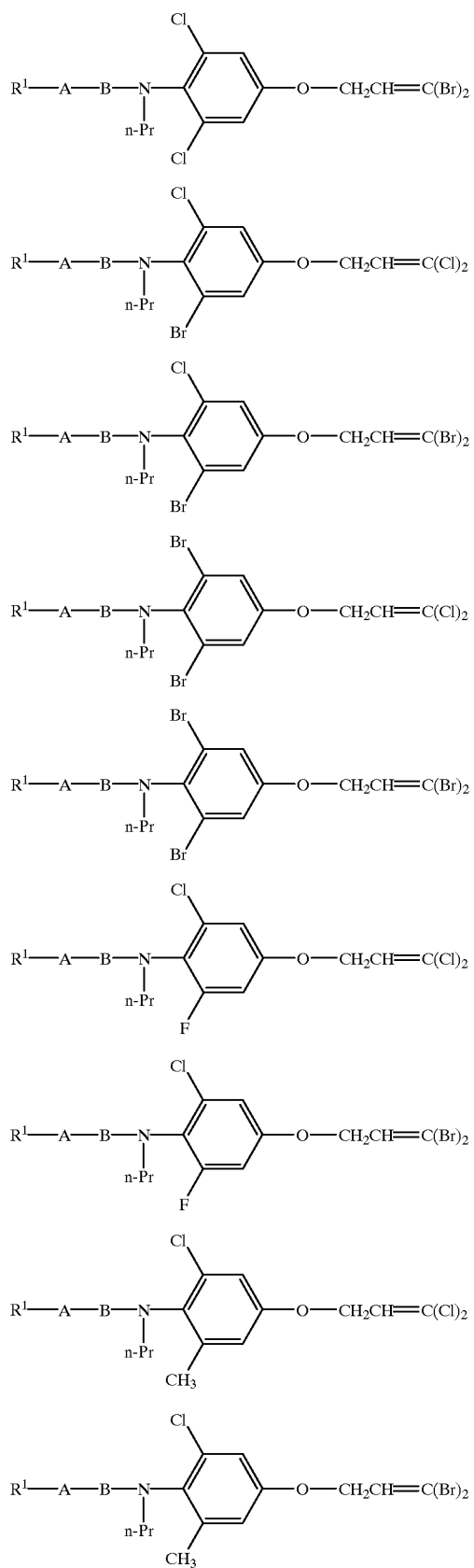
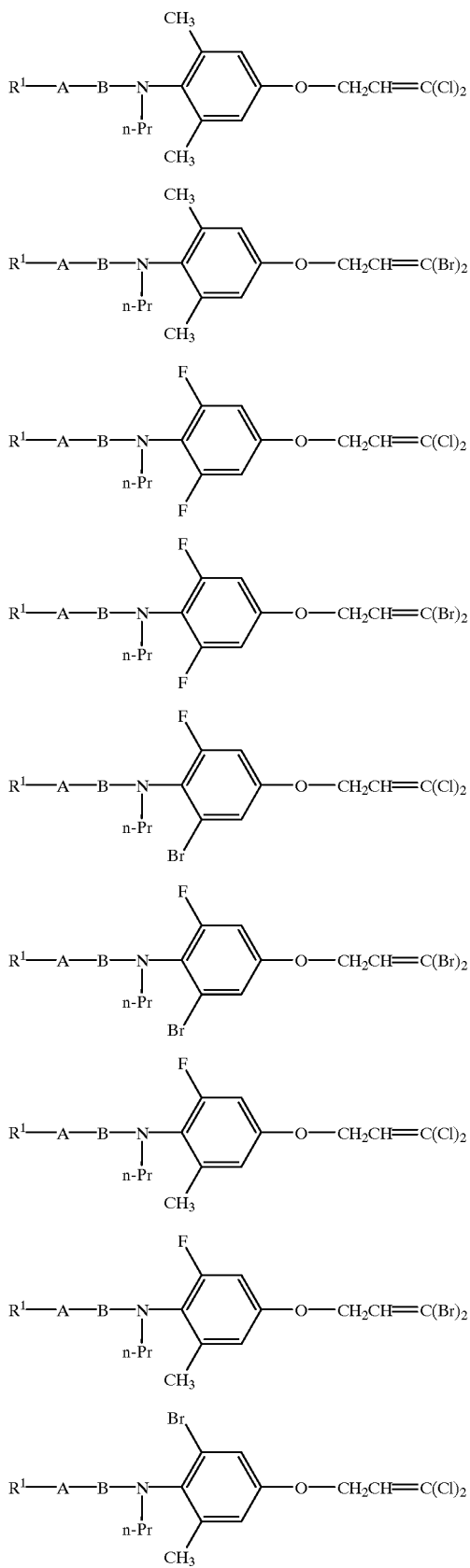

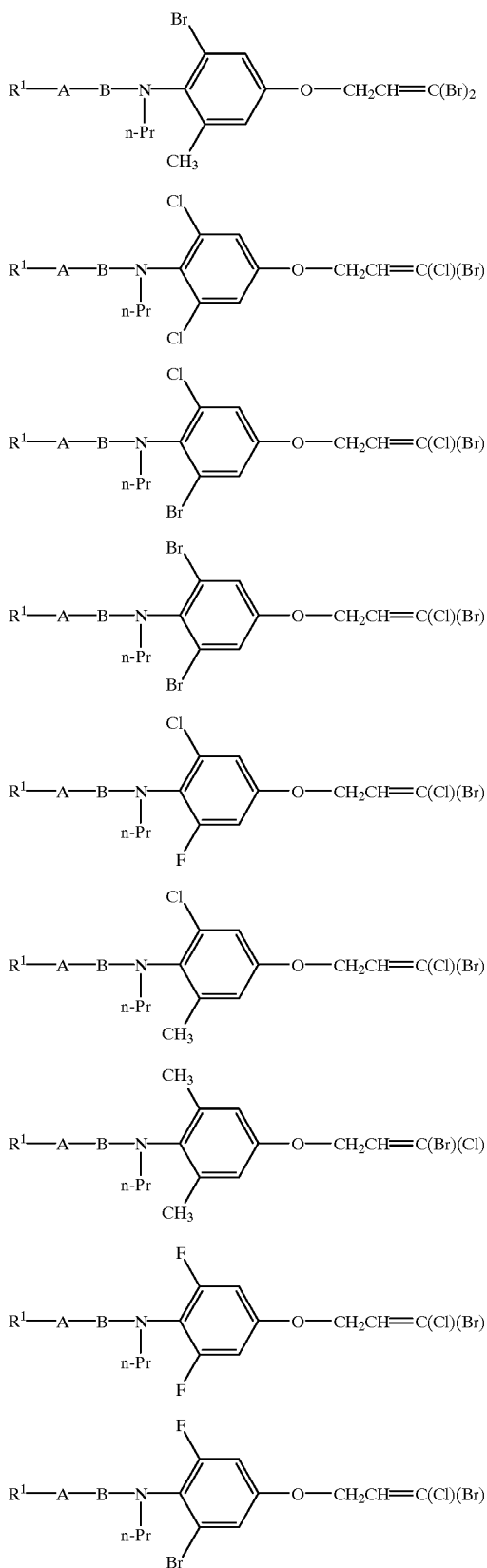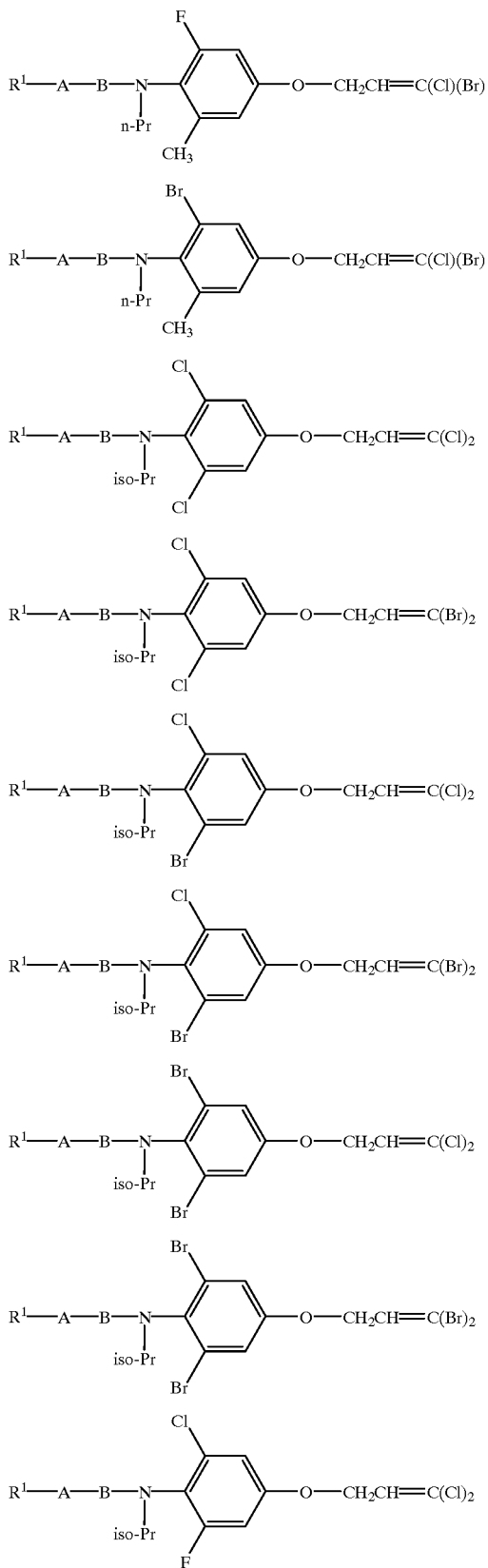

-continued
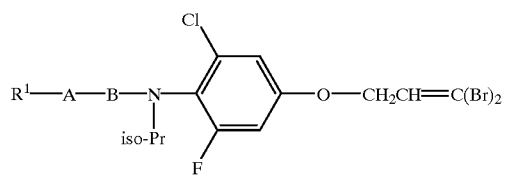
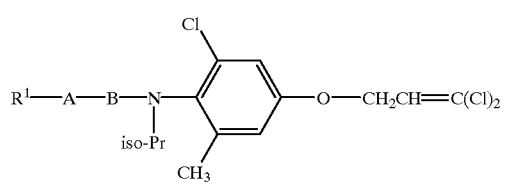
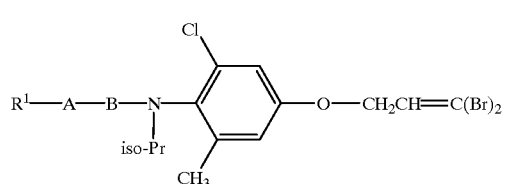
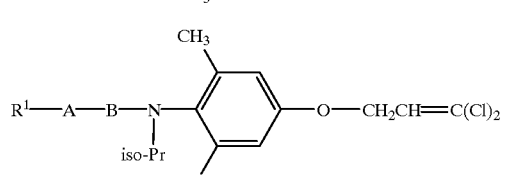
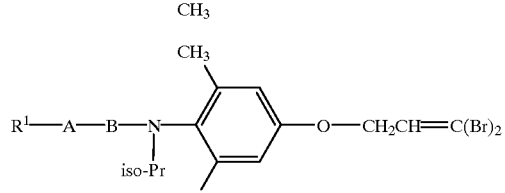
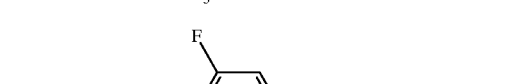
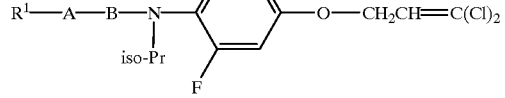
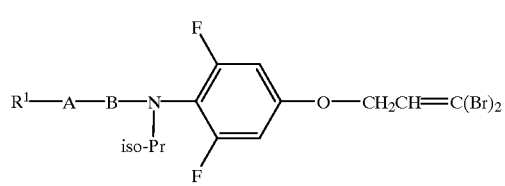
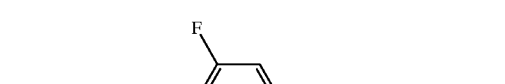
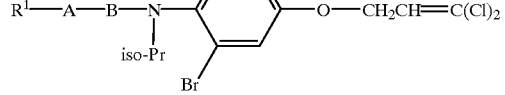
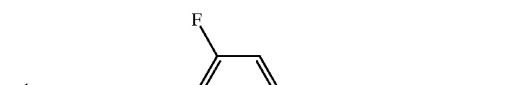
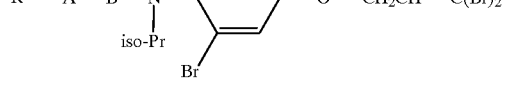
-continued
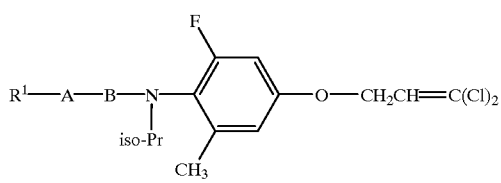
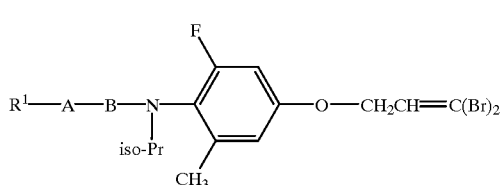
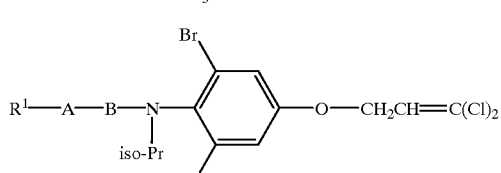
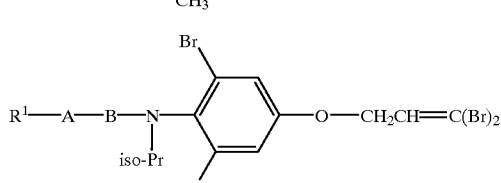
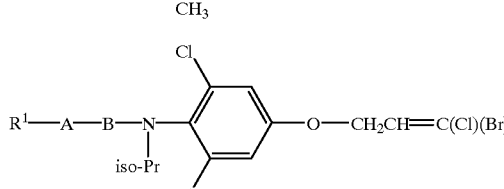
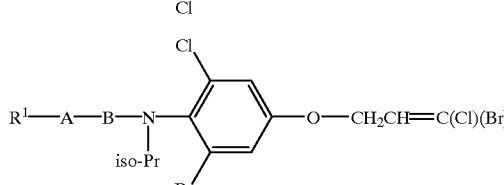
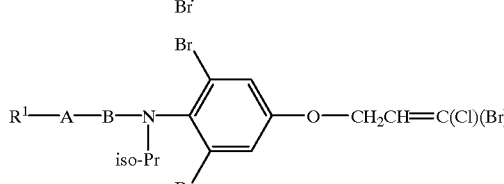
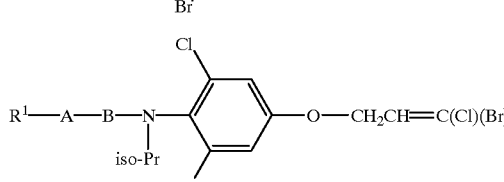
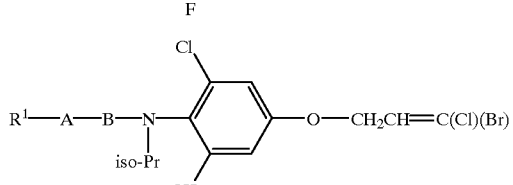

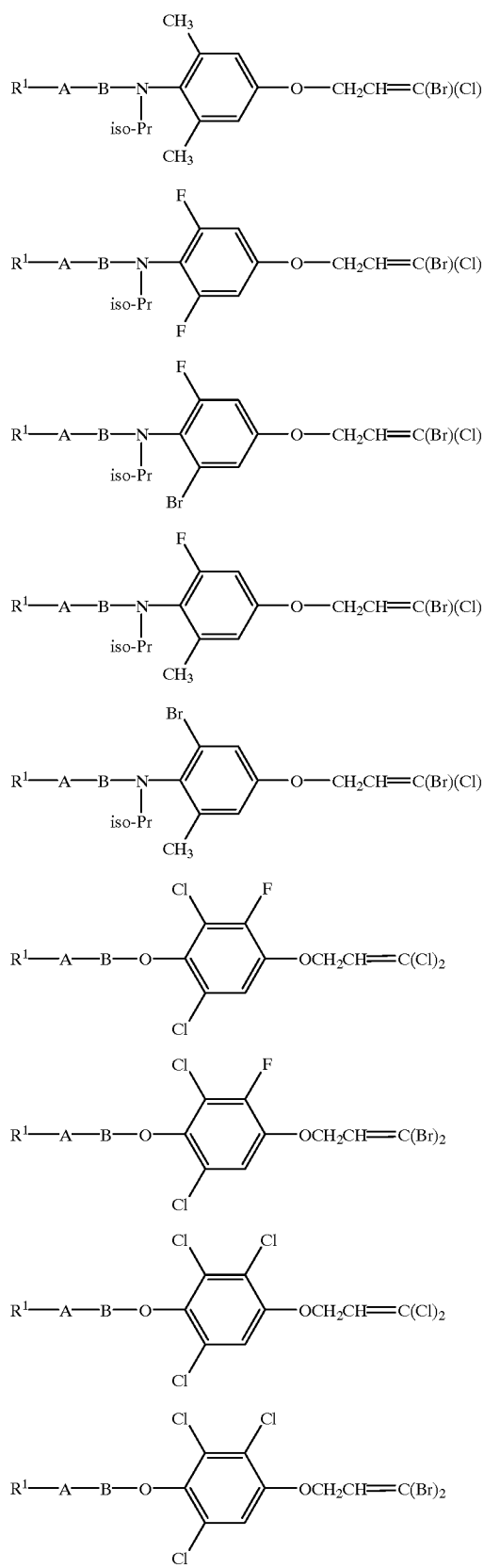
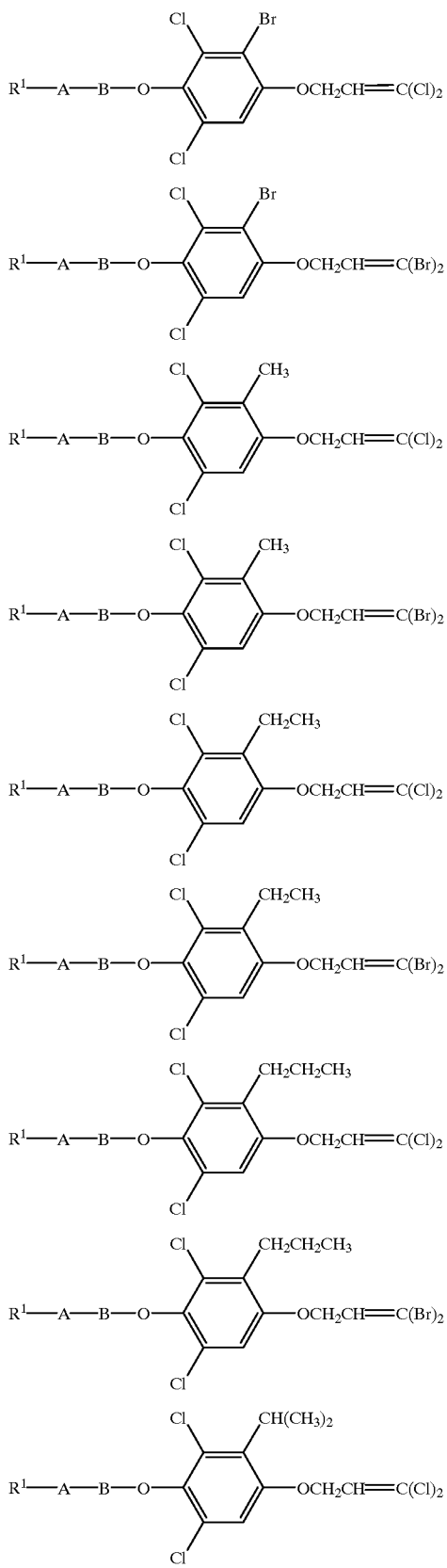

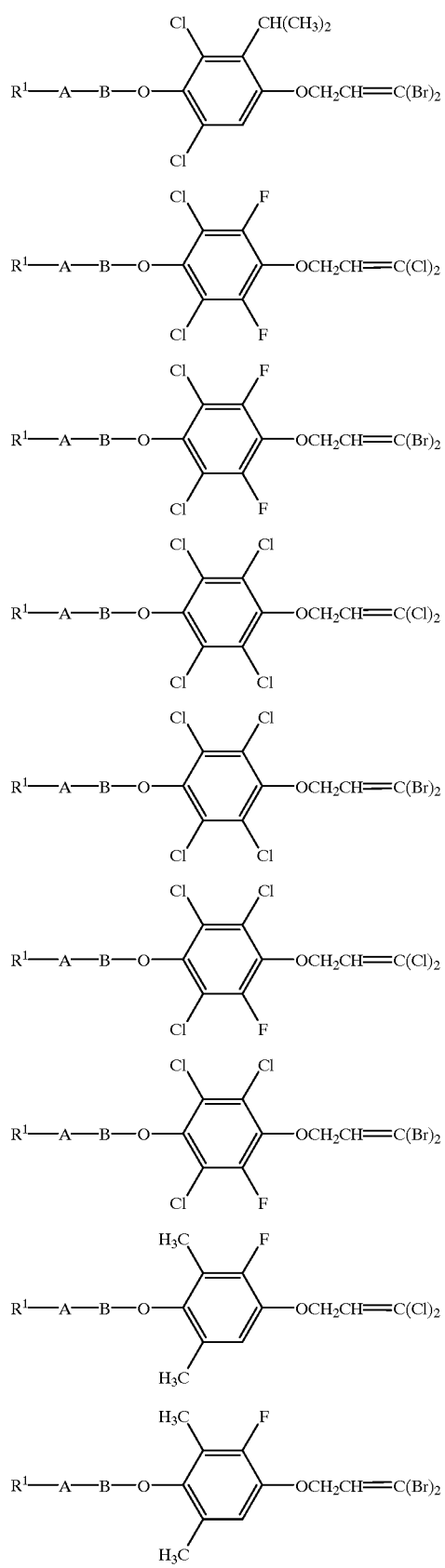
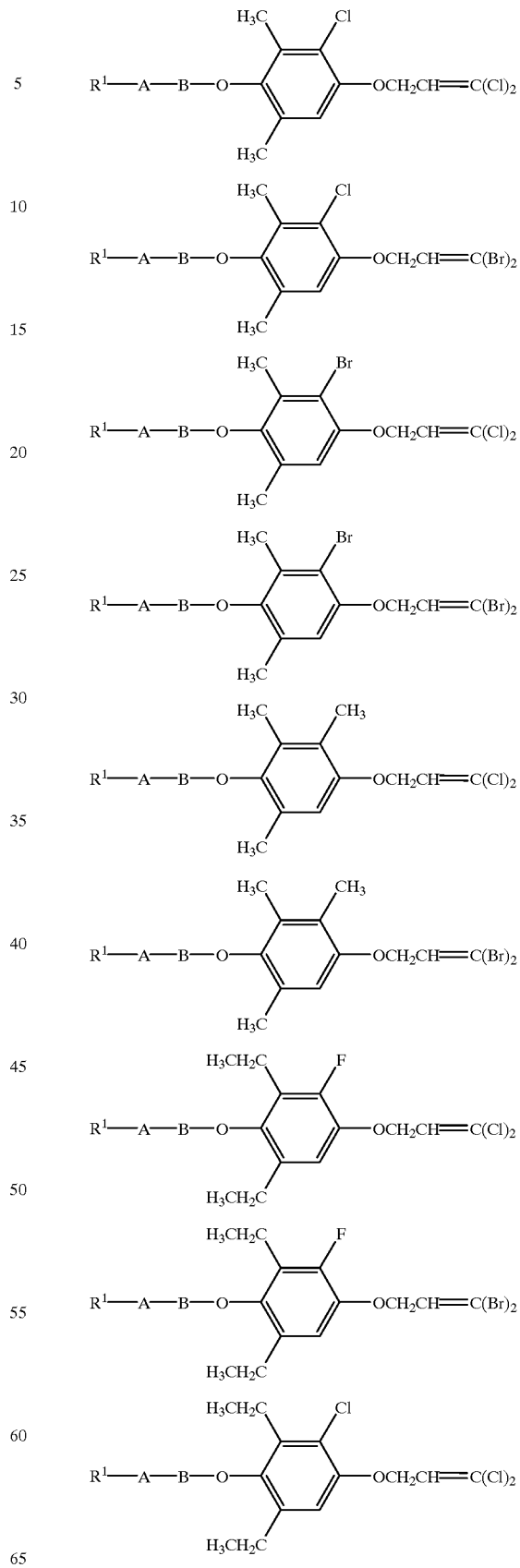

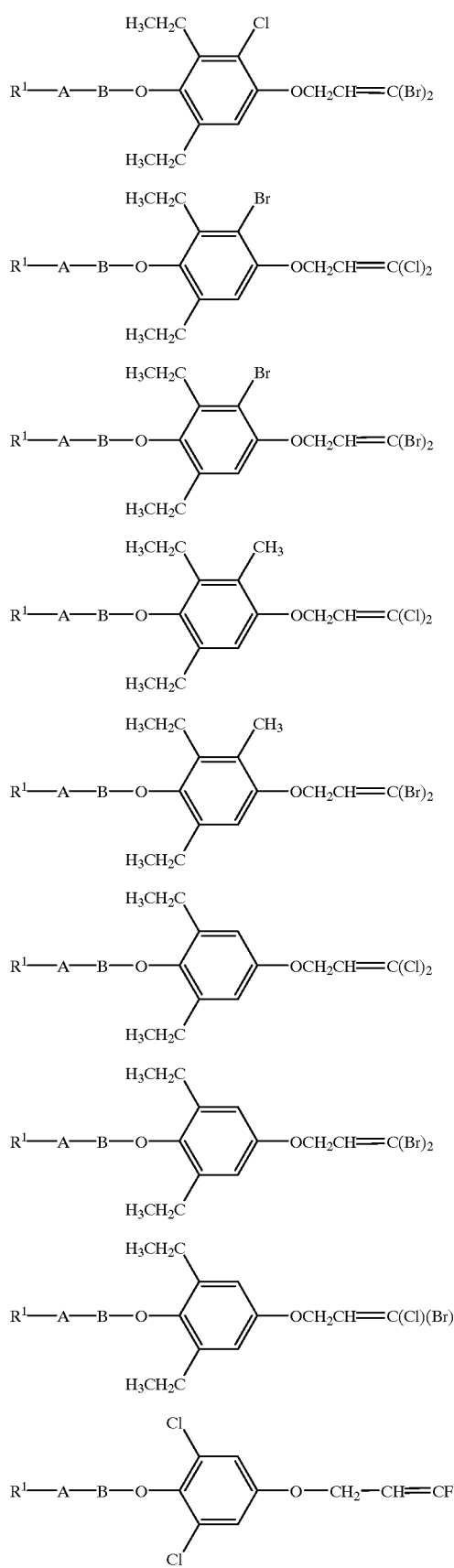
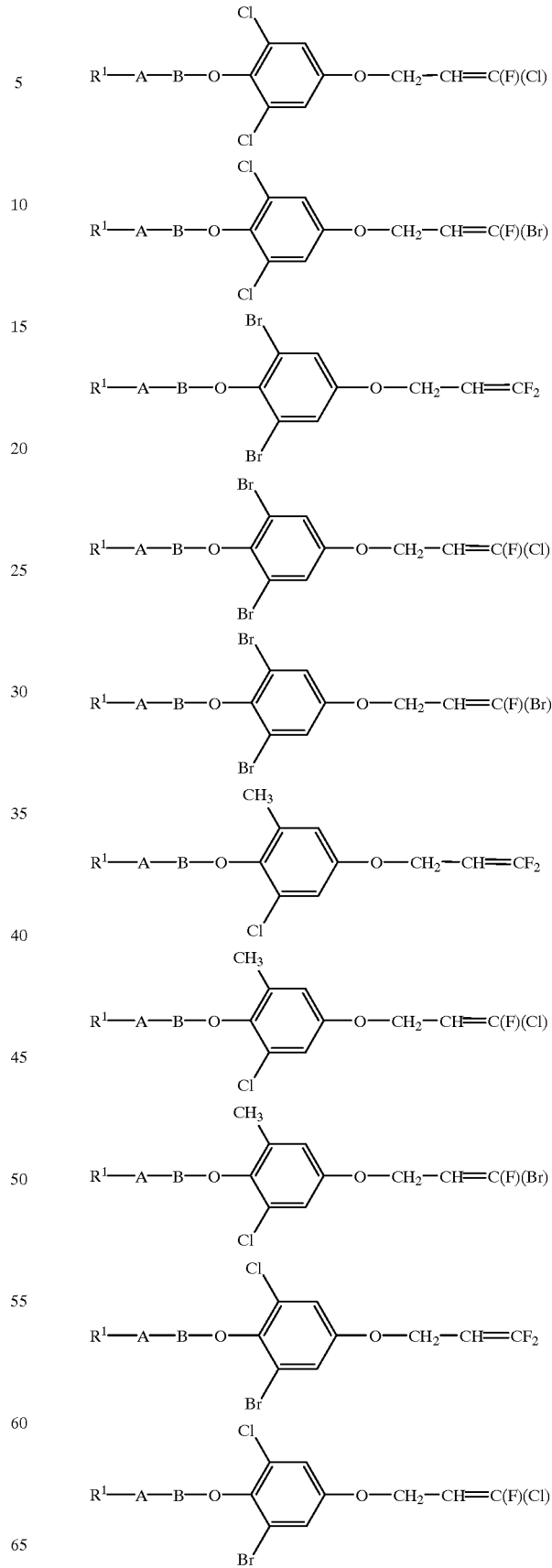

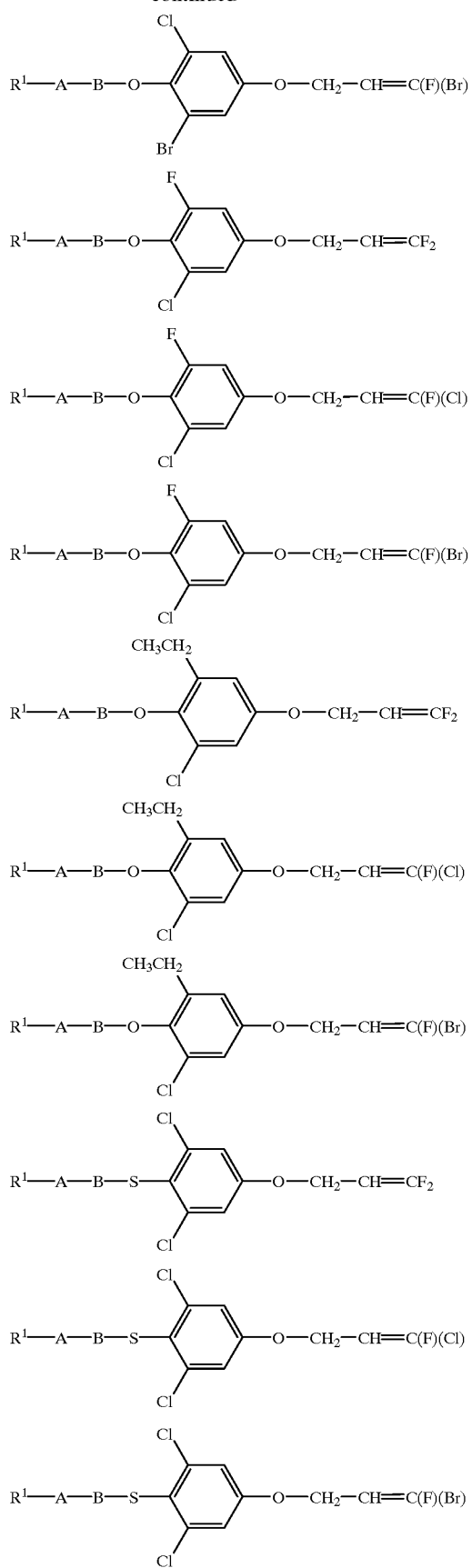
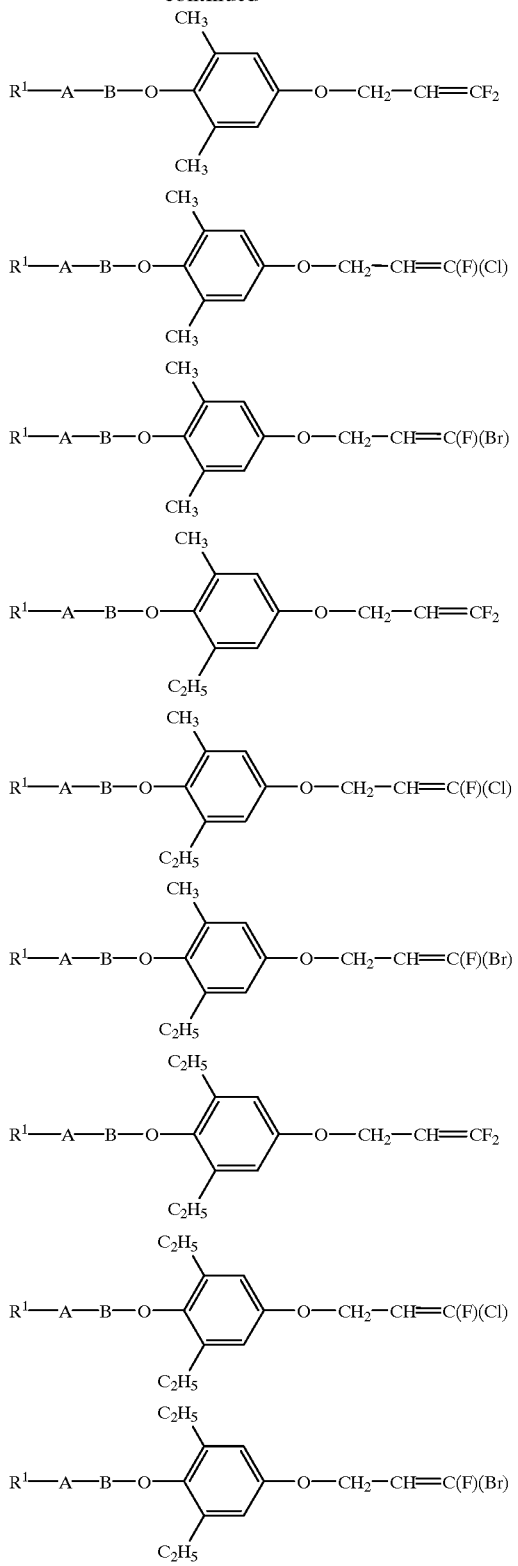
In these examples, R¹—A—B is as defined below.
R¹—O—(CH₂)₂
R¹—O—(CH₂)₂
R¹—O—(CH₂)₄
R¹—O—(CH₂)₅

$R^1$—O—$(CH_2)_6$
$R^1$—O—$(CH_2)_7$
$R^1$—O—$CH(CH_3)CH_2$
$R^1$—O—$CH(CH_3)(CH_2)_2$
$R^1$—O—$CH(CH_3)(CH_2)_3$
$R^1$—O—$CH(CH_3)(CH_2)_4$
$R^1$—O—$CH(CH_3)(CH_2)_5$
$R^1$—O—$CH(CH_3)(CH_2)_6$
$R^1$—O—$CH(CH_3)CH(CH_3)$
$R^1$—O—$CH(CH_3)CH_2CH(CH_3)$
$R^1$—O—$CH(CH_3)CH_2CH_2CH(CH_3)$
$R^1$—O—$CH_2C(CH_3)_2CH_2$
$R^1$—O—$CH_2C(CH_2CH_3)_2CH_2$
$R^1$—O—$CH_2CH(CH_3)$
$R^1$—O—$(CH_2)_2CH(CH_3)$
$R^1$—O—$(CH_2)_3CH(CH_3)$
$R^1$—O—$(CH_2)_4CH(CH_3)$
$R^1$—O—$(CH_2)_5CH(CH_3)$
$R^1$—O—$(CH_2)_6CH(CH_3)$
$R^1$—O—$CH_2CH=CHCH_2$
$R^1$—O—$CH_2C\equiv CCH_2$
$R^1$—S—$(CH_2)_2$
$R^1$—S—$(CH_2)_3$
$R^1$—S—$(CH_2)_4$
$R^1$—S—$(CH_2)_5$
$R^1$—S—$(CH_2)_6$
$R^1$—S—$(CH_2)_7$
$R^1$—S—$CH(CH_3)CH_2$
$R^1$—S—$CH(CH_3)(CH_2)_2$
$R^1$—S—$CH(CH_3)(CH_2)_3$
$R^1$—S—$CH(CH_3)(CH_2)_4$
$R^1$—S—$CH(CH_3)(CH_2)_5$
$R^1$—S—$CH(CH_3)(CH_2)_6$
$R^1$—S—$CH(CH_3)CH(CH_3)$
$R^1$—S—$CH(CH_3)CH_2CH(CH_3)$
$R^1$—S—$CH(CH_3)CH_2CH_2CH(CH_3)$
$R^1$—S—$CH_2C(CH_3)_2CH_2$
$R^1$—S—$CH_2C(CH_2CH_3)_2CH_2$
$R^1$—S—$CH_2CH(CH_3)$
$R^1$—S—$(CH_2)_2CH(CH_3)$
$R^1$—S—$(CH_2)_3CH(CH_3)$
$R^1$—S—$(CH_2)_4CH(CH_3)$
$R^1$—S—$(CH_2)_5CH(CH_3)$
$R^1$—S—$(CH_2)_6CH(CH_3)$
$R^1$—S—$CH_2CH=CHCH_2$
$R^1$—S—$CH_2C\equiv CCH_2$
$R^1$—S(=O)—$(CH_2)_2$
$R^1$—S(=O)—$(CH_2)_3$
$R^1$—S(=O)—$(CH_2)_4$
$R^1$—S(=O)—$(CH_2)_5$
$R^1$—S(=O)—$(CH_2)_6$
$R^1$—S(=O)—$(CH_2)_7$
$R^1$—S(=O)—$CH(CH_3)CH_2$
$R^1$—S(=O)—$CH(CH_3)(CH_2)_2$
$R^1$—S(=O)—$CH(CH_3)(CH_2)_3$
$R^1$—S(=O)—$CH(CH_3)(CH_2)_4$
$R^1$—S(=O)—$CH(CH_3)(CH_2)_5$
$R^1$—S(=O)—$CH(CH_3)(CH_2)_6$
$R^1$—S(=O)—$CH(CH_3)CH(CH_3)$
$R^1$—S(=O)—$CH(CH_3CH_2CH(CH_3)$
$R^1$—S(=O)—$CH(CH_3CH_2CH_2CH(CH_3)$
$R^1$—S(=O)—$CH_2C(CH_3)_2CH_2$
$R^1$—S(=O)—$CH_2C(CH_2CH_3)_2CH_2$
$R^1$—S(=O)—$CH_2CH(CH_3)$
$R^1$—S(=O)—$(CH_2)_2CH(CH_3)$
$R^1$—S(=O)—$(CH_2)_3CH(CH_3)$
$R^1$—S(=O)—$(CH_2)_4CH(CH_3)$
$R^1$—S(=O)—$(CH_2)_5CH(CH_3)$
$R^1$—S(=O)—$(CH_2)_6CH(CH_3)$
$R^1$—S(=O)—$CH_2CH=CHCH_2$
$R^1$—S(=O)—$CH_2C\equiv CCH_2$
$R^1$—$SO_2$—$(CH_2)_2$
$R^1$—$SO_2$—$(CH_2)_3$
$R^1$—$SO_2$—$(CH_2)_4$
$R^1$—$SO_2$—$(CH_2)_5$
$R^1$—$SO_2$—$(CH_2)_6$
$R^1$—$SO_2$—$(CH_2)_7$
$R^1$—$SO_2$—$CH(CH_3)CH_2$
$R^1$—$SO_2$—$CH(CH_3)(CH_2)_2$
$R^1$—$SO_2$—$CH(CH_3)(CH_2)_3$
$R^1$—$SO_2$—$CH(CH_3)(CH_2)_4$
$R^1$—$SO_2$—$CH(CH_3)(CH_2)_5$
$R^1$—$SO_2$—$CH(CH_3)(CH_2)_6$
$R^1$—$SO_2$—$CH(CH_3)CH(CH_3)$
$R^1$—$SO_2$—$CH(CH_3)CH_2CH(CH_3)$
$R^1$—$SO_2$—$CH(CH_3)CH_2CH_2CH(CH_3)$
$R^1$—$SO_2$—$CH_2C(CH_3)_2CH_2$
$R^1$—$SO_2$—$CH_2C(CH_2CH_3)_2CH_2$
$R^1$—$SO_2$—$CH_2CH(CH_3)$
$R^1$—$SO_2$—$(CH_2)_2CH(CH_3)$
$R^1$—$SO_2$—$(CH_2)_3CH(CH_3)$
$R^1$—$SO_2$—$(CH_2)_4CH(CH_3)$
$R^1$—$SO_2$—$(CH_2)_5CH(CH_3)$
$R^1$—$SO_2$—$(CH_2)_6CH(CH_3)$
$R^1$—$SO_2$—$CH_2CH=CHCH_2$
$R^1$—$SO_2$—$CH_2C\equiv CCH_2$
$R^1$—NH—$(CH_2)_2$
$R^1$—NH—$(CH_2)_3$
$R^1$—NH—$(CH_2)_4$
$R^1$—NH—$(CH_2)_5$
$R^1$—NH—$(CH_2)_6$
$R^1$—NH—$(CH_2)_7$
$R^1$—NH—$CH(CH_3)CH_2$
$R^1$—NH—$CH(CH_3)(CH_2)_2$
$R^1$—NH—$CH(CH_3)(CH_2)_3$
$R^1$—NH—$CH(CH_3)(CH_2)_4$
$R^1$—NH—$CH(CH_3)(CH_2)_5$
$R^1$—NH—$CH(CH_3)(CH_2)_6$
$R^1$—NH—$CH(CH_3)CH(CH_3)$
$R^1$—NH—$CH(CH_3)CH_2CH(CH_3)$
$R^1$—NH—$CH(CH_3)CH_2CH_2CH(CH_3)$
$R^1$—NH—$CH_2C(CH_3)_2CH_2$ R$^1$—NH—CH$_2$C(CH$_2$CH$_3$)$_2$CH$_2$
R$^1$—NH—CH$_2$CH(CH$_3$)
R$^1$—NH—(CH$_2$)$_2$CH(CH$_3$)
R$^1$—NH—(CH$_2$)$_3$CH(CH$_3$)
R$^1$—NH—(CH$_2$)$_4$CH(CH$_3$)
R$^1$—NH—(CH$_2$)$_5$CH(CH$_3$)
R$^1$—NH—(CH$_2$)$_6$CH(CH$_3$)
R$^1$—NH—CH$_2$CH=CHCH$_2$
R$^1$—NH—CH$_2$C≡CCH$_2$
R$^1$—N(CH$_3$)—(CH$_2$)$_2$
R$^1$—N(CH$_3$)—(CH$_2$)$_3$
R$^1$—N(CH$_3$)—(CH$_2$)$_4$
R$^1$—N(CH$_3$)—(CH$_2$)$_5$
R$^1$—N(CH$_3$)—(CH$_2$)$_6$
R$^1$—N(CH$_3$)—(CH$_2$)$_7$
R$^1$—N(CH$_2$CH$_3$)—(CH$_2$)$_2$
R$^1$—N(CH$_2$CH$_3$)—(CH$_2$)$_3$
R$^1$—N(CH$_2$CH$_3$)—(CH$_2$)$_4$
R$^1$—N(CH$_2$CH$_3$)—(CH$_2$)$_5$
R$^1$—N(CH$_2$CH$_3$)—(CH$_2$)$_6$
R$^1$—N(CH$_2$CH$_3$)—(CH$_2$)$_7$
R$^1$—N(CH$_2$CH$_2$CH$_3$)—(CH$_2$)$_2$
R$^1$—N(CH$_2$CH$_2$CH$_3$)—(CH$_2$)$_3$
R$^1$—N(CH$_2$CH$_2$CH$_3$)—(CH$_2$)$_4$
R$^1$—N(CH$_2$CH$_2$CH$_3$)—(CH$_2$)$_5$
R$^1$—N(CH$_2$CH$_2$CH$_3$)—(CH$_2$)$_6$
R$^1$—N(CH$_2$CH$_2$CH$_3$)—(CH$_2$)$_7$
R$^1$—N(CH(CH$_3$)$_2$)—(CH$_2$)$_2$
R$^1$—N(CH(CH$_3$)$_2$)—(CH$_2$)$_3$
R$^1$—N(CH(CH$_3$)$_2$)—(CH$_2$)$_4$
R$^1$—N(CH(CH$_3$)$_2$)—(CH$_2$)$_5$
R$^1$—N(CH(CH$_3$)$_2$)—(CH$_2$)$_6$
R$^1$—N(CH(CH$_3$)$_2$)—(CH$_2$)$_7$ wherein R$^1$ is as defined in Tables 1 to 3 in which "Ac" means acetyl.

| R$^1$ |
|---|
| HO—(CH$_2$)$_2$ |
| HO—(CH$_2$)$_3$ |
| HO—(CH$_2$)$_4$ |
| HO—(CH$_2$)$_5$ |
| HO—CH$_2$CH(CH$_2$)CH$_2$ |
| HO—CH$_2$C(CH$_3$)$_2$CH$_2$ |
| CH$_3$CH(OH)CH$_2$ |
| CH$_3$CH$_2$CH(OH)CH$_2$ |
| CH$_3$CH(OH)(CH$_2$)$_2$ |
| CF$_3$CH(OH)CH$_2$ |
| CF$_3$CCl$_2$CH(OH)CH$_2$ |
| CF$_3$CCl$_2$CH(OH)(CH$_2$)$_2$ |
| CF$_3$CHClCH(OH)CH$_2$ |
| CF$_3$CHClCH(OH)(CH$_2$)$_2$ |
| CF$_3$CBr$_2$CH(OH)CH$_2$ |
| CF$_3$CBr$_2$CH(OH)(CH$_2$)$_2$ |
| HO—CH$_2$CH(CH$_3$) |
| CF$_3$CH(OH)CH(CH$_3$) |
| CF$_3$CCl$_2$CH(OH)CH(CH$_3$) |
| CF$_3$CHClCH(OH)CH(CH$_3$) |
| CF$_3$CBr$_2$CH(OH)CH(CH$_3$) |
| CF$_3$CH$_2$CH(OH)CH$_2$ |
| CF$_3$CH$_2$CH(OH)(CH$_2$)$_2$ |
| F—(CH$_2$)$_2$ |
| F—(CH$_2$)$_3$ |

-continued

| R$^1$ |
|---|
| F—(CH$_2$)$_4$ |
| F—(CH$_2$)$_5$ |
| F—CH$_2$CH(CH$_3$)CH$_2$ |
| F—CH$_2$C(CH$_3$)$_2$CH$_2$ |
| CH$_3$CHFCH$_2$ |
| CH$_3$CH$_2$CHFCH$_2$ |
| CH$_3$CHF(CH$_2$)$_2$ |
| CF$_3$CHFCH$_2$ |
| CF$_3$CCl$_2$CHFCH$_2$ |
| CF$_3$CCl$_2$CHF(CH$_2$)$_2$ |
| CF$_3$CHClCHFCH$_2$ |
| CF$_3$CHClCHF(CH$_2$)$_2$ |
| CF$_3$CBr$_2$CHFCH$_2$ |
| CF$_3$CBr$_2$CHF(CH$_2$)$_2$ |
| F—CH$_2$CH(CH$_3$) |
| CF$_3$CHFCH(CH$_3$) |
| CF$_3$CCl$_2$CHFCH(CH$_3$) |
| CF$_3$CHClCHFCH(CH$_3$) |
| CF$_3$CBr$_2$CHFCH(CH$_3$) |
| CF$_3$CH$_2$CHFCH$_2$ |
| CF$_3$CH$_2$CHF(CH$_2$)$_2$ |
| Cl—(CH$_2$)$_2$ |
| Cl—(CH$_2$)$_3$ |
| Cl—(CH$_2$)$_4$ |
| Cl—(CH$_2$)$_5$ |
| Cl—CH$_2$CH(CH$_3$)CH$_2$ |
| Cl—CH$_2$C(CH$_3$)$_2$CH$_2$ |
| CH$_3$CHClCH$_2$ |
| CH$_3$CH$_2$CHClCH$_2$ |
| CH$_2$CHCl(CH$_2$)$_2$ |
| CH$_3$CHCl(CH$_2$)$_3$ |
| CH$_3$CHCl(CH$_2$)$_4$ |
| CF$_3$CHClCH$_2$ |
| CF$_3$CCl$_2$CHClCH$_2$ |
| CF$_3$CCl$_2$CHCl(CH$_2$)$_2$ |
| CF$_3$CHClCHClCH$_2$ |
| CF$_3$CHClCHCl(CH$_2$)$_2$ |
| CF$_3$CBr$_2$CHClCH$_2$ |
| CF$_3$CBr$_2$CHCl(CH$_2$)$_2$ |
| Cl—CH$_2$CH(CH$_3$) |
| CF$_3$CHClCH(CH$_3$) |
| CF$_3$CCl$_2$CHClCH(CH$_3$) |
| CF$_3$CHClCHClCH(CH$_3$) |
| CF$_3$CBr$_2$CHClCH(CH$_3$) |
| CF$_3$CH$_2$CHClCH$_2$ |
| CF$_3$CH$_2$CHCl(CH$_2$)$_2$ |
| Br—(CH$_2$)$_2$ |
| Br—(CH$_2$)$_3$ |
| Br—(CH$_2$)$_4$ |
| Br—(CH$_2$)$_5$ |
| Br—CH$_2$CH(CH$_3$)CH$_2$ |
| Br—CH$_2$C(CH$_3$)$_2$CH$_2$ |
| CH$_3$CHBrCH$_2$ |
| CH$_3$CH$_2$CHBrCH$_2$ |
| CH$_3$CHBr(CH$_2$)$_2$ |
| CF$_3$CHBrCH$_2$ |
| CF$_3$CCl$_2$CHBrCH$_2$ |
| CF$_3$CCl$_2$CHBr(CH$_2$)$_2$ |
| CF$_3$CHClCHBrCH$_2$ |
| CF$_3$CHClCHBr(CH$_2$)$_2$ |
| CF$_3$CBr$_2$CHBrCH$_2$ |
| CF$_3$CBr$_2$CHBr(CH$_2$)$_2$ |
| Br—CH$_2$CH(CH$_3$) |
| CF$_3$CHBrCH(CH$_3$) |
| CF$_3$CCl$_2$CHBrCH(CH$_3$) |
| CF$_3$CHClCHBrCH(CH$_3$) |
| CF$_3$CBr$_2$CHBrCH(CH$_3$) |
| CF$_3$CH$_2$CHBrCH$_2$ |
| CF$_3$CH$_2$CHBr(CH$_2$)$_2$ |
| CF$_3$CH$_2$ |
| CF$_3$CF$_2$CH$_2$ |
| CF$_3$(CF$_2$)$_2$CH$_2$ |
| CF$_3$(CH$_2$)$_2$ |
| CF$_3$(CH$_2$)$_3$ |
| FCH$_2$CH$_2$ |
| CHF$_2$CH$_2$ |
| CHF$_2$CF$_2$CH$_2$ |

-continued

| $R^1$ |
|---|
| $CF_3CHFCF_2CH_2$ |
| $CHF_2(CF_2)_3CH_2$ |
| $CHF_2(CF_2)_4CH_2$ |
| $CH(CF_3)(CH_3)$ |
| $CH(CF_3CF_2)(CH_3)$ |
| $CH(CF_3)_2$ |
| $CCl_3CH_2$ |
| $CBr_3CH_2$ |
| $AcO-(CH_2)_2$ |
| $AcO-(CH_2)_3$ |
| $AcO-(CH_2)_4$ |
| $AcO-(CH_2)_5$ |
| $AcO-CH_2CH(CH_3)CH_2$ |
| $AcO-CH_2C(CH_3)_2CH_2$ |
| $CH_3CH(OAc)CH_2$ |
| $CH_3CH_2CH(OAc)CH_2$ |
| $CH_3CH(OAc)(CH_2)_2$ |
| $CF_3CH(OAc)CH_2$ |
| $CF_3CCl_2CH(OAc)CH_2$ |
| $CF_3CCl_2CH(OAc)(CH_2)_2$ |
| $CF_3CHClCH(OAc)CH_2$ |
| $CF_3CHClCH(OAc)(CH_2)_2$ |
| $CF_3CBr_2CH(OAc)CH_2$ |
| $CF_3CBr_2CH(OAc)(CH_2)_2$ |
| $AcO-CH_2CH(CH_3)$ |
| $CF_3CH(OAc)(CH(CH_3)$ |
| $CF_3CCl_2CH(OAc)CH(CH_3)$ |
| $CF_3CHClCH(OAc)CH(CH_3)$ |
| $CF_3CBr_2CH(OAc)CH(CH_3)$ |
| $CF_3CH_2CH(OAc)CH_2$ |
| $CF_3CH_2CH(OAc)(CH_2)_2$ |
| $CH_3CH_2COO-(CH_2)_2$ |
| $CH_3CH_2COO-(CH_2)_3$ |
| $CH_3CH(OCOCH_2CH_3)CH_2$ |
| $CF_3CH(OCOCH_2CH_3)CH_2$ |
| $CF_3CCl_2CH(OCOCH_2CH_3)CH_2$ |
| $CF_3CCl_2CH(OCOCH_2CH_3)(CH_2)_2$ |
| $CH_3(CH_2)_2COO-(CH_2)_2$ |
| $CH_3(CH_2)_2COO-(CH_2)_3$ |
| $CH_3CH(OCO(CH_2)_2CH_3)CH_2$ |
| $CF_3CH(OCO(CH_2)_2CH_3)CH_2$ |
| $CF_3CCl_2CH-(OCO(CH_2)_2CH_3)CH_2$ |
| $CF_3CCl_2CH-(OCO(CH_2)_2CH_3)(CH_2)_2$ |
| $(CH_3)_2CHCOO-(CH_2)_2$ |
| $(CH_3)_2CHCOO-(CH_2)_3$ |
| $CH_3CH(OCOCH(CH_3)_2)CH_2$ |
| $CF_3CH(OCOCH(CH_3)_2)CH_2$ |
| $CF_3CCl_2CH-(OCOCH(CH_3)_2)CH_2$ |
| $CF_3CCl_2CH-(OCOCH(CH_3)_2)(CH_2)_2$ |
| $CH_3(CH_2)_3COO-(CH_2)_2$ |
| $CH_3(CH_2)_3COO-(CH_2)_3$ |
| $CH_3CH(OCO(CH_2)_3CH_3)CH_2$ |
| $CF_3CH(OCO(CH_2)_3CH_3)CH_2$ |
| $CF_3CCl_2CH-(OCO(CH_2)_3CH_3)CH_2$ |
| $CF_3CCl_2CH-(OCO(CH_2)_3CH_3)(CH_2)_2$ |
| $(CH_3)_2CHCH_2COO-(CH_2)_2$ |
| $(CH_3)_2CHCH_2COO-(CH_2)_3$ |
| $CH_3CH(OCOCH_2CH(CH_3)_2)CH_2$ |
| $CF_3CH(OCOCH_2CH(CH_3)_2)CH_2$ |
| $CF_3CCl_2CH-(OCOCH_2CH(CH_3)_2)CH_2$ |
| $CF_3CCl_2CH-(OCOCH_2CH(CH_3)_2)(CH_2)_2$ |
| $CH_3CH_2CH(CH_3)COO-(CH_2)_2$ |
| $CH_3CH_2CH(CH_3)COO-(CH_2)_3$ |
| $CH_3CH(OCOCH(CH_3)CH_2CH_3)CH_2$ |
| $CF_3CH(OCOCH(CH_3)CH_2CH_3)CH_2$ |
| $CF_3CCl_2CH-(OCOCH(CH_3)CH_2CH_3)CH_2$ |
| $CF_3CCl_2CH-(OCOCH(CH_3)CH_2CH_3)(CH_2)_2$ |
| $(CH_3)_3CCOO-(CH_2)_2$ |
| $(CH_3)_3CCOO-(CH_2)_3$ |
| $CH_3CH(OCOC(CH_3)_3)CH_2$ |
| $CF_3CH(OCOC(CH_3)_3)CH_2$ |
| $CF_3CCl_2CH(OCOC(CH_3)_3)CH_2$ |
| $CF_3CCl_2CH-(OCOC(CH_3)_3)(CH_2)_2$ |
| $CH_2ClCOO-(CH_2)_2$ |
| $CH_2ClCOO-(CH_2)_3$ |
| $CH_3CH(OCOCH_2Cl)CH_2$ |
| $CF_3CH(OCOCH_2Cl)CH_2$ |

-continued

| $R^1$ |
|---|
| $CF_3CCl_2CH(OCOCH_2Cl)CH_2$ |
| $CF_3CCl_2CH(OCOCH_2Cl)(CH_2)_2$ |
| $CHCl_2COO-(CH_2)_2$ |
| $CHCl_2COO-(CH_2)_3$ |
| $CH_3CH(OCOCHCl_2)CH_2$ |
| $CF_3CH(OCOCHCl_2)CH_2$ |
| $CF_3CCl_2CH(OCOCHCl_2)CH_2$ |
| $CF_3CCl_2CH(OCOCHCl_2)(CH_2)_2$ |
| $CCl_3COO-(CH_2)_2$ |
| $CCl_3COO-(CH_2)_3$ |
| $CH_3CH(OCOCCl_3)CH_2$ |
| $CF_3CH(OCOCCl_3)CH_2$ |
| $CF_3CCl_2CH(OCOCCl_3)CH_2$ |
| $CF_3CCl_2CH(OCOCCl_3)(CH_2)_2$ |
| $CF_3COO-(CH_2)_2$ |
| $CF_3COO-(CH_2)_3$ |
| $CH_3CH(OCOCF_3)CH_2$ |
| $CF_3CH(OCOCF_3)CH_2$ |
| $CF_3CCl_2CH(OCOCF_3)CH_2$ |
| $CF_3CCl_2CH(OCOCF_3)(CH_2)_2$ |
| $CF_2ClCOO-(CH_2)_2$ |
| $CF_2ClCOO-(CH_2)_3$ |
| $CH_3CH(OCOCF_2Cl)CH_2$ |
| $CF_3CH(OCOCF_2Cl)CH_2$ |
| $CF_3CCl_2CH(OCOCF_2Cl)CH_2$ |
| $CF_3CCl_2CH(OCOCF_2Cl)(CH_2)_2$ |
| $CF_3CF_2COO-(CH_2)_2$ |
| $CF_3CF_2COO-(CH_2)_3$ |
| $CH_3CH(OCOCF_2CF_3)CH_2$ |
| $CF_3CH(OCOCF_2CF_3)CH_2$ |
| $CF_3CCl_2CH(OCOCF_2CF_3)CH_2$ |
| $CF_3CCl_2CH-(OCOCF_2CF_3)(CH_2)_2$ |
| $CF_3CF_2CF_2COO-(CH_2)_2$ |
| $CF_3CF_2CF_2COO-(CH_2)_3$ |
| $CH_3CH(OCOCF_2CF_2CF_3)CH_2$ |
| $CF_3CH(OCOCF_2CF_2CF_3)CH_2$ |
| $CF_3CCl_2CH(OCOCF_2CF_2CF_3)CH_2$ |
| $CF_3CCl_2CH-(OCOCF_2CF_2CF_3)(CH_2)_2$ |
| $CH_3O-(CH_2)_2$ |
| $CH_3O-(CH_2)_3$ |
| $CH_3O-(CH_2)_4$ |
| $CH_3O-(CH_2)_5$ |
| $CH_3O-CH_2CH(CH_3)CH_2$ |
| $CH_3O-CH_2C(CH_3)_2CH_2$ |
| $CH_3CH(OCH_3)CH_2$ |
| $CH_3CH_2CH(OCH_3)CH_2$ |
| $CH_3CH(OCH_3)(CH_2)_2$ |
| $CF_3CH(OCH_3)CH_2$ |
| $CF_3CCl_2CH(OCH_3)CH_2$ |
| $CF_3CCl_2CH(OCH_3)(CH_2)_2$ |
| $CF_3CHClCH(OCH_3)CH_2$ |
| $CF_3CHClCH(OCH_3)(CH_2)_2$ |
| $CF_3CBr_2CH(OCH_3)CH_2$ |
| $CF_3CBr_2CH(OCH_3)(CH_2)_2$ |
| $CH_3O-CH_2CH(CH_3)$ |
| $CF_3CH(OCH_3)CH(CH_3)$ |
| $CF_3CCl_2CH(OCH_3)CH(CH_3)$ |
| $CF_3CHClCH(OCH_3)CH(CH_3)$ |
| $CF_3CBr_2CH(OCH_3)CH(CH_3)$ |
| $CF_3CH_2CH(OCH_3)(CH_2)_2$ |
| $CH_3CH_2O-(CH_2)_2$ |
| $CH_3CH_2O-(CH_2)_3$ |
| $CH_3CH_2O-(CH_2)_4$ |
| $CH_3CH_2O-(CH_2)_5$ |
| $CH_3CH_2O-CH_2CH(CH_3)CH_2$ |
| $CH_3CH_2O-CH_2C(CH_3)_2CH_2$ |
| $CH_3CH(OCH_2CH_3)CH_2$ |
| $CH_3CH_2CH(OCH_2CH_3)CH_2$ |
| $CH_3CH(OCH_2CH_3)(CH_2)_2$ |
| $CF_3CH(OCH_2CH_3)CH_2$ |
| $CF_3CCl_2CH(OCH_2CH_3)CH_2$ |
| $CF_3CCl_2CH(OCH_2CH_3)(CH_2)_2$ |
| $CF_3CHClCH(OCH_2CH_3)CH_2$ |
| $CF_3CHClCH(OCH_2CH_3)(CH_2)_2$ |
| $CF_3CBr_2CH(OCH_2CH_3)CH_2$ |
| $CF_3CBr_2CH(OCH_2CH_3)(CH_2)_2$ |
| $CH_3CH_2O-CH_2CH(CH_3)$ |

| R¹ |
|---|
| CF₃CH(OCH₂CH₃)CH(CH₃) |
| CF₃CCl₂CH—(OCH₂CH₃)CH(CH₃) |
| CF₃CHClCH(OCH₂CH₃)CH(CH₃) |
| CF₃CBr₂CH(OCH₂CH₃)CH(CH₃) |
| CF₃CH₂CH(OCH₂CH₃)CH₂ |
| CF₃CH₂CH(OCH₂CH₃)(CH₂)₂ |
| CH₃(CH₂)₂O—(CH₂)₂ |
| CH₃(CH₂)₂O—(CH₂)₃ |
| CH₃(CH₂)₂O—(CH₂)₄ |
| CH₃CH(O(CH₂)₂CH₃)CH₂ |
| CH₃CH(O(CH₂)₂CH₃)(CH₂)₂ |
| (CH₃)₂CHO—(CH₂)₂ |
| (CH₃)₂CHO—(CH₂)₃ |
| (CH₃)₂CHO—(CH₂)₄ |
| CH₃CH(OCH(CH₃)₂)CH₂ |
| CH₃CH(OCH(CH₃)₂)(CH₂)₂ |
| FCH₂CH₂O—(CH₂)₂ |
| FCH₂CH₂O—(CH₂)₃ |
| FCH₂CH₂O—(CH₂)₄ |
| CH₃CH(OCH₂CH₂F)CH₂ |
| CH₃CH(OCH₂CH₂F)(CH₂)₂ |
| ClCH₂CH₂O—(CH₂)₂ |
| ClCH₂CH₂O—(CH₂)₃ |
| ClCH₂CH₂O—(CH₂)₄ |
| CH₃CH(OCH₂CH₂Cl)CH₂ |
| CH₃CH(OCH₂CH₂Cl)(CH₂)₂ |
| BrCH₂CH₂O—(CH₂)₂ |
| BrCH₂CH₂O—(CH₂)₃ |
| BrCH₂CH₂O—(CH₂)₄ |
| CH₃CH(OCH₂CH₂Br)CH₂ |
| CH₃CH(OCH₂CH₂Br)(CH₂)₂ |
| CF₃CH₂O—(CH₂)₂ |
| CF₃CH₂O—(CH₂)₃ |
| CF₃CH₂O—(CH₂)₄ |
| CH₃CH(OCH₂CF₃)CH₂ |
| CH₃CH(OCH₂CF₃)(CH₂)₂ |
| CCl₃CH₂O—(CH₂)₂ |
| CCl₃CH₂O—(CH₂)₃ |
| CCl₃CH₂O—(CH₂)₄ |
| CH₃CH(OCH₂Cl₃)CH₂ |
| CH₃CH(OCH₂Cl₃)(CH₂)₂ |
| CBr₃CH₂O—(CH₂)₂ |
| CBr₃CH₂O—(CH₂)₃ |
| CBr₃CH₂O—(CH₂)₄ |
| CH₃CH(OCH₂Br₃)CH₂ |
| CH₃CH(OCH₂Br₃)(CH₂)₂ |
| CF₃CF₂CH₂O—(CH₂)₂ |
| CF₃CF₂CH₂O—(CH₂)₃ |
| CF₃CF₂CH₂O—(CH₂)₄ |
| CH₃CH(OCH₂CF₂CF₃)CH₂ |
| CH₃CH(OCH₂CF₂CF₃)(CH₂)₂ |
| (CF₃)₂CHO—(CH₂)₂ |
| (CF₃)₂CHO—(CH₂)₃ |
| (CF₃)₂CHO—(CH₂)₄ |
| CH₃CH(OCH(CF₃)₂)CH₂ |
| CH₃CH(OCH(CF₃)₂)(CH₂)₂ |
| CH₂=CHCH₂O—(CH₂)₂ |
| CH₂=CHCH₂O—(CH₂)₃ |
| CH₂=CHCH₂O—(CH₂)₄ |
| CH₃CH(OCH₂CH=CH₂)CH₂ |
| CF₃CH(OCH₂CH=CH₂)(CH₂)₂ |
| Cl₂C=CHCH₂O—(CH₂)₂ |
| Cl₂C=CHCH₂O—(CH₂)₃ |
| Cl₂C=CHCH₂O—(CH₂)₄ |
| CH₃CH(OCH₂CH=CCl₃)CH₂ |
| CH₃CH(OCH₂CH=CCl₃)(CH₂)₂ |
| ClCH=CHCH₂O—(CH₂)₂ |
| ClCH=CHCH₂O—(CH₂)₃ |
| ClCH=CHCH₂O—(CH₂)₄ |
| CH₃CH(OCH₂CH=CHCl)CH₂ |
| CH₃CH(OCH₂CH=CHCl)(CH₂)₂ |
| HC≡CCH₂O—(CH₂)₂ |
| HC≡CCH₂O—(CH₂)₃ |
| HC≡CCH₂O—(CH₂)₄ |
| CH₃CH(OCH₂C≡CH)CH₂ |
| CH₃CH(OCH₂C≡CH)(CH₂)₂ |
| Cl—C≡CCH₂O—(CH₂)₂ |
| Cl—C≡CCH₂O—(CH₂)₃ |
| Cl—C≡CCH₂O—(CH₂)₃ |
| CH₃CH(CH₂C≡CCl)CH₂ |
| CH₃CH(CH₂C≡CCl)(CH₂)₂ |
| CH₃S—(CH₂)₂ |
| CH₃S—(CH₂)₃ |
| CH₃S—(CH₂)₄ |
| CH₃S—(CH₂)₅ |
| CH₃S—CH₂CH(CH₃)CH₂ |
| CH₃S—CH₂C(CH₃)₂CH₂ |
| CH₃CH(SCH₃)CH₂ |
| CH₃CH₂CH(SCH₃)CH₂ |
| CH₃CH(SCH₃)(CH₂)₂ |
| CF₃CH(SCH₃)CH₂ |
| CF₃CCl₂CH(SCH₃)CH₂ |
| CF₃CCl₂CH(SCH₃)(CH₂)₂ |
| CF₃CHClCH(SCH₃)CH₂ |
| CF₃CHClCH(SCH₃)(CH₂)₂ |
| CF₃CBr₂CH(SCH₃)CH₂ |
| CF₃CBr₂CH(SCH₃)(CH₂)₂ |
| CH₃S—CH₂CH(CH₃) |
| CF₃CH(SCH₃)CH(CH₃) |
| CF₃CCl₂CH(SCH₃)CH(CH₃) |
| CF₃CHClCH(SCH₃)CH(CH₃) |
| CF₃CBr₂CH(SCH₃)CH(CH₃) |
| CF₃CH₂CH(SCH₃)CH₂ |
| CF₃CH₂CH(SCH₃)(CH₂)₂ |
| CH₃CH₂S—(CH₂)₂ |
| CH₃CH₂S—(CH₂)₃ |
| CH₃CH₂S—(CH₂)₄ |
| CH₃CH₂S—(CH₂)₅ |
| CH₃CH₂S—CH₂CH(CH₃)CH₂ |
| CH₃CH₂S—CH₂C(CH₃)₂CH₂ |
| CH₃CH(SCH₂CH₃)CH₂ |
| CH₃CH₂CH(SCH₂CH₃)CH₂ |
| CH₃CH(SCH₂CH₃)(CH₂)₂ |
| CF₃CH(SCH₂CH₃)CH₂ |
| CF₃CCl₂CH(SCH₂CH₃)CH₂ |
| CF₃CCl₂CH(SCH₂CH₃)(CH₂)₂ |
| CF₃CHClCH(SCH₂CH₃)CH₂ |
| CF₃CHClCH(SCH₂CH₃)(CH₂)₂ |
| CF₃CBr₂CH(SCH₂CH₃)CH₂ |
| CF₃CBr₂CH(SCH₂CH₃)(CH₂)₂ |
| CH₃CH₂S—CH₂CH(CH₃) |
| CF₃CH(SCH₂CH₃)CH(CH₃) |
| CF₃CCl₂CH(SCH₂CH₃)CH(CH₃) |
| CF₃CHClCH(SCH₂CH₃)CH(CH₃) |
| CF₃CBr₂CH(SCH₂CH₃)CH(CH₃) |
| CF₃CH₂CH(SCH₂CH₃)CH₂ |
| CF₃CH₂CH(SCH₂CH₃)(CH₂)₂ |
| CH₂=CHCH₂S—(CH₂)₂ |
| CH₂=CHCH₂S—(CH₂)₃ |
| CH₂=CHCH₂S—(CH₂)₄ |
| CH₃CH(SCH₂CH=CH₂)CH₂ |
| CH₃CH(SCH₂CH=CH₂)(CH₂)₂ |
| Cl₂C=CHCH₂S—(CH₂)₂ |
| Cl₂C=CHCH₂S—(CH₂)₃ |
| Cl₂C=CHCH₂S—(CH₂)₄ |
| CH₃CH(SCH₂CH=CCl₂)CH₂ |
| CH₃CH(SCH₂CH=CCl₂)(CH₂)₂ |
| ClCH=CHCH₂S—(CH₂)₂ |
| ClCH=CHCH₂S—(CH₂)₃ |
| ClCH=CHCH₂S—(CH₂)₄ |
| CH₃CH(SCH₂CH=CHCl)CH₂ |
| CH₃CH(SCH₂CH=CHCl)(CH₂)₂ |
| HC≡CCH₂S—(CH₂)₂ |
| HC≡CCH₂S—(CH₂)₃ |
| HC≡CCH₂S—(CH₂)₄ |
| CH₃CH(SCH₂C≡CH)CH₂ |
| CH₃CH(SCH₂C≡CH)(CH₂)₂ |
| Cl—C≡CCH₂S—(CH₂)₂ |
| Cl—C≡CCH₂S—(CH₂)₃ |
| Cl—C≡CCH₂S—(CH₂)₄ |
| CH₃CH(SCH₂C≡CCl)CH₂ |
| CH₃CH(SCH₂C≡CCl)(CH₂)₂ |
| CH₃(CH₂)₂S—(CH₂)₂ |
| CH₃(CH₂)₂S—(CH₂)₃ |

-continued

| R¹ |
|---|
| CH₃(CH₂)₂S—(CH₂)₄ |
| CH₃CH(S(CH₂)₂CH₃)CH₂ |
| CH₃CH(S(CH₂)₂CH₃)(CH₂)₂ |
| (CH₃)₂CHS—(CH₂)₂ |
| (CH₃)₂CHS—(CH₂)₃ |
| (CH₃)₂CHS—(CH₂)₄ |
| CH₃CH(SCH(CH₃)₂)CH₂ |
| CH₃CH(SCH(CH₃)₂)(CH₂)₂ |
| FCH₂CH₂S—(CH₂)₂ |
| FCH₂CH₂S—(CH₂)₃ |
| FCH₂CH₂S—(CH₂)₄ |
| CH₃CH(SCH₂F)CH₂ |
| CH₃CH(SCH₂F)(CH₂)₂ |
| CF₃CH₂S—(CH₂)₂ |
| CF₃CH₂S—(CH₂)₃ |
| CF₃CH₂S—(CH₂)₄ |
| CH₃CH(SCH₂CF₃)CH₂ |
| CH₃CH(SCH₂CF₃)(CH₂)₂ |
| CCl₃CH₂S—(CH₂)₂ |
| CCl₃CH₂S—(CH₂)₃ |
| CCl₃CH₂S—(CH₂)₄ |
| CH₃CH(SCH₂CCl₃)CH₂ |
| CH₃CH(SCH₂CCl₃)(CH₂)₂ |
| CBr₃CH₂S—(CH₂)₂ |
| CBr₃CH₂S—(CH₂)₃ |
| CBr₃CH₂S—(CH₂)₄ |
| CH₃CH(SCH₂CBr₃)CH₂ |
| CH₃CH(SCH₂CBr₃)(CH₂)₂ |
| CF₃CF₂CH₂S—(CH₂)₂ |
| CF₃CF₂CH₂S—(CH₂)₃ |
| CF₃CF₂CH₂S—(CH₂)₄ |
| CH₃CH(SCH₂CF₂CF₃)CH₂ |
| CH₃CH(SCH₂CF₂CF₃)(CH₂)₂ |
| (CF₃)₂CHS—(CH₂)₂ |
| (CF₃)₂CHS—(CH₂)₃ |
| (CF₃)₂CHS—(CH₂)₄ |
| CH₃CH(SCH(CF₃)₂)CH₂ |
| CH₃CH(SCH(CF₃)₂)(CH₂)₂ |
| CH₃CONH—(CH₂)₂ |
| CH₃CONH—(CH₂)₃ |
| CH₃CONH—(CH₂)₄ |
| CH₃CH(NHCOCH₃)CH₂ |
| CH₃CH(NHCOCH₃)(CH₂)₂ |
| CH₃CH₂CONH—(CH₂)₂ |
| CH₃CH₂CONH—(CH₂)₃ |
| CH₃CH₂CONH—(CH₂)₄ |
| CH₃CH(NHCOCH₂CH₃)CH₂ |
| CH₃CH(NHCOCH₂CH₃)(CH₂)₂ |
| CH₃(CH₂)₂CONH—(CH₂)₂ |
| CH₃(CH₂)₂CONH—(CH₂)₃ |
| CH₃(CH₂)₂CONH—(CH₂)₄ |
| CH₃CH(NHCO(CH₂)₂CH₃)CH₂ |
| CH₃CH(NHCO(CH₂)₂CH₃)(CH₂)₂ |
| (CH₃)₂CHCONH—(CH₂)₂ |
| (CH₃)₂CHCONH—(CH₂)₃ |
| (CH₃)₂CHCONH—(CH₂)₄ |
| CH₃CH(NHCOCH(CH₃)₂)CH₂ |
| CH₃CH(NHCOCH(CH₃)₂)(CH₂)₂ |
| CH₃(CH₂)₃CONH—(CH₂)₂ |
| CH₃(CH₂)₃CONH—(CH₂)₃ |
| CH₃(CH₂)₃CONH—(CH₂)₄ |
| CH₃CH(NHCO(CH₂)₃CH₃)CH₂ |
| CH₃CH(NHCO(CH₂)₃CH₃)(CH₂)₂ |
| (CH₃)₂CHCH₂CONH—(CH₂)₂ |
| (CH₃)₂CHCH₂CONH—(CH₂)₃ |
| (CH₃)₂CHCH₂CONH—(CH₂)₄ |
| CH₃CH(NHCOCH₂CH(CH₃)₂)CH₂ |
| CH₃CH—(NHCOCH₂CH(CH₃)₂)(CH₂)₂ |
| CH₃CH₂CH(CH₃)CONH—(CH₂)₂ |
| CH₃CH₂CH(CH₃)CONH—(CH₂)₃ |
| CH₃CH₂CH(CH₃)CONH—(CH₂)₄ |
| CH₃CH(NHCOCH(CH₃)CH₂CH₃)CH₂ |
| CH₃CH—(NHCOCH(CH₃)CH₂CH₃)(CH₂)₂ |
| (CH₃)₃CCONH—(CH₂)₂ |
| (CH₃)₃CCONH—(CH₂)₃ |
| (CH₃)₃CCONH—(CH₂)₄ |
| CH₃CH(NHCO(CH₃)₃)CH₂ |
| CH₃CH(NHCO(CH₃)₃)(CH₂)₂ |
| CH₂ClCONH—(CH₂)₂ |
| CH₂ClCONH—(CH₂)₃ |
| CH₂ClCONH—(CH₂)₄ |
| CH₃CH(NHCOCH₂Cl)CH₂ |
| CH₃CH(NHCOCH₂Cl)(CH₂)₂ |
| CF₃CONH—(CH₂)₂ |
| CF₃CONH—(CH₂)₃ |
| CF₃CONH—(CH₂)₄ |
| CH₃CH(NHCOCF₃)CH₂ |
| CH₃CH(NHCOCF₃)(CH₂)₂ |
| CH₃NH—(CH₂)₂ |
| CH₃NH—(CH₂)₃ |
| CH₃NH—(CH₂)₄ |
| CH₃CH(NHCH₃)CH₂ |
| CH₃CH(NHCH₃)(CH₂)₂ |
| CH₃CH₂NH—(CH₂)₂ |
| CH₃CH₂NH—(CH₂)₃ |
| CH₃CH₂NH—(CH₂)₄ |
| CH₃CH(NHCH₂CH₃)CH₂ |
| CH₃CH(NHCH₂CH₃)(CH₂)₂ |
| CH₃(CH₂)₂NH—(CH₂)₂ |
| CH₃(CH₂)₂NH—(CH₂)₃ |
| CH₃(CH₂)₂NH—(CH₂)₄ |
| CH₃CH(NH(CH₂)₂CH₃)CH₂ |
| CH₃CH(NH(CH₂)₂CH₃)(CH₂)₂ |
| CH₃(CH₂)₃NH—(CH₂)₂ |
| CH₃(CH₂)₃NH—(CH₂)₃ |
| CH₃(CH₂)₃NH—(CH₂)₄ |
| CH₃CH(NH(CH₂)₃CH₃)CH₂ |
| CH₃CH(NH(CH₂)₃CH₃)(CH₂)₂ |
| (CH₃)₂CHNH—(CH₂)₂ |
| (CH₃)₂CHNH—(CH₂)₃ |
| (CH₃)₂CHNH—(CH₂)₄ |
| CH₃CH(NHCH(CH₃)₂)CH₂ |
| CH₃CH(NHCH(CH₃)₂)(CH₂)₂ |
| (CH₃)₂N—(CH₂)₂ |
| (CH₃)₂N—(CH₂)₃ |
| (CH₃)₂N—(CH₂)₄ |
| CH₃CH(N(CH₃)₂)CH₂ |
| CH₃CH(N(CH₃)₂)(CH₂)₂ |
| (CH₃CH₂)₂N—(CH₂)₂ |
| (CH₃CH₂)₂N—(CH₂)₃ |
| (CH₃CH₂)₂N—(CH₂)₄ |
| CH₃CH(N(CH₂CH₃)₂)CH₂ |
| CH₃CH(N(CH₂CH₃)₂)(CH₂)₂ |
| (CH₃(CH₂)₂)₂N—(CH₂)₂ |
| (CH₃(CH₂)₂)₂N—(CH₂)₃ |
| (CH₃(CH₂)₂)₂N—(CH₂)₄ |
| CH₃CH—(N(CH₂C≡CH)₂)(CH₂)₂ |
| Cl—C≡CCH₂NH—(CH₂)₂ |
| Cl—C≡CCH₂NH—(CH₂)₃ |
| Cl—C≡CCH₂NH—(CH₂)₄ |
| CH₃CH(NHCH₂C≡C—Cl)CH₂ |
| CH₃CH—(NHCH₂C≡C—Cl)(CH₂)₂ |
| CH₃OOCCH₂ |
| CH₃OOC(CH₂)₂ |
| CH₃OOC(CH₂)₃ |
| CH₃OOC(CH₂)₄ |
| CH₃OOCCH(CH₃) |
| CH₃OOCCH₂CH(OH)CH₂ |
| CH₃OOCCHClCH(OH)CH₂ |
| CH₃OOCCCl₂CH(OH)CH₂ |
| CH₃OOCCH₂CH(OOCCH₃)CH₂ |
| CH₃OOCCHClCH(OOCCH₃)CH₂ |
| CH₃OOCCCl₂CH(OOCCH₃)CH₂ |
| (CH₃OOC)₂CH |
| C₂H₅OOCCH₂ |
| C₂H₅OOC(CH₂)₂ |
| C₂H₅OOC(CH₂)₃ |
| C₂H₅OOC(CH₂)₄ |
| C₂H₅OOCCH(CH₃) |
| C₂H₅OOCCH₂CH(OH)CH₂ |
| C₂H₅OOCCHClCH(OH)CH₂ |
| C₂H₅OOCCCl₂CH(OH)CH₂ |
| C₂H₅OOCCH₂CH(OOCCH₃)CH₂ |
| C₂H₅OOCCHClCH(OOCCH₃)CH₂ |

-continued

| R¹ |
|---|
| C₂H₅OOCCl₂CH(OOCCH₃)CH₂ |
| (C₂H₅OOC)₂CH |
| CH₃(CH₂)₂OOCCH₂ |
| CH₃(CH₂)₂OOC(CH₂)₂ |
| CH₃(CH₂)₂OOC(CH₂)₃ |
| CH₃(CH₂)₂OOCCH(CH₃) |
| (CH₃)₂CHOOCCH₂ |
| (CH₃)₂CHOOC(CH₂)₂ |
| (CH₃)₂CHOOC(CH₂)₃ |
| (CH₃)₂CHOOCCH(CH₃) |
| CH₃(CH₂)₃OOCCH₂ |
| CH₃(CH₂)₃OOC(CH₂)₂ |
| CH₃(CH₂)₃OOC(CH₂)₂ |
| CH₃(CH₂)₃OOCCH(CH₃) |
| CF₃CH₂OOCCH₂ |
| CF₃CH₂OOC(CH₂)₂ |
| CF₃CH₂OOC(CH₂)₃ |
| CF₃CH₂OOCCH(CH₃) |
| CCl₃CH₂OOCCH₂ |
| CCl₃CH₂OOC(CH₂)₂ |
| CCl₃CH₂OOC(CH₂)₃ |
| CCl₃CH₂OOCCH(CH₃) |
| CBr₃CH₂OOCCH₂ |
| CBr₃CH₂OOC(CH₂)₂ |
| CBr₃CH₂OOC(CH₂)₃ |
| CBr₃CH₂OOCCH(CH₃) |
| (CF₃)₂CHOOCCH₂ |
| (CF₃)₂CHOOC(CH₂)₂ |
| (CF₃)₂CHOOC(CH₂)₃ |
| (CF₃)₂CHOOCCH(CH₃) |
| CH₂=CHCH₂OOCCH₂ |
| CH₂=CHCH₂OOC(CH₂)₂ |
| CH₂=CHCH₂OOC(CH₂)₃ |
| CH₂=CHCH₂OOCCH(CH₃) |
| (CH₃)₂C=CHCH₂OOCCH₂ |
| (CH₃)₂C=CHCH₂OOC(CH₂)₂ |
| (CH₃)₂C=CHCH₂OOC(CH₂)₃ |
| (CH₃)₂C=CHCH₂OOCCH(CH₃) |
| Cl₂C=CHCH₂OOCCH₂ |
| Cl₂C=CHCH₂OOC(CH₂)₂ |
| Cl₂C=CHCH₂OOC(CH₂)₃ |
| Cl₂C=CHCH₂OOCCH(CH₃) |
| ClCH=CHCH₂OOCCH₂ |
| ClCH=CHCH₂OOC(CH₂)₂ |
| ClCH=CHCH₂OOC(CH₂)₃ |
| ClCH=CHCH₂OOCCH(CH₃) |
| Br₂C=CHCH₂OOCCH₂ |
| Br₂C=CHCH₂OOC(CH₂)₂ |
| Br₂C=CHCH₂OOC(CH₂)₃ |
| Br₂C=CHCH₂OOCCH(CH₃) |
| HC≡CCH₂OOCCH₂ |
| HC≡CCH₂OOC(CH₂)₂ |
| HC≡CCH₂OOC(CH₂)₃ |
| HC≡CCH₂OOCCH(CH₃) |
| ClC≡CCH₂OOCCH₂ |
| ClC≡CCH₂OOC(CH₂)₂ |
| ClC≡CCH₂OOC(CH₂)₃ |
| ClC≡CCH₂OOCCH(CH₃) |
| N≡CCH₂ |
| N≡C(CH₂)₂ |
| N≡C(CH₂)₃ |
| N≡C(CH₂)₄ |
| N≡CCH(CH₃) |
| N≡CCH₂CH(OH)CH₂ |
| N≡CCHClCH(OH)CH₂ |
| N≡CCCl₂CH(OH)CH₂ |
| N≡CCH₂CH(OOCCH₃)CH₂ |
| N≡CCHClCH(OOCCH₃)CH₂ |
| N≡CCCl₂CH(OOCCH₃)CH₂ |
| (N≡C)₂CH |
| O₂NCH₂ |
| O₂N(CH₂)₂ |
| CH₃NHC(=O)CH₂ |
| CH₃NHC(=O)(CH₂)₂ |
| CH₃NHC(=O)(CH₂)₃ |
| CH₃NHC(=O)CH(CH₃) |
| CH₃CH₂NHC(=O)CH₂ |
| CH₃CH₂NHC(=O)(CH₂)₂ |
| CH₃CH₂NHC(=O)(CH₂)₃ |
| CH₃CH₂NHC(=O)CH(CH₃) |
| CH₃(CH₂)₂NHC(=O)CH₂ |
| CH₃(CH₂)₂NHC(=O)(CH₂)₂ |
| CH₃(CH₂)₂NHC(=O)(CH₂)₃ |
| CH₃(CH₂)₂NHC(=O)CH(CH₃) |
| CH₃(CH₂)₃NHC(=O)CH₂ |
| CH₃(CH₂)₃NHC(=O)(CH₂)₂ |
| CH₃(CH₂)₃NHC(=O)(CH₂)₃ |
| CH₃(CH₂)₃NHC(=O)CH(CH₃) |
| (CH₃)₂CHNHC(=O)CH₂ |
| (CH₃)₂CHNHC(=O)(CH₂)₂ |
| (CH₃)₂CHNHC(=O)(CH₂)₃ |
| (CH₃)₂CHNHC(=O)CH(CH₃) |
| (CH₃)₂NC(=O)CH₂ |
| (CH₃)₂NC(=O)(CH₂)₂ |
| (CH₃)₂NC(=O)(CH₂)₃ |
| (CH₃)₂NC(=O)CH(CH₃) |
| (CH₃CH₂)₂NC(=O)CH₂ |
| (CH₃CH₂)₂NC(=O)(CH₂)₂ |
| (CH₃CH₂)₂NC(=O)(CH₂)₃ |
| (CH₃CH₂)₂NC(=O)CH(CH₃) |
| (CH₃(CH₂)₂)₂NC(=O)CH₂ |
| (CH₃(CH₂)₂)₂NC(=O)—(CH₂)₂ |
| (CH₃(CH₂)₂)₂NC(=O)—(CH₂)₃ |
| (CH₃(CH₂)₂)₂NC(=O)—CH(CH₃) |
| (CH₃(CH₂)₃)₂NC(=O)CH₂ |
| (CH₃(CH₂)₃)₂NC(=O)—(CH₂)₂ |
| (CH₃(CH₂)₃)₂NC(=O)—(CH₂)₃ |
| (CH₃(CH₂)₃)₂NC(=O)—CH(CH₃) |
| ((CH₃)₂CH)₂NC(=O)CH₂ |
| ((CH₃)₂CH)₂NC(=O)(CH₂)₂ |
| ((CH₃)₂CH)₂NC(=O)(CH₂)₃ |
| ((CH₃)₂CH)₂NC(=O)CH(CH₃) |
| CH₂=CHCH₂NHC(=O)CH₂ |
| CH₂=CHCH₂NHC(=O)(CH₂)₂ |
| CH₂=CHCH₂NHC(=O)(CH₂)₃ |
| CH₂=CHCH₂NHC(=O)CH(CH₃) |
| (CH₂=CHCH₂)₂NHC(=O)CH₂ |
| (CH₂=CHCH₂)₂NHC(=O)—(CH₂)₂ |
| (CH₂=CHCH₂)₂NHC(=O)—(CH₂)₃ |
| (CH₂=CHCH₂)₂NHC(=O)—CH(CH₃) |
| Cl₂C=CHCH₂NHC(=O)CH₂ |
| Cl₂C=CHCH₂NHC(=O)(CH₂)₂ |
| Cl₂C=CHCH₂NHC(=O)(CH₂)₃ |
| Cl₂C=CHCH₂NHC(=O)CH(CH₃) |
| (Cl₂C=CHCH₂)₂NHC(=O)CH₂ |
| (Cl₂C=CHCH₂)₂NHC(=O)—(CH₂)₂ |
| (Cl₂C=CHCH₂)₂NHC(=O)—(CH₂)₃ |
| (Cl₂C=CHCH₂)₂NHC(=O)—CH(CH₃) |
| CF₃CH₂NHC(=O)CH₂ |
| CF₃CH₂NHC(=O)(CH₂)₂ |
| CF₃CH₂NHC(=O)(CH₂)₃ |
| CF₃CH₂NHC(=O)CH(CH₃) |
| HC≡CCH₂NHC(=O)CH₂ |
| HC≡CCH₂NHC(=O)(CH₂)₂ |
| HC≡CCH₂NHC(=O)(CH₂)₃ |
| HC≡CCH₂NHC(=O)CH(CH₃) |
| (HC≡CCH₂)₂NC(=O)CH₂ |
| (HC≡CCH₂)₂NC(=O)(CH₂)₂ |
| (HC≡CCH₂)₂NC(=O)(CH₂)₃ |
| (HC≡CCH₂)₂NC(=O)CH(CH₃) |
| Cl—C≡CCH₂NHC(=O)CH₂ |
| Cl—C≡CCH₂NHC(=O)(CH₂)₂ |
| Cl—C≡CCH₂NHC(=O)(CH₂)₃ |
| Cl—C≡CCH₂NHC(=O)CH(CH₃) |
| (CH₃O)₂CHCH₂ |
| (CH₃O)₂CH(CH₂)₂ |
| (CH₃O)₂CH(CH₂)₃ |
| (CH₃O)₂CH(CH₂)₄ |
| (CH₃O)₂CHCH(CH₃)CH₂ |
| (CH₃O)₂CHC(CH₃)₂CH₂ |
| (CH₃O)₂CHCH(CH₃) |
| (CH₃O)₂CHCH(CH₂CH₃) |
| (CH₃O)₂CHCH(CH₂CH₂CH₃) |
| (CH₃O)₂CHCH(CH₂CH(CH₃)₂) |

| R$^1$ |
|---|
| (CH$_3$O)$_2$C(CF$_3$)CH$_2$ |
| (CH$_3$O)$_2$C(CH$_3$)CH$_2$ |
| (CH$_3$O)$_2$C(CH$_3$)(CH$_2$)$_2$ |
| (CH$_3$O)$_2$C(CH$_3$)(CH$_2$)$_3$ |
| (CH$_3$O)$_2$C(CCl$_2$CF$_3$)CH$_2$ |
| (CH$_3$O)$_2$C(CCl$_2$CF$_3$)(CH$_2$)$_2$ |
| (CH$_3$O)$_2$C(CCl$_2$CF$_3$)(CH$_2$)$_3$ |
| (CH$_3$O)$_2$C(CHClCF$_3$)CH$_2$ |
| (CH$_3$O)$_2$C(CHClCF$_3$)(CH$_2$)$_2$ |
| (CH$_3$O)$_2$C(CHClCF$_3$)(CH$_2$)$_3$ |
| (CH$_3$O)$_2$C(CBr$_2$CF$_3$)CH$_2$ |
| (CH$_3$O)$_2$C(CBr$_2$CF$_3$)(CH$_2$)$_2$ |
| (CH$_3$O)$_2$C(CBr$_2$CF$_3$)(CH$_2$)$_3$ |
| (CH$_3$O)$_2$C(CHBrCF$_3$)CH$_2$ |
| (CH$_3$O)$_2$C(CHBrCF$_3$)(CH$_2$)$_2$ |
| (CH$_3$O)$_2$C(CHBrCF$_3$)(CH$_2$)$_3$ |
| (CH$_3$O)$_2$C(CH$_2$CF$_3$)CH$_2$ |
| (CH$_3$O)$_2$C(CH$_2$CF$_3$)(CH$_2$)$_2$ |
| (CH$_3$O)$_2$C(CH$_2$CF$_3$)(CH$_2$)$_3$ |
| (CH$_3$CH$_2$O)$_2$CHCH$_2$ |
| (CH$_3$CH$_2$O)$_2$CH(CH$_2$)$_2$ |
| (CH$_3$CH$_2$O)$_2$CH(CH$_2$)$_3$ |
| (CH$_3$CH$_2$O)$_2$CH(CH$_2$)$_4$ |
| (CH$_3$CH$_2$O)$_2$CHCH(CH$_3$)CH$_2$ |
| (CH$_3$CH$_2$O)$_2$CHC(CH$_3$)$_2$CH$_2$ |
| (CH$_3$CH$_2$O)$_2$CHCH(CH$_3$) |
| (CH$_3$CH$_2$O)$_2$CHCH(CH$_2$CH$_3$) |
| (CH$_3$CH$_2$O)$_2$CHCH(CH$_2$CH$_2$—CH$_3$) |
| (CH$_3$CH$_2$O)$_2$CHCH—(CH$_2$CH(CH$_3$)$_2$) |
| (CH$_3$CH$_2$O)$_2$C(CF$_3$)CH$_2$ |
| (CH$_3$CH$_2$O)$_2$C(CH$_3$)(CH$_2$)$_2$ |
| (CH$_3$CH$_2$O)$_2$C(CH$_3$)(CH$_2$)$_3$ |
| (CH$_3$CH$_2$O)($_2$C(CCl$_2$CF$_3$)CH$_2$ |
| (CH$_3$CH$_2$O)$_2$C—(Cl$_2$CF$_3$)(CH$_2$)$_2$ |
| (CH$_3$CH$_2$O)$_2$C—(Cl$_2$CF$_3$)(CH$_2$)$_3$ |
| (CH$_3$CH$_2$O)$_2$C(CHClCF$_3$)CH$_2$ |
| (CH$_3$CH$_2$O)$_2$C(CHClCF$_3$)(CH$_2$)$_2$ |
| (CH$_3$CH$_2$O)$_2$C(CHClCF$_3$)(CH$_2$)$_3$ |
| (CH$_3$CH$_2$O)$_2$C(CBr$_2$CF$_3$)CH$_2$ |
| (CH$_3$CH$_2$O)$_2$C—(CBr$_2$CF$_3$)(CH$_2$)$_2$ |
| (CH$_3$CH$_2$O)$_2$C—(CBr$_2$CF$_3$)(CH$_2$)$_3$ |
| (CH$_3$CH$_2$O)$_2$C(CHBrCF$_3$)CH$_2$ |
| (CH$_3$CH$_2$O)$_2$C(CBrCF$_3$)(CH$_2$)$_2$ |
| (CH$_3$CH$_2$O)$_2$C(CBrCF$_3$)(CH$_2$)$_3$ |
| (CH$_3$CH$_2$O)$_2$C(CH$_2$CF$_3$)CH$_2$ |
| (CH$_3$CH$_2$O)$_2$C(CH$_2$CF$_3$)(CH$_2$)$_2$ |
| (CH$_3$CH$_2$O)$_2$C(CH$_2$CF$_3$)(CH$_2$)$_3$ |
| (CH$_3$(CH$_2$)$_2$O)$_2$CHCH$_2$ |
| (CH$_3$(CH$_2$)$_2$O)$_2$CH(CH$_2$)$_2$ |
| (CH$_3$(CH$_2$)$_2$O)$_2$CH(CH$_2$)$_3$ |
| (CH$_3$(CH$_2$)$_2$O)$_2$CH(CH$_2$)$_4$ |
| (CH$_3$CH$_2$O)$_2$C(CH$_3$)CH$_2$ |
| (CH$_3$(CH$_2$)$_2$O)$_2$—CHCH(CH$_3$)CH$_2$ |
| (CH$_3$(CH$_2$)$_2$O)$_2$CHCH(CH$_3$) |
| (CH$_3$(CH$_2$)$_2$O)$_2$C(CH$_3$)CH$_2$ |
| (CH$_3$(CH$_2$)$_2$O)$_2$—C(CH$_3$)(CH$_2$)$_2$ |
| (CH$_3$(CH$_2$)$_2$O)$_2$C(CF$_3$)CH$_2$ |
| (CH$_3$(CH$_2$)$_2$O)$_2$—C(CH$_2$CF$_3$)CH$_2$ |
| (CH$_3$(CH$_2$)$_2$O)$_2$—C(CCl$_2$CF$_3$)CH$_2$ |
| ((CH$_3$)$_2$CHO)$_2$CHCH$_2$ |
| ((CH$_3$)$_2$CHO)$_2$CH(CH$_2$)$_2$ |
| ((CH$_3$)$_2$CHO)$_2$CH(CH$_2$)$_3$ |
| ((CH$_3$)$_2$CHO)$_2$CH(CH$_2$)$_4$ |
| ((CH$_3$)$_2$CHO)$_2$CHCH(CH$_3$)CH$_2$ |
| ((CH$_3$)$_2$CHO)$_2$CHCH(CH$_3$) |
| ((CH$_3$)$_2$CHO)$_2$C(CH$_3$)CH$_2$ |
| ((CH$_3$)$_2$CHO)$_2$C(CH$_2$CF$_3$)CH$_2$ |
| ((CH$_3$)$_2$CHO)$_2$C(CH$_3$)(CH$_2$)$_2$ |
| ((CH$_3$)$_2$CHO)$_2$C(CF$_3$)CH$_2$ |
| ((CH$_3$)$_2$CHO)$_2$—C(CCl$_2$CF$_3$)CH$_2$ |
| (FCH$_2$CH$_2$O)$_2$CHCH$_2$ |
| (FCH$_2$CH$_2$O)$_2$CH(CH$_2$)$_2$ |
| (FCH$_2$CH$_2$O)$_2$CH(CH$_2$)$_3$ |
| (FCH$_2$CH$_2$O)$_2$CH(CH$_2$)$_4$ |
| (FCH$_2$CH$_2$O)$_2$CHCH(CH$_3$)CH$_2$ |
| (FCH$_2$CH$_2$O)$_2$CHCH(CH$_3$) |
| (FCH$_2$CH$_2$O)$_2$C(CH$_3$)CH$_2$ |
| (FCH$_2$CH$_2$O)$_2$C(CH$_2$CF$_3$)CH$_2$ |
| (FCH$_2$CH$_2$O)$_2$C(CH$_3$)(CH$_2$)$_2$ |
| (FCH$_2$CH$_2$O)$_2$C(CF$_3$)CH$_2$ |
| (FCH$_2$CH$_2$O)$_2$C(CCl$_2$CF$_3$)CH$_2$ |
| (ClCH$_2$CH$_2$O)$_2$CHCH$_2$ |
| (ClCH$_2$CH$_2$O)$_2$CH(CH$_2$)$_2$ |
| (ClCH$_2$CH$_2$O)$_2$CH(CH$_2$)$_3$ |
| (ClCH$_2$CH$_2$O)$_2$CH(CH$_2$)$_4$ |
| (ClCH$_2$CH$_2$O)$_2$CHCH(CH$_3$)CH$_2$ |
| (ClCH$_2$CH$_2$O)$_2$CHCH(CH$_3$) |
| (ClCH$_2$CH$_2$O)$_2$C(CH$_3$)CH$_2$ |
| (ClCH$_2$CH$_2$O)$_2$C(CH$_3$)(CH$_2$)$_2$ |
| (ClCH$_2$CH$_2$O)$_2$C(CF$_3$)CH$_2$ |
| (ClCH$_2$CH$_2$O)$_2$C(CH$_2$CF$_3$)CH$_2$ |
| (ClCH$_2$CH$_2$O)$_2$C(CCl$_2$CF$_3$)CH$_2$ |
| (BrCH$_2$CH$_2$O)$_2$CHCH$_2$ |
| (BrCH$_2$CH$_2$O)$_2$CH(CH$_2$)$_2$ |
| (BrCH$_2$CH$_2$O)$_2$CH(CH$_2$)$_3$ |
| (BrCH$_2$CH$_2$O)$_2$CH(CH$_2$)$_4$ |
| (BrCH$_2$CH$_2$O)$_2$CHCH(CH$_3$)CH$_2$ |
| (BrCH$_2$CH$_2$O)$_2$CHCH(CH$_3$) |
| (BrCH$_2$CH$_2$O)$_2$C(CH$_3$)CH$_2$ |
| (BrCH$_2$CH$_2$O)$_2$C(CH$_3$)(CH$_2$)$_2$ |
| (BrCH$_2$CH$_2$O)$_2$C(CF$_3$)CH$_2$ |
| (BrCH$_2$CH$_2$O)$_2$C(CH$_2$CF$_3$)CH$_2$ |
| (BrCH$_2$CH$_2$O)$_2$—C(CCl$_2$CF$_3$)CH$_2$ |
| (CF$_3$CH$_2$O)$_2$CHCH$_2$ |
| (CF$_3$CH$_2$O)$_2$CH(CH$_2$)$_2$ |
| (CF$_3$CH$_2$O)$_2$CH(CH$_2$)$_3$ |
| (CF$_3$CH$_2$O)$_2$CH(CH$_2$)$_4$ |
| (CF$_3$CH$_2$O)$_2$CHCH(CH$_3$)CH$_2$ |
| (CF$_3$CH$_2$O)$_2$CHCH(CH$_3$) |
| (CF$_3$CH$_2$O)$_2$C(CH$_3$)CH$_2$ |
| (CF$_3$CH$_2$O)$_2$C(CH$_3$)(CH$_2$)$_2$ |
| (CF$_3$CH$_2$O)$_2$C(CF$_3$)CH$_2$ |
| (CF$_3$CH$_2$O)$_2$C(CH$_2$CF$_3$)CH$_2$ |
| (CF$_3$CH$_2$O)$_2$C(CCl$_2$CF$_3$)CH$_2$ |
| (CCl$_3$CH$_2$O)$_2$CHCH$_2$ |
| (CCl$_3$CH$_2$O)$_2$CH(CH$_2$)$_2$ |
| (CCl$_3$CH$_2$O)$_2$CH(CH$_2$)$_3$ |
| (CCl$_3$CH$_2$O)$_2$CH(CH$_2$)$_4$ |
| (CCl$_3$CH$_2$O)$_2$CHCH(CH$_3$)CH$_2$ |
| (CCl$_3$CH$_2$O)$_2$CHCH(CH$_3$) |
| (CCl$_3$CH$_2$O)$_2$C(CH$_3$)CH$_2$ |
| (CCl$_3$CH$_2$O)$_2$C(CH$_3$)(CH$_2$)$_2$ |
| (CCl$_3$CH$_2$O)$_2$C(CF$_3$)CH$_2$ |
| (CCl$_3$CH$_2$O)$_2$C(CH$_2$CF$_3$)CH$_2$ |
| (CCl$_3$CH$_2$O)$_2$C(CCl$_2$CF$_3$)CH$_2$ |
| (CBr$_3$CH$_2$O)$_2$CHCH$_2$ |
| (CBr$_3$CH$_2$O)$_2$CH(CH$_2$)$_2$ |
| (CBr$_3$CH$_2$O)$_2$CH(CH$_2$)$_3$ |
| (CBr$_3$CH$_2$O)$_2$CH(CH$_2$)$_4$ |
| (CBr$_3$CH$_2$O)$_2$CHCH(CH$_3$)CH$_2$ |
| (CBr$_3$CH$_2$O)$_2$CHCH(CH$_3$) |
| (CBr$_3$CH$_2$O)$_2$C(CH$_3$)CH$_2$ |
| (CBr$_3$CH$_2$O)$_2$C(CH$_3$)(CH$_2$)$_2$ |
| (CBr$_3$CH$_2$O)$_2$C(CF$_3$)CH$_2$ |
| (CBr$_3$CH$_2$O)$_2$C(CH$_2$CF$_3$)CH$_2$ |
| (CBr$_3$CH$_2$O)$_2$C(CCl$_2$CF$_3$)CH$_2$ |
| (CF$_3$CF$_2$CH$_2$O)$_2$CHCH$_2$ |
| (CF$_3$CF$_2$CH$_2$O)$_2$CH(CH$_2$)$_2$ |
| (CF$_3$CF$_2$CH$_2$O)$_2$CH(CH$_2$)$_3$ |
| (CF$_3$CF$_2$CH$_2$O)$_2$CH(CH$_2$)$_4$ |
| (CF$_3$CF$_2$CH$_2$O)$_2$CHCH(CH$_3$)CH$_2$ |
| (CF$_3$CF$_2$CH$_2$O)$_2$CHCH(CH$_3$) |
| (CF$_3$CF$_2$CH$_2$O)$_2$C(CH$_3$)CH$_2$ |
| (CF$_3$CF$_2$CH$_2$O)$_2$C(CH$_3$)(CH$_2$)$_2$ |
| (CF$_3$CF$_2$CH$_2$O)$_2$C(CF$_3$)CH$_2$ |
| (CF$_3$CF$_2$CH$_2$O)$_2$C(CH$_2$CF$_3$)CH$_2$ |
| (CF$_3$CF$_2$CH$_2$O)$_2$—C(CCl$_2$CF$_3$)CH$_2$ |
| ((CF$_3$)$_2$CHO)$_2$CHCH$_2$ |
| ((CF$_3$)$_2$CHO)$_2$CH(CH$_2$)$_2$ |
| ((CF$_3$)$_2$CHO)$_2$CH(CH$_2$)$_3$ |
| ((CF$_3$)$_2$CHO)$_2$CH(CH$_2$)$_4$ |
| ((CF$_3$)$_2$CHO)$_2$CHCH(CH$_3$)CH$_2$ |
| ((CF$_3$)$_2$CHO)$_2$CHCH(CH$_3$) |
| ((CF$_3$)$_2$CHO)$_2$C(CH$_3$)CH$_2$ |

| -continued |
|---|
| R¹ |

((CF$_3$)$_2$CHO)$_2$C(CH$_3$)(CH$_2$)$_2$
((CF$_3$)$_2$CHO)$_2$C(CF$_3$)CH$_2$
((CF$_3$)$_2$CHO)$_2$C(CH$_2$CF$_3$)CH$_2$
((CF$_3$)$_2$CHO)$_2$—C(CCl$_2$CF$_3$)CH$_2$
(CH$_2$=CHCH$_2$O)$_2$CHCH$_2$
(CH$_2$=CHCH$_2$O)$_2$CH(CH$_2$)$_2$
(CH$_2$=CHCH$_2$O)$_2$CH(CH$_2$)$_3$
(CH$_2$=CHCH$_2$O)$_2$CH(CH$_2$)$_4$
(CH$_2$=CHCH$_2$O)$_2$—CHCH(CH$_3$)CH$_2$
(CH$_2$=CHCH$_2$O)$_2$CHCH(CH$_3$)
(CH$_2$=CHCH$_2$O)$_2$C(CH$_3$)CH$_2$
(CH$_2$=CHCH$_2$O)$_2$—C(CH$_3$)(CH$_2$)$_2$
(CH$_2$=CHCH$_2$O)$_2$C(CF$_3$)CH$_2$
(CH$_2$=CHCH$_2$O)$_2$—C(CH$_2$CF$_3$)CH$_2$
(CH$_2$=CHCH$_2$O)$_2$—C(CCl$_2$CF$_3$)CH$_2$
(CH$_3$CH=CHCH$_2$O)$_2$CHCH$_2$
(CH$_3$CH=CHCH$_2$O)$_2$CH(CH$_2$)$_2$
(CH$_3$CH=CHCH$_2$O)$_2$CH(CH$_2$)$_3$
(CH$_3$CH=CHCH$_2$O)$_2$CH(CH$_2$)$_4$
(CH$_3$CH=CHCH$_2$O)$_2$—CHCH(CH$_3$)CH$_2$
(CH$_3$CH=CHCH$_2$O)$_2$CHCH(CH$_3$)
(CH$_3$CH=CHCH$_2$O)$_2$C(CH$_3$)CH$_2$
(CH$_3$CH=CHCH$_2$O)$_2$—C(CH$_3$)(CH$_2$)$_2$
(CH$_3$CH=CHCH$_2$O)$_2$C(CF$_3$)CH$_2$
(CH$_3$CH=CHCH$_2$O)$_2$—C(CH$_2$CF$_3$)CH$_2$
(CH$_3$CH=CHCH$_2$O)$_2$—C(CCl$_2$CF$_3$)CH$_2$
((CH$_3$)$_2$C=CHCH$_2$O)$_2$CHCH$_2$
((CH$_3$)$_2$C=CHCH$_2$O)$_2$CH(CH$_2$)$_2$
((CH$_3$)$_2$C=CHCH$_2$O)$_2$CH(CH$_2$)$_3$
((CH$_3$)$_2$C=CHCH$_2$O)$_2$CH(CH$_2$)$_4$
((CH$_3$)$_2$C=CHCH$_2$O)$_2$—CHCH(CH$_3$)CH$_2$
((CH$_3$)$_2$C=CHCH$_2$O)$_2$CHCH(CH$_3$)
((CH$_3$)$_2$C=CHCH$_2$O)$_2$—C(CH$_3$)CH$_2$
((CH$_3$)$_2$C=CHCH$_2$O)$_2$—C(CH$_3$)(CH$_2$)$_2$
((CH$_3$)$_2$C=CHCH$_2$O)$_2$—C(CF$_3$)CH$_2$
((CH$_3$)$_2$C=CHCH$_2$O)$_2$—C(CH$_2$CF$_3$)CH$_2$
((CH$_3$)$_2$C=CHCH$_2$O)$_2$—C(CCl$_2$CF$_3$)CH$_2$
(Cl$_2$C=CHCH$_2$O)$_2$CHCH$_2$
(Cl$_2$C=CHCH$_2$O)$_2$CH(CH$_2$)$_2$
(Cl$_2$C=CHCH$_2$O)$_2$CH(CH$_2$)$_3$
(Cl$_2$C=CHCH$_2$O)$_2$CH(CH$_2$)$_4$
(Cl$_2$C=CHCH$_2$O)$_2$—CHCH(CH$_3$)CH$_2$
(Cl$_2$C=CHCH$_2$O)$_2$CHCH(CH$_3$)
(Cl$_2$C=CHCH$_2$O)$_2$C(CH$_3$)CH$_2$
(Cl$_2$C=CHCH$_2$O)$_2$—C(CH$_3$)(CH$_2$)$_2$
(Cl$_2$C=CHCH$_2$O)$_2$C(CF$_3$)CH$_2$
(Cl$_2$C=CHCH$_2$O)$_2$—C(CH$_2$CF$_3$)CH$_2$
(Cl$_2$C=CHCH$_2$O)$_2$—C(CCl$_2$CF$_3$)CH$_2$
(ClCH=CHCH$_2$O)$_2$CHCH$_2$
(ClCH=CHCH$_2$O)$_2$CH(CH$_2$)$_2$
(ClCH=CHCH$_2$O)$_2$CH(CH$_2$)$_3$
(ClCH=CHCH$_2$O)$_2$CH(CH$_2$)$_4$
(ClCH=CHCH$_2$O)$_2$CHCH(CH$_3$)CH$_2$
(ClCH=CHCH$_2$O)$_2$CHCH(CH$_3$)
(ClCH=CHCH$_2$O)$_2$C(CH$_3$)CH$_2$
(ClCH=CHCH$_2$O)$_2$C(CH$_3$)(CH$_2$)$_2$
(ClCH=CHCH$_2$O)$_2$C(CF$_3$)CH$_2$
(ClCH=CHCH$_2$O)$_2$C(CH$_2$CF$_3$)CH$_2$
(ClCH=CHCH$_2$O)$_2$C(CCl$_2$CF$_3$)CH$_2$
(Br$_2$C=CHCH$_2$O)$_2$CHCH$_2$
(Br$_2$C=CHCH$_2$O)$_2$CH(CH$_2$)$_2$
(Br$_2$C=CHCH$_2$O)$_2$CH(CH$_2$)$_3$
(Br$_2$C=CHCH$_2$O)$_2$CH(CH$_2$)$_4$
(Br$_2$C=CHCH$_2$O)$_2$CHCH(CH$_3$)CH$_2$
(Br$_2$C=CHCH$_2$O)$_2$CHCH(CH$_3$)
(Br$_2$C=CHCH$_2$O)$_2$C(CH$_3$)CH$_2$
(Br$_2$C=CHCH$_2$O)$_2$C(CH$_3$)(CH$_2$)$_2$
(Br$_2$C=CHCH$_2$O)$_2$C(CF$_3$)CH$_2$
(Br$_2$C=CHCH$_2$O)$_2$C(CH$_2$CF$_3$)CH$_2$
(Br$_2$C=CHCH$_2$O)$_2$—C(CCl$_2$CF$_3$)CH$_2$
(BrCH=CHCH$_2$O)$_2$CHCH$_2$
(BrCH=CHCH$_2$O)$_2$CH(CH$_2$)$_2$
(BrCH=CHCH$_2$O)$_2$CH(CH$_2$)$_3$
(BrCH=CHCH$_2$O)$_2$CH(CH$_2$)$_4$
(BrCH=CHCH$_2$O)$_2$CHCH(CH$_3$)CH$_2$
(BrCH=CHCH$_2$O)$_2$CHCH(CH$_3$)
(BrCH=CHCH$_2$O)$_2$C(CH$_3$)CH$_2$

| -continued |
|---|
| R¹ |

(BrCH=CHCH$_2$O)$_2$C(CH$_3$)(CH$_2$)$_2$
(BrCH=CHCH$_2$O)$_2$C(CF$_3$)CH$_2$
(BrCH=CHCH$_2$O)$_2$C(CH$_2$CF$_3$)CH$_2$
(BrCH=CHCH$_2$O)$_2$—C(CCl$_2$CF$_3$)CH$_2$
(CF$_3$CCl=CHCH$_2$O)$_2$CHCH$_2$
(CF$_3$CCl=CHCH$_2$O)$_2$CH(CH$_2$)$_2$
(CF$_3$CCl=CHCH$_2$O)$_2$CH(CH$_2$)$_3$
(CF$_3$CCl=CHCH$_2$O)$_2$CH(CH$_2$)$_4$
(CF$_3$CCl=CHCH$_2$O)$_2$—CHCH(CH$_3$)CH$_2$
(CF$_3$CCl=CHCH$_2$O)$_2$CHCH(CH$_3$)
(CF$_3$CCl=CHCH$_2$O)$_2$C(CH$_3$)CH$_2$
(CF$_3$CCl=CHCH$_2$O)$_2$—C(CH$_3$)(CH$_2$)$_2$
(CF$_3$CCl=CHCH$_2$O)$_2$C(CF$_3$)CH$_2$
(CF$_3$CCl=CHCH$_2$O)$_2$—C(CH$_2$CF$_3$)CH$_2$
(CF$_3$CCl=CHCH$_2$O)$_2$—C(CCl$_2$CF$_3$)CH$_2$
HC≡CCH$_2$O)$_2$CHCH$_2$
HC≡CCH$_2$O)$_2$CH(CH$_2$)$_2$
HC≡CCH$_2$O)$_2$CH(CH$_2$)$_3$
HC≡CCH$_2$O)$_2$CH(CH$_2$)$_4$
HC≡CCH$_2$O)$_2$CHCH(CH$_3$)CH$_2$
HC≡CCH$_2$O)$_2$CHCH(CH$_3$)
HC≡CCH$_2$O)$_2$C(CH$_3$)CH$_2$
HC≡CCH$_2$O)$_2$C(CH$_3$)(CH$_2$)$_2$
HC≡CCH$_2$O)$_2$C(CF$_3$)CH$_2$
HC≡CCH$_2$O)$_2$C(CH$_2$CF$_3$)CH$_2$
HC≡CCH$_2$O)$_2$C(CCl$_2$CF$_3$)CH$_2$
ClC≡CCH$_2$O)$_2$CHCH$_2$
(ClC≡CCH$_2$O)$_2$CH(CH$_2$)$_2$
(ClC≡CCH$_2$O)$_2$CH(CH$_2$)$_3$
(ClC≡CCH$_2$O)$_2$CH(CH$_2$)$_4$
(ClC≡CCH$_2$O)$_2$CHCH(CH$_3$)CH$_2$
(ClC≡CCH$_2$O)$_2$CHCH(CH$_3$)
(ClC≡CCH$_2$O)$_2$C(CH$_3$)CH$_2$
(ClC≡CCH$_2$O)$_2$C(CH$_3$)(CH$_2$)$_2$
(ClC≡CCH$_2$O)$_2$C(CF$_3$)CH$_2$
(ClC≡CCH$_2$O)$_2$C(CH$_2$CF$_3$)CH$_2$
(ClC≡CCH$_2$O)$_2$C(CCl$_2$CF$_3$)CH$_2$
(CH$_3$(CH$_2$)$_3$O)$_2$CHCH$_2$
(CH$_3$(CH$_2$)$_3$O)$_2$CH(CH$_2$)$_2$
(CH$_3$(CH$_2$)$_3$O)$_2$CH(CH$_2$)$_3$
(CH$_3$(CH$_2$)$_3$O)$_2$C(CH$_3$)$_2$
(CH$_3$(CH$_2$)$_3$O)$_2$C(CF$_3$)CH$_2$
((CH$_3$)$_2$CHCH$_2$O)$_2$CHCH$_2$
((CH$_3$)$_2$CHCH$_2$O)$_2$CH(CH$_2$)$_2$
((CH$_3$)$_2$CHCH$_2$O)$_2$CH(CH$_2$)$_3$
((CH$_3$)$_2$CHCH$_2$O)$_2$CH(CH$_3$)$_3$
((CH$_3$)$_2$CHCH$_2$O)$_2$C(CH$_3$)(CH$_2$)$_2$
((CH$_3$)$_2$CHCH$_2$O)$_2$C(CF$_3$)CH$_2$
(CH$_3$CH$_2$CH(CH$_3$)O)$_2$CHCH$_2$
(CH$_3$CH$_2$CH(CH$_3$)O)$_2$—CH(CH$_2$)$_2$
(CH$_3$CH$_2$CH(CH$_3$)O)$_2$—CH(CH$_2$)$_3$
(CH$_3$CH$_2$CH(CH$_3$)O)$_2$—C(CH$_3$)CH$_2$
(CH$_3$CH$_2$CH(CH$_3$)O)$_2$—C(CF$_3$)CH$_2$
(CH$_3$(CH$_2$)$_4$O)$_2$CHCH$_2$
(CH$_3$(CH$_2$)$_4$O)$_2$CH(CH$_2$)$_2$
(CH$_3$(CH$_2$)$_4$O)$_2$CH(CH$_2$)$_3$
(CH$_3$(CH$_2$)$_4$O)$_2$C(CH$_3$)CH$_2$
(CH$_3$(CH$_2$)$_4$O)$_2$C(CF$_3$)CH$_2$
(CH$_3$(CH$_2$)$_5$O)$_2$CHCH$_2$
(CH$_3$(CH$_2$)$_5$O)$_2$CH(CH$_2$)$_2$
(CH$_3$(CH$_2$)$_5$O)$_2$CH(CH$_2$)$_3$
(CH$_3$(CH$_2$)$_5$O)$_2$C(CH$_3$)CH$_2$
(CH$_3$(CH$_2$)$_5$O)$_2$C(CF$_3$)CH$_2$
(CH$_3$CHClCH$_2$O)$_2$CHCH$_2$
(CH$_3$CHClCH$_2$O)$_2$CH(CH$_2$)$_2$
(CH$_3$CHClCH$_2$O)$_2$CH(CH$_2$)$_3$
(CH$_3$CHClCH$_2$O)$_2$C(CH$_3$)CH$_2$
(CH$_3$CHClCH$_2$O)$_2$C(CF$_3$)CH$_2$
(ClCH$_2$(CH$_2$)$_2$O)$_2$CHCH$_2$
(ClCH$_2$(CH$_2$)$_2$O)$_2$CH(CH$_2$)$_2$
(ClCH$_2$(CH$_2$)$_2$O)$_2$CH(CH$_2$)$_3$
(ClCH$_2$(CH$_2$)$_2$O)$_2$C(CH$_3$)CH$_2$
(ClCH$_2$(CH$_2$)$_2$O)$_2$C(CF$_3$)CH$_2$
(BrCH$_2$(CH$_2$)$_2$O)$_2$CHCH$_2$
(BrCH$_2$(CH$_2$)$_2$O)$_2$CH(CH$_2$)$_2$
(BrCH$_2$(CH$_2$)$_2$O)$_2$CH(CH$_2$)$_3$
(BrCH$_2$(CH$_2$)$_2$O)$_2$C(CH$_3$)CH$_2$

-continued

| R¹ |
|---|
| (BrCH$_2$(CH$_2$)$_2$O)$_2$C(CF$_3$)CH$_2$ |
| (CH(BrCH$_2$)(CH$_3$)CH$_2$O)$_2$CHCH$_2$ |
| (CH(BrCH$_2$)(CH$_3$)CH$_2$O)$_2$—CH(CH$_2$)$_2$ |
| (CH(BrCH$_2$)(CH$_3$)CH$_2$O)$_2$—CH(CH$_2$)$_2$ |
| (CH(BrCH$_2$)(CH$_3$)CH$_2$O)$_2$—C(CH$_3$)CH$_2$ |
| (CH(BrCH$_2$)(CH$_3$)CH$_2$O)$_2$—C(CF$_3$)CH$_2$ |
| (ClCH$_2$(CH$_2$)$_3$O)$_2$CHCH$_2$ |
| (ClCH$_2$(CH$_2$)$_3$O)$_2$CH(CH$_2$)$_2$ |
| (ClCH$_2$(CH$_2$)$_3$O)$_2$CH(CH$_2$)$_3$ |
| (ClCH$_2$(CH$_2$)$_3$O)$_2$C(CH$_3$)CH$_2$ |
| (ClCH$_2$(CH$_2$)$_3$O)$_2$—C(CF$_3$)CH$_2$ |
| ClCH$_2$(CH$_2$)$_4$O)$_2$CHCH$_2$ |
| (ClCH$_2$(CH$_2$)$_4$O)$_2$—CH(CH$_2$)$_2$ |
| (ClCH$_2$(CH$_2$)$_4$O)$_2$—CH(CH$_2$)$_3$ |
| (ClCH$_2$(CH$_2$)$_4$O)$_2$—C(CH$_3$)CH$_2$ |
| (ClCH$_2$(CH$_2$)$_4$O)$_2$—C(CF$_3$)CH$_2$ |
| (ClCH$_2$(CH$_2$)$_5$O)$_2$CHCH$_2$ |
| (ClCH$_2$(CH$_2$)$_5$O)$_2$—CH(CH$_2$)$_2$ |
| (ClCH$_2$(CH$_2$)$_5$O)$_2$—CH(CH$_2$)$_3$ |
| (ClCH$_2$(CH$_2$)$_5$O)$_2$—C(CH$_3$)CH$_2$ |
| (ClCH$_2$(CH$_2$)$_5$O)$_2$—C(CF$_3$)CH$_2$ |
| (BrCH$_2$(CH$_2$)$_3$O)$_2$CHCH$_2$ |
| (BrCH$_2$(CH$_2$)$_3$O)$_2$—CH(CH$_2$)$_2$ |
| (BrCH$_2$(CH$_2$)$_3$O)$_2$—CH(CH$_2$)$_3$ |
| (BrCH$_2$(CH$_2$)$_3$O)$_2$C(CH$_3$)CH$_2$ |
| (BrCH$_2$(CH$_2$)$_3$O)$_2$C(CF$_3$)CH$_2$ |
| (BrCH$_2$(CH$_2$)$_4$O)$_2$CHCH$_2$ |
| (BrCH$_2$(CH$_2$)$_4$O)$_2$CH(CH$_2$)$_2$ |
| (BrCH$_2$(CH$_2$)$_4$O)$_2$CH(CH$_2$)$_3$ |
| (BrCH$_2$(CH$_2$)$_4$O)$_2$C(CH$_3$)CH$_2$ |
| (BrCH$_2$(CH$_2$)$_4$O)$_2$C(CF$_3$)CH$_2$ |
| (BrCH$_2$(CH$_2$)$_5$O)$_2$CHCH$_2$ |
| (BrCH$_2$(CH$_2$)$_5$O)$_2$CH(CH$_2$)$_2$ |
| (BrCH$_2$(CH$_2$)$_5$O)$_2$CH(CH$_2$)$_2$ |
| (BrCH$_2$(CH$_2$)$_5$O)$_2$C(CH$_3$)CH$_2$ |
| (BrCH$_2$(CH$_2$)$_5$O)$_2$C(CF$_3$)CH$_2$ |
| (Cl$_2$CHCH$_2$O)$_2$CHCH$_2$ |
| (Cl$_2$CHCH$_2$O)$_2$CH(CH$_2$)$_2$ |
| (Cl$_2$CHCH$_2$O)$_2$CH(CH$_2$)$_3$ |
| (Cl$_2$CHCH$_2$O)$_2$C(CH$_3$)CH$_2$ |
| (Cl$_2$CHCH$_2$O)$_2$C(CF$_3$)CH$_2$ |
| (BrCH$_2$CH(Br)CH$_2$O)$_2$CHCH$_2$ |
| (BrCH$_2$CH(Br)CH$_2$O)$_2$CH(CH$_2$)$_2$ |
| (BrCH$_2$CH(Br)CH$_2$O)$_2$CH(CH$_2$)$_3$ |
| (BrCH$_2$CH(Br)CH$_2$O)$_2$C(CH$_3$)CH$_2$ |
| (BrCH$_2$CH(Br)CH$_2$O)$_2$C(CF$_3$)CH$_2$ |
| (BrCH$_2$CH(Br)CH$_2$O)$_2$—C(CH$_2$CF$_3$)CH$_2$ |
| (CF$_3$(CF$_2$)$_2$CH$_2$O)$_2$CHCH$_2$ |
| (CF$_3$(CF$_2$)$_2$CH$_2$O)$_2$—CH(CH$_2$)$_2$ |
| (CF$_3$(CF$_2$)$_2$CH$_2$O)$_2$—CH(CH$_2$)$_3$ |
| (CF$_3$(CF$_2$)$_2$CH$_2$O)$_2$—C(CH$_3$)CH$_2$ |
| (CF$_3$(CF$_2$)$_2$CH$_2$O)$_2$—C(CF$_3$)CH$_2$ |
| (CF$_3$(CH$_2$)$_2$O)$_2$CHCH$_2$ |
| (CF$_3$(CH$_2$)$_2$O)$_2$CH(CH$_2$)$_2$ |
| (CF$_3$(CH$_2$)$_2$O)$_2$CH(CH$_2$)$_3$ |
| (CF$_3$(CH$_2$)$_2$O)$_2$C(CH$_3$)CH$_2$ |
| (CF$_3$(CH$_2$)$_2$O)$_2$C(CF$_3$)CH$_2$ |
| (CF$_3$(CH$_2$)$_2$O)$_2$—C(CH$_2$CF$_3$)CH$_2$ |
| (CF$_3$(CH$_2$)$_3$O)$_2$CHCH$_2$ |
| (CF$_3$(CH$_2$)$_3$O)$_2$CH(CH$_2$)$_2$ |
| (CF$_3$(CH$_2$)$_3$O)$_2$CH(CH$_2$)$_3$ |
| (CF$_3$(CH$_2$)$_3$O)$_2$C(CH$_3$)CH$_2$ |
| (CF$_3$(CH$_2$)$_3$O)$_2$C(CF$_3$)CH$_2$ |
| (CF$_3$(CH$_2$)$_3$O)$_2$—C(CH$_2$CF$_3$)CH$_2$ |
| (CHF$_2$CH$_2$O)$_2$CHCH$_2$ |
| (CHF$_2$CH$_2$O)$_2$CH(CH$_2$)$_2$ |
| (CHF$_2$CH$_2$O)$_2$CH(CH$_2$)$_3$ |
| (CHF$_2$CH$_2$O)$_2$C(CH$_3$)CH$_2$ |
| (CHF$_2$CH$_2$O)$_2$C(CF$_3$)CH$_2$ |
| (CHF$_2$CH$_2$O)$_2$C(CH$_2$CF$_3$)CH$_2$ |
| (CHF$_2$CF$_2$CH$_2$O)$_2$CHCH$_2$ |
| (CHF$_2$CF$_2$CH$_2$O)$_2$CH(CH$_2$)$_2$ |
| (CHF$_2$CF$_2$CH$_2$O)$_2$CH(CH$_2$)$_3$ |
| (CHF$_2$CF$_2$CH$_2$O)$_2$C(CH$_3$)CH$_2$ |
| (CHF$_2$CF$_2$CH$_2$O)$_2$C(CF$_3$)CH$_2$ |
| (CHF$_2$CF$_2$CH$_2$O)$_2$C(CH$_2$CF$_3$)CH$_2$ |
| (CF$_3$CHFCF$_2$CH$_2$O)$_2$CHCH$_2$ |
| (CF$_3$CHFCF$_2$CH$_2$O)$_2$CH(CH$_2$)$_2$ |
| (CF$_3$CHFCF$_2$CH$_2$O)$_2$CH(CH$_2$)$_3$ |
| (CF$_3$CHFCF$_2$CH$_2$O)$_2$C(CH$_3$)CH$_2$ |
| (CF$_3$CHFCF$_2$CH$_2$O)$_2$C(CF$_3$)CH$_2$ |
| (CF$_3$CHFCF$_2$CH$_2$O)$_2$—C(CH$_2$CF$_3$)CH$_2$ |
| (CHF$_2$(CF$_2$)$_3$CH$_2$O)$_2$CHCH$_2$ |
| (CHF$_2$(CF$_2$)$_3$CH$_2$O)$_2$—CH(CH$_2$)$_2$ |
| (CHF$_2$(CF$_2$)$_3$CH$_2$O)$_2$—CH(CH$_2$)$_3$ |
| (CHF$_2$(CF$_2$)$_3$CH$_2$O)$_2$—C(CH$_3$)CH$_2$ |
| (CHF$_2$(CF$_2$)$_3$CH$_2$O)$_2$—C(CF$_3$)CH$_2$ |
| (CHF$_2$(CF$_2$)$_3$CH$_2$O)$_2$—C(CH$_2$CF$_3$)CH$_2$ |
| (CHF$_2$(CF$_2$)$_4$CH$_2$O)$_2$CHCH$_2$ |
| (CHF$_2$(CF$_2$)$_4$CH$_2$O)$_2$—CH(CH$_2$)$_2$ |
| (CHF$_2$(CF$_2$)$_4$CH$_2$O)$_2$—CH(CH$_2$)$_3$ |
| (CHF$_2$(CF$_2$)$_4$CH$_2$O)$_2$—C(CH$_3$)CH$_2$ |
| (CHF$_2$(CF$_2$)$_4$CH$_2$O)$_2$—C(CF$_3$)CH$_2$ |
| (CHF$_2$(CF$_2$)$_4$CH$_2$O)$_2$—C(CH$_2$CF$_3$)CH$_2$ |
| (CH(CF$_3$)(CH$_3$)O)$_2$CHCH$_2$ |
| (CH(CF$_3$)(CH$_3$)O)$_2$CH(CH$_2$)$_2$ |
| (CH(CF$_3$)(CH$_3$)O)$_2$CH(CH$_2$)$_3$ |
| (CH(CF$_3$)(CH$_3$)O)$_2$C(CH$_3$)CH$_2$ |
| (CH(CF$_3$)(CH$_3$)O)$_2$C(CF$_3$)CH$_2$ |
| (CH(CF$_3$)(CH$_3$)O)$_2$—C(CH$_2$CF$_3$)CH$_2$ |
| (CH(CF$_3$CF$_2$)(CH$_3$)O)$_2$CHCH$_2$ |
| (CH(CF$_3$CF$_2$)(CH$_3$)O)$_2$—CH(CH$_2$)$_2$ |
| (CH(CF$_3$CF$_2$)(CH$_3$)O)$_2$—CH(CH$_2$)$_3$ |
| (CH(CF$_3$CF$_2$)(CH$_3$)O)$_2$—C(CH$_3$)CH$_2$ |
| (CH(CF$_3$CF$_2$)(CH$_3$)O)$_2$—C(CF$_3$)CH$_2$ |
| (CH(CF$_3$CF$_2$)(CH$_3$)O)$_2$—C(CH$_2$CF$_3$)CH$_2$ |
| (CH(CH$_2$Br)(CH$_3$)O)$_2$CHCH$_2$ |
| (CH(CH$_2$Br)(CH$_3$)O)$_2$CH(CH$_2$)$_2$ |
| (CH(CH$_2$Br)(CH$_3$)O)$_2$CH(CH$_2$)$_3$ |
| (CH(CH$_2$Br)(CH$_3$)O)$_2$C(CH$_3$)CH$_2$ |
| (CH(CH$_2$Br)(CH$_3$)O)$_2$C(CF$_3$)CH$_2$ |
| (CH(CH$_2$Br)(CH$_3$)O)$_2$—C(CH$_2$CF$_3$)CH$_2$ |
| (CH(CH$_2$F)$_2$O)$_2$CHCH$_2$ |
| (CH(CH$_2$F)$_2$O)$_2$CH(CH$_2$)$_2$ |
| (CH(CH$_2$F)$_2$O)$_2$CH(CH$_2$)$_3$ |
| (CH(CH$_2$F)$_2$O)$_2$C(CH$_3$)CH$_2$ |
| (CH(CH$_2$F)$_2$O)$_2$C(CF$_3$)CH$_2$ |
| (CH(CH$_2$F)$_2$O)$_2$C(CH$_2$CF$_3$)CH$_2$ |
| (CH(CH$_2$Cl)$_2$O)$_2$CHCH$_2$ |
| (CH(CH$_2$Cl)$_2$O)$_2$CH(CH$_2$)$_2$ |
| (CH(CH$_2$Cl)$_2$O)$_2$CH(CH$_2$)$_3$ |
| (CH(CH$_2$Cl)$_2$O)$_2$C(CH$_3$)(CH$_2$ |
| (CH(CH$_2$Cl)$_2$O)$_2$C(CF$_3$)CH$_2$ |
| (CH(CH$_2$Cl)$_2$O)$_2$—C(CH$_2$CF$_3$)CH$_2$ |
| (CH(CH$_2$Br)$_2$O)$_2$CHCH$_2$ |
| (CH(CH$_2$Br)$_2$O)$_2$CH(CH$_2$)$_2$ |
| (CH(CH$_2$Br)$_2$O)$_2$CH(CH$_2$)$_3$ |
| (CH(CH$_2$Br)$_2$O)$_2$C(CH$_3$)CH$_2$ |
| (CH(CH$_2$Br)$_2$O)$_2$C(CF$_3$)CH$_2$ |
| (CH(CH$_2$Br)$_2$O)$_2$—C(CH$_2$CF$_3$)CH$_2$ |
| (CH(CH$_2$Br)(CH$_2$CH$_2$Br)O)$_2$—CHCH$_2$ |
| (CH(CH$_2$Br)(CH$_2$CH$_2$Br)O)$_2$—(CH(CH$_2$)$_2$ |
| (CH(CH$_2$Br)(CH$_2$CH$_2$Br)O)$_2$—CH(CH$_2$)$_3$ |
| (CH(CH$_2$Br)(CH$_2$CH$_2$Br)O)$_2$—C(CH$_3$)CH$_2$ |
| (CH(CH$_2$Br)(CH$_2$CH$_2$Br)O)$_2$—C(CF$_3$)CH$_2$ |
| (CH(CH$_2$Br)(CH$_2$CH$_2$Br)O)$_2$—C(CH$_2$CF$_3$)CH$_2$ |
| (CH$_3$CH$_2$CH=CHCH$_2$O)$_2$CHCH$_2$ |
| (CH$_3$CH$_2$CH=CHCH$_2$O)$_2$—CH(CH$_2$)$_2$ |
| (CH$_3$CH$_2$CH=CHCH$_2$O)$_2$—CH(CH$_2$)$_3$ |
| (CH$_3$CH$_2$CH=CHCH$_2$O)$_2$—C(CH$_3$)CH$_2$ |
| (CH$_3$CH$_2$CH=CHCH$_2$O)$_2$—C(CF$_3$)CH$_2$ |
| (CH$_3$CH$_2$CH=CHCH$_2$O)$_2$—C(CH$_2$CF$_3$)CH$_2$ |
| (CH$_3$(CH$_2$)$_2$CH=CHCH$_2$O)$_2$—CHCH$_2$ |
| (CH$_3$(CH$_2$)$_2$CH=CHCH$_2$O)$_2$—CH(CH$_2$)$_2$ |
| (CH$_3$(CH$_2$)$_2$CH=CHCH$_2$O)$_2$—CH(CH$_2$)$_3$ |
| (CH$_3$(CH$_2$)$_2$CH=CHCH$_2$O)$_2$—C(CH$_3$)CH$_2$ |
| (CH$_3$(CH$_2$)$_2$CH=CHCH$_2$O)$_2$—C(CF$_3$)CH$_2$ |
| (CH$_3$(CH$_2$)$_2$CH=CHCH$_2$O)$_2$—C(CH$_2$CF$_3$)CH$_2$ |
| (CH$_2$=C(CH$_3$)CH$_2$O)$_2$CHCH$_2$ |
| (CH$_2$=C(CH$_3$)CH$_2$O)$_2$—CH(CH$_2$)$_2$ |
| (CH$_2$=C(CH$_3$)CH$_2$O)$_2$—CH(CH$_2$)$_3$ |
| (CH$_2$=C(CH$_3$)CH$_2$O)$_2$—C(CH$_3$)CH$_2$ |
| (CH$_2$=C(CH$_3$)CH$_2$O)$_2$—C(CF$_3$)CH$_2$ |
| (CH$_2$=C(CH$_3$)CH$_2$O)$_2$—C(CH$_2$CF$_3$)CH$_2$ |

-continued

R¹

(ClCH=CClCH₂O)₂CHCH₂
(ClCH=CClCH₂O)₂CH(CH₂)₂
(ClCH=CClCH₂O)₂CH(CH₂)₃
(ClCH=CClCH₂O)₂C(CH₃)CH₂
(ClCH=CClCH₂O)₂C(CF₃)CH₂
(ClCH=CClCH₂O)₂—C(CH₂CF₃)CH₂
(CH₂=CClCH₂O)₂CHCH₂
(CH₂=CClCH₂O)₂CH(CH₂)₂
(CH₂=CClCH₂O)₂CH(CH₂)₃
(CH₂=CClCH₂O)₂C(CH₃)CH₂
(CH₂=CClCH₂O)₂C(CF₃)CH₂
(CH₂=CClCH₂O)₂—C(CH₂CF₃)CH₂
(CH₂=CBrCH₂O)₂CHCH₂
(CH₂=CBrCH₂O)₂CH(CH₂)₂
(CH₂=CBrCH₂O)₂CH(CH₂)₃
(CH₂=CBrCH₂O)₂C(CH₃)CH₂
(CH₂=CBrCH₂O)₂C(CF₃)CH₂
(CH₂=CBrCH₂O)₂C(CH₂CF₃)CH₂
(CH₃CCl=CHCH₂O)₂CHCH₂
(CH₃CCl=CHCH₂O)₂CH(CH₂)₂
(CH₃CCl=CHCH₂O)₂CH(CH₂)₃
(CH₃CCl=CHCH₂O)₂C(CH₃)CH₂
(CH₃CCl=CHCH₂O)₂C(CF₃)CH₂
(CH₃CCl=CHCH₂O)₂—C(CH₂CF₃)CH₂
(CF₃CH=CHCH₂O)₂CHCH₂
(CF₃CH=CHCH₂O)₂CH(CH₂)₂
(CF₃CH=CHCH₂O)₂CH(CH₂)₃
(CF₃CH=CHCH₂O)₂C(CH₃)CH₂
(CF₃CH=CHCH₂O)₂C(CF₃)CH₂
(CF₃CH=CHCH₂O)₂—C(CH₂CF₃)CH₂
((CF₃)₂C=CHCH₂O)₂CHCH₂
((CF₃)₂C=CHCH₂O)₂CH(CH₂)₂
((CF₃)₂C=CHCH₂O)₂CH(CH₂)₃
((CF₃)₂C=CHCH₂O)₂C(CH₃)CH₂
((CF₃)₂C=CHCH₂O)₂C(CF₃)CH₂
((CF₃)₂C=CHCH₂O)₂—C(CH₂CF₃)CH₂
(CH₂=C(CF₃)CH₂O)₂CHCH₂
(CH₂=C(CF₃)CH₂O)₂—CH(CH₂)₂
(CH₂=C(CF₃)CH₂O)₂—CH(CH₂)₃
(CH₂=C(CF₃)CH₂O)₂—C(CH₃)CH₂
(CH₂=C(CF₃)CH₂O)₂—C(CF₃)CH₂
(CH₂=C(CF₃)CH₂O)₂—C(CH₂CF₃)CH₂
(Cl₂C=CHCH₂CH₂O)₂CHCH₂
(Cl₂C=CHCH₂CH₂O)₂—CH(CH₂)₂
(Cl₂C=CHCH₂CH₂O)₂—CH(CH₂)₃
(Cl₂C=CHCH₂CH₂O)₂—C(CH₃)CH₂
(Cl₂C=CHCH₂CH₂O)₂—C(CF₃)CH₂
(Cl₂C=CHCH₂CH₂O)₂—C(CH₂CF₃)CH₂
(ClCH=CHCH₂CH₂O)₂CHCH₂
(ClCH=CHCH₂CH₂O)₂CH(CH₂)₂
(ClCH=CHCH₂CH₂O)₂CH(CH₂)₃
(ClCH=CHCH₂CH₂O)₂C(CH₃)CH₂
(ClCH=CHCH₂CH₂O)₂C(CF₃)CH₂
(ClCH=CHCH₂CH₂O)₂—C(CH₂CF₃)CH₂
(BrCH=CHCH₂CH₂O)₂CHCH₂
(BrCH=CHCH₂CH₂O)₂CH(CH₂)₂
(BrCH=CHCH₂CH₂O)₂CH(CH₂)₃
(BrCH=CHCH₂CH₂O)₂C(CH₃)CH₂
(BrCH=CHCH₂CH₂O)₂C(CF₃)CH₂
(BrCH=CHCH₂CH₂O)₂—C(CH₂CF₃)CH₂
(Br₂C=CHCH₂CH₂O)₂CHCH₂
(Br₂C=CHCH₂CH₂O)₂CH(CH₂)₂
(Br₂C=CHCH₂CH₂O)₂CH(CH₂)₃
(Br₂C=CHCH₂CH₂O)₂C(CH₃)CH₂
(Br₂C=CHCH₂CH₂O)₂C(CF₃)CH₂
(Br₂C=CHCH₂CH₂O)₂—C(CH₂CF₃)CH₂
(CF₃CH=CHCH₂CH₂O)₂CHCH₂
(CF₃CH=CHCH₂CH₂O)₂—CH(CH₂)₂
(CF₃CH=CHCH₂CH₂O)₂—CH(CH₂)₃
(CF₃CH=CHCH₂CH₂O)₂—C(CH₃)CH₂
(CF₃CH=CHCH₂CH₂O)₂—C(CF₃)CH₂
(CF₃CH=CHCH₂CH₂O)₂—C(CH₂CF₃)CH₂
(CF₃CCl=CHCH₂CH₂O)₂CHCH₂
(CF₃CCl=CHCH₂CH₂O)₂—CH(CH₂)₂
(CF₃CCl=CHCH₂CH₂O)₂—CH(CH₂)₃
(CF₃CCl=CHCH₂CH₂O)₂—C(CH₃)CH₂
(CF₃CCl=CHCH₂CH₂O)₂—C(CF₃)CH₂

-continued

R¹

(CF₃CCl=CHCH₂CH₂O)₂—C(CH₂CF₃)CH₂
((CF₃)₂C=CHCH₂CH₂O)₂CHCH₂
((CF₃)₂C=CHCH₂CH₂O)₂—CH(CH₂)₂
((CF₃)₂C=CHCH₂CH₂O)₂—CH(CH₂)₃
((CF₃)₂C=CHCH₂CH₂O)₂—C(CH₃)CH₂
((CF₃)₂C=CHCH₂CH₂O)₂—C(CF₃)CH₂
((CF₃)₂C=CHCH₂CH₂O)₂—C(CH₂CF₃)CH₂
(CH₃C≡CCH₂O)₂CHCH₂
(CH₃C≡CCH₂O)₂CH(CH₂)₂
(CH₃C≡CCH₂O)₂CH(CH₂)₃
(CH₃C≡CCH₂O)₂C(CH₃)CH₂
(CH₃C≡CCH₂O)₂C(CF₃)CH₂
(CH₃C≡CCH₂O)₂—C(CH₂CF₃)CH₂
(CF₃C≡CCH₂O)₂CHCH₂
(CF₃C≡CCH₂O)₂CH(CH₂)₂
(CF₃C≡CCH₂O)₂CH(CH₂)₃
(CF₃C≡CCH₂O)₂C(CH₃)CH₂
(CF₃C≡CCH₂O)₂C(CF₃)CH₂
(CF₃C≡CCH₂O)₂—C(CH₂CF₃)CH₂
(BrC≡CCH₂O)₂CHCH₂
(BrC≡CCH₂O)₂CH(CH₂)₂
(BrC≡CCH₂O)₂CH(CH₂)₃
(BrC≡CCH₂O)₂C(CH₃)CH₂
(BrC≡CCH₂O)₂C(CF₃)CH₂
(BrC≡CCH₂O)₂C(CH₂CF₃)CH₂
(FC≡CCH₂O)₂CHCH₂
(FC≡CCH₂O)₂CH(CH₂)₂
(FC≡CCH₂O)₂CH(CH₂)₃
(FC≡CCH₂O)₂C(CH₃)CH₂
(FC≡CCH₂O)₂C(CF₃)CH₂
(FC≡CCH₂O)₂C(CH₂CF₃)CH₂
(CH₂=CHCH₂CH₂O)₂CHCH₂
(CH₂=CHCH₂CH₂O)₂—CH(CH₂)₂
(CH₂=CHCH₂CH₂O)₂—CH(CH₂)₃
(CH₂=CHCH₂CH₂O)₂—C(CH₃)CH₂
(CH₂=CHCH₂CH₂O)₂—C(CF₃)CH₂
(CH₂=CHCH₂CH₂O)₂—C(CH₂CF₃)CH₂
(CH(CH₂Cl)(CH₃)O)₂CHCH₂
(CH(CH₂Cl)(CH₃)O)₂—CH(CH₂)₂
(CH(CH₂Cl)(CH₃)O)₂—CH(CH₂)₃
(CH(CH₂Cl)(CH₃)O)₂—C(CH₃)CH₂
(CH(CH₂Cl)(CH₃)O)₂—C(CF₃)CH₂
(CH(CH₂Cl)(CH₃)O)₂—C(CH₂CF₃)CH₂
(CH₃S)₂CHCH₂
(CH₃S)₂CH(CH₂)₂
(CH₃S)₂CH(CH₂)₃
(CH₃S)₂CH(CH₂)₄
(CH₃S)₂CHCH(CH₃)CH₂
(CH₃S)₂CHC(CH₃)₂CH₂
(CH₃S)₂CHCH(CH₃)
(CH₃S)₂CHCH(CH₂CH₃)
(CH₃S)₂CHCH(CH₂CH₂CH₃)
(CH₃S)₂CHCH(CH₂CH(CH₃)₂)
(CH₃S)₂C(CF₃)CH₂
(CH₃S)₂C(CH₃)CH₂
(CH₃S)₂C(CH₃)CH₂)₂
(CH₃S)₂C(CH₃)CH₂)₃
(CH₃S)₂C(CHClCF₃)CH₂
(CH₃S)₂C(CHClCF₃)(CH₂)₂
(CH₃S)₂C(CHClCF₃)(CH₂)₃
(CH₃S)₂C(CBr₂CF₃)CH₂
(CH₃S)₂C(CBr₂CF₃)(CH₂)₂
(CH₃S)₂C(CBr₂CF₃)(CH₂)₃
(CH₃S)₂C(CHBrCF₃)CH₂
(CH₃S)₂C(CHBrCF₃)(CH₂)₂
(CH₃S)₂C(CHBrCF₃)(CH₂)₃
(CH₃S)₂C(CH₂CF₃)CH₂
(CH₃S)₂C(CH₂CF₃)(CH₂)₂
(CH₃S)₂C(CH₂CF₃)(CH₂)₃
(CH₃CH₂S)₂CHCH₂
(CH₃CH₂S)₂CH(CH₂)₂
(CH₃CH₂S)₂CH(CH₂)₃
(CH₃CH₂S)₂CH(CH₂)₄
(CH₃CH₂S)₂CHCH(CH₃)CH₂
(CH₃CH₂S)₂CHC(CH₃)₂CH₂
(CH₃CH₂S)₂CHCH(CH₃)
(CH₃CH₂S)₂CHCH(CH₂CH₃)

| R¹ |
|---|
| (CH₃CH₂S)₂—CHCH(CH₂CH₂CH₃) |
| (CH₃CH₂S)₂—CHCH(CH₂CH(CH₃)₂) |
| (CH₃CH₂S)₂C(CF₃)CH₂ |
| (CH₃CH₂S)₂C(CH₃)CH₂ |
| (CH₃CH₂S)₂C(CH₃)(CH₂)₂ |
| (CH₃CH₂S)₂C(CH₃)(CH₂)₃ |
| (CH₃CH₂S)₂C(CCl₂CF₃)CH₂ |
| (CH₃CH₂S)₂—C(CCl₂CF₃)(CH₂)₂ |
| (CH₃CH₂S)₂—C(CCl₂CF₃)(CH₂)₃ |
| (CH₃CH₂S)₂C(CHClCF₃)CH₂ |
| (CH₃CH₂S)₂—C(CHClCF₃)(CH₂)₂ |
| (CH₃CH₂S)₂—C(CHClCF₃)(CH₂)₃ |
| (CH₃CH₂S)₂C(CBr₂CF₃)CH₂ |
| (CH₃CH₂S)₂—C(CBr₂CF₃)(CH₂)₂ |
| (CH₃CH₂S)₂—C(CBr₂CF₃)(CH₂)₃ |
| (CH₃CH₂S)₂C(CHBrCF₃)CH₂ |
| (CH₃CH₂S)₂C(CHBrCF₃)(CH₂)₂ |
| (CH₃CH₂S)₂C(CHBrCF₃)(CH₂)₃ |
| (CH₃CH₂S)₂C(CH₂CF₃)CH₂ |
| (CH₃CH₂S)₂C(CH₂CF₃)(CH₂)₂ |
| (CH₃CH₂S)₂C(CH₂CF₃)(CH₂)₃ |
| (CH₃(CH₂)₂S)₂CHCH₂ |
| (CH₃(CH₂)₂S)₂CH(CH₂)₂ |
| (CH₃(CH₂)₂S)₂CH(CH₂)₃ |
| (CH₃(CH₂)₂S)₂CH(CH₂)₄ |
| (CH₃(CH₂)₂S)₂—CHCH(CH₃)CH₂ |
| (CH₃(CH₂)₂S)₂CHCH(CH₃) |
| (CH₃(CH₂)₂S)₂C(CH₃)CH₂ |
| (CH₃(CH₂)₂S)₂—C(CH₃)(CH₂)₂ |
| (CH₃(CH₂)₂S)₂C(CF₃)CH₂ |
| (CH₃(CH₂)₂S)₂—C(CH₂CF₃)CH₂ |
| (CH₃(CH₂)₂S)₂—C(CCl₂CF₃)CH₂ |
| ((CH₃)₂CHS)₂CHCH₂ |
| ((CH₃)₂CHS)₂CH(CH₂)₂ |
| ((CH₃)₂CHS)₂CH(CH₂)₃ |
| ((CH₃)₂CHS)₂CH(CH₂)₄ |
| ((CH₃)₂CHS)₂CHCH(CH₃)CH₂ |
| ((CH₃)₂CHS)₂CHCH(CH₃) |
| ((CH₃)₂CHS)₂C(CH₃)CH₂ |
| ((CH₃)₂CHS)₂C(CH₃)(CH₂)₂ |
| ((CH₃)₂CHS)₂C(CF₃)CH₂ |
| ((CH₃)₂CHS)₂C(CH₂CF₃)CH₂ |
| ((CH₃)₂CHS)₂—C(CCl₂CF₃)CH₂ |
| (FCH₂CH₂S)₂CHCH₂ |
| (FCH₂CH₂S)₂CH(CH₂)₂ |
| (FCH₂CH₂S)₂CH(CH₂)₃ |
| (FCH₂CH₂S)₂CH(CH₂)₄ |
| (FCH₂CH₂S)₂CHCH(CH₃)CH₂ |
| (FCH₂CH₂S)₂CHCH(CH₃) |
| (FCH₂CH₂S)₂C(CH₃)CH₂ |
| (FCH₂CH₂S)₂C(CH₃)(CH₂)₂ |
| (FCH₂CH₂S)₂C(CF₃)CH₂ |
| (FCH₂CH₂S)₂C(CH₂CF₃)CH₂ |
| (FCH₂CH₂S)₂C(CCl₂CF₃)CH₂ |
| (CF₃CH₂S)₂CHCH₂ |
| (CF₃CH₂S)₂CH(CH₂)₂ |
| (CF₃CH₂S)₂CH(CH₂)₃ |
| (CF₃CH₂S)₂CH(CH₂)₄ |
| (CF₃CH₂S)₂CHCH(CH₃)CH₂ |
| (CF₃CH₂S)₂CHCH(CH₃) |
| (CF₃CH₂S)₂C(CH₃)CH₂ |
| (CF₃CH₂S)₂C(CH₃)(CH₂)₂ |
| (CF₃CH₂S)₂C(CF₃)CH₂ |
| (CF₃CH₂S)₂C(CH₂CF₃)CH₂ |
| (CF₃CH₂S)₂C(CCl₂CF₃)CH₂ |
| (CCl₃CH₂S)₂CHCH₂ |
| (CCl₃CH₂S)₂CH(CH₂)₂ |
| (CCl₃CH₂S)₂CH(CH₂)₃ |
| (CCl₃CH₂S)₂CH(CH₂)₄ |
| (CCl₃CH₂S)₂CHCH(CH₃)CH₂ |
| (CCl₃CH₂S)₂CHCH(CH₃) |
| (CCl₃CH₂S)₂C(CH₃)CH₂ |
| (CCl₃CH₂S)₂C(CH₃)(CH₂)₂ |
| (CCl₃CH₂S)₂C(CF₃)CH₂ |
| (CCl₃CH₂S)₂C(CH₂CF₃)CH₂ |
| (CCl₃CH₂S)₂C(CCl₂CF₃)CH₂ |
| (CBr₃CH₂S)₂CHCH₂ |
| (CBr₃CH₂S)₂CH(CH₂)₂ |
| (CBr₃CH₂S)₂CH(CH₂)₃ |
| (CBr₃CH₂S)₂CH(CH₂)₄ |
| (CBr₃CH₂S)₂CHCH(CH₃)CH₂ |
| (CBr₃CH₂S)₂CHCH(CH₃) |
| (CBr₃CH₂S)₂C(CH₃)CH₂ |
| (CBr₃CH₂S)₂C(CH₃)(CH₂)₂ |
| (CBr₃CH₂S)₂C(CF₃)CH₂ |
| (CBr₃CH₂S)₂C(CH₂CF₃)CH₂ |
| (CBr₃CH₂S)₂C(CCl₂CF₃)CH₂ |
| (CF₃CF₂CH₂S)₂CHCH₂ |
| (CF₃CF₂CH₂S)₂CH(CH₂)₂ |
| (CF₃CF₂CH₂S)₂CH(CH₂)₃ |
| (CF₃CF₂CH₂S)₂CH(CH₂)₄ |
| (CF₃CF₂CH₂S)₂—CHCH(CH₃)CH₂ |
| (CF₃CF₂CH₂S)₂CHCH(CH₃) |
| (CF₃CF₂CH₂S)₂C(CH₃)CH₂ |
| (CF₃CF₂CH₂S)₂—C(CH₃)(CH₂)₂ |
| (CF₃CF₂CH₂S)₂C(CF₃)CH₂ |
| (CF₃CF₂CH₂S)₂—C(CH₂CF₃)CH₂ |
| (CF₃CF₂CH₂S)₂—C(CCl₂CF₃)CH₂ |
| ((CF₃)₂CHS)₂CHCH₂ |
| ((CF₃)₂CHS)₂CH(CH₂)₂ |
| ((CF₃)₂CHS)₂CH(CH₂)₃ |
| ((CF₃)₂CHS)₂CH(CH₂)₄ |
| ((CF₃)₂CHS)₂CHCH(CH₃)CH₂ |
| ((CF₃)₂CHS)₂CHCH(CH₃) |
| ((CF₃)₂CHS)₂C(CH₃)CH₂ |
| ((CF₃)₂CHS)₂C(CH₃)(CH₂)₂ |
| ((CF₃)₂CHS)₂C(CF₃)CH₂ |
| ((CF₃)₂CHS)₂C(CH₂CF₃)CH₂ |
| ((CF₃)₂CHS)₂C(CCl₂CF₃)CH₂ |
| (CH₂=CHCH₂S)₂CHCH₂ |
| (CH₂=CHCH₂S)₂CH(CH₂)₂ |
| (CH₂=CHCH₂S)₂CH(CH₂)₃ |
| (CH₂=CHCH₂S)₂CH(CH₂)₄ |
| (CH₂=CHCH₂S)₂CHCH(CH₃)CH₂ |
| (CH₂=CHCH₂S)₂CHCH(CH₃) |
| (CH₂=CHCH₂S)₂C(CH₃)CH₂ |
| (CH₂=CHCH₂S)₂—C(CH₃)(CH₂)₂ |
| (CH₂=CHCH₂S)₂C(CF₃)CH₂ |
| (CH₂=CHCH₂S)₂—C(CH₂CF₃)CH₂ |
| (CH₂=CHCH₂S)₂—C(CCl₂CF₃)CH₂ |
| (Cl₂C=CHCH₂S)₂CHCH₂ |
| (Cl₂C=CHCH₂S)₂CH(CH₂)₂ |
| (Cl₂C=CHCH₂S)₂CH(CH₂)₃ |
| (Cl₂C=CHCH₂S)₂CH(CH₂)₄ |
| (Cl₂C=CHCH₂S)₂—CHCH(CH₃)CH₂ |
| (Cl₂C=CHCH₂S)₂CHCH(CH₃) |
| (Cl₂C=CHCH₂S)₂C(CH₃)CH₂ |
| (Cl₂C=CHCH₂S)₂—C(CH₃)(CH₂)₂ |
| (Cl₂C=CHCH₂S)₂C(CF₃(CH₂ |
| (Cl₂C=CHCH₂S)₂—C(CH₂CF₃)CH₂ |
| (Cl₂C=CHCH₂S)₂—C(CCl₂CF₃)CH₂ |
| (HC≡CCH₂S)₂CHCH₂ |
| (HC≡CCH₂S)₂CH(CH₂)₂ |
| (HC≡CCH₂S)₂CH(CH₂)₃ |
| (HC≡CCH₂S)₂CH(CH₂)₄ |
| (HC≡CCH₂S)₂CHCH(CH₃)CH₂ |
| (HC≡CCH₂S)₂CHCH(CH₃) |
| (HC≡CCH₂S)₂C(CH₃)CH₂ |
| (HC≡CCH₂S)₂C(CH₃)(CH₂)₂ |
| (HC≡CCH₂S)₂C(CF₃)CH₂ |
| (HC≡CCH₂S)₂C(CH₂CF₃)CH₂ |
| (HC≡CCH₂S)₂—C(CCl₂CF₃)CH₂ |
| (ClC≡CCH₂S)₂CHCH₂ |
| (ClC≡CCH₂S)₂CH(CH₂)₂ |
| (ClC≡CCH₂S)₂CH(CH₂)₃ |
| (ClC≡CCH₂S)₂CH(CH₂)₄ |
| (ClC≡CCH₂S)₂CHCH(CH₃)CH₂ |
| (ClC≡CCH₂S)₂CHCH(CH₃) |
| (ClC≡CCH₂S)₂C(CH₃)CH₂ |
| (ClC≡CCH₂S)₂C(CH₃)(CH₂)₂ |
| (ClC≡CCH₂S)₂C(CF₃)CH₂ |
| (ClC≡CCH₂S)₂C(CH₂CF₃)CH₂ |
| (ClC≡CCH₂S)₂C(CCl₂CF₃)CH₂ |
| (CH₃(CH₂)₃S)₂CHCH₂ |

-continued

| $R^1$ |
|---|
| $(CH_3(CH_2)_3S)_2CH(CH_2)_2$ |
| $(CH_3(CH_2)_3S)_2CH(CH_2)_3$ |
| $(CH_3(CH_2)_3S)_2C(CH_3)CH_2$ |
| $(CH_3(CH_2)_3S)_2C(CF_3)CH_2$ |
| $((CH_3)_2CHCH_2S)_2CHCH_2$ |
| $((CH_3)_2CHCH_2S)_2CH(CH_2)_2$ |
| $((CH_3)_2CHCH_2S)_2CH(CH_2)_3$ |
| $((CH_3)_2CHCH_2S)_2C(CH_3)CH_2$ |
| $((CH_3)_2CHCH_2S)_2C(CF_3)CH_2$ |
| $(CH_3(CH_2)_4S)_2CHCH_2$ |
| $(CH_3(CH_2)_4S)_2CH(CH_2)_2$ |
| $(CH_3(CH_2)_4S)_2CH(CH_2)_3$ |
| $(CH_3(CH_2)_4S)_2C(CH_3)CH_2$ |
| $(CH_3(CH_2)_4S)_2C(CF_3)CH_2$ |
| $(CF_3(CF_2)_2CH_2S)_2CHCH_2$ |
| $(CF_3(CF_2)_2CH_2S)_2-CH(CH_2)_2$ |
| $(CF_3(CF_2)_2CH_2S)_2-CH(CH_2)_3$ |
| $(CF_3(CF_2)_2CH_2S)_2-C(CH_3)CH_2$ |
| $(CF_3(CF_2)_2CH_2S)_2-C(CF_3)CH_2$ |
| $(CF_3(CH_2)_2S)_2CHCH_2$ |
| $(CF_3(CH_2)_2S)_2CH(CH_2)_2$ |
| $(CF_3(CH_2)_2S)_2CH(CH_2)_3$ |
| $(CF_3(CH_2)_2S)_2C(CH_3)CH_2$ |
| $(CF_3(CH_2)_2S)_2C(CF_3)CH_2$ |
| $(CHF_2CH_2S)_2CHCH_2$ |
| $(CHF_2CH_2S)_2CH(CH_2)_2$ |
| $(CHF_2CH_2S)_2CH(CH_2)_3$ |
| $(CHF_2CH_2S)_2C(CH_3)CH_2$ |
| $(CHF_2CH_2S)_2C(CF_3)CH_2$ |
| $(CHF_2CF_2CH_2S)_2CHCH_2$ |
| $(CHF_2CF_2CH_2S)_2CH(CH_2)_2$ |
| $(CHF_2CF_2CH_2S)_2CH(CH_2)_3$ |
| $(CHF_2CF_2CH_2S)_2C(CH_3)CH_2$ |
| $(CHF_2CF_2CH_2S)_2C(CF_3)CH_2$ |
| $(CH(CF_3)(CH_3)S)_2CHCH_2$ |
| $(CH(CF_3)(CH_3)S)_2CH(CH_2)_2$ |
| $(CH(CF_3)(CH_3)S)_2CH(CH_2)_3$ |
| $(CH(CF_3)(CH_3)S)_2C(CH_3)CH_2$ |
| $(CH(CF_3)(CH_3)S)_2C(CF_3)CH_2$ |
| $(CH(CH_2F)_2S)_2CHCH_2$ |
| $(CH(CH_2F)_2S)_2CH(CH_2)_2$ |
| $(CH(CH_2F)_2S)_2CH(CH_2)_3$ |
| $(CH(CH_2F)_2S)_2C(CH_3)CH_2$ |
| $(CH(CH_2F)_2S)_2C(CF_3)CH_2$ |
| $(CH_2=C(CH_3)CH_2S)_2CHCH_2$ |
| $(CH_2=C(CH_3)CH_2S)_2-CH(CH_2)_2$ |
| $(CH_2=C(CH_3)CH_2S)_2-CH(CH_2)_3$ |
| $(CH_2=C(CH_3)CH_2S)_2-C(CH_3)CH_2$ |
| $(CH_2=C(CH_3)CH_2S)_2-C(CF_3)CH_2$ |
| $(ClCH=CClCH_2S)_2CHCH_2$ |
| $(ClCH=CClCH_2S)_2CH(CH_2)_2$ |
| $(ClCH=CClCH_2S)_2CH(CH_2)_3$ |
| $(ClCH=CClCH_2S)_2C(CH_3)CH_2$ |
| $(ClCH=CClCH_2S)_2C(CF_3)CH_2$ |
| $(CH_2=CClCH_2S)_2CHCH_2$ |
| $(CH_2=CClCH_2S)_2CH(CH_2)_2$ |
| $(CH_2=CClCH_2S)_2CH(CH_2)_3$ |
| $(CH_2=CClCH_2S)_2C(CH_3)CH_2$ |
| $(CH_2=CClCH_2S)_2C(CF_3)CH_2$ |
| $(CH_3CCl=CHCH_2S)_2CHCH_2$ |
| $(CH_3CCl=CHCH_2S)_2CH(CH_2)_2$ |
| $(CH_3CCl=CHCH_2S)_2CH(CH_2)_3$ |
| $(CH_3CCl=CHCH_2S)_2C(CH_3)CH_2$ |
| $(CH_3CCl=CHCH_2S)_2C(CF_3)CH_2$ |
| $((CF_3)_2C=CHCH_2S)_2CHCH_2$ |
| $((CF_3)_2C=CHCH_2S)_2-CH(CH_2)_2$ |
| $((CF_3)_2C=CHCH_2S)_2-CH(CH_2)_3$ |
| $((CF_3)_2C=CHCH_2S)_2-C(CH_3)CH_2$ |
| $((CF_3)_2C=CHCH_2S)_2-C(CF_3)CH_2$ |
| $(CH_3CH=CHCH_2S)_2CHCH_2$ |
| $(CH_3CH=CHCH_2S)_2CH(CH_2)_2$ |
| $(CH_3CH=CHCH_2S)_2CH(CH_2)_3$ |
| $(CH_3CH=CHCH_2S)_2C(CH_3)CH_2$ |
| $(CH_3CH=CHCH_2S)_2C(CF_3)CH_2$ |
| $((CH_3)_2C=CHCH_2S)_2CHCH_2$ |
| $((CH_3)_2C=CHCH_2S)_2-CH(CH_2)_2$ |
| $((CH_3)_2C=CHCH_2S)_2-CH(CH_2)_3$ |

-continued

| $R^1$ |
|---|
| $((CH_3)_2C=CHCH_2S)_2C(CH_3)CH_2$ |
| $((CH_3)_2C=CHCH_2S)_2C(CF_3)CH_2$ |
| $(ClCH=CHCH_2S)_2CHCH_2$ |
| $(ClCH=CHCH_2S)_2CH(CH_2)_2$ |
| $(ClCH=CHCH_2S)_2CH(CH_2)_3$ |
| $(ClCH=CHCH_2S)_2C(CH_3)CH_2$ |
| $(ClCH=CHCH_2S)_2C(CF_3)CH_2$ |
| $(BrCH=CHCH_2S)_2CHCH_2$ |
| $(BrCH=CHCH_2S)_2CH(CH_2)_2$ |
| $(BrCH=CHCH_2S)_2CH(CH_2)_3$ |
| $(BrCH=CHCH_2S)_2C(CH_3)CH_2$ |
| $(BrCH=CHCH_2S)_2C(CF_3)CH_2$ |
| $(Br_2C=CHCH_2S)_2CHCH_2$ |
| $(Br_2C=CHCH_2S)_2CH(CH_2)_2$ |
| $(Br_2C=CHCH_2S)_2CH(CH_2)_3$ |
| $(Br_2C=CHCH_2S)_2C(CH_3)CH_2$ |
| $(Br_2C=CHCH_2S)_2C(CF_3)CH_2$ |
| $(CF_3CCl=CHCH_2S)_2CHCH_2$ |
| $(CF_3CCl=CHCH_2S)_2CH(CH_2)_2$ |
| $(CF_3CCl=CHCH_2S)_2CH(CH_2)_3$ |
| $(CF_3CCl=CHCH_2S)_2C(CH_3)CH_2$ |
| $(CF_3CCl=CHCH_2S)_2C(CF_3)CH_2$ |
| $(CH_3C\equiv CCH_2S)_2CHCH_2$ |
| $(CH_3C\equiv CCH_2S)_2CH(CH_2)_2$ |
| $(CH_3C\equiv CCH_2S)_2CH(CH_2)_3$ |
| $(CH_3C\equiv CCH_2S)_2C(CH_3)CH_2$ |
| $(CH_3C\equiv CCH_2S)_2C(CF_3)CH_2$ |
| $(CF_3C\equiv CCH_2S)_2CHCH_2$ |
| $(CF_3C\equiv CCH_2S)_2CH(CH_2)_2$ |
| $(CF_3C\equiv CCH_2S)_2CH(CH_2)_3$ |
| $(CF_3C\equiv CCH_2S)_2C(CH_3)CH_2$ |
| $(CF_3C\equiv CCH_2S)_2C(CF_3)CH_2$ |
| $(BrC\equiv CCH_2S)_2CHCH_2$ |
| $(BrC\equiv CCH_2S)_2CH(CH_2)_2$ |
| $(BrC\equiv CCH_2S)_2CH(CH_2)_3$ |
| $(BrC\equiv CCH_2S)_2C(CH_3)CH_2$ |
| $(BrC\equiv CCH_2S)_2C(CF_3)CH_2$ |
| $(FC\equiv CCH_2S)_2CHCH_2$ |
| $(FC\equiv CCH_2S)_2CH(CH_2)_2$ |
| $(FC\equiv CCH_2S)_2CH(CH_2)_3$ |
| $(FC\equiv CCH_2S)_2C(CH_3)CH_2$ |
| $(FC\equiv CCH_2S)_2C(CF_3)CH_2$ |
| $(CH_2=CH(CH_2)_2S)_2CHCH_2$ |
| $(CH_2=CH(CH_2)_2S)_2-CH(CH_2)_2$ |
| $(CH_2=CH(CH_2)_2S)_2-CH(CH_2)_3$ |
| $(CH_2=CH(CH_2)_2S)_2-C(CH_3)CH_2$ |
| $CH_3C(=O)CH_2$ |
| $CH_3CH_2C(=O)CH_2$ |
| $CH_3(CH_2)_2C(=O)CH_2$ |
| $CH_3(CH_2)_3C(=O)CH_2$ |
| $(CH_3)_2CHC(=O)CH_2$ |
| $(CH_3)_3CC(=O)CH_2$ |
| $(CH_3)_2CHCH_2C(=O)CH_2$ |
| $CH_3C(=O)(CH_2)_2$ |
| $CH_3C(=O)(CH_2)_3$ |
| $CH_3C(=O)(CH_2)_4$ |
| $CF_3C(=O)CH_2$ |
| $CF_3CCl_2C(=O)CH_2$ |
| $CF_3CCl_2C(=O)CH_2CH_2$ |
| $CF_3CBr_2C(=O)CH_2$ |
| $CF_3CBr_2C(=O)CH_2CH_2$ |
| $CF_3CHClC(=O)CH_2$ |
| $CF_3CHClC(=O)CH_2CH_2$ |
| $CF_3CH_2C(=O)CH_2$ |
| $CF_3CH_2C(=O)CH_2CH_2$ |
| $CH_3C(=O)CH(CH_3)$ |
| $CF_3C(=O)CH(CH_3)$ |
| $CF_3CH_2C(=O)CH(CH_3)$ |
| $CF_3CCl_2C(=O)CH(CH_3)$ |
| $(CH_2=CH(CH_2)_2S)_2-C(CF_3)CH_2$ |

TABLE 2

$$R^1 = Q^1 = \begin{matrix} R^8 \\ \diagdown \\ R^7 \end{matrix} C = R^7 \left( \begin{matrix} R^5 \\ | \\ C \\ | \\ R^6 \end{matrix} \right)_n$$

| $R^3$ | $R^9$ | $R^7$ | $\left(\begin{matrix}R^5\\|\\C\\|\\R^6\end{matrix}\right)_n$ |
|---|---|---|---|
| Cl | Cl | H | —CH$_2$— |
| Br | Cl | H | —CH$_2$— |
| F | Cl | H | —CH$_2$— |
| CF$_3$ | Cl | H | —CH$_2$— |
| CF$_3$CF$_2$ | Cl | H | —CH$_2$— |
| CF$_3$(CF$_2$)$_2$ | Cl | H | —CH$_2$— |
| CF$_3$(CF$_2$)$_3$ | Cl | H | —CH$_2$— |
| CF$_3$(CF$_2$)$_5$ | Cl | H | —CH$_2$— |
| CF$_2$Cl | Cl | H | —CH$_2$— |
| CF$_2$Br | Cl | H | —CH$_2$— |
| H | Cl | H | —CH$_2$— |
| CH$_3$ | Cl | H | —CH$_2$— |
| CH$_3$CH$_2$ | Cl | H | —CH$_2$— |
| CH$_3$(CH$_2$)$_2$ | Cl | H | —CH$_2$— |
| (CH$_3$)$_2$CH | Cl | H | —CH$_2$— |
| CH$_3$(CH$_2$)$_3$ | Cl | H | —CH$_2$— |
| (CH$_3$)$_2$CHCH$_2$ | Cl | H | —CH$_2$— |
| CH$_3$CH$_2$CH(CH$_3$) | Cl | H | —CH$_2$— |
| (CH$_3$)$_3$C | Cl | H | —CH$_2$— |
| CH$_3$(CH$_2$)$_4$ | Cl | H | —CH$_2$— |
| CH$_3$(CH$_2$)$_5$ | Cl | H | —CH$_2$— |
| CN | Cl | H | —CH$_2$— |
| NO$_2$ | Cl | H | —CH$_2$— |
| CH$_3$C(=O) | Cl | H | —CH$_2$— |
| CF$_3$C(=O) | Cl | H | —CH$_2$— |
| CH$_3$OOC | Cl | H | —CH$_2$— |
| CH$_3$CH$_2$OOC | Cl | H | —CH$_2$— |
| (CH$_3$)$_2$CHOOC | Cl | H | —CH$_2$— |
| CF$_3$CH$_2$OOC | Cl | H | —CH$_2$— |
| (CH$_2$)$_3$NC(=O) | Cl | H | —CH$_2$— |
| (CH$_3$CH$_2$)$_2$NC(=O) | Cl | H | —CH$_2$— |
| (CH$_3$CH$_2$CH$_2$)NC(=O) | Cl | H | —CH$_2$— |
| Br | Br | H | —CH$_2$— |
| F | Br | H | —CH$_2$— |
| CF$_3$ | Br | H | —CH$_2$— |
| CF$_3$CF$_2$ | Br | H | —CH$_2$— |
| CF$_3$(CF$_2$)$_2$ | Br | H | —CH$_2$— |
| CF$_3$(CF$_{23}$ | Br | H | —CH$_2$— |
| CF$_3$(CF$_2$)$_5$ | Br | H | —CH$_2$— |
| CF$_2$Cl | Br | H | —CH$_2$— |
| CF$_2$Br | Br | H | —CH$_2$— |
| H | Br | H | —CH$_2$— |
| CH$_3$ | Br | H | —CH$_2$— |
| CH$_3$CH$_2$ | Br | H | —CH$_2$— |
| CH$_3$(CH$_2$)$_2$ | Br | H | —CH$_2$— |
| (CH$_3$)$_2$CH | Br | H | —CH$_2$— |
| CH$_3$(CH$_2$)$_3$ | Br | H | —CH$_2$— |
| (CH$_3$)$_2$CHCH$_2$ | Br | H | —CH$_2$— |
| CH$_3$CH$_2$CH(CH$_3$) | Br | H | —CH$_2$— |
| (CH$_3$)$_3$C | Br | H | —CH$_2$— |
| CH$_3$(CH$_2$)$_4$ | Br | H | —CH$_2$— |
| CH$_3$(CH$_2$)$_5$ | Br | H | —CH$_2$— |
| CN | Br | H | —CH$_2$— |
| NO$_2$ | Br | H | —CH$_2$— |
| CH$_3$C(=O) | Br | H | —CH$_2$— |
| CF$_3$C(=O) | Br | H | —CH$_2$— |
| CH$_3$OOC | Br | H | —CH$_2$— |
| CH$_3$CH$_2$OOC | Br | H | —CH$_2$— |
| (CH$_3$)$_2$CHOOC | Br | H | —CH$_2$— |
| CF$_3$CH$_2$OOC | Br | H | —CH$_2$— |
| (CH$_3$)$_2$NC(=O) | Br | H | —CH$_2$— |
| (CH$_3$CH$_2$)$_2$NC(=O) | Br | H | —CH$_2$— |
| (CH$_3$CH$_2$CH$_2$)$_2$NC(=O) | Br | H | —CH$_2$— |
| F | F | H | —CH$_2$— |

TABLE 2-continued $$R^1 = Q^1 = \begin{matrix} R^8 \\ \diagdown \\ R^7 \diagup \end{matrix} C = R^7 \left( \begin{matrix} R^5 \\ | \\ C \\ | \\ R^6 \end{matrix} \right)_n$$

$$\left( \begin{matrix} R^5 \\ | \\ C \\ | \\ R^6 \end{matrix} \right)_n$$

| $R^3$ | $R^9$ | $R^7$ | $\left( \begin{matrix} R^5 \\ | \\ C \\ | \\ R^6 \end{matrix} \right)_n$ |
|---|---|---|---|
| $CF_3$ | F | H | —$CH_2$— |
| $CF_2Cl$ | F | H | —$CH_2$— |
| $CF_2Br$ | F | H | —$CH_2$— |
| H | F | H | —$CH_2$— |
| $CH_3$ | F | H | —$CH_2$— |
| $CH_3CH_2$ | F | H | —$CH_2$— |
| $CH_3C(=O)$ | F | H | —$CH_2$— |
| $CF_3C(=O)$ | F | H | —$CH_2$— |
| $CH_3CH_2OOC$ | F | H | —$CH_2$— |
| $CF_3CH_2OOC$ | F | H | —$CH_2$— |
| $(CH_3)_2NC(=O)$ | F | H | —$CH_2$— |
| H | H | H | —$CH_2$— |
| $CH_3$ | H | H | —$CH_2$— |
| $CH_3CH_2$ | H | H | —$CH_2$— |
| $CH_3(CH_2)_2$ | H | H | —$CH_2$— |
| $(CH_3)_2CH$ | H | H | —$CH_2$— |
| $CH_3(CH_2)_3$ | H | H | —$CH_2$— |
| $(CH_3)_2CHCH_2$ | H | H | —$CH_2$— |
| $CH_3CH_2CH(CH_3)$ | H | H | —$CH_2$— |
| $(CH_3)_3C$ | H | H | —$CH_2$— |
| $CH_3(CH_2)_4$ | H | H | —$CH_2$— |
| $CH_3(CH_2)_5$ | H | H | —$CH_2$— |
| CN | H | H | —$CH_2$— |
| $NO_2$ | H | H | —$CH_2$— |
| $CH_3C(=O)$ | H | H | —$CH_2$— |
| $CF_3C(=O)$ | H | H | —$CH_2$— |
| $CH_3OOC$ | H | H | —$CH_2$— |
| $CH_3CH_2OOC$ | H | H | —$CH_2$— |
| $(CH_3)_2CHOOC$ | H | H | —$CH_2$— |
| $CF_3CH_2OOC$ | H | H | —$CH_2$— |
| $(CH_3)_2NC(=O)$ | H | H | —$CH_2$— |
| $(CH_3CH_2)_2NC(=O)$ | H | H | —$CH_2$— |
| $(CH_3CH_2CH_2)_2NC(=O)$ | H | H | —$CH_2$— |
| $CH_3$ | $CH_3$ | H | —$CH_2$— |
| $CH_3CH_2$ | $CH_3$ | H | —$CH_2$— |
| $CH_3(CH_2)_2$ | $CH_3$ | H | —$CH_2$— |
| $(CH_3)_2CH$ | $CH_3$ | H | —$CH_2$— |
| $CH_3(CH_2)_3$ | $CH_3$ | H | —$CH_2$— |
| $(CH_3)_2CHCH_2$ | $CH_3$ | H | —$CH_2$— |
| $CH_3CH_2CH(CH_3)$ | $CH_3$ | H | —$CH_2$— |
| $(CH_3)_3C$ | $CH_3$ | H | —$CH_2$— |
| $CH_3(CH_2)_4$ | $CH_3$ | H | —$CH_2$— |
| $CH_3(CH_2)_5$ | $CH_3$ | H | —$CH_2$— |
| CN | $CH_3$ | H | —$CH_2$— |
| $NO_2$ | $CH_3$ | H | —$CH_2$— |
| $CH_3C(=O)$ | $CH_3$ | H | —$CH_2$— |
| $CF_3C(=O)$ | $CH_3$ | H | —$CH_2$— |
| $CH_3OOC$ | $CH_3$ | H | —$CH_2$— |
| $CH_3CH_2OOC$ | $CH_3$ | H | —$CH_2$— |
| $(CH_3)_2CHOOC$ | $CH_3$ | H | —$CH_2$— |
| $CF_3CH_2OOC$ | $CH_3$ | H | —$CH_2$— |
| $(CH_3)_2NC(=O)$ | $CH_3$ | H | —$CH_2$— |
| $(CH_3CH_2)_2NC(=O)$ | $CH_3$ | H | —$CH_2$— |
| $(CH_3CH_2CH_2)_2NC(=O)$ | $CH_3$ | H | —$CH_2$— |
| $CH_3CH_2$ | $CH_3CH_2$ | H | —$CH_2$— |
| $CF_3$ | $CF_3$ | H | —$CH_2$— |
| $CH_3$ | $CF_3$ | H | —$CH_2$— |
| H | $CF_3$ | H | —$CH_2$— |
| CN | CN | H | —$CH_2$— |
| $CH_3OOC$ | CN | H | —$CH_2$— |
| $CH_3CH_2OOC$ | CN | H | —$CH_2$— |
| $CH_3OOC$ | $CH_3C(=O)$ | H | —$CH_2$— |
| $CH_3CH_2OOC$ | $CH_3C(=O)$ | H | —$CH_2$— |
| $CH_3OOC$ | $CF_3C(=O)$ | H | —$CH_2$— |

TABLE 2-continued

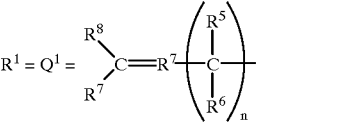

| R³ | R⁹ | R⁷ | $\left(\begin{array}{c}R^5\\|\\C\\|\\R^6\end{array}\right)_n$ |
|---|---|---|---|
| CH₃CH₂OOC | CF₃C(=O) | H | —CH₂— |
| CH₃OOC | CH₃OOC | H | —CH₂— |
| CH₃CH₂OOC | CH₃CH₂OOC | H | —CH₂— |
| H | H | Cl | —CH₂— |
| Cl | H | Cl | —CH₂— |
| Cl | Cl | Cl | —CH₂— |
| H | H | Br | —CH₂— |
| Br | H | Br | —CH₂— |
| Br | Br | Br | —CH₂— |
| Cl | Cl | CH₃ | —CH₂— |
| Br | Cl | CH₃ | —CH₂— |
| F | Cl | CH₃ | —CH₂— |
| CF₃ | Cl | CH₃ | —CH₂— |
| CF₂Cl | Cl | CH₃ | —CH₂— |
| CF₂Br | Cl | CH₃ | —CH₂— |
| H | Cl | CH₃ | —CH₂— |
| CH₃ | Cl | CH₃ | —CH₂— |
| CN | Cl | CH₃ | —CH₂— |
| NO₂ | Cl | CH₃ | —CH₂— |
| CH₃C(=O) | Cl | CH₃ | —CH₂— |
| CF₃C(=O) | Cl | CH₃ | —CH₂— |
| CH₃CH₂OOC | Cl | CH₃ | —CH₂— |
| CF₃CH₂OOC | Cl | CH₃ | —CH₂— |
| (CH₃)₂NC(=O) | Cl | CH₃ | —CH₂— |
| Br | Br | CH₃ | —CH₂— |
| F | Br | CH₃ | —CH₂— |
| CF₃ | Br | CH₃ | —CH₂— |
| CF₂Cl | Br | CH₃ | —CH₂— |
| CF₂Br | Br | CH₃ | —CH₂— |
| H | Br | CH₃ | —CH₂— |
| CH₃ | Br | CH₃ | —CH₂— |
| CN | Br | CH₃ | —CH₂— |
| NO₂ | Br | CH₃ | —CH₂— |
| CH₃C(=O) | Br | CH₃ | —CH₂— |
| CF₃C(=O) | Br | CH₃ | —CH₂— |
| CH₃CH₂OOC | Br | CH₃ | —CH₂— |
| CF₃CH₂OOC | Br | CH₃ | —CH₂— |
| (CH₃)₂NC(=O) | Br | CH₃ | —CH₂— |
| F | F | CH₃ | —CH₂— |
| CF₂Cl | F | CH₃ | —CH₂— |
| CF₂Br | F | CH₃ | —CH₂— |
| H | F | CH₃ | —CH₂— |
| CH₃ | F | CH₃ | —CH₂— |
| CH₃C(=O) | F | CH₃ | —CH₂— |
| CF₃C(=O) | F | CH₃ | —CH₂— |
| CH₃CH₂OOC | F | CH₃ | —CH₂— |
| CF₃CH₂OOC | F | CH₃ | —CH₂— |
| (CH₃)₂N | F | CH₃ | —CH₂— |
| H | H | CH₃ | —CH₂— |
| CH₃ | H | CH₃ | —CH₂— |
| CH₃CH₂ | H | CH₃ | —CH₂— |
| CN | H | CH₃ | —CH₂— |
| NO₂ | H | CH₃ | —CH₂— |
| CH₃C(=O) | H | CH₃ | —CH₂— |
| CF₃C(=O) | H | CH₃ | —CH₂— |
| CH₃CH₂OOC | H | CH₃ | —CH₂— |
| CF₃CH₂OOC | H | CH₃ | —CH₂— |
| (CH₃)₂NC(=O) | H | CH₃ | —CH₂— |
| CH₃ | CH₃ | CH₃ | —CH₂— |
| CN | CN | CH₃ | —CH₂— |
| CH₃OOC | CN | CH₃ | —CH₂— |
| CH₃CH₂OOC | CN | CH₃ | —CH₂— |
| CH₃OOC | CH₃C(=O) | CH₃ | —CH₂— |
| CH₃CH₂OOC | CH₃C(=O) | CH₃ | —CH₂— |

TABLE 2-continued $$R^1 = Q^1 = \underset{R^7}{\overset{R^8}{C}}=R^7 \left(\underset{R^6}{\overset{R^5}{C}}\right)_n$$

$$\left(\underset{R^6}{\overset{R^5}{C}}\right)_n$$

| R³ | R⁹ | R⁷ | $\left(\underset{R^6}{\overset{R^5}{C}}\right)_n$ |
|---|---|---|---|
| CH₃OOC | CF₃C(=O) | CH₃ | —CH₂— |
| CH₃CH₂OOC | CF₃C(=O) | CH₃ | —CH₂— |
| CH₃OOC | CH₃OOC | CH₃ | —CH₂— |
| CH₃CH₂OOC | CH₃CH₂OOC | CH₃ | —CH₂— |
| Cl | Cl | CF₃ | —CH₂— |
| Br | Cl | CF₃ | —CH₂— |
| F | Cl | CF₃ | —CH₂— |
| CF₃ | Cl | CF₃ | —CH₂— |
| CF₂Cl | Cl | CF₃ | —CH₂— |
| CF₂Br | Cl | CF₃ | —CH₂— |
| H | Cl | CF₃ | —CH₂— |
| CH₃ | Cl | CF₃ | —CH₂— |
| CN | Cl | CF₃ | —CH₂— |
| NO₂ | Cl | CF₃ | —CH₂— |
| CH₃C(=O) | Cl | CF₃ | —CH₂— |
| CF₃C(=O) | Cl | CF₃ | —CH₂— |
| CH₃CH₂OOC | Cl | CF₃ | —CH₂— |
| CF₃CH₂OOC | Cl | CF₃ | —CH₂— |
| (CH₃)₂N | Cl | CF₃ | —CH₂— |
| Br | Br | CF₃ | —CH₂— |
| F | Br | CF₃ | —CH₂— |
| CF₃ | Br | CF₃ | —CH₂— |
| CF₂Cl | Br | CF₃ | —CH₂— |
| CF₂Br | Br | CF₃ | —CH₂— |
| H | Br | CF₃ | —CH₂— |
| CH₃ | Br | CF₃ | —CH₂— |
| CN | Br | CF₃ | —CH₂— |
| NO₂ | Br | CF₃ | —CH₂— |
| CH₃C(=O) | Br | CF₃ | —CH₂— |
| CF₃C(=O) | Br | CF₃ | —CH₂— |
| CH₃CH₂OOC | Br | CF₃ | —CH₂— |
| CF₃CH₂OOC | Br | CF₃ | —CH₂— |
| (CH₃)₂NC(=O) | Br | CF₃ | —CH₂— |
| F | F | CF₃ | —CH₂— |
| H | F | CF₃ | —CH₂— |
| CH₃ | F | CF₃ | —CH₂— |
| CH₃C(=O) | F | CF₃ | —CH₂— |
| CF₃C(=O) | F | CF₃ | —CH₂— |
| CH₃CH₂OOC | F | CF₃ | —CH₂— |
| CF₃CH₂OOC | F | CF₃ | —CH₂— |
| (CH₃)₂NC(=O) | F | CF₃ | —CH₂— |
| H | H | CF₃ | —CH₂— |
| CH₃ | H | CF₃ | —CH₂— |
| CH₃CH₂ | H | CF₃ | —CH₂— |
| CN | H | CF₃ | —CH₂— |
| NO₂ | H | CF₃ | —CH₂— |
| CH₃C(=O) | H | CF₃ | —CH₂— |
| CF₃C(=O) | H | CF₃ | —CH₂— |
| CH₃CH₂OOC | H | CF₃ | —CH₂— |
| CF₃CH₂OOC | H | CF₃ | —CH₂— |
| (CH₃)₂NC(=O) | H | CF₃ | —CH₂— |
| CH₃ | CH₃ | CF₃ | —CH₂— |
| CN | CN | CF₃ | —CH₂— |
| CH₃OOC | CN | CF₃ | —CH₂— |
| CH₃CH₂OOC | CN | CF₃ | —CH₂— |
| CH₃OOC | CH₃C(=O) | CF₃ | —CH₂— |
| CH₃CH₂OOC | CH₃C(=O) | CF₃ | —CH₂— |
| CH₃OOC | CF₃C(=O) | CF₃ | —CH₂— |
| CH₃CH₂OOC | CF₃C(=O) | CF₃ | —CH₂— |
| CH₃OOC | CH₃OOC | CF₃ | —CH₂— |
| CH₃CH₂OOC | CH₃CH₂OOC | CF₃ | —CH₂— |
| Cl | Cl | H | —(CH₂)₂— |
| Br | Cl | H | —(CH₂)₂— |
| F | Cl | H | —(CH₂)₂— |

TABLE 2-continued

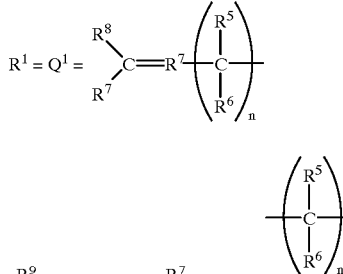

| $R^3$ | $R^9$ | $R^7$ | $-\left(\underset{R^6}{\overset{R^5}{\underset{|}{C}}}\right)_n-$ |
|---|---|---|---|
| $CF_3$ | Cl | H | $-(CH_2)_2-$ |
| $CF_2Cl$ | Cl | H | $-(CH_2)_2-$ |
| $CF_2Br$ | Cl | H | $-(CH_2)_2-$ |
| H | Cl | H | $-(CH_2)_2-$ |
| $CH_3$ | Cl | H | $-(CH_2)_2-$ |
| $CH_3CH_2$ | Cl | H | $-(CH_2)_2-$ |
| $CH_3(CH_2)_2$ | Cl | H | $-(CH_2)_2-$ |
| $(CH_3)_2CH$ | Cl | H | $-(CH_2)_2-$ |
| $CH_3(CH_2)_3$ | Cl | H | $-(CH_2)_2-$ |
| $(CH_3)_2CHCH_2$ | Cl | H | $-(CH_2)_2-$ |
| $CH_3CH_2CH(CH_3)$ | Cl | H | $-(CH_2)_2-$ |
| $(CH_3)_3C$ | Cl | H | $-(CH_2)_2-$ |
| $CH_3(CH_2)_4$ | Cl | H | $-(CH_2)_2-$ |
| $CH_3(CH_2)_5$ | Cl | H | $-(CH_2)_2-$ |
| CN | Cl | H | $-(CH_2)_2-$ |
| $NO_2$ | Cl | H | $-(CH_2)_2-$ |
| $CH_3C(=O)$ | Cl | H | $-(CH_2)_2-$ |
| $CF_3C(=O)$ | Cl | H | $-(CH_2)_2-$ |
| $CH_3OOC$ | Cl | H | $-(CH_2)_2-$ |
| $CH_3CH_2OOC$ | Cl | H | $-(CH_2)_2-$ |
| $(CH_3)_2CHOOC$ | Cl | H | $-(CH_2)_2-$ |
| $CF_3CH_2OOC$ | Cl | H | $-(CH_2)_2-$ |
| $(CH_3)_2NC(=O)$ | Cl | H | $-(CH_2)_2-$ |
| $(CH_3CH_2)_2NC(=O)$ | Cl | H | $-(CH_2)_2-$ |
| $(CH_3CH_2CH_2)_2NC(=O)$ | Cl | H | $-(CH_2)_2-$ |
| Br | Br | H | $-(CH_2)_2-$ |
| F | Br | H | $-(CH_2)_2-$ |
| $CF_3$ | Br | H | $-(CH_2)_2-$ |
| $CF_2Cl$ | Br | H | $-(CH_2)_2-$ |
| $CF_2Br$ | Br | H | $-(CH_2)_2-$ |
| H | Br | H | $-(CH_2)_2-$ |
| $CH_3$ | Br | H | $-(CH_2)_2-$ |
| $CH_3CH_2$ | Br | H | $-(CH_2)_2-$ |
| $CH_3(CH_2)_2$ | Br | H | $-(CH_2)_2-$ |
| $(CH_3)_2CH_2$ | Br | H | $-(CH_2)_2-$ |
| $CH_3(CH_2)_3$ | Br | H | $-(CH_2)_2-$ |
| $(CH_3)_2CHCH_2$ | Br | H | $-(CH_2)_2-$ |
| $CH_3CH_2CH(CH_3)$ | Br | H | $-(CH_2)_2-$ |
| $(CH_3)_3C$ | Br | H | $-(CH_2)_2-$ |
| $CH_3(CH_2)_4$ | Br | H | $-(CH_2)_2-$ |
| $CH_3(CH_2)_5$ | Br | H | $-(CH_2)_2-$ |
| CN | Br | H | $-(CH_2)_2-$ |
| $NO_2$ | Br | H | $-(CH_2)_2-$ |
| $CH_3C(=O)$ | Br | H | $-(CH_2)_2-$ |
| $CF_3C(=O)$ | Br | H | $-(CH_2)_2-$ |
| $CH_3OOC$ | Br | H | $-(CH_2)_2-$ |
| $CH_3CH_2OOC$ | Br | H | $-(CH_2)_2-$ |
| $(CH_3)_2CHOOC$ | Br | H | $-(CH_2)_2-$ |
| $CF_3CH_2OOC$ | Br | H | $-(CH_2)_2-$ |
| $(CH_3)_2NC(=O)$ | Br | H | $-(CH_2)_2-$ |
| $(CH_3CH_2)_2NC(=O)$ | Br | H | $-(CH_2)_2-$ |
| $(CH_3CH_2CH_2)_2NC(=O)$ | Br | H | $-(CH_2)_2-$ |
| F | F | H | $-(CH_2)_2-$ |
| $CF_3$ | F | H | $-(CH_2)_2-$ |
| $CF_2Cl$ | F | H | $-(CH_2)_2-$ |
| $CF_2Br$ | F | H | $-(CH_2)_2-$ |
| H | F | H | $-(CH_2)_2-$ |
| $CH_3$ | F | H | $-(CH_2)_2-$ |
| $CH_3CH_2$ | F | H | $-(CH_2)_2-$ |
| $CH_3C(=O)$ | F | H | $-(CH_2)_2-$ |
| $CF_3C(=O)$ | F | H | $-(CH_2)_2-$ |
| $CH_3OOC$ | F | H | $-(CH_2)_2-$ |
| $CH_3CH_2OOC$ | F | H | $-(CH_2)_2-$ |
| $(CH_3)_2NC(=O)$ | F | H | $-(CH_2)_2-$ |

TABLE 2-continued

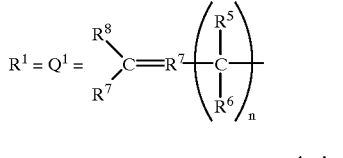

| R³ | R⁹ | R⁷ | $\left(\begin{array}{c}R^5\\|\\C\\|\\R^6\end{array}\right)_n$ |
|---|---|---|---|
| H | H | H | —(CH$_2$)$_2$— |
| CH$_3$ | H | H | —(CH$_2$)$_2$— |
| CH$_3$CH$_2$ | H | H | —(CH$_2$)$_2$— |
| CH$_3$(CH$_2$)$_2$ | H | H | —(CH$_2$)$_2$— |
| (CH$_3$)$_2$CH$_2$ | H | H | —(CH$_2$)$_2$— |
| CH$_3$(CH$_2$)$_3$ | H | H | —(CH$_2$)$_2$— |
| (CH$_3$)$_2$CHCH$_2$ | H | H | —(CH$_2$)$_2$— |
| CH$_3$CH$_2$CH(CH$_3$) | H | H | —(CH$_2$)$_2$— |
| (CH$_3$)$_3$C | H | H | —(CH$_2$)$_2$— |
| CH$_3$(CH$_2$)$_4$ | H | H | —(CH$_2$)$_2$— |
| CH$_3$(CH$_2$)$_5$ | H | H | —(CH$_2$)$_2$— |
| CN | H | H | —(CH$_2$)$_2$— |
| NO$_2$ | H | H | —(CH$_2$)$_2$— |
| CH$_3$C(=O) | H | H | —(CH$_2$)$_2$— |
| CF$_3$C(=O) | H | H | —(CH$_2$)$_2$— |
| CH$_3$OOC | H | H | —(CH$_2$)$_2$— |
| CH$_3$CH$_2$OOC | H | H | —(CH$_2$)$_2$— |
| (CH$_3$)$_2$CHOOC | H | H | —(CH$_2$)$_2$— |
| CF$_3$CH$_2$OOC | H | H | —(CH$_2$)$_2$— |
| (CH$_3$)$_2$NC(=O) | H | H | —(CH$_2$)$_2$— |
| (CH$_3$CH$_2$)$_2$NC(=O) | H | H | —(CH$_2$)$_2$— |
| (CH$_3$CH$_2$CH$_2$)$_2$NC(=O) | H | H | —(CH$_2$)$_2$— |
| CH$_3$ | CH$_3$ | H | —(CH$_2$)$_2$— |
| CH$_3$CH$_2$ | CH$_3$ | H | —(CH$_2$)$_2$— |
| CH$_3$(CH$_2$)$_2$ | CH$_3$ | H | —(CH$_2$)$_2$— |
| (CH$_3$)$_2$CH | CH$_3$ | H | —(CH$_2$)$_2$— |
| CH$_3$(CH$_2$)$_3$ | CH$_3$ | H | —(CH$_2$)$_2$— |
| (CH$_3$)$_2$CHCH$_2$ | CH$_3$ | H | —(CH$_2$)$_2$— |
| CH$_3$CH$_2$CH(CH$_3$) | CH$_3$ | H | —(CH$_2$)$_2$— |
| (CH$_3$)$_3$C | CH$_3$ | H | —(CH$_2$)$_2$— |
| CH$_3$(CH$_2$)$_4$ | CH$_3$ | H | —(CH$_2$)$_2$— |
| CH$_3$(CH$_2$)$_5$ | CH$_3$ | H | —(CH$_2$)$_2$— |
| CN | CH$_3$ | H | —(CH$_2$)$_2$— |
| NO$_2$ | CH$_3$ | H | —(CH$_2$)$_2$— |
| CH$_3$C(=O) | CH$_3$ | H | —(CH$_2$)$_2$— |
| CF$_3$C(=O) | CH$_3$ | H | —(CH$_2$)$_2$— |
| CH$_3$OOC | CH$_3$ | H | —(CH$_2$)$_2$— |
| CH$_3$CH$_2$OOC | CH$_3$ | H | —(CH$_2$)$_2$— |
| (CH$_3$)$_2$CHOOC | CH$_3$ | H | —(CH$_2$)$_2$— |
| CF$_3$CH$_2$OOC | CH$_3$ | H | —(CH$_2$)$_2$— |
| (CH$_3$)$_2$NC(=O) | CH$_3$ | H | —(CH$_2$)$_2$— |
| (CH$_3$CH$_2$)$_2$NC(=O) | CH$_3$ | H | —(CH$_2$)$_2$— |
| (CH$_3$CH$_2$CH$_2$)$_2$NC(=O) | CH$_3$ | H | —(CH$_2$)$_2$— |
| CH$_3$CH$_2$ | CH$_3$CH$_2$ | H | —(CH$_2$)$_2$— |
| CF$_3$ | CF$_3$ | H | —(CH$_2$)$_2$— |
| CH$_3$ | CF$_3$ | H | —(CH$_2$)$_2$— |
| H | CF$_3$ | H | —(CH$_2$)$_2$— |
| CN | CN | H | —(CH$_2$)$_2$— |
| CH$_3$OOC | CN | H | —(CH$_2$)$_2$— |
| CH$_3$CH$_2$OOC | CN | H | —(CH$_2$)$_2$— |
| CH$_3$OOC | CH$_3$C(=O) | H | —(CH$_2$)$_2$— |
| CH$_3$CH$_2$OOC | CH$_3$C(=O) | H | —(CH$_2$)$_2$— |
| CH$_3$OOC | CF$_3$C(=O) | H | —(CH$_2$)$_2$— |
| CH$_3$CH$_2$OOC | CF$_3$C(=O) | H | —(CH$_2$)$_2$— |
| CH$_3$OOC | CH$_3$OOC | H | —(CH$_2$)$_2$— |
| CH$_3$CH$_2$OOC | CH$_3$CH$_2$OOC | H | —(CH$_2$)$_2$— |
| Cl | Cl | H | —(CH$_2$)$_3$— |
| Br | Cl | H | —(CH$_2$)$_3$— |
| F | Cl | H | —(CH$_2$)$_3$— |
| CF$_2$ | Cl | H | —(CH$_2$)$_3$— |
| CF$_2$Cl | Cl | H | —(CH$_2$)$_3$— |
| CF$_2$Br | Cl | H | —(CH$_2$)$_3$— |
| H | Cl | H | —(CH$_2$)$_3$— |
| CH$_3$ | Cl | H | —(CH$_2$)$_3$— |

TABLE 2-continued $$R^1 = Q^1 = \begin{matrix} R^8 \\ \diagdown \\ R^7 \end{matrix} C = R^7 {\left(\begin{matrix} R^5 \\ | \\ C \\ | \\ R^6 \end{matrix}\right)}_n$$

| R³ | R⁹ | R⁷ | $\left(\begin{matrix} R^5 \\ \| \\ C \\ \| \\ R^6 \end{matrix}\right)_n$ |
|---|---|---|---|
| CH₃CH₂ | Cl | H | —(CH₂)₃— |
| CN | Cl | H | —(CH₂)₃— |
| NO₂ | Cl | H | —(CH₂)₃— |
| CH₃C(=O) | Cl | H | —(CH₂)₃— |
| CF₃C(=O) | Cl | H | —(CH₂)₃— |
| CH₃CH₂OOC | Cl | H | —(CH₂)₃— |
| CF₃CH₂OOC | Cl | H | —(CH₂)₃— |
| (CH₃)₂NC(=O) | Cl | H | —(CH₂)₃— |
| Br | Br | H | —(CH₂)₃— |
| F | Br | H | —(CH₂)₃— |
| CF₃ | Br | H | —(CH₂)₃— |
| CF₂Cl | Br | H | —(CH₂)₃— |
| CF₂Br | Br | H | —(CH₂)₃— |
| H | Br | H | —(CH₂)₃— |
| CH₃ | Br | H | —(CH₂)₃— |
| CH₃CH₂ | Br | H | —(CH₂)₃— |
| CN | Br | H | —(CH₂)₃— |
| NO₂ | Br | H | —(CH₂)₃— |
| CH₃C(=O) | Br | H | —(CH₂)₃— |
| CF₃C(=O) | Br | H | —(CH₂)₃— |
| CH₃CH₂OOC | Br | H | —(CH₂)₃— |
| CH₃CH₂OOC | Br | H | —(CH₂)₃— |
| (CH₃)₂NC(=O) | Br | H | —(CH₂)₃— |
| F | F | H | —(CH₂)₃— |
| CF₃ | F | H | —(CH₂)₃— |
| CF₂Cl | F | H | —(CH₂)₃— |
| CF₂Br | F | H | —(CH₂)₃— |
| H | F | H | —(CH₂)₃— |
| CH₃ | F | H | —(CH₂)₃— |
| CH₃CH₂ | F | H | —(CH₂)₃— |
| CH₃C(=O) | F | H | —(CH₂)₃— |
| CF₃C(=O) | F | H | —(CH₂)₃— |
| CH₃CH₂OOC | F | H | —(CH₂)₃— |
| CH₃CH₂OOC | F | H | —(CH₂)₃— |
| (CH₃)₂NC(=O) | F | H | —(CH₂)₃— |
| H | H | H | —(CH₂)₃— |
| CH₃ | H | H | —(CH₂)₃— |
| CH₃CH₂ | H | H | —(CH₂)₃— |
| CH₃(CH₂)₂ | H | H | —(CH₂)₃— |
| (CH₃)₂CH | H | H | —(CH₂)₃— |
| CH₃(CH₂)₃ | H | H | —(CH₂)₃— |
| (CH₃)₂CHCH₂ | H | H | —(CH₂)₃— |
| CH₃CH₂CH(CH₃) | H | H | —(CH₂)₃— |
| (CH₃)₃C | H | H | —(CH₂)₃— |
| CH₃(CH₂)₄ | H | H | —(CH₂)₃— |
| CH₃(CH₂)₅ | H | H | —(CH₂)₃— |
| CN | H | H | —(CH₂)₃— |
| NO₂ | H | H | —(CH₂)₃— |
| CH₃C(=O) | H | H | —(CH₂)₃— |
| CF₃C(=O) | H | H | —(CH₂)₃— |
| CH₃OOC | H | H | —(CH₂)₃— |
| CH₃CH₂OOC | H | H | —(CH₂)₃— |
| (CH₃)₂CHOOC | H | H | —(CH₂)₃— |
| CF₃CH₂OOC | H | H | —(CH₂)₃— |
| (CH₃)₂NC(=O) | H | H | —(CH₂)₃— |
| (CH₃CH₂)₂NC(=O) | H | H | —(CH₂)₃— |
| (CH₃CH₂CH₂)₂NC(=O) | H | H | —(CH₂)₃— |
| CH₃ | CH₃ | H | —(CH₂)₃— |
| CH₃CH₂ | CH₃ | H | —(CH₂)₃— |
| CN | CH₃ | H | —(CH₂)₃— |
| NO₂ | CH₃ | H | —(CH₂)₃— |
| CH₃C(=O) | CH₃ | H | —(CH₂)₃— |
| CF₃C(=O) | CH₃ | H | —(CH₂)₃— |
| CH₃OOC | CH₃ | H | —(CH₂)₃— |

TABLE 2-continued

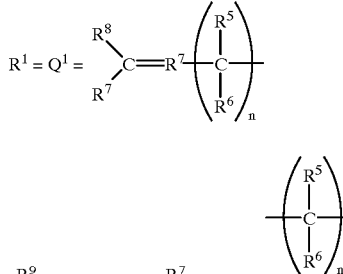

| R³ | R⁹ | R⁷ | $\left(\begin{array}{c}R^5\\|\\-C-\\|\\R^6\end{array}\right)_n$ |
|---|---|---|---|
| CH₃CH₂OOC | CH₃ | H | —(CH₂)₃— |
| (CH₃)₂CHOOC | CH₃ | H | —(CH₂)₃— |
| CF₃CH₂OOC | CH₃ | H | —(CH₂)₃— |
| (CH₃)₂NC(=O) | CH₃ | H | —(CH₂)₃— |
| (CH₃CH₂)₂NC(=O) | CH₃ | H | —(CH₂)₃— |
| (CH₃CH₂CH₂)₂NC(=O) | CH₃ | H | —(CH₂)₃— |
| CH₃CH₂ | CH₃CH₂ | H | —(CH₂)₃— |
| CF₃ | CF₃ | H | —(CH₂)₃— |
| CH₃ | CF₃ | H | —(CH₂)₃— |
| H | CF₃ | H | —(CH₂)₃— |
| CN | CN | H | —(CH₂)₃— |
| CH₃OOC | CN | H | —(CH₂)₃— |
| CH₃CH₂OOC | CN | H | —(CH₂)₃— |
| CH₃OOC | CH₃C(=O) | H | —(CH₂)₃— |
| CH₃CH₂OOC | CH₃C(=O) | H | —(CH₂)₃— |
| CH₃OOC | CF₃C(=O) | H | —(CH₂)₃— |
| CH₃CH₂OOC | CF₃C(=O) | H | —(CH₂)₃— |
| CH₃OOC | CH₃OOC | H | —(CH₂)₃— |
| CH₃CH₂OOC | CH₃CH₂OOC | H | —(CH₂)₃— |
| Cl | Cl | H | —(CH₂)₄— |
| Br | Br | H | —(CH₂)₄— |
| F | F | H | —(CH₂)₄— |
| Cl | CF₃ | H | —(CH₂)₄— |
| H | H | H | —(CH₂)₄— |
| Cl | CN | H | —(CH₂)₄— |
| Cl | CH₃CH₂OOC | H | —(CH₂)₄— |
| Cl | Cl | H | —CH(CH₃)CH₂— |
| Br | Br | H | —CH(CH₃)₂CH₂— |
| F | F | H | —CH(CH₃)₂CH₂— |
| Cl | CF₃ | H | —CH(CH₃)₂CH₂— |
| H | H | H | —CH(CH₃)₂CH₂— |
| Cl | CN | H | —CH(CH₃)₂CH₂— |
| Cl | CH₃CH₂OOC | H | —CH(CH₃)₂CH₂— |
| Cl | Cl | H | —C(CH₃)₂CH₂— |
| Br | Br | H | —C(CH₃)₂CH₂— |
| F | F | H | —C(CH₃)₂CH₂— |
| Cl | CF₃ | H | —C(CH₃)₂CH₂— |
| H | H | H | —C(CH₃)₂CH₂— |
| Cl | CN | H | —C(CH₃)₂CH₂— |
| Cl | CH₃CH₂OOC | H | —C(CH₃)₂CH₂— |
| Cl | Cl | H | —CH(CH₃)— |
| Br | Br | H | —CH(CH₃)— |
| F | F | H | —CH(CH₃)— |
| Cl | CF₃ | H | —CH(CH₃)— |
| H | H | H | —CH(CH₃)— |
| Cl | CN | H | —CH(CH₃)— |
| Cl | CH₃CH₂OOC | H | —CH(CH₃)— |
| Cl | Cl | H | —C(CH₂CH₃)— |
| Br | Br | H | —C(CH₂CH₃)— |
| F | F | H | —C(CH₂CH₃)— |
| Cl | CF₃ | H | —C(CH₂CH₃)— |
| H | H | H | —C(CH₂CH₃)— |
| Cl | CN | H | —C(CH₂CH₃)— |
| Cl | CH₃CH₂OOC | H | —C(CH₂CH₃)— |
| Cl | Cl | H | —CH(CH₂CH₂CH₃)— |
| Br | Br | H | —CH(CH₂CH₂CH₃)— |
| F | F | H | —CH(CH₂CH₂CH₃)— |
| Cl | CF₃ | H | —CH(CH₂CH₂CH₃)— |
| H | H | H | —CH(CH₂CH₂CH₃)— |
| Cl | CN | H | —CH(CH₂CH₂CH₃)— |
| Cl | CH₃CH₂OOC | H | —CH(CH₂CH₂CH₃)— |
| Cl | Cl | H | —CH(CH₂CH(CH₃)₂)— |
| Br | Br | H | —CH(CH₂CH(CH₃)₂)— |
| F | F | H | —CH(CH₂CH(CH₃)₂)— |

TABLE 2-continued

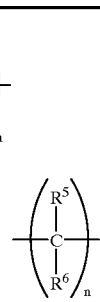

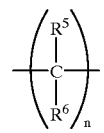

| R³ | R⁹ | R⁷ | $\left(\begin{array}{c}R^5\\|\\C\\|\\R^6\end{array}\right)_n$ |
|---|---|---|---|
| Cl | CF₃ | H | —CH(CH₂CH(CH₃)₂)— |
| H | H | H | —CH(CH₂CH(CH₃)₂)— |
| Cl | CN | H | —CH(CH₂CH(CH₃)₂)— |
| Cl | CH₃CH₂OOC | H | —CH(CH₂CH(CH₃)₂)— |
| Cl | Cl | CH₃ | —(CH₂)₂— |
| Br | Br | CH₃ | —(CH₂)₂— |
| F | F | CH₃ | —(CH₂)₂— |
| Cl | CF₃ | CH₃ | —(CH₂)₂— |
| H | H | CH₃ | —(CH₂)₂— |
| Cl | CN | CH₃ | —(CH₂)₂— |
| Cl | CH₃CH₂OOC | CH₃ | —(CH₂)₂— |
| Cl | Cl | CF₃CH₂ | —CH₂— |
| Br | Br | CF₃CH₂ | —CH₂— |
| F | F | CF₃CH₂ | —CH₂— |
| Cl | CF₃ | CF₃CH₂ | —CH₂— |
| H | H | CF₃CH₂ | —CH₂— |
| Cl | CN | CF₃CH₂ | —CH₂— |
| Cl | CH₃CH₂OOC | CF₃CH₂ | —CH₂— |
| Cl | Cl | CF₃CH₂ | —(CH₂)₂— |
| Br | Br | CF₃CH₂ | —(CH₂)₂— |
| F | F | CF₃CH₂ | —(CH₂)₂— |
| Cl | CF₃ | CF₃CH₂ | —(CH₂)₂— |
| H | H | CF₃CH₂ | —(CH₂)₂— |
| Cl | CN | CF₃CH₂ | —(CH₂)₂— |
| Cl | CH₃CH₂OOC | CF₃CH₂ | —(CH₂)₂— |

TABLE 3

$R^1 = Q^2 = R^8{-}C{\equiv}C{-}\left(\begin{array}{c}R^5\\|\\C\\|\\R^6\end{array}\right)_n{-}$

| R⁸ | $\left(\begin{array}{c}R^5\\|\\C\\|\\R^6\end{array}\right)_n$ |
|---|---|
| Cl | —CH₂— |
| Br | —CH₂— |
| F | —CH₂— |
| CF₃ | —CH₂— |
| CF₃CF₂ | —CH₂— |
| CF₃(CF₂)₂ | —CH₂— |
| CF₃(CF₂)₃ | —CH₂— |
| CF₃(CF₂)₅ | —CH₂— |
| CF₂Cl | —CH₂— |
| CF₂Br | —CH₂— |
| H | —CH₂— |
| CH₃ | —CH₂— |
| CH₃CH₂ | —CH₂— |
| CH₃(CH₂)₂ | —CH₂— |
| (CH₃)₂CH | —CH₂— |
| CH₃(CH₂)₃ | —CH₂— |
| (CH₃)₂CHCH₂ | —CH₂— |
| CH₃CH₂CH(CH₃) | —CH₂— |
| (CH₃)₃C | —CH₂— |
| CH₃(CH₂)₄ | —CH₂— |
| CH₃(CH₂)₅ | —CH₂— |
| CN | —CH₂— |
| NO₂ | —CH₂— |
| CH₃C(=O) | —CH₂— |
| CF₃C(=O) | —CH₂— |
| CH₃OOC | —CH₂— |
| CH₃CH₂OOC | —CH₂— |
| (CH₃)₂CHOOC | —CH₂— |
| CF₃CH₂OOC | —CH₂— |
| (CH₃)₂NC(=O) | —CH₂— |
| (CH₃CH₂)₂NC(=O) | —CH₂— |
| (CH₃CH₂CH₂)₂NC(=O) | —CH₂— |
| Cl | —(CH₂)₂— |
| Br | —(CH₂)₂— |
| F | —(CH₂)₂— |
| CF₃ | —(CH₂)₂— |
| CF₂Cl | —(CH₂)₂— |
| CF₂Br | —(CH₂)₂— |

TABLE 3-continued $$R^1 = Q^2 = R^8—C\equiv C\left(\begin{array}{c}R^5\\|\\C\\|\\R^6\end{array}\right)_n$$

$$R^8\left(\begin{array}{c}R^5\\|\\C\\|\\R^6\end{array}\right)_n$$

| $R^8$ | |
|---|---|
| H | —(CH$_2$)$_2$— |
| CH$_3$ | —(CH$_2$)$_2$— |
| CH$_3$CH$_2$ | —(CH$_2$)$_2$— |
| CN | —(CH$_2$)$_2$— |
| NO$_2$ | —(CH$_2$)$_2$— |
| CH$_3$C(=O) | —(CH$_2$)$_2$— |
| CF$_3$C(=O) | —(CH$_2$)$_2$— |
| CH$_3$CH$_2$OOC | —(CH$_2$)$_2$— |
| CF$_3$CH$_2$OOC | —(CH$_2$)$_2$— |
| (CH$_3$)$_2$NC(=O) | —(CH$_2$)$_2$— |
| H | —(CH$_2$)$_3$— |
| CH$_3$ | —(CH$_2$)$_3$— |
| Cl | —(CH$_2$)$_3$— |
| Br | —(CH$_2$)$_3$— |
| F | —(CH$_2$)$_3$— |
| CF$_3$ | —(CH$_2$)$_3$— |
| CN | —(CH$_2$)$_3$— |
| CH$_3$OOC | —(CH$_2$)$_3$— |
| CH$_3$CH$_2$OOC | —(CH$_2$)$_3$— |
| H | —(CH$_2$)$_4$— |
| CH$_3$ | —(CH$_2$)$_4$— |
| Cl | —(CH$_2$)$_4$— |
| Br | —(CH$_2$)$_4$— |
| F | —(CH$_2$)$_4$— |
| CF$_3$ | —(CH$_2$)$_4$— |
| CN | —(CH$_2$)$_4$— |
| CH$_3$OOC | —(CH$_2$)$_4$— |
| CH$_3$CH$_2$OOC | —(CH$_2$)$_4$— |
| H | —CH(CH$_3$)CH$_2$— |
| CH$_3$ | —CH(CH$_3$)CH$_2$— |
| Cl | —CH(CH$_3$)CH$_2$— |
| Br | —CH(CH$_3$)CH$_2$— |
| F | —CH(CH$_3$)CH$_2$— |
| CF$_3$ | —CH(CH$_3$)CH$_2$— |
| CN | —CH(CH$_3$)CH$_2$— |
| CH$_3$OOC | —CH(CH$_3$)CH$_2$— |
| CH$_3$CH$_2$OOC | —CH(CH$_3$)CH$_2$— |
| H | —CH(CH$_3$)— |
| CH$_3$ | —CH(CH$_3$)— |
| Cl | —CH(CH$_3$)— |
| Br | —CH(CH$_3$)— |
| F | —CH(CH$_3$)— |
| CF$_3$ | —CH(CH$_3$)— |
| CN | —CH(CH$_3$)— |
| CH$_3$OOC | —CH(CH$_3$)— |
| CH$_3$CH$_2$OOC | —CH(CH$_3$)— |
| H | —CH(CH$_2$CH$_3$)— |
| CH$_3$ | —CH(CH$_2$CH$_3$)— |
| Cl | —CH(CH$_2$CH$_3$)— |
| Br | —CH(CH$_2$CH$_3$)— |
| F | —CH(CH$_2$CH$_3$)— |
| CF$_3$ | —CH(CH$_2$CH$_3$)— |
| CN | —CH(CH$_2$CH$_3$)— |
| CH$_3$OOC | —CH(CH$_2$CH$_3$)— |
| CH$_3$CH$_2$OOC | —CH(CH$_2$CH$_3$)— |

The aldehyde compounds of the general formula [X], which are intermediates for the production of the present compounds, can be produced, for example, according to the following scheme 2:

SCHEME 2

[VII] + L—CH$_2$CH(OC$_2$H$_5$)$_2$

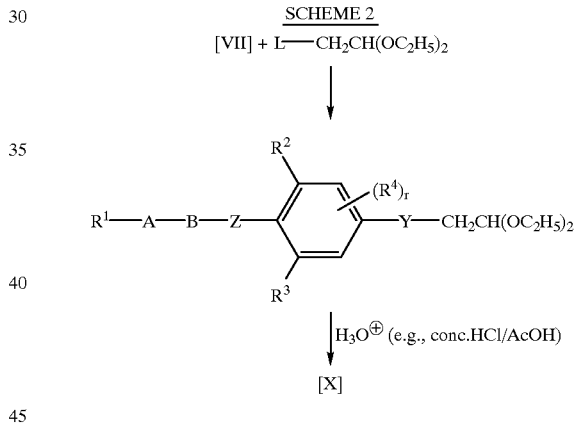

$\Big\downarrow$ H$_3$O$^\oplus$ (e.g., conc.HCl/AcOH)

[X]

wherein all the symbols are as defined above.

The compounds of the general formula [VII], which are intermediates for the production of the present compounds, can be produced, for example, according to the following schemes 3 to 9:

SCHEME 3

(when Y and Z are both oxygen)

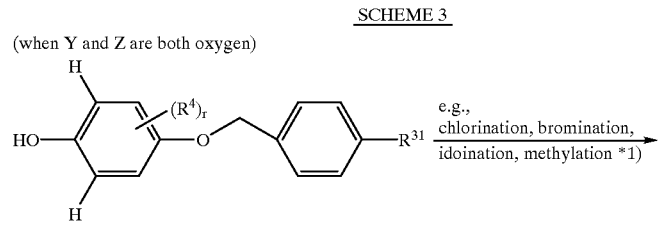

e.g., chlorination, bromination, idoination, methylation *1)

-continued
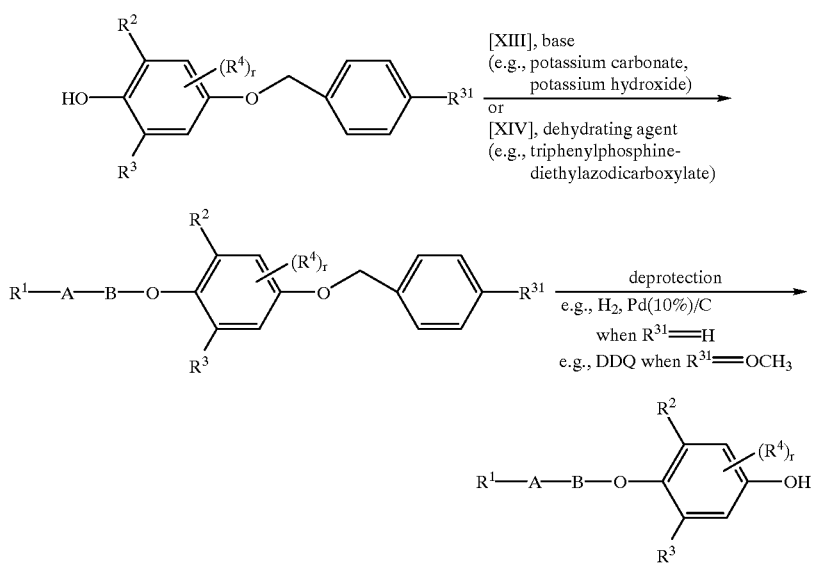
*1): e.g., Tetrahedron Lett., 889(1974)
SCHEME 4
(when Y and Z are both oxygen)
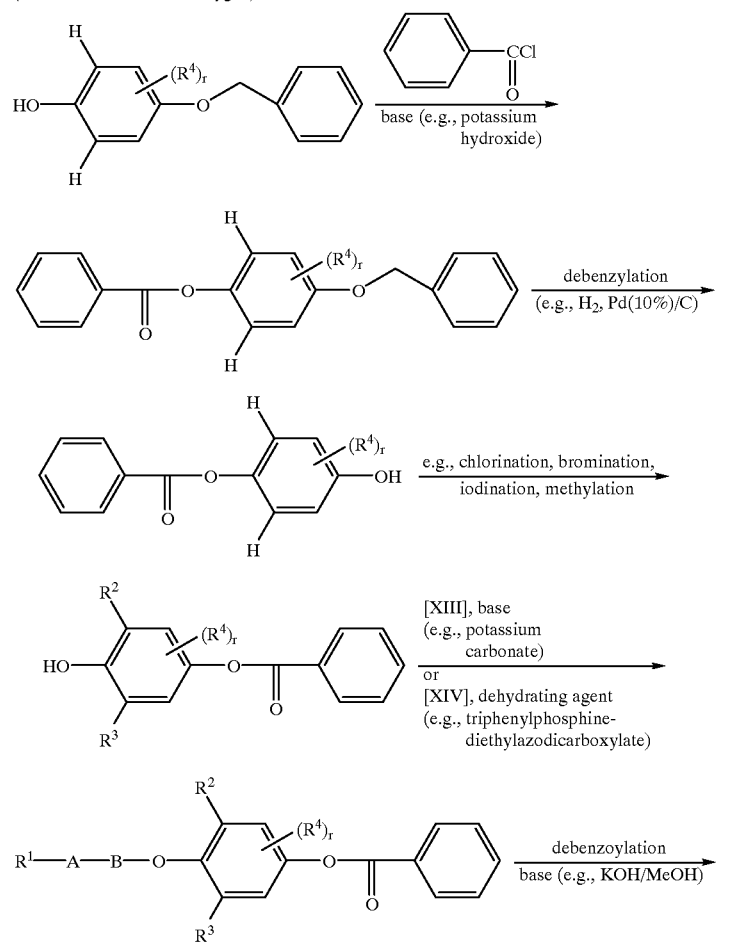

-continued
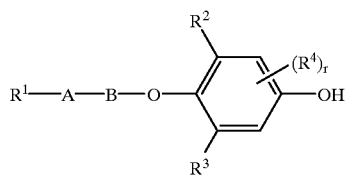
SCHEME 5
(Y and Z are both oxygen.)
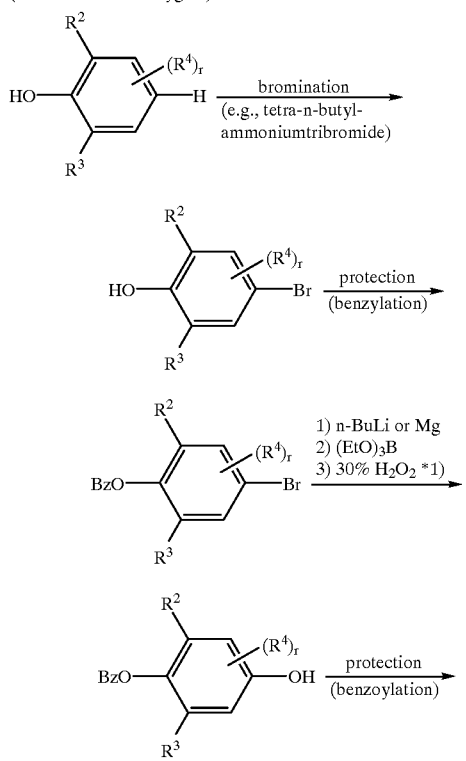
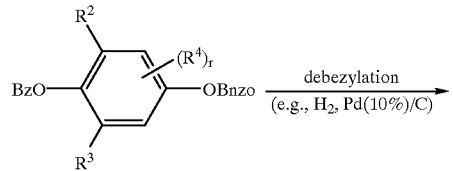
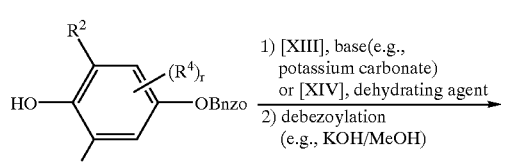
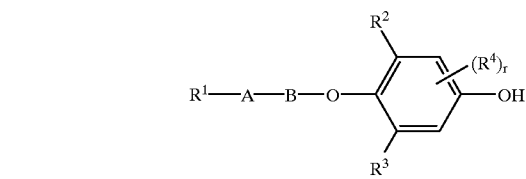
*1): J. Org. Chem., 22, 1001(1957)
SCHEME 6
(when Y and Z are not both oxygen)
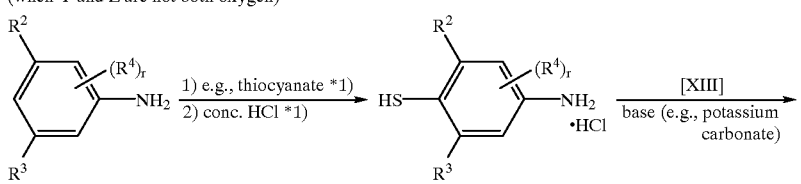

-continued
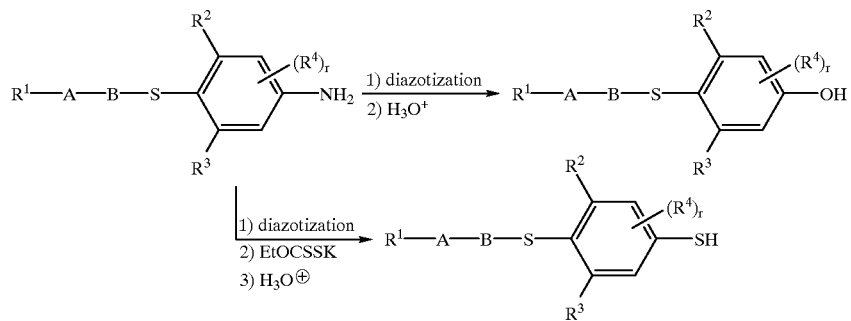
*1): JP 60-181067 A

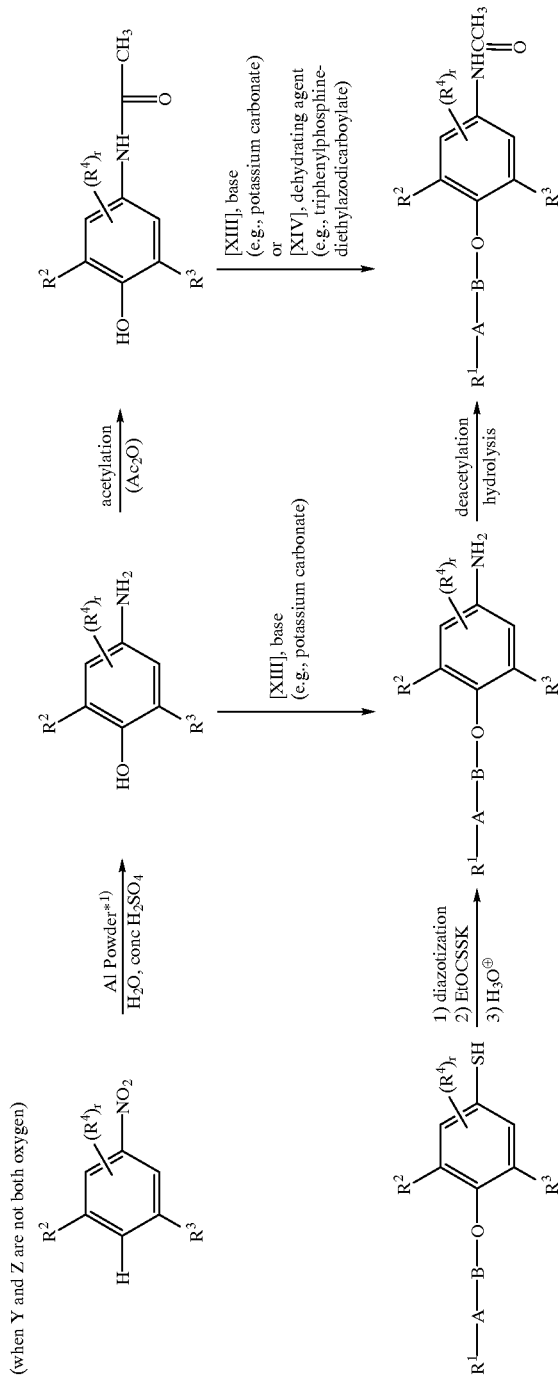

SCHEME 8
(when Y is oxygen)
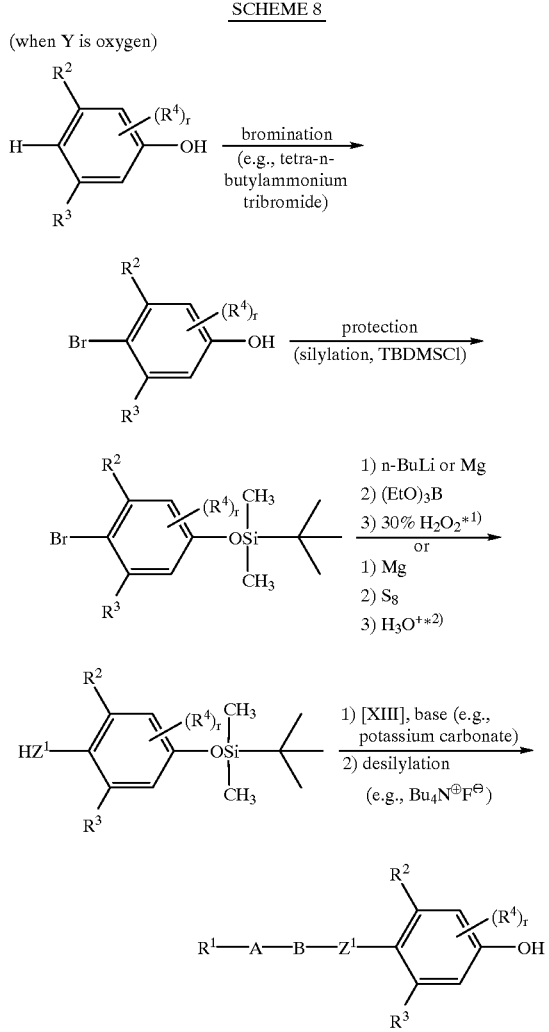
*1) J. Org. Chem., 22, 1001 (1957)
*2) Ber., 72, 594 (1939)
SCHEME 9
(when Y is oxygen)
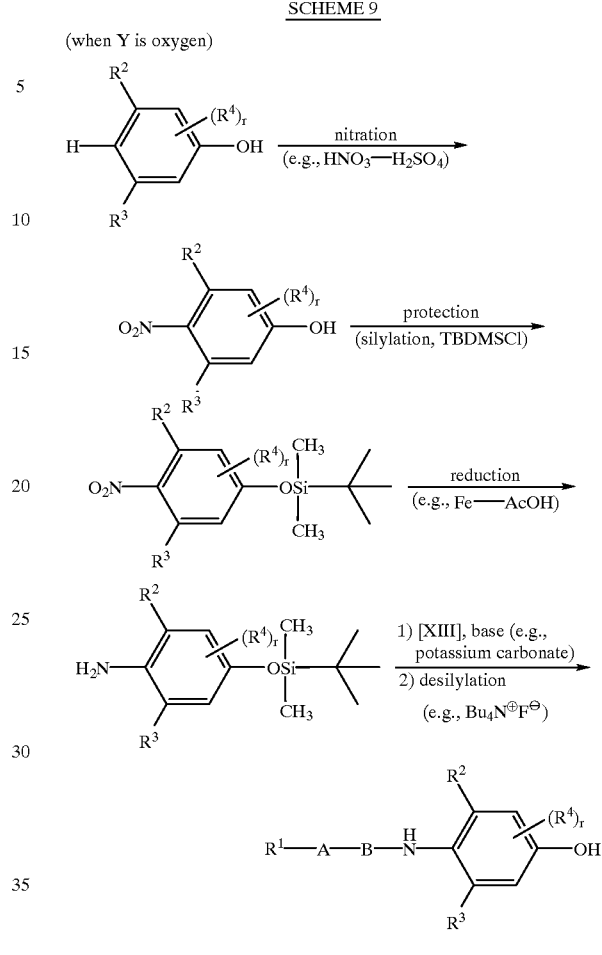
*1) J. Org. Chem., 22, 1001 (1957)
*2) Ber., 72, 594 (1939)
The compounds of the general formula [XII], which are intermediates for the production of the present compounds, can be produced, for example, according to the following scheme 10:
SCHEME 10
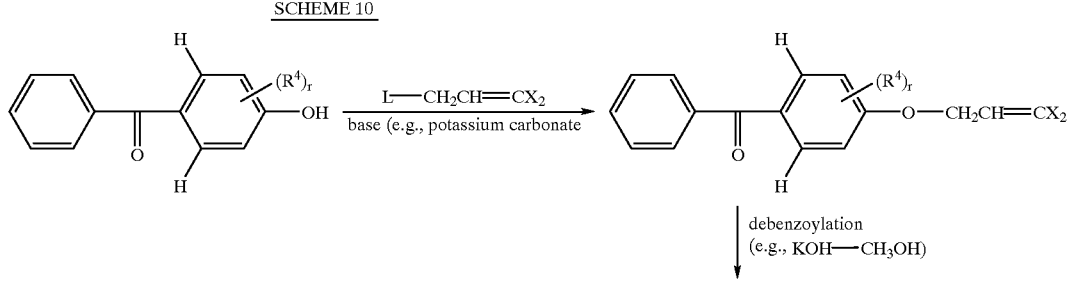

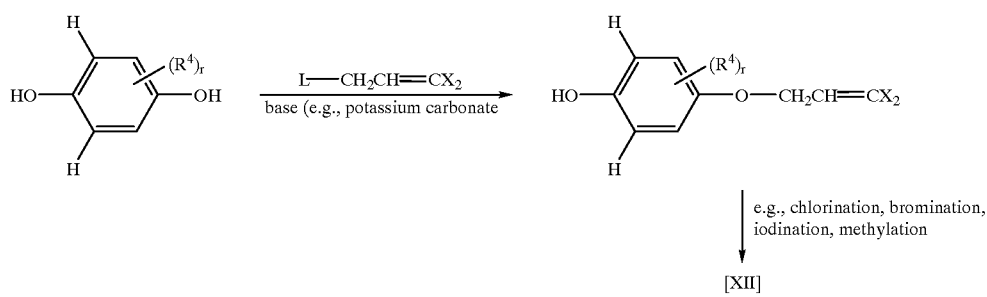
The compounds of the general formula [XV] or [XVII], which are intermediates for the production of the present compounds, can be produced, for example, according to the following scheme 11:
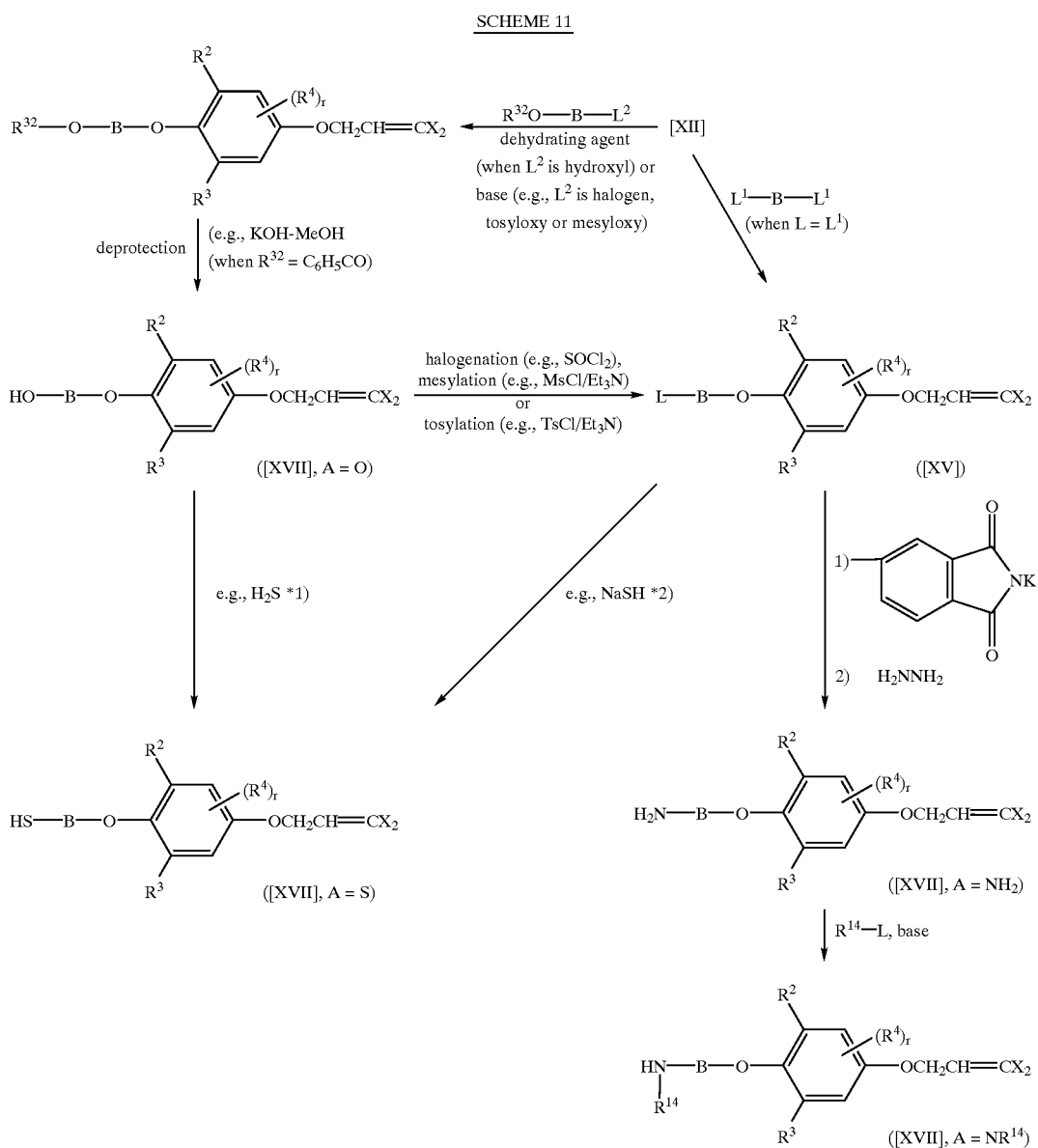

*1) e.g., R. L. Kramer et al., J. Am. Chem. Soc., 43,880 (1921)
*2) e.g., L. M. Ellis et al., J. Am. Chem. Soc., 54,1674 (1932)

The halide compounds of the general formula [VIII] and the alcohol compounds of the general formula [IX], which are intermediates for the production of the present compounds, can be obtained from commercial sources or can be produced according to the following scheme 12:

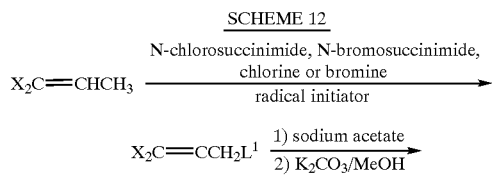

-continued mesyl chloride or
$$X_2C{=\!\!=}CCH_2OH \xrightarrow[\text{base}]{\text{tosyl chloride}} X_2C{=\!\!=}CCH_2L^3$$

wherein $L^1$ is chlorine or bromine, $L^3$ is mesyloxy or tosyloxy, and X is as defined above.

The compounds of the general formula [XIII], [XIV] and [XVIII] which are intermediates for the production of the present compounds, can be produced, for example, according to the following scheme 13 or 14:

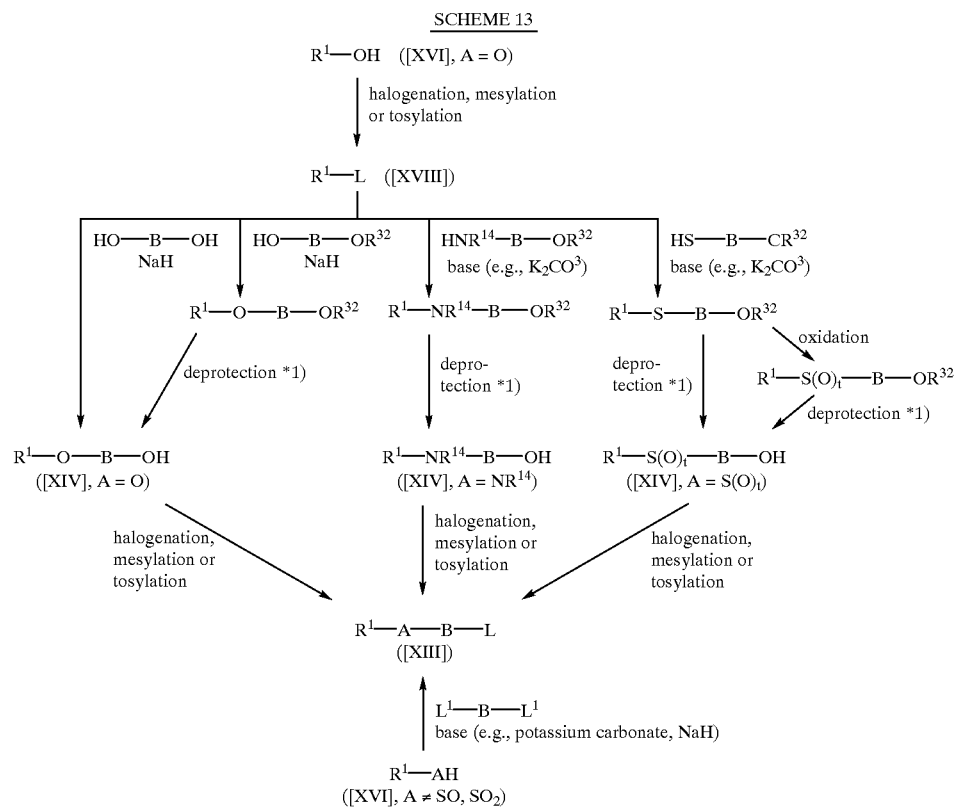

*1) e.g., KOH-MeOH when $R^{32}$ is $C_6H_5CO$

SCHEME 14

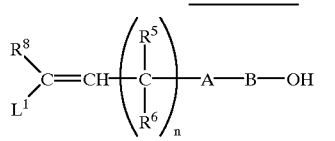

([XIV], R¹ = Q¹, R⁷ = H, R⁹ = L¹)

↓ NaOCH₃/DMF

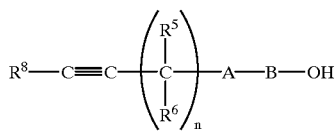

([XIV], R¹ = Q²)

wherein all the symbols are as defined above.

The carbonyl compounds of the general formula [XXI] (including the compounds of the general formula [VI]), the compounds of the general formula [XXX], carboxylic acid compounds of the general formula [XXXIII] and the compounds of the general formula [XXXX], which are intermediates for the production of the present compounds, can be produced, for example, according to the following scheme 15 or 16:

SCHEME 15
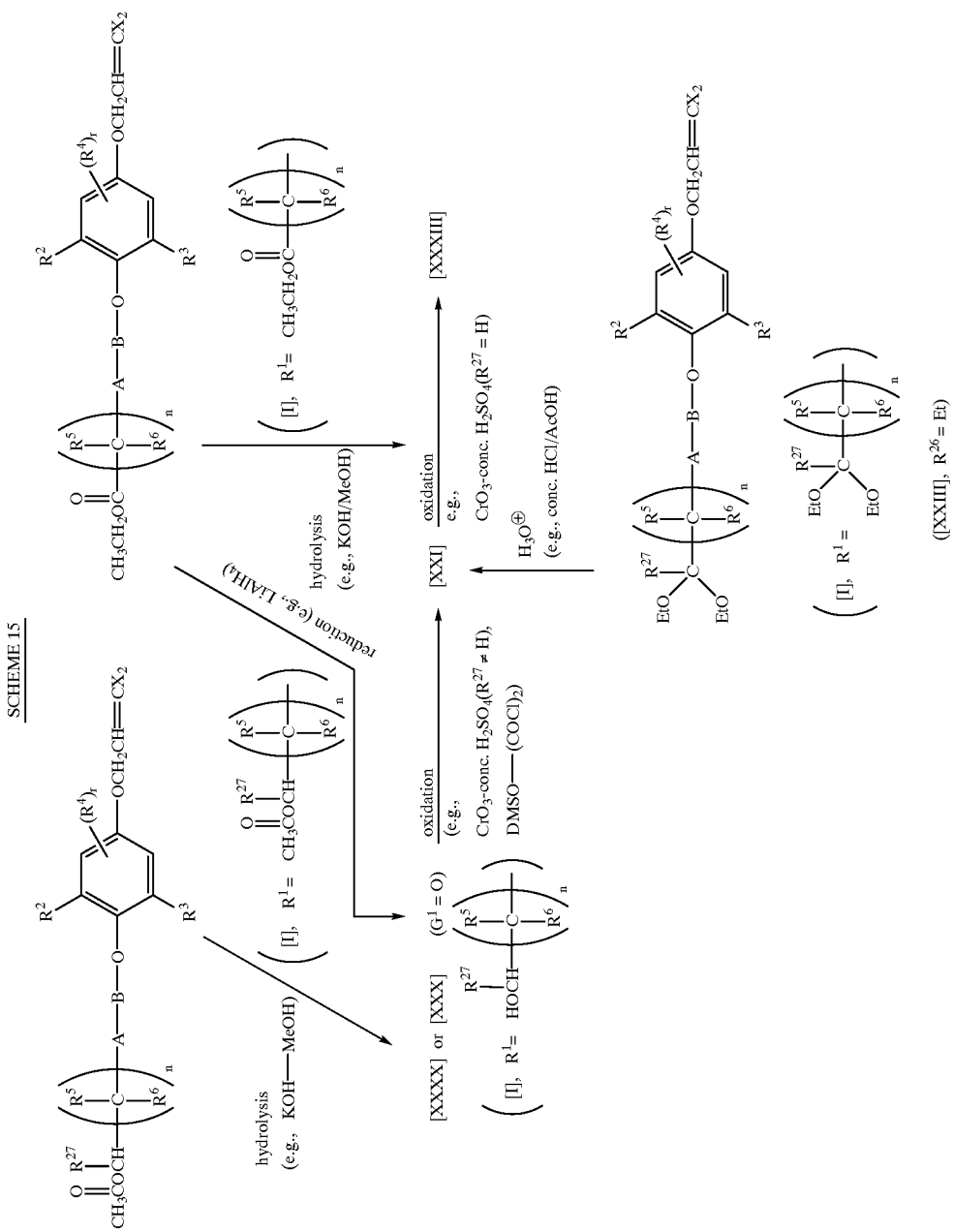

SCHEME 16

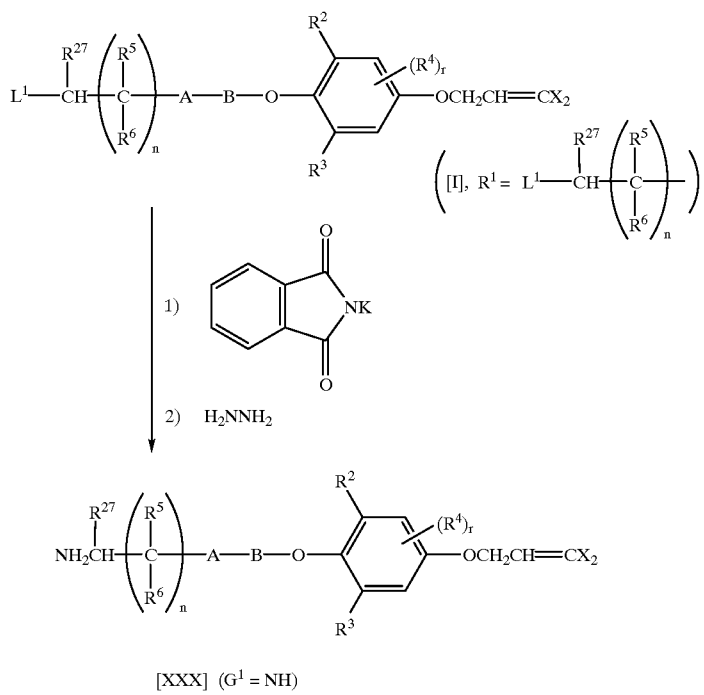

[XXX] (G¹ = NH)

wherein all the symbols are as defined above.

The compounds of the general formula [XXVI] or [XXVII], which are intermediates for the production of the present compounds, can be obtained from commercial sources or can be produced according to the following scheme 17:

SCHEME 17

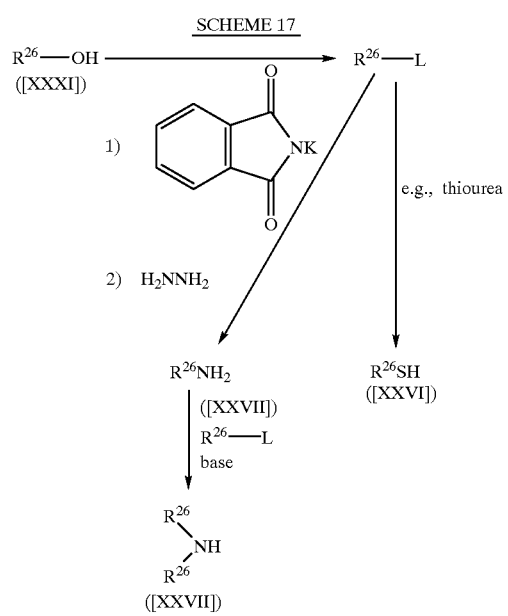

wherein all the symbols are as defined above.

The compounds of the general formula [XXXVIII] can be produced, for example, according to the following scheme 18:

SCHEME 18

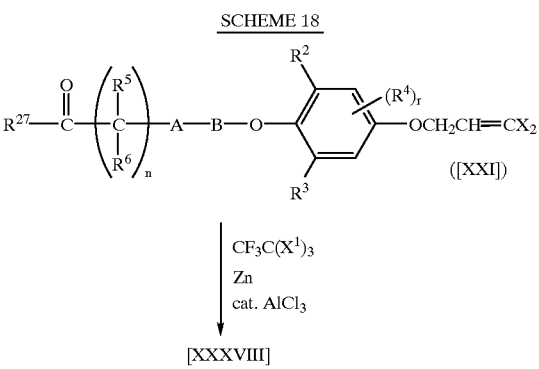

wherein all the symbols are as defined above.

The present compounds are satisfactorily effective for the control of various noxious insects, mites and ticks, examples of which are as follows:

Hemiptera:
Delphacidae such as *Laodelphax striatellus, Nilaparvata lugens* and *Sogatella furcifera,* Deltocephalidae such as *Nephotettix cincticeps* and *Nephotettix virescens,* Aphididae, Pentatomidae, Aleyrodidae, Coccidae, Tingidae, Psyllidae , etc.

Lepidoptera:
Pyralidae such as *Chilo suppressalis, Cnaphalocrocis medinalis, Ostrinia nubilalis, Parapediasia teterrella, Notarcha derogata* and *Plodia interpunctella,* Noctuidae such as *Spodoptera litura, Spodoptera exigua, Spodoptera littoralis, Pseudaletia separata, Mamestra brassicae, Agrotis ipsilon,* Trichoplusia spp., Heliothis spp., Helicoverpa spp. and Earias spp., Pieridae such as Pieris *rapae crucivora,* Tortricidae such as Adoxophyes spp., Carposinidae such as *Grapholita molesta, Cydia pomonella* and *Carposina*

*niponensis,* Lyonetiidae such as Lyonetia spp., Lymantriidae such as Lymantria spp. and Euproctis spp., Yponomeutidae such as *Plutella xylostella,* Gelechiidae such as *Pectinophora gossypiella,* Arctiidae such as *Hyphantria cunea,* Tineidae such as *Tinea translucens* and *Tineola bisselliella,* etc.

Diptera:

Culex such as *Culex pipiens pallens* and *Cules tritaeniorhynchus,* Aedes such as *Aedes aegypti* and *Aedes albopictus,* Anopheles such as *Anophelinae sinensis,* Chironomidae, Muscidae such as Musca domestica and *Muscina stabulans,* Calliphoridae, Sarcophagidae, *Fannia canicularis,* Anthomyiidae such as *Delia platura* and *Delia antiqua,* Trypetidae, Drosophilidae, Psychodidae, Tabanidae, Simuliidae, Stomoxyinae, Agromyzidae, etc.

Coleoptera:

Diabrotica such as *Diabrotica virgifera* and *Diabrotica undecimpunctata,* Scarabaeidae such as *Anomala cuprea* and *Anomala rufocuprea,* Curculionidae such as *Sitophilus oryzae, Lissorhoptrus oryzophilus* and *Callosobruchus chinensis,* Tenebrionidae such as *Tenebrio molitor* and *Tribolium castaneum,* Chrysomelidae such as *Phyllotreta striolata* and *Aulacophora femoralis,* Anobiidae, Epilachna spp. such as *Epilachna vigintioctopunctata,* Lyctidae, Bostrychidae, Cerambycidae, Paederusfuscipes, etc.

Dictyoptera:

*Blattella germanica, Periplaneta fuliginosa, Peroplaneta americana, Perilaneta brunnea, Blana orientalis,* etc.

Thysanoptera:

*Thrips palmi, Thrips hawaiiensis,* etc.

Hymenoptera:

Formicidae, Vespidae, Bethylidae, Tenthredinidae such as *Athalia rosae aponensis,* etc.

Orthoptera:

Gryllotalpidae, Acrididae, etc.

Siphonaptera:

*Purex irritans* etc.

Anoplura:

*Pediculus humanus capitis, Phthirus pubis,* etc.

Isoptera (termites):

*Reticulitermes speratus, Coptotermes formosanus,* etc.

Acarina:

plant parasitic Tetranychidae such as *Tetranychus uriticae, Panonychus citri, Tetranychus cinnabarinus* and *Panonychus ulmi,* Eriophyidae such as *Acaphylla theae,* and *Aculops pelekassi,* animal parasitic Ixodidae such as *Boophilus microphus,* house dust mites, etc.

The present compounds are also effective for the control of various noxious insects, mites and ticks having resistance to conventional insecticides and acaricides.

When the present compounds are used as active ingredients of insecticidal/acaricidal agents, they may be used as such without any addition of other ingredients. The present compounds are, however, usually formulated into dosage forms such as oil sprays, emulsifiable concentrates, wettable powders, flowable concentrates, granules, dusts, aerosols, fumigants (foggings) and poison baits. These dosage forms are usually prepared by mixing the present compounds with solid carriers, liquid carriers, gaseous carriers or baits, and if necessary, adding surfactants and other auxiliaries used for formulation.

Each of the dosage forms usually contains at least one of the present compounds as an active ingredient in an amount of 0.01% to 95% by weight.

Examples of the solid carrier to be used for formulation may include fine powder or granules of clay materials such as kaolin clay, diatomaceous earth, synthetic hydrated silicon oxide, bentonite, Fubasami clay and acid clay; various kinds of talc, ceramics and other inorganic minerals such as sericite, quartz, sulfur, active carbon, calcium carbonate and hydrated silica; and chemical fertilizers such as ammonium sulfate, ammonium phosphate, ammonium nitrate, urea and ammonium chloride.

Examples of the liquid carrier may include water; alcohols such as methanol and ethanol; ketones such as acetone and methyl ethyl ketone; aromatic hydrocarbons such as benzene, toluene, xylene, ethylbenzene and methylnaphthalene; aliphatic hydrocarbons such as hexane, cyclohexane, kerosine and gas oil; esters such as ethyl acetate and butyl acetate; nitriles such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane and carbon tetrachloride; dimethyl sulfoxide; and vegetable oils such as soybean oil and cottonseed oil.

Examples of the gaseous carrier or propellant may include flon gas, butane gas, LPG (liquefied petroleum gas), dimethyl ether and carbon dioxide.

Examples of the surfactant may include alkyl sulfates, alkyl sulfonates, alkyl arylsulfonates, alkyl aryl ethers and their polyoxyethylene derivatives, polyethylene glycol ethers, polyhydric alcohol esters and sugar alcohol derivatives.

Examples of the auxiliaries used for formulation, such as fixing agents or dispersing agents, may include casein, gelatin, polysaccharides such as starch, gum arabic, cellulose derivatives and alginic acid, lignin derivatives, bentonite, sugars, and synthetic water-soluble polymers such as polyvinyl alcohol, polyvinyl pyrrolidone and polyacrylic acid.

Examples of the stabilizer may include PAP (isopropyl acid phosphate), BHT (2,6-di-tert-butyl-4-methylphenol), BHA (mixtures of 2-tert-butyl-4-methoxyphenol and 3-tert-butyl-4-methoxyphenol), vegetable oils, mineral oils, surfactants, fatty acids and their esters.

Examples of the base material to be used in the poison baits may include bait materials such as grain powder, vegetable oils, sugars and crystalline cellulose; antioxidants such as dibutylhydroxytoluene and nordihydroguaiaretic acid; preservatives such as dehydroacetic acid; substances for preventing erroneous eating, such as red pepper powder, attractant flavors such as cheese flavor or onion flavor.

The dosage forms thus obtained are used as such or after diluted with water. The dosage forms may also be used in combination with other insecticides, nematocides, acaricides, bactericides, fungicides, herbicides, plant growth regulators, synergists, fertilizers, soil conditioners and/or animal feed under non-mixing conditions or pre-mixing conditions.

Examples of the insecticide, nematocide and/or acaricide which can be used may include organophosphorus compounds such as Fenitrothion [O,O-dimethyl O-(3-methyl-4-nitrophenyl)phosphorothioate], Fenthion [O,O-dimethyl O-(3-methyl-4-(methylthio)phenyl)phophorothioate], Diazinon [O,O-diethyl-O-2-isopropyl-6-methylpyrimidin-4-ylphosphorothioate], Chlorpyriphos [O,O-diethyl-O-3,5,6-trichloro-2-pyridylphosphorothioate], Acephate [O,S-dimethylacetylphosphoramidothioate], Methidathion [S-2,3-dihydro-5-methoxy-2-oxo-1,3,4-thiadiazol-3-ylmethyl O,O-dimethylphosphorodithioate], Disulfoton [O,O-diethyl S-2-ethylthioethylphosphorothioate], DDVP [2,2-dichlorovinyldimethylphosphate], Sulprofos [O-ethyl O-4-(methylthio)phenyl S-propyl phosphorodithioate], Cyanophos [O-4-cyanophenyl O,O-dimethylphosphorothioate], Dioxabenzofos [2-methoxy-4H-1,3,2-benzodioxaphosphinine-2-sulfide], Dimethoate [O,O-dimethyl-S-(N-methylcarbamoylmethyl)dithiophosphate], Phenthoate [ethyl 2-dimethoxyphosphinothioylthio(phenyl) acetate], Malathion [diethyl(dimethoxyphosphinothioylthio) succinate], Trichlorfon [dimethyl 2,2,2-trichloro-1-hydroxyethylphosphonate], Azinphos-methyl [S-3,4-dihydro-4-oxo-1,2,3-benzotriazin-3-ylmethyl O,O-dimethylphosphorodithioate], Monocrotophos [dimethyl (E)-1-methyl-2-(methylcarbamoyl)vinylphosphate], Ethion [O,O,O',O'-tetraethyl S,S'-methylenebis (phosphorodithioate)] and Profenofos [O,-4-bromo-2-chlorophenyl O-ethyl S-propyl phosphorothioate]; carbamate compounds such as BPMC [2-sec-butylphenylmethylcarbamate], Benfuracarb [ethyl N-[2,3-dihydro-2,2-dimethylbenzofuran-7-yloxycarbonyP(methyl) aminothio]-N-isopropyl-β-alaninate], Propoxur [2-isopropoxyphenyl N-methylcarbamate], Carbosulfan [2,3-dihydro-2,2-dimethyl-7-benzo[b]furanyl N-dibutylamrinothio-N-methylcarbamate], Carbaril [1-naphthyl-N-methylcarbamate], Methomyl [S-methyl-N-[(methylcarbamoyl)oxy]thioacetimidate], Ethiofencarb [2-(ethylthiomethyl)phenylmethylcarbamate], Aldicarb [2-methyl-2-(methylthio)propanaldehyde O-methylcarbamoyloxime], Oxamyl [N,N-dimethyl-2-methylcarbamoyloxyimino-2-(methylthio)acetamide], Fenothiocarb [S-(4-phenoxybutyl)-N, Ndimethylthiocarbamate], Thiodicarb [3,7,9,13-tetramethyl-5,11-dioxa-2,8,14-trithia-4,7, 9,12-tetraazapentadeca-3,12-diene-6,10-dione] and Alanycarb [ethyl (Z)-N-benzyl-N-{[methyl(1-methylthioethylideneamninooxycarbonyl)amino]thio}-β-alaninate]; pyrethroid compounds such as Etofenprox [2-(4-ethoxyphenyl)-2-methylpropyl-3-phenoxybenzylether], Fenvalerate [(RS)-α-cyano-3-phenoxybenzyl (RS)-2-(4-chlorophenyl)-3-methylbutyrate], Esfenvalerate [(S)-α-cyano-3-phenoxybenzyl (S)-2-(4-chlorophenyl)-3-methylbutyrate], Fenpropathrin [(RS)-α-cyano-3-phenoxybenzyl 2,2,3,3-tetramethylcyclopropanecarboxylate], Cypermethrin [(RS)-α-cyano-3-phenoxybenzyl (1RS,3RS)-3-(2,2-dichlorovinyl)-2,2-dimethylcyclopropanecarboxylate], Perrnethrin [3-phenoxybenzyl (1RS, 3RS)-3-(2,2-dichlorovinyl)-2,2-dimethylcyclopropanecarboxylate], Cyhalothrin [(RS)-α-cyano-3-phenoxybenzyl (Z)-(1RS)-cis-3-(2-chloro-3,3,3-trifluoroprop-5-enyl)-2,2-dimethylcyclopropanecarboxylate], Deltamethrin [(S)-α-cyano-m-phenoxybenzyl (1R,3R)-3-(2,2-dibromovinyl)-2,2-dimethylcyclopropanecarboxylate], Cycloprothrin [(RS)-α-cyano-3-phenoxybenzyl (RS)-2,2-dichloro-1-(4-ethoxyphenyl)cyclopropanecarboxylate], Fluvalinate [α-cyano-3-phenoxybenzyl N-(2-chloro-α,α,α-trifluoro-p-tolyl)-D-valinate], Bifenthrin [2-methylbiphenyl-3-ylmethyl) (Z)-(1RS)-cis-3-(2-chloro-3,3,3-trifluoroprop-1-enyl)-2,2-dimethylcyclopropanecarboxylate], Acrinathrin [(S)-α-cyano-(3-phenoxyphenyl)methyl [1R-{1α(S*),3α(Z)}]-2,2-dimethyl-3-[3-oxo-3-(2,2,2-trifluoro-1-(trifluoromethyl)ethoxy-1-propenyl] cyclopropanecarboxylate], 2-methyl-2-(4-bromodifluoromethoxyphenyl)propyl (3-phenoxybenzyl) ether, Traromethrin [(S)-α-cyano-3-phenoxylbenzyl (1R, 3R)-3-[(1'RS)(1',1',2',2'-tetrabromoethyl)]-2,2-dimethylcyclopropanecarboxylate] and Silafluofen [4-ethoxyphenyl [3-(4-fluoro-3-phenoxyphenyl)propyl] dimethylsilane]; thiadiazine derivatives such as Buprofezin [2-tert-butylimino-3-isopropylphenyl-1,3,5-thiadiazin-4-one]; nitroimidazolidine derivatives such as Imidacloprid [1-(6-chloro-3-pyridylmethyl)-N-nitroimidazolidin-2-ylidenamine]; Nereistoxin derivatives such as Cartap [S,S'-(2-dimethylaminotrimethylene)bis(thiocarbamate)], Thiocyclam [N,N-dimethyl-1,2,3-trithian-5-ylamine] and Bensultap [S,S'-2-dimethylaminotrimethylene di(benzenethiosulfonate)]; N-cyanoarnidine derivatives such as acetamiprid [N-cyano-N'-methyl-N'-(6-chloro-3-pyridylmethyl)acetamidine]; chlorinated hydrocarbon compounds such as Endosulfan [6,7,8,9,10,10-hexachloro-1,5, 5a,6,9,9a-hexahydro-6,9-methano-2,4,3-benzodioxathiepinoxide], γ-BHC [1,2,3 ,4,5,6-hexachlorocyclohexane] and Kelthane [1,1-bis (chlorophenyl)-2,2,2-trichloroethanol]; benzoylphenylurea compounds such as Chlorfluazuron [1-(3,5-dichloro-4-(3-chloro-5-trifluoromethylpyridin-2-yloxy)phenyl)-3-(2,6-difluorobenzoyl)urea], Teflubenzuron [1-(3,5-dichloro-2,4-difluorophenyl)-3-(2,6-difluorobenzoyl)urea] and Fulphenoxron [1-(4-(2-chloro-4-trifluoromethylphenoxy)-2-fluorophenyl)-3-(2,6-difluorobenzoyl)urea]; formamidine derivatives such as Amitraz [N,N'-[(methylimino) dimethylidine]-di-2,4-xylidine] and Chlordimeform [N'-(4-chloro-2-methylphenyl)-N,N-dimethylmethanimidamide]; thiourea derivatives such as Diafenthiuron [N-(2,6-diisopropyl-4-phenoxyphenyl)-N'-tert-butylcarbodiimide]; Bromopropylate [isopropyl 4,4'-dibromobenzylate], Tetradifon [4-chlorophenyl 2,4,5-trichlorophenylsulfone], Quinomethionate [S,S-6-methylquinoxaline-2,3-diyldithiocarbonate], Propargite [2-(4-tert-butylphenoxy) cyclohexyl prop-2-yl sulfite], Fenbutatin oxide [bis[tris(2-methyl-2-phenylpropyl)tin]oxide], Hexythiazox [(4RS, 5RS)-5-(4-chlorophenyl)-N-chlorohexyl-4-methyl-2-oxo-1, 3-thiazolidine-3-carboxamide], Chlofentezine [3,6-bis(2-chlorophenyl)-1,2,4,5-tetrazine], Pyridaben [2-tert-butyl-5-(4-tert-butylbenzylthio)-4-chloropyridazin-3(2H)-one], Fenpyroximate [tert-butyl (E)-4-[(1,3-dimethyl-5--phenoxypyrazol-4-yl)methyleneaminooxymethyl] benzoate], Tebfenpyrad [N-4-tert-butylbenzyl)-4-chloro-3-ethyl-1-methyl-5-pyrazolecarboxamide], polynactin complexes including tetranactin, dinactin and trinactin; Milbemectin, Avermectin, Ivermectin, Azadilactin [AZAD], Pyrimidifen [5-chloro-N-[2-{4-(2-ethoxyethyl)-2,3-dimethylphenoxy }ethyl]-6-ethylpyrimidin-4-amine], Chlorfenapyr [4-bromo-2-(4-chlorophenyl)-1-ethoxymethyl-5-trifluoromethylpyrrole-3-carbonitrile], Tebfenozide [N-tert-butyl-N'-(4-ethylbenzoyl)-3,5-dimethylbenzohydrazide] and phenylpyrazole derivatives.

When the present compounds are used as active ingredients of insecticidal/acaricidal agents for agriculture, the application amount thereof is usually in the range of 0.1 to 100 g per 10 ares. In the case of emulsifiable concentrates, wettable powders and flowable concentrates, which are used after diluted with water, the application concentration thereof is usually in the range of 1 to 10,000 ppm. In the case of granules and dusts, they are applied as such without any dilution. When the present compounds are used as active ingredients of insecticidal/acaricidal agents for epidemic prevention, they are formulated into dosage forms such as emulsifiable concentrates, wettable powders and flowable concentrates, which are applied after diluted with water to a typical concentration of 0.1 to 500 ppm; or they are formulated into dosage forms such as oil sprays, aerosols, fumigants and poisonous baits, which are applied as such without any dilution.

The application amount and application concentration may vary with the conditions including types of dosage forms, application time, place and method, kinds of noxious insects, mites and ticks, and degree of damage, and they can be increased or decreased without limitation to the above range.

The present invention will be further illustrated by the following production examples, formulation examples and test examples; however, the present invention is not limited to these examples.

The following are production examples for the present compounds according to various production processes.

PRODUCTION EXAMPLE 1

Production of compound (2) by production process E

To a mixture of 1.30 g of 3-(3,3-dichloro-2-propenyloxy) propanol, 2.02 g of 2,6-dichloro-4-(3,3-dichloro-2-propenyloxy)phenol, 1.89 g of triphenylphosphine and 20 ml of tetrahydrofuran was slowly added dropwise 1.42 g of diisopropyl azodicarboxylate with stirring under ice cooling. After stirring at room temperature for 24 hours, the reaction mixture was concentrated. The residue was subjected to silica gel chromatography, which afforded 0.15 g of 3,5-dichloro-1-(3,3-dichloro-2-propenyloxy)-4-(3-(3,3-dichloro-2-propenyloxy)propyloxy)benzene (yield, 4.7%), $n_D^{18.5}$ 1.5530.

PRODUCTION EXAMPLE 2

Production of compound (3) by production process E

To a mixture of 0.30 g of 4-(3,3-dichloro-2-propenyloxy) butanol, 0.43 g of 2,6-dichloro-4-(3,3-dichloro-2-propenyloxy)phenol, 0.39 g of triphenylphosphine and 15 ml of tetrahydrofuran was slowly added dropwise 0.30 g of diisopropyl azodicarboxylate with stirring under ice cooling. After stirring at room temperature for 24 hours, the reaction mixture was concentrated. The residue was subjected to silica gel chromatography, which afforded 0.34 g of 3,5-dichloro-1-(3,3-dichloro-2-propenyloxy)-4-(4-(3,3-dichloro-2-propenyloxy)butyloxy)benzene (yield, 73%), $n_D^{24.5}$ 1.5519.

PRODUCTION EXAMPLE 3

Production of compound (14) by production process E

To a mixture of 0.22 g of 4-(2-propenyloxy)pentanol, 0.43 g of 2,6-dichloro- 4-(3,3-dichloro-2-propenyloxy)phenol, 0.39 g of triphenylphosphine and 15 ml of tetrahydrofuran was slowly added dropwise 0.30 g of diisopropyl azodicarboxylate with stirring under ice cooling. After stirring at room temperature for 24 hours, the reaction mixture was concentrated. The residue was subjected to silica gel chromatography, which afforded 0.54 g of 3,5-dichloro-1-(3,3-dichloro-2-propenyloxy)-4-(5-(2-propenyloxy)pentyloxy)benzene (yield, 87%), $n_D^{23.5}$ 1.5378.

PRODUCTION EXAMPLE 4

Production of compound (12) by production process A

A reaction vessel was charged with 0.30 g of 3-ethyl-5-methyl-4-,(4-(3-methyl-2-butenyloxy)butyloxy)phenol, 0.16 g of 1,1,3-trichloro-1-propene, 0.15 g of potassium carbonate and 10 ml of N,N-dimethylformamide. After stirring at room temperature for 24 hours, the reaction mixture was poured into water and extracted twice with 50 ml of diethyl ether. The diethyl ether layers were combined, washed with water, dried over magnesium sulfate and then concentrated. The residue was subjected to silica gel chromatography, which afforded 0.28 g of 3-ethyl-5-methyl-1-(3,3-dichloro-2-propenyloxy)-4-(4-(3-methyl-2-butenyloxy)butyloxy)benzene (yield, 70%), $n_D^{24.2}$ 1.5168.

PRODUCTION EXAMPLE 5

Production of compound (11) by production process A

A reaction vessel was charged with 0.35 g of 3,5-diethyl-4-(4-(3,3-dichloro-2-propenyloxy)butyloxy)phenol, 0.16 g of 1,1,3-trichloro-1-propene, 0.15 g of potassium carbonate and 10 ml of N,N-dimethylformamide. After stirring at room temperature for 24 hours, the reaction mixture was poured into water and extracted twice with 50 ml of diethyl ether. The diethyl ether layers were combined, washed with water, dried over magnesium sulfate and then concentrated. The residue was subjected to silica gel chromatography, which afforded 0.33 g of 3,5-diethyl-1-(3,3-dichloro-2-propenyloxy)-4-(4-(3,3-dichloro-2-propenyloxy)butyloxy) benzene (yield, 72%), $n_D^{24.4}$ 1.5311.

PRODUCTION EXAMPLE 6

Production of compound (34) by production process N

A mixture of 1.21 g of 4-(2,6-dichloro-4-(3,3-dichloro-2-propenyloxy)phenoxy)butyloxyacetaldehyde, 0.87 g of triphenylphosphine and 10 ml of diglyme was stirred at 160° C., to which a solution (5 ml) of 0.69 g of sodium chlorodifluoroacetate in diglyme heated to 60° C. was added dropwise. After stirring at 160° C. for 1.5 hours, the reaction mixture was returned to room temperature, poured into water and extracted twice with 50 ml of diethyl ether. The diethyl ether layers were combined, washed with water, dried over magnesium sulfate and then concentrated to give a crude product. The crude product was subjected to silica gel chromatography, which afforded 0.21 g of 3,5-dichloro-1-(3,3-dichloro-2-propenyloxy)-4-(4-(3,3-difluoro-2-propenyloxy)butyloxy)benzene (yield, 16%), $n_D^{23.0}$ 1.5219.

PRODUCTION EXAMPLE 7

Production of compound (17) by method (i) in production process R

A solution of 0.36 g of 3,5-dichloro-1-(3,3-dichloro-2-propenyloxy)-4-(4-(3-chloro-4,4-difluoro-2-hydroxy-3-butenyloxy)butyloxy)benzene in 5 ml of dichloromethane was slowly added dropwise to a solution of 0.12 g of diethylaminosulfur trifluoride (DAST) in 10 ml of dichloromethane with stirring at −78° C. After complement of the dropwise addition, the reaction mixture was returned to room temperature over 30 minutes and poured into water. The dichloromethane layer was separated, washed with water, dried over magnesium sulfate and then evaporated to give a crude product. The crude product was subjected to silica gel chromatography, which afforded 0.20 g of (Z)-3, 5-dichloro-1-(3,3-dichloro-2-propenyloxy)-4-(4-(3-chloro-4,4,4-trifluoro-2-butenyloxy)butyloxy)benzene (yield, 55%), $n_D^{23.7}$ 1.5160.

PRODUCTION EXAMPLE 8

Production of compound (38) by method (i) in production process O

To a mixture of 1.21 g of 5-(2,6-dichloro-4-(3,3-dichloro-2-propenyloxy)phenoxy)pentyloxyacetaldehyde, 0.57 g of zinc dust and 10 ml of N,N-dimethylformamide was added 0.82 g of 1,1,1-trichlorotrifluoroethane. After stirring at room temperature for 1.5 hours, 0.44 g of acetic anhydride was added. The reaction mixture was stirred at room temperature for 3 hours and then filtered. The filtrate was poured into 20 ml of diluted hydrochloric acid and extracted twice with 50 ml of diethyl ether. The diethyl ether layers were combined, washed with water, dried over magnesium sulfate and then evaporated to give a crude product. The crude product was subjected to silica gel chromatography, which afforded 0.21 g of (Z)-3,5-dichloro-1-(3,3-dichloro-2-propenyloxy)-4-(5-(3-chloro-4,4,4-trifluoro-2-butenyloxy) pentyloxy)benzene [the integrated $CF_3$ signal ratio of Z/E= 94/6 as determined by $^{19}$F-NMR (CDCl$_3$/CFCl$_3$)] (yield, 14%), $n_D^{26.5}$ 1.5123.

PRODUCTION EXAMPLE 9

Production of compound (43) by method (v) in production process O

A mixture of 0.57 g of 3,5-dichloro-1-(3,3-dichloro-2-propenyloxy)-4-(4-(4,4-dichloro-5,5,5-trifluoro-3-hydroxypentyloxy)butyloxy)benzene, 0.16 g of pyridine, 0.12 g of acetic anhydride, 10 mg of N,N-dimethyl-4-aminopyridine and 20 ml of N,N-dimethylformamide was stirred at room temperature for 30 minutes, to which 0.078 g of zinc dust was added. The reaction mixture was further stirred at room temperature for 1 hour, poured into 20 ml of diluted hydrochloric acid and extracted twice with 50 ml of diethyl ether. The diethyl ether layers were combined, washed with water, dried over magnesium sulfate and then evaporated to give a crude product. The crude product was subjected to silica gel chromatography, which afforded 0.41 g of (Z)-3,5-dichloro-1-(3,3-dichloro-2-propenyloxy)-4-(4-(4-chloro-5,5,5-trifluoro-3-pentenyloxy)butyloxy)benzene [the integrated $CF_3$ signal ratio of Z/E=93/7 as determined by $^{19}$F-NMR (CDCl$_3$/CFCl$_3$)] (yield, 79%), $n_D^{30.0}$ 1.5057.

PRODUCTION EXAMPLE 10

Production of compound (39) by method (ii) in production process R

To a mixture of 0.50 g of 3,5-dichloro-1-(3,3-dichloro-2-propenyloxy)-4-(4-(3-chloro-4,4-difluoro-2-hydroxy-3-butenyloxy)butyloxy)benzene, 0.17 g of pyridine and 10 ml of chloroform was added 0.13 g of thionyl chloride. After stirring at 50° C. for 6 hours, the reaction mixture was poured into 10 ml of diluted hydrochloric acid and extracted twice with 50 ml of diethyl ether. The diethyl ether layers were combined, washed with water, dried over magnesium sulfate and then evaporated to give a crude product. The crude product was subjected to silica gel chromatography, which afforded 0.21 g of (Z)-3,5-dichloro-1-(3,3-dichloror2-propenyloxy) 4(4-(3,4-dichloro-4,4-difluoro-2-butenyloxy) butyloxy)benzene (yield, 40%), $n_D^{26.5}$ 1.5295.

PRODUCTION EXAMPLE 11

Production of compound (48) by the method (i) in production process O

To a mixture of 0.60 g of 4-(2,6-dichloro-4-(3,3-dichloro-2-propenyloxy)phenoxy)butyloxyacetaldehyde, 0.29 g of zinc dust and 10 ml of N,N-dimethylformamide was added ethyl trichloroacetate with stirring at room temperature. After stirring at room temperature for 2 hours, the reaction mixture was poured into 10 ml of diluted hydrochloric acid and extracted twice with diethyl ether. The diethyl ether layers were combined, washed with water, dried over magnesium sulfate and then evaporated to give a crude product. The crude product was subjected to silica gel chromatography, which afforded 0.04 g of 3,5-dichloro-1-(3,3-dichloro-2-propenyloxy)-4-(4-(3-chloro-3-ethoxycarbonyl-2-propenyloxy)butyloxy)benzene (yield, 5%), $n_D^{23.0}$ 1.5348.

PRODUCTION EXAMPLE 12

Production of compound (49) by method (v) in production process O

A mixture of 0.26 g of 3,5-dichloro-1-(3,3-dichloro-2-propenyloxy)-4-(4-(3-cyano-3,3-dichloro-2-hydroxypropyloxy)butyloxy)benzene, 0.079 g of pyridine, 0.077 g of acetic anhydride, 10 mg of N,N-dimethyl-4-aminopyridine and 10 ml of N,N-dimethylformamide was stirred at room temperature for 30 minutes, to which 0.065 g of zinc dust was added. The reaction mixture was further stirred at room temperature for 1 hour, poured into 20 ml of diluted hydrochloric acid and extracted twice with diethyl ether. The diethyl ether layers were combined, washed with water, dried over magnesium sulfate and then evaporated to give a crude product. The crude product was subjected to silica gel chromatography, which afforded 0.19 g of 3,5-dichloro-1-(3,3-dichloro-2-propenyloxy)-4-(4-(3-chloro-3-cyano-2-propenyloxy)butyloxy)benzene (yield, 83%), $n_D^{23.0}$ 1.5410.

PRODUCTION EXAMPLE 13

Production of compound (23) by production process E

To a mixture of 0.20 g of 4-(3-chloro-2-propynyloxy) butanol, 0.32 g of 2,6-dichloro-4-(3,3-dichloro-2-propenyloxy)phenol, 0.32 g of triphenylphosphine and 15 ml of tetrahydrofuran was slowly added dropwise 0.27 g of diisopropyl azodicarboxylate with stirring under ice cooling. After stirring at room temperature for 24 hours, the reaction mixture was concentrated. The residue was subjected to silica gel chromatography, which afforded 0.38 g of 3,5-dichloro-1-(3,3-dichloro-2-propenyloxy)-4-(4-(3-chloro-2-propynyloxy)butyloxy)benzene (yield, 71%), $n_D^{23.5}$ 1.5511.

PRODUCTION EXAMPLE 14

Production of compound (47) by production process H

A mixture of 0.39 g of 4-(2,6-diethyl-4-(3,3-dichloro-2-propenyloxy)phenoxy)butyloxyacetaldehyde, 0.24 g of 1-propanol and 10 ml of cyclohexane was stirred at room temperature, to which 0.038 g of p-tolunesulfonic acid hydrate and 0.40 g of powdered molecular sieves SA were added. After stirring at room temperature for 30 minutes, the reaction mixture was filtered. The filtrate was added to water and extracted twice with diethyl ether. The diethyl ether layers were combined, washed with water, dried over magnesium sulfate and then evaporated to give a crude product. The crude product was subjected to silica gel chromatography, which afforded 0.38 g of 3,5-diethyl-1-(3, 3-dichloro-2-propenyloxy)-4-(4-(2,2-dipropyloxyethoxy) butyloxy)benzene (yield, 77%), $n_D^{23.5}$ 1.4975.

PRODUCTION EXAMPLE 15

Production of compound (25) by production process E

To a mixture of 2.30 g of 4-(2,2-diethoxyethoxy)butanol, 2.94 g of 2,6-dichloro-4-(3,3-dichloro-2-propenyloxy) phenol, 2.94 g of triphenylphosphine and 30 ml of tetrahydrofuran was slowly added dropwise 2.48 g of diisopropyl azodicarboxylate with stirring under ice cooling. After stirring at room temperature for 24 hours, the reaction mixture was concentrated. The residue was subjected to silica gel chromatography, which afforded 4.48 g of 3,5-dichloro-1-(3,3-dichloro-2-propenyloxy)-4-(4-(2,2-diethoxyethoxy) butyloxy)benzene (yield, 73%), $n_D^{24.5}$ 1.5165.

PRODUCTION EXAMPLE 16

Production of compound (53) by production process A

A reaction vessel was charged with 19.9 g of 3,5-diethyl-4-(4-(2,2-diethoxyethoxy)butyloxy)phenol, 9.20 g of 1,1,3-trichloro-1-propene, 9.15 g of potassium carbonate and 200 ml of N,N-dimethylformamide. After stirring at room temperature for 24 hours, the reaction mixture was poured into water and extracted twice with diethyl ether. The diethyl ether layers were combined, washed with water, dried over magnesium sulfate and then concentrated. The residue was subjected to silica gel chromatography, which afforded 25.4 g of 3,5-diethyl-1-(3,3-dichloro-2-propenyloxy)-4-(4-(2,2-diethoxyethoxy)butyloxy (yield, 91%), $n_D^{26.0}$ 1.4991.

PRODUCTION EXAMPLE 17

Production of compound (37) by method (ii) in production process O

To a mixture of 2.01 g of 4-(2,6-dichloro-4-(3,3-dichloro-2-propenyloxy)phenoxy)butyloxyacetaldehyde, 1.31 g of zinc dust and 10 ml of N,N-dimethylformamide was added 4.12 g of 1,1,1-trichlorotrifluoroethane. After stirring at room temperature for 1.5 hours, the reaction mixture was filtered. The filtrate was poured into 20 ml of diluted hydrochloric acid and extracted twice with 50 ml of ethyl acetate. The ethyl acetate layers were combined, washed with water, dried over magnesium sulfate and then evaporated to give a crude product. The crude product was subjected to silica gel chromatography, which afforded 1.76 g of 3,5-dichloro-1-(3,3-dichloro-2-propenyloxy)-4-(4-(3,3-dichloro-4,4,4-trifluoro-2-hydroxybutyloxy)butyloxy)benzene (yield, 63%), $n_D^{24.2}$ 1.5188.

PRODUCTION EXAMPLE 18

Production of compound (50) by method (ii) in production process o

To a mixture of 0.60 g of 4-(2,6-dichloro-4-(3,3-dichloro-2-propenyloxy)phenoxy)butyloxyacetaldehyde, 0.29 g of zinc dust and 10 ml of N,N-dimethylformamide was added 0.040 g of trichloroacetonitrile with stirring at room temperature. After stirring at room temperature for 2 hours, the reaction mixture was poured into 10 ml of diluted hydrochloric acid and extracted twice with diethyl ether. The diethyl ether layers were combined, washed with water; dried over magnesium sulfate and then evaporated to give a crude product. The crude product was subjected to silica gel chromatography, which afforded 0.35 g of 3,5-dichloro-1-(3,3-dichloro-2-propenyloxy)-4-(4-(3-cyano-3,3-dichloro-2-hydroxypropyloxy)butyloxy)benzene (yield, 46%), $n_D^{24.0}$ 1.5460.

PRODUCTION EXAMPLE 19

Production of compound (51) by production process L

A mixture of 0.28 g of 3,5-dichloro-1-(3,3-dichloro-2-propenyloxy)-4-(4-(3,3-dichloro-4,4,4-trifluoro-2-hydroxybutyloxy)butyloxy)benzene, which is one of the present compounds produced in Production Example 17, 0.079 g of pyridine, 0.077 g of acetic anhydride, 10 mg of N,N-dimethyl-4-amino-pyridine (DMAP) and 10 ml of N,N-dimethylformamide was stirred at room temperature for 30 minutes. The reaction mixture was poured into 20 ml of diluted hydrochloric acid and extracted twice with diethyl ether. The diethyl ether layers were combined, washed with water, dried over magnesium sulfate and then evaporated to give a crude product. The crude product was subjected to silica gel chromatography, which afforded 0.28 g of 3,5-dichloro-1-(3,3-dichloro-2-propenyloxy) -4-(4-(3,3-dichloro-4,4,4-trifluoro-2-acetoxybutyloxy)butyloxy) benzene (yield, 94%), $n_D^{23.0}$ 1.4958.

PRODUCTION EXAMPLE 20

Production of compound (55) by method (i) in production process O

To a mixture of 0.12 g of aluminum chloride and 50 ml of N,N-dimethylformamide was added 3.04 g of 1,1,1-trichlorotrifluoroethane. After stirring at room temperature for 1 hour, 1.21 g of 5-(2,6-diethyl-4-(3,3-dichloro-2-propenyloxy)phenoxy)pentyloxyacetaldehyde was added, and the reaction mixture was further stirred at room temperature for 4 hours, to which 1.38 g of acetic anhydride was added. After stirring at room temperature for 1 hour, 0.88 g of zinc dust was added, and the reaction mixture was stirred at room temperature for 12 hours and filtered. The filtrate was poured into 50 ml of diluted hydrochloric acid and extracted twice with 100 ml of diethyl ether. The diethyl ether layers were combined, washed with water, dried over magnesium sulfate and then evaporated to give a crude product. The crude product was subjected to silica gel chromatography, which afforded 2.91 g of (Z)-3,5-diethyl-1-(3,3-dichloro-2-propenyloxy)-4-(5-(3-chloro-4,4,4-trifluoro-2-butenyloxy)pentyloxy)benzene (yield, 72%), $n_D^{26.0}$ 1.4958.

PRODUCTION EXMAPLE 21

Production of compound (109) by production process H

To a mixture of 0.39 g of 4-(2,6-diethyl-4-(3,3-dichloro-2-propenyloxy)phenoxy)butyloxyacetaldehyde, 0.16 g of 1-propanethiol and 10 ml of chloroform was slowly added dropwise 0.16 g of trimethylsilyl chloride with stirring at room temperature. After stirring at room temperature for 3 hours, the reaction mixture was poured into 5% aqueous sodium carbonate solution and extracted twice with diethyl ether. The diethyl ether layers were combined, washed with water, dried over magnesium sulfate and then evaporated to give a crude product. The crude product was subjected to silica gel chromatography, which afforded 0.20 g of 3,5-diethyl-1-(3,3-dichloro-2-propenyloxy)-4-(4-(2,2-di(propylthio)ethoxy)butyloxy)benzene (yield, 41%), $n_D^{26.4}$ 1.5300.

PRODUCTION EXAMPLE 22

Production of compound (104) by production process F

A reaction vessel was charged with 0.42 g of 3,5-dichloro-4-(4-bromobutyloxy)-1-(3,3-dichloro-2-propenyloxy) benzene, 0.25 g of 1,1,1,3,3,3-hexafluoro-2-propanol, 0.17 g of potassium carbonate and 10 ml of N,N-dimethylformamide. After stirring at room temperature for 48 hours, the reaction mixture was poured into water and extracted twice with diethyl ether. The diethyl ether layers were combined, washed with water, dried over magnesium sulfate and then concentrated. The residue was subjected to silica gel chromatography, which afforded 0.077 g of 3,5-dichloro-1-(3,3-dichloro-2 -propenyloxy)-4-(4-(1,1,1,3,3,3-hexafluoro-2-propyloxy)butyloxy)benzene (yield, 15%), $n_D^{24.0}$ 1.4805.

PRODUCTION EXAMPLE 23

Production of compound (102) by production process H

First, 0.39 g of 4-(2,6-diethyl-4-(3,3-dichloro-2-propenyloxy)phenoxy)butyloxyacetaldehyde was dissolved in 10 ml of anhydrous methanol, to which 5 mg of ammonium chloride was added, and the mixture was heated under reflux for 3 hours After left alone for cooling, the reaction mixture was mixed with 10 ml of saturated aqueous sodium hydrogencarbonate solution. The methanol was distilled out, and the residue was extracted twice with diethyl ether. The diethyl ether layers were combined, washed with water, dried over anhydrous magnesium sulfate and then concentrated to give a crude product. The crude product was subjected to silica gel chromatography, which afforded 0.31 g of 3,5-diethyl-1-(3,3-dichloro-2-propenyloxy)-4-(4-(2,2-dimethoxyethoxy)butyloxy)benzene (yield, 71%), $n_D^{24.0}$ 1.5068.

The following are specific examples of the present compounds with their compound numbers and physical properties, if measured.

(1) 3,5-Dichloro-1-(3,3-dichloro-2-propenyloxy)-4-(2-(3,3-dichloro-2-propenyloxy)ethoxy)benzene $n_D^{25.2}$ 1.5474
(2) 3,5-Dichloro-1-(3,3-dichloro-2-propenyloxy)-4-(3-(3,3-dichloro-2-propenyloxy)propyloxy)benzene $n_D^{18.5}$ 1.5530
(3) 3,5-Dichloro-1-(3,3-dichloro-2-propenyloxy)-4-(4-(3,3-dichloro-2-propenyloxy)butyloxy)benzene $n_D^{24.5}$ 1.5519
(4) 3,5-Dichloro-1-(3,3-dichloro-2-propenyloxy)-4-(5-(3,3-dichloro-2-propenyloxy)pentyloxy)benzene $n_D^{29.4}$ 1.5382
(5) 3,5-Dichloro-1-(3,3-dichloro-2-propenyloxy)-4-(6-(3,3-dichloro-2-propenyloxy)hexyloxy)benzene
(6) 3,5-Dichloro-1-(3,3-dichloro-2-propenyloxy)-4-(3-(3-methyl-2-butenyloxy)propyloxy)benzene
(7) 3,5-Dichloro-1-(3,3-dichloro-2-propenyloxy)-4-(4-(3-methyl-2-butenyloxy)butyloxy)benzene $n_D^{24.3}$ 1.5348
(8) 3,5-Dichloro-1-(3,3-dichloro-2-propenyloxy)-4-(4-(3-chloro-2-butenyloxy)butyloxy)benzene $n_D^{20.0}$ 1.5464
(9) 3,5-Dichloro-1-(3,3-dichloro-2-propenyloxy)-4-(4-(3-chloro-2-propenyloxy)butyloxy)benzene $n_D^{20.0}$ 1.5503
(10) 3-Ethyl-5-methyl-1-(3,3-dichloro-2-propenyloxy)-4-(4-(3,3-dichloro-2-propenyloxy)butyloxy)benzene $n_D^{24.4}$ 1.5325
(11) 3,5-Diethyl-1-(3,3-dichloro-2-propenyloxy)-4-(4-(3,3-dichloro-2-propenyloxy)butyloxy)benzene $n_D^{24.4}$ 1.5311
(12) 3-Ethyl-5-methyl-1-(3,3-dichloro-2-propenyloxy)-4-(4-(3-methyl-2-butenyloxy)butyloxy)benzene $n_D^{24.2}$ 1.5168
(13) 3,5-Diethyl-1-(3,3-dichloro-2-propenyloxy)-4-(4-(3-methyl-2-butenyloxy)butyloxy)benzene
(14) 3,5-Dichloro-1-(3,3-dichloro-2-propenyloxy)-4-(5-(2-propenyloxy)pentyloxy)benzene $n_D^{23.5}$ 1.5378
(15) 3,5-Dichloro-1-(3,3-dibromo-2-propenyloxy)-4-(4-(3,3-dichloro-2-propenyloxy)butyloxy)benzene $n_D^{22.5}$ 1.5705
(16) 3,5-Dichloro-1-(3,3-dichloro-2-propenyloxy)-4-(4-(3,3-dibromo-2-propenyloxy)butyloxy)benzene $n_D^{23.0}$ 1.5660
(17) (Z)-3,5-dichloro-1-(3,3-dichloro-2-propenyloxy)-4-(4-(3-chloro-4,4,4-trifluoro-2-butenyloxy)butyloxy)benzene $n_D^{23.7}$ 1.5160
(18) 3,5-Dichloro-1-(3,3-dichloro-2-propenyloxy)-4-(4-(3-trifluoromethyl-2-butenyloxy)butyloxy)benzene
(19) 3-Ethyl-5-methyl-1-(3,3-dibromo-2-propenyloxy)-4-(4-(3-methyl-2-butenyloxy)butyloxy)benzene $n_D^{21.7}$ 1.5390
(20) Ethyl-5-methyl-1-(3,3-dibromo-2-propenyloxy)-4-(4-(3,3-dichloro-2-propenyloxy)butyloxy)benzene $n_D^{24.4}$ 1.5501
(21) 3,5-Diethyl-1-(3,3-dibromo-2-propenyloxy)-4-(4-(3,3-dichloro-2-propenyloxy)butyloxy)benzene $n_D^{24.4}$ 1.5491
(22) 3,5-Dichloro-1-(3,3-dichloro-2-propenyloxy)-4-(2-(2-ethoxyethoxy)ethoxy)benzene $n_D^{20.5}$ 1.5311
(23) 3,5-Dichloro-1-(3,3-dichloro-2-propenyloxy)-4-(4-(3-chloro-2-propynyloxy)butyloxy)benzene $n_D^{23.5}$ 1.5511
(24) 3,5-Dichloro-1-(3,3-dichloro-2-propenyloxy)-4-(4-(2-propenyloxy)butyloxy)benzene $n_D^{24.4}$ 1.5378
(25) 3,5-Dichloro-1-(3,3-dichloro-2-propenyloxy)-4-(4-(2,2-diethoxyethoxy)butyloxy)benzene $n_D^{23.7}$ 1.5166
(26) 3,5-Dichloro-1-(3,3-dichloro-2-propenyloxy)-4-(4-(2-chloro-2-propenyloxy)butyloxy)benzene $n_D^{23.7}$ 1.5450
(27) 3,5-Dichloro-1-(3,3-dichloro-2-propenyloxy)-4-(4-(3,3-dichloro-2-propenyloxy)-2-butenyloxy)benzene $n_D^{23.7}$ 1.5640
(28) 3,5-Dichloro-1-(3,3-dichloro-2-propenyloxy)-4-(5-(3,3-dichloro-2-propenyloxy)pentyloxy)benzene $n_D^{22.5}$ 1.5676
(29) 3,5-Dichloro-1-(3,3-dichloro-2-propenyloxy)-4-(5-(3,3-dichloro-2-propenyloxy)pentyloxy)benzene $n_D^{22.5}$ 1.5252
(30) 3-Ethyl-5-methyl-1-(3,3-dichloro-2-propenyloxy)-4-(5-(3,3-dichloro-2-propenyloxy)pentyloxy)benzene $n_D^{22.5}$ 1.5230

-continued

(31) 3,5-Diethyl-1-(3,3-dibromo-2-propenyloxy)-4-(5-(3,3-dichloro-2-propenyloxy)pentyloxy)benzene $n_D^{22.5}$ 1.5341
(32) 3-Ethyl-5-methyl-1-(3,3-dibromo-2-propenyloxy)-4-(5-(3,3-dichloro-2-propenyloxy)pentyloxy)benzene $n_D^{22.5}$ 1.5391
(33) 3,5-Dichloro-1-(3,3-dichloro-2-propenyloxy)-4-(5-(2,2-diethoxyethoxy)pentyloxy)benzene $n_D^{23.8}$ 1.5148
(34) 3,5-Dichloro-1-(3,3-dichloro-2-propenyloxy)-4-(4-(3,3-difluoro-2-propenyloxy)butyloxy)benzene $n_D^{23.0}$ 1.5219
(35) (Z)-3,5-dichloro-1-(3,3-dichloro-2-propenyloxy)-4-(4-(2,3-dichloro-2-propenyloxy)butyloxy)benzene $n_D^{25.0}$ 1.5502
(36) (E)-3,5-dichloro-1-(3,3-dichloro-2-propenyloxy)-4-(4-(2,3-dichloro-2-propenyloxy)butyloxy)benzene $n_D^{25.0}$ 1.5502
(37) 3,5-Dichloro-1-(3,3-dichloro-2-propenyloxy)-4-(4-(3,3-dichloro-4,4,4-trifluoro-2-hydroxybutyloxy)butyloxy)benzene $n_D^{24.2}$ 1.5188
(38) (Z)-3,5-dichloro-1-(3,3-dichloro-2-propenyloxy)-4-(5-(3-chloro-4,4,4-trifluoro-2-butenyloxy)pentyloxy)benzene $n_D^{26.5}$ 1.5123
(39) (Z)-3,5-dichloro-1-(3,3-dichloro-2-propenyloxy)-4-(4-(3,4-dichloro-4,4-difluoro-2-butenyloxy)butyloxy)benzene $n_D^{26.5}$ 1.5295
(40) 3,5-Dichloro-1-(3,3-dichloro-2-propenyloxy)-4-(5-(3,3-diethoxypropyloxy)pentyloxy)benzene $n_D^{26.5}$ 1.5090
(41) 3,5-Dichloro-1-(3,3-dichloro-2-propenyloxy)-4-(4-(3,3-diethoxypropyloxy)butyloxy)benzene $n_D^{26.5}$ 1.5064
(42) (Z)-3,5-dichloro-1-(3,3-dichloro-2-propenyloxy)-4-(5-(4-chloro-5,5,5-trifluoro-3-pentyloxy)pentyloxy)benzene $n_D^{30.0}$ 1.5028
(43) (Z)-3,5-dichloro-1-(3,3-dichloro-2-propenyloxy)-4-(4-(4-chloro-5,5,5-trifluoro-3-pentenyloxy)butyloxy)benzene $n_D^{30.0}$ 1.5057
(44) 3,5-Dichloro-1-(3,3-dichloro-2-propenyloxy)-4-(5-(4,4-dichloro-5,5,5-trifluoro-3-hydroxypentyloxy)pentyloxy)benzene $n_D^{30.0}$ 1.5122
(45) 3,5-Dichloro-1-(3,3-dichloro-2-propenyloxy)-4-(4-(4,4-dichloro-5,5,5-trifluoro-3-hydroxypentyloxy)butyloxy)benzene $n_D^{30.0}$ 1.5161
(46) 3,5-Dichloro-1-(3,3-dichloro-2-propenyloxy)-4-(4-(2,2-diisopropyloxyethoxy)butyloxy)benzene
(47) 3,5-Diethyl-1-(3,3-dichloro-2-propenyloxy)-4-(4-(2,2-diisopropyloxyethoxy)butyloxy)benzene $n_D^{23.5}$ 1.4955
(48) 3,5-Dichloro-1-(3,3-dichloro-2-propenyloxy)-4-(4-(3-chloro-3-ethoxy-carbonyl-2-propenyloxy)butyloxy)benzene $n_D^{23.0}$ 1.5438
(49) 3,5-Dichloro-1-(3,3-dichloro-2-propenyloxy)-4-(4-(3-chloro-3-cyano-2-propenyloxy)butyloxy)benzene $n_D^{23.0}$ 1.5410
(50) 3,5-Dichloro-1-(3,3-dichloro-2-propenyloxy)-4-(4-(3-cyano-3,3-dichloro-2-hydroxypropyloxy)butyloxy)benzene $n_D^{24.0}$ 1.5460
(51) 3,5-Dichloro-1-(3,3-dichloro-2-propenyloxy)-4-(4-(3,3-dichloro-4,4,4-trifluoro-2-acetoxybutyloxy)butyloxy)benzene $n_D^{23.0}$ 1.4958
(52) 3,5-Diethyl-1-(3,3-dichloro-2-propenyloxy)-4-(4-(2,2-diethoxyethoxy)butyloxy)benzene $n_D^{26.0}$ 1.4991
(53) 3,5-Diethyl-1-(3,3-dichloro-2-propenyloxy)-4-(5-(2,2-diethoxyethoxy)pentyloxy)benzene $n_D^{26.0}$ 1.4982
(54) (Z)-3,5-diethyl-1-(3,3-dichloro-2-propenyloxy)-4-(4-(3-chloro-4,4,4-trifluoro-2-butenyloxy)butyloxy)benzene $n_D^{26.0}$ 1.4975
(55) (Z)-3,5-diethyl-1-(3,3-dichloro-2-propenyloxy)-4-(5-(3-chloro-4,4,4-trifluoro-2-butenyloxy)pentyloxy)benzene $n_D^{26.0}$ 1.4958
(56) 3,5-Diethyl-1-(3,3-dichloro-2-propenyloxy)-4-(4-(3,3-dibromo-2-propenyloxy)butyloxy)benzene
(57) 3-Ethyl-5-methyl-1-(3,3-dichloro-2-propenyloxy)-4-(4-(3,3-dibromo-2-propenyloxy)butyloxy)benzene
(58) 3,5-Dichloro-1-(3,3-dichloro-2-propenyloxy)-4-(5-(3,3-dibromo-2-propenyloxy)pentyloxy)benzene
(59) 3,5-Diethyl-1-(3,3-dichloro-2-propenyloxy)-4-(5-(3,3-dibromo-2-propenyloxy)pentyloxy)benzene
(60) 3-Ethyl-5-methyl-1-(3,3-dichloro-2-propenyloxy)-4-(5-(3,3-dibromo-2-propenyloxy)pentyloxy)benzene
(61) 3-Ethyl-5-methyl-1-(3,3-dichloro-2-propenyloxy)-4-(4-(3-chloro-4,4,4-trifluoro-2-butenyloxy)butyloxy)benzene
(62) 3-Ethyl-5-methyl-1-(3,3-dichloro-2-propenyloxy)-4-(5-(3-chloro-4,4,4-trifluoro-2-butenyloxy)pentyloxy)benzene
(63) 3,5-Diethyl-1-(3,3-dichloro-2-propenyloxy)-4-(4-(4-chloro-5,5,5-trifluoro-3-pentyloxy)butyloxy)benzene
(64) 3-Ethyl-5-methyl-1-(3,3-dichloro-2-propenyloxy)-4-(4-(4-chloro-5,5,5-trifluoro-3-pentyloxy)butyloxy)benzene
(65) 3,5-Diethyl-1-(3,3-dichloro-2-propenyloxy)-4-(5-(4-chloro-5,5,5-trifluoro-3-pentenyloxy)pentyloxy)benzene
(66) 3-Ethyl-5-methyl-1-(3,3-dichloro-2-propenyloxy)-4-(5-(4-chloro-5,5,5-trifluoro-3-

-continued pentenyloxy)pentyloxy)benzene
(67) 3-Ethyl-5-methyl-1-(3,3-dichloro-2-propenyloxy)-4-(4-(2,2-diisopropyloxyethoxy)butyloxy)benzene
(68) 3,5-Dichloro-1-(3,3-dichloro-2-propenyloxy)-4-(5-(2,2-diisopropyloxyethoxy)pentyloxy)benzene
(69) 3,5-Diethyl-1-(3,3-dichloro-2-propenyloxy)-4-(5-(2,2-diisopropyloxyethoxy)pentyloxy)benzene
(70) 3-Ethyl-5-methyl-1-(3,3-dichloro-2-propenyloxy)-4-(5-(2,2-diisopropyloxyethoxy)pentyloxy)benzene
(71) 3,5-Dichloro-1-(3,3-dichloro-2-propenyloxy)-4-(4-(2,2-dipropyloxyethoxy)butyloxy)benzene
(72) 3,5-Diethyl-1-(3,3-dichloro-2-propenyloxy)-4-(4-(2,2-dipropyloxyethoxy)butyloxy)benzene    $n_D^{23.5}$ 1.4975
(73) 3-Ethyl-5-methyl-1-(3,3-dichloro-2-propenyloxy)-4-(4-(2,2-dipropyloxyethoxy)butyloxy)benzene
(74) 3,5-Dichloro-1-(3,3-dichloro-2-propenyloxy)-4-(5-(2,2-dipropyloxyethoxy)pentyloxy)benzene
(75) 3,5-Diethyl-1-(3,3-dichloro-2-propenyloxy)-4-(5-(2,2-dipropyloxyethoxy)pentyloxy)benzene
(76) 3-Ethyl-5-methyl-1-(3,3-dichloro-2-propenyloxy)-4-(5-(2,2-dipropyloxyethoxy)pentyloxy)benzene
(77) 3-Ethyl-5-methyl-1-(3,3-dichloro-2-propenyloxy)-4-(4-(2,2-diethoxyethoxy)butyloxy)benzene
(78) 3-Ethyl-5-methyl-1-(3,3-dichloro-2-propenyloxy)-4-(5-(2,2-diethoxyethoxy)pentyloxy)benzene
(79) 3,5-Diethyl-1-(3,3-dichloro-2-propenyloxy)-4-(4-(3,3-diethoxypropyloxy)butyloxy)benzene
(80) 3-Ethyl-5-methyl-1-(3,3-dichloro-2-propenyloxy)-4-(4-(3,3-diethoxypropyloxy)butyloxy)benzene
(81) 3,5-Diethyl-1-(3,3-dichloro-2-propenyloxy)-4-(5-(3,3-diethoxypropyloxy)pentyloxy)benzene
(82) 3-Ethyl-5-methyl-1-(3,3-dichloro-2-propenyloxy)-4-(5-(3,3-diethoxypropyloxy)pentyloxy)benzene
(83) 3,5-Dichloro-1-(3,3-dichloro-2-propenyloxy)-4-(5-(2,2-dimethoxyethoxy)pentyloxy)benzene
(84) 3,5-Diethyl-1-(3,3-dichloro-2-propenyloxy)-4-(5-(2,2-dimethoxyethoxy)pentyloxy)benzene
(85) 3-Ethyl-5-methyl-1-(3,3-dichloro-2-propenyloxy)-4-(5-(2,2-dimethoxyethoxy)pentyloxy)benzene
(86) 3,5-Dichloro-1-(3,3-dichloro-2-propenyloxy)-4-(5-(2,2-di(propylthio)ethoxy)pentyloxy)benzene
(87) 3,5-Diethyl-1-(3,3-dichloro-2-propenyloxy)-4-(5-(2,2-di(propylthio)ethoxy)pentyloxy)benzene
(88) 3-Ethyl-5-methyl-1-(3,3-dichloro-2-propenyloxy)-4-(5-(2,2-di(propylthio)ethoxy)pentyloxy)benzene
(89) 3,5-Dichloro-1-(3,3-dichloro-2-propenyloxy)-4-(5-(2,2-di(2,2,2-trichloroethoxy)ethoxy)pentyloxy)benzene
(90) 3,5-Diethyl-1-(3,3-dichloro-2-propenyloxy)-4-(5-(2,2-di(2,2,2-trichloroethoxy)ethoxy)pentyloxy)benzene
(91) 3-Ethyl-5-methyl-1-(3,3-dichloro-2-propenyloxy)-4-(5-(2,2-di(2,2,2-trichloroethoxy)ethoxy)pentyloxy)benzene
(92) 3,5-Dichloro-1-(3,3-dichloro-2-propenyloxy)-4-(5-(2,2-di(ethylthio)ethoxy)pentyloxy)benzene
(93) 3,5-Diethyl-1-(3,3-dichloro-2-propenyloxy)-4-(5-(2,2-di(ethylthio)ethoxy)pentyloxy)benzene
(94) 3-Ethyl-5-methyl-1-(3,3-dichloro-2-propenyloxy)-4-(5-(2,2-di(ethylthio)ethoxy)pentyloxy)benzene
(95) 3,5-Dichloro-1-(3,3-dichloro-2-propenyloxy)-4-(4-(2,2-dibutyloxyethoxy)butyloxy)benzene
(96) 3,5-Diethyl-1-(3,3-dichloro-2-propenyloxy)-4-(4-(2,2-dibutyloxyethoxy)butyloxy)benzene    $n_D^{22.5}$ 1.4950
(97) 3-Ethyl-5-methyl-1-(3,3-dichloro-2-propenyloxy)-4-(4-(2,2-dibutyloxyethoxy)butyloxy)benzene
(98) 3,5-Dichloro-1-(3,3-dichloro-2-propenyloxy)-4-(5-(2,2-dibutyloxyethoxy)pentyloxy)benzene
(99) 3,5-Diethyl-1-(3,3-dichloro-2-propenyloxy)-4-(5-(2,2-dibutyloxyethoxy)pentyloxy)benzene
(100) 3-Ethyl-5-methyl-1-(3,3-dichloro-2-propenyloxy)-4-(2,2-dibutyloxyethoxy)pentyloxy)benzene
(101) 3,5-Dichloro-1-(3,3-dichloro-2-propenyloxy)-4-(4-(2,2-dimethoxyethoxy)butyloxy)benzene
(102) 3,5-Diethyl-1-(3,3-dichloro-2-propenyloxy)-4-(4-(2,2-dimethoxyethoxy)butyloxy)benzene    $n_D^{24.0}$ 1.5068
(103) 3-Ethyl-5-methyl-1-(3,3-dichloro-2-propenyloxy)-4-(4-(2,2-dimethoxyethoxy)butyloxy)benzene
(104) 3,5-Dichloro-1-(3,3-dichloro-2-propenyloxy)-4-(4-(1,1,1,3,3,3-hexafluoro-2-propyloxy)butyloxy)benzene    $n_D^{24.0}$ 1.4805
(105) 3,5-Dichloro-1-(3,3-dichloro-2-propenyloxy)-4-(5-(1,1,1,3,3,3-hexafluoro-2-propyloxy)pentyloxy)benzene
(106) 3,5-Dichloro-1-(3,3-dichloro-2-propenyloxy)-4-(4-(2,2,2-trifluoroethoxy)butyloxy)benzene
(107) 3,5-Dichloro-1-(3,3-dichloro-2-propenyloxy)-4-(5-(2,2,2-trifluoroethoxy)pentyloxy)benzene
(108) 3,5-Dichloro-1-(3,3-dichloro-2-propenyloxy)-4-(4-(2,2-di(propylthio)ethoxy)butyloxy)benzene
(109) 3,5-Diethyl-1-(3,3-dichloro-2-propenyloxy)-4-(4-(2,2-di(propylthio)ethoxy)butyloxy)benzene    $n_D^{26.4}$ 1.5300
(110) 3-Ethyl-5-methyl-1-(3,3-dichloro-2-propenyloxy)-4-(4-(2,2-di(propylthio)ethoxy)butyloxy)benzene
(111) 3,5-Dichloro-1-(3,3-dichloro-2-propenyloxy)-4-(3-(3-chloro-4,4,4-trifluoro-2-butenyloxy)propyloxy)benzene
(112) 3,5-Dichloro-1-(3,3-dichloro-2-propenyloxy)-4-(1-methyl-4-(3-chloro-4,4,4-trifluoro-2-butenyloxy)butyloxy)benzene
(113) 3,5-Dichloro-1-(3,3-dichloro-2-propenyloxy)-4-(1-methyl-4-(3,3-dichloro-2-propenyloxy)butyloxy)benzene
(114) 3,5-Dichloro-1-(3,3-dichloro-2-propenyloxy)-4-(4-(3-chloro-4,4,4-trifluoro-2-butenyloxy)pentyloxy)benzene
(115) 3,5-Dichloro-1-(3,3-dichloro-2-propenyloxy)-4-(4-(3,3-dichloro-2-propenyloxy)pentyloxy)benzene
(116) 3,5-Dichloro-1-(3,3-dichloro-2-propenyloxy)-4-(1-methyl-3-(3-chloro-4,4,4-trifluoro-2-butenyloxy)propyloxy)benzene
(117) 3,5-Dichloro-1-(3,3-dichloro-2-propenyloxy)-4-(1-methyl-3-(3,3-dichloro-2-propenyloxy)propyloxy)benzene
(118) 3,5-Dichloro-1-(3,3-dichloro-2-propenyloxy)-4-(3-(3-chloro-4,4,4-trifluoro-2-butenyloxy)butyloxy)benzene
(119) 3,5-Dichloro-1-(3,3-dichloro-2-propenyloxy)-4-(3-(3,3-dichloro-2-propenyloxy)butyloxy)benzene
(120) 3,5-Dichloro-1-(3,3-dichloro-2-propenyloxy)-4-(2,2-dimethyl-3-(3-chloro-4,4,4-trifluoro-2-butenyloxy)propyloxy)benzene
(121) 3,5-Dichloro-1-(3,3-dichloro-2-propenyloxy)-4-(2,2-dimethyl-3-(3,3-dichloro-2-propenyloxy)propyloxy)benzene
(122) 3,5-Dichloro-1-(3,3-dichloro-2-propenyloxy)-4-(2-ethyl-2-methyl-3-(3-chloro-4,4,4-trifluoro-2-butenyloxy)propyloxy)benzene
(123) 3,5-Dichloro-1-(3,3-dichloro-2-propenyloxy)-4-(2-ethyl-2-methyl-3-(3,3-dichloro-2-propenyloxy)propyloxy)benzene
(124) 3,5-Dichloro-1-(3,3-dichloro-2-propenyloxy)-4-(1-methyl-4-(3-chloro-4,4,4-trifluoro-2-butenyloxy)pentyloxy)benzene
(125) 3,5-Dichloro-1-(3,3-dichloro-2-propenyloxy)-4-(1-methyl-4-(3,3-dichloro-2-propenyloxy)pentyloxy)benzene
(126) 3,5-Dichloro-1-(3,3-dichloro-2-propenyloxy)-4-(1-methyl-3-(3-chloro-4,4,4-trifluoro-2-butenyloxy)butyloxy)benzene
(127) 3,5-Dichloro-1-(3,3-dichloro-2-propenyloxy)-4-(1-methyl-3-(3,3-dichloro-2-propenyloxy)butyloxy)benzene
(128) 3,5-Dichloro-1-(3,3-dichloro-2-propenyloxy)-4-(2-methyl-3-(3-chloro-4,4,4-trifluoro-2-butenyloxy)butyloxy)benzene
(129) 3,5-Dichloro-1-(3,3-dichloro-2-propenyloxy)-4-(2-methyl-3-(3,3-dichloro-2-propenyloxy)propyloxy)benzene The following are production examples for the intermediate compounds of the general formula [XIV].

INTERMEDIATE PRODUCTION EXAMPLE 1

In a reaction vessel containing 7.61 g of 1,3-propanediol was put 2.20 g of 60% sodium hydride (in oil), and the mixture was stirred until the evolution of hydrogen gas ceased, to which 7.28 g of 1,1,3-trichloro-1-propene was added dropwise under ice cooling. The reaction mixture was slowly warmed and stirred at 60° C. for 3 hours, which was then poured into water and extracted twice with diethyl ether. The diethyl ether layers were combined, washed with water, dried over magnesium sulfate and then concentrated to give a crude product. The crude product was subjected to silica gel chromatography, which afforded 5.48 g of 3-(3,3-dichloro-2-propenyloxy)propanol (yield, 60%).

$^1$H-NMR (CDCl$_3$/TMS) δ (ppm): 1.85 (2H, dt), 3.63 (2H, t), 3.77 (2H, t), 4.11 (2H, d), 6.04 (1H, t)

INTERMEDIATE PRODUCTION EXAMPLE 2

In a reaction vessel containing 9.02 g of 1,4-butanediol was put 2.20 g of 60% sodium hydride (in oil), and the mixture was stirred until the evolution of hydrogen gas ceased, to which 7.28 g of 1,1,3-trichloro-1-propene was added dropwise under ice cooling. The reaction mixture was slowly warmed and stirred at 60° C. for 3 hours, which was then poured into water and extracted twice with diethyl ether. The diethyl ether layers were combined, washed with water, dried over magnesium sulfate and then concentrated to give a crude product. The crude product was subjected to silica gel chromatography, which afforded 1.40 g of 4-(3,3-dichloro-2-propenyloxy)butanol (yield, 14%).

$^1$5H-NMR (CDCl$_3$/TMS) δ (ppm): 1.66 (4H, br s), 3.48 (2H, t), 3.66 (2H, t), 4.11 (2H, d), 6.03 (1H, t)

INTERMEDIATE PRODUCTION EXAMPLE 3

In a reaction vessel containing 10.42 g of 1,5-pentanediol was put 2.20 g of 60% sodium hydride (in oil), and the mixture was stirred until the evolution of hydrogen gas ceased, to which 3.83 g of 3-chloro-1-propene was added dropwise under ice cooling. The reaction mixture was slowly warmed and stirred at 60° C. for 3 hours, which was then poured into water and extracted twice with diethyl ether. The diethyl ether layers were combined, washed with water, dried over magnesium sulfate and then concentrated to give a crude product. The crude product was subjected to silica gel chromatography, which afforded 1.50 g of 5-(3-chloro-1-propenyloxy)pentanol (yield, 21%).

$^1$H-NMR (CDCl$_3$/TMS) δ (ppm): 1.4–1.7 (6H, m), 3.44 (2H, t), 3.65 (2H, t), 3.96 (2H, d), 5.17 (1H, d), 5.26 (1H, d), 5.92 (1H, m)

INTERMEDIATE PRODUCTION EXAMPLE 4

To a mixture of 56.3 g of 1,4-butanediol and 400 ml of N,N-dimethylformamide was slowly added 11.0 g of 60% sodium hydride (in oil) with stirring under ice cooling. After stirring at room temperature for 12 hours, 49.3 g of bromoacetaldehyde diethylacetal was added dropwise to the reaction mixture, which was stirred at 60° C. for 8 hours. The reaction mixture was poured into ice water and extracted twice with ethyl acetate. The ethyl acetate layers were combined, washed with water, dried over magnesium sulfate and then concentrated to give a crude product. The crude product was subjected to silica gel chromatography, which afforded 21.6 g of 4-(2,2-diethoxyethoxy)butanol (yield, 41%), $n_D^{23.2}$ 1.4314.

INTERMEDIATE PRODUCTION EXAMPLE 5

In a reaction vessel containing 10 ml of N,N-dimethylformamide and 0.088 g of 60% sodium hydride (in oil) was put 0.070 g of methanol under ice cooling, and the mixture was stirred until the evolution of hydrogen gas ceased, to which 0.40 g of 4-(3,3-dichloro-2-propenyloxy) butanol was added. After stirring at 50° C. for 3 hours, the reaction mixture was poured into diluted hydrochloric acid and extracted twice with diethyl ether. The diethyl ether layers were combined, washed with water, dried over magnesium sulfate and then concentrated to give a crude product. The crude product was subjected to silica gel chromatography, which afforded 0.20 g of 4-(3-chloro-2-propynyloxy)butanol (yield, 62%), $n_D^{24.6}$ 1.4720.

The following are production examples for the intermediate compounds of the general formula [XII].

INTERMEDIATE PRODUCTION EXAMPLE 6

A reaction vessel was charged with 30.5 g of 4-hydroxyphenyl benzoate, 21.6 g of potassium carbonate, 20.8 g of 1,1,3-trichloropropene and 100 ml of N,N-dimethylformamide. After stirring at room temperature for 15 hours, the reaction mixture was poured into water and extracted twice with 150 ml of diethyl ether. The diethyl ether layers were combined, washed with water, dried over anhydrous magnesium sulfate and then concentrated to give a crude product. The crude product was subjected to silica gel chromatography, which afforded 44.1 g of 4-(3,3-dichloro-2-propenyloxy)phenyl benzoate (yield, 96%).

A reaction vessel was charged with 44.1 g of 4-(3,3-dichloro-2-propenyloxy)phenyl benzoate and 400 ml of methanol, to which 33 g of 30% potassium hydroxide solution was slowly added dropwise under ice cooling. After stirring for 1 hour, the reaction mixture was weakly acidified by the addition of 10% hydrochloric acid and extracted twice with 150 ml of diethyl ether under salting out. The diethyl ether layers were combined, washed with water, dried over anhydrous magnesium sulfate and then concentrated to give a crude product. The crude product was subjected to silica gel chromatography, which afforded 26.0 g of 4-(3,3-dichloro-2-propenyloxy)phenol (yield, 87%).

A reaction vessel was charged with 26.0 g of 4-(3,3-dichloro-2-propenyloxy)phenol and 500 ml of carbon tetrachloride, to which a solution of 27.1 g of tert-butyl hypochlorite dissolved in 20 ml of carbon tetrachloride was slowly added dropwise. After 24 hours, the reaction mixture was poured into water and the organic layer (carbon tetrachloride layer). was separated. The organic layer was washed with water, dried over anhydrous magnesium sulfate and then concentrated to give a crude product. The crude product was subjected to silica gel chromatography, which afforded 11.0 g of 2,6-dichloro-4-(3,3-dichloro-2-propenyloxy)phenol (yield, 32%), $n_D^{22.5}$ 1.5895.

The following are production examples for the intermediate compounds of the general formula [VII] (including compounds of the general formula [IV]).

INTERMEDIATE PRODUCTION EXAMPLE 7

Production of intermediate compound 12)

A mixture of 27 g of 2-ethyl-6-methylaniline, 36 ml of concentrated sulfuric acid and 100 ml of water was stirred at a temperature of 0° C. to 5° C., during which a solution of 16.1 g of sodium nitrite dissolved in 50 ml of water was added dropwise to the mixture. After completion of the dropwise addition, 150 g of chilled water, 1.5 g of urea and 150 g of ice were added thereto.

This aqueous solution was added dropwise to a mixture of 100 ml of sulfuric acid, 100 ml of water and 150 g of sodium sulfate heated at 135° C. with stirring. At the same time as the dropwise addition, steam distillation was carried out. After completion of the dropwise addition, an aqueous solution obtained by the steam distillation was subjected to salting out with sodium chloride, dried over anhydrous magnesium sulfate and then concentrated to give a crude product. The crude product was subjected to silica gel chromatography, which 16 g of 2-ethyl-6-methylphenol (yield, 59%).

Then, 16 g of 2-ethyl-6-methylphenol was dissolved in 200 ml of chloroform, to which 56.6 g of tetrabutylammonium tribromide was added in portions with stirring at 0° C. After stirring at room temperature for 1 hour, the solvent was distilled out under reduced pressure. The residue was dissolved in 300 ml of diethyl ether, washed with 10% hydrochloric acid and then water, dried over anhydrous magnesium sulfate and then concentrated to give a crude product. The crude product was subjected to silica gel chromatography, which afforded 23 g of 4-bromo-2-ethyl-6-methylphenol (yield, 92%).

To a mixture of 26 g of 4-bromo-2-ethyl-6-methylphenol, 24.8 g of benzyl bromide and 200 ml of N,N-dimethylformamide was added 21.7 g of potassium carbonate with stirring at room temperature. After stirring at room temperature for 24 hours, the reaction mixture was poured into ice water and extracted twice with 500 ml of diethyl ether. The diethyl ether layers were combined, washed with water, dried over anhydrous magnesium sulfate and then concentrated to give a crude product. The crude product was subjected to silica gel chromatography, which afforded 35.6 g of 4-bromo-2-ethyl-6-methyl-1-benzyloxybenzene (yield, 97%).

Then, 35.6 g of 4-bromo-2-ethyl-6-methyl-1-benzyloxybenzene was dissolved in 250 ml of tetrahydrofuran, to which 69 ml of a solution of n-butyl lithium in hexane (1.69 mol/l) was added dropwise with stirring at −70° C. After further stirring at −70° C. for 2 hours, a solution of 12.1 g of trimethoxyboran dissolved in 50 ml of tetrahydrofuran was added dropwise to the reaction solution. After completion of the dropwise addition, the reaction mixture was returned to room temperature and stirred for 1 hour, which was poured into ice water, weakly acidified by the addition of 10% hydrochloric acid and extracted twice with 500 ml of diethyl ether. The diethyl ether layers were combined, washed with water, dried over anhydrous magnesium sulfate and then concentrated. To the residue was added 120 m of toluene, to which 33 ml of 30% aqueous hydrogen peroxide solution was added dropwise with heating at 0° C. under stirring. After heating under reflux for 1 hour, the reaction mixture was returned to room temperature, washed once with water, twice with 10% aqueous ammonium ferrous sulfate solution and further once with water, and the toluene layer was dried over anhydrous magnesium sulfate and then concentrated to give a crude product. The crude product was subjected to silica gel chromatography, which afforded 26.2 g of 4-benzyloxy-3-ethyl-5-methylphenol (yield, 93%).

To a mixture of 6.3 g of 4-benzyloxy-3-ethyl-5-methylphenol, 3.2 g of triethylamine and 50 ml of chloroform was added dropwise 4.0 g of benzoyl chloride with stirring at 0° C. After stirring at room temperature for 6 hours, the reaction mixture was concentrated under reduced pressure. To the residue was added 100 ml of 10% hydrochloric acid, which was extracted with 100 ml of ethyl acetate. The ethyl acetate layer was washed with 10% hydrochloric acid, aqueous sodium hydrogencarbonate solution and then saturated sodium chloride solution, dried over anhydrous magnesium sulfate and then concentrated under reduced pressure, which afforded 8.4 g of crude 4-benzyloxy-3-ethyl-5-methylphenyl benzoate (yield, 93%).

Then, 8.4 g of crude 4-benzyloxy-3-ethyl-5-methylphenyl benzoate was dissolved in 100 ml of ethyl acetate, and the solution was put in a reaction vessel. The air in the reaction vessel was replaced with nitrogen gas. To the vessel was added 0.5 g of 10% palladium on carbon, and the nitrogen gas in the vessel was replaced with hydrogen gas, followed by vigorous stirring at room temperature for 24 hours. The hydrogen gas in the vessel was replaced with nitrogen gas, and the reaction mixture was filtered through cerite. The filtrate was concentrated under reduced pressure, which afforded 5.9 g of 2-ethyl-6-methyl-4-benzoyloxyphenol (yield, 95%).

To a mixture of 0.52 g of 4-(3-methyl-2-butenyloxy)butanol, 0.77 g of 2-ethyl-6-methyl-4-benzoyloxyphenol, 0.87 g of triphenylphosphine and 20 ml of tetrahydrofuran was slowly added dropwise 0.73 g of diisopropyl azodicarboxylate with stirring under ice cooling. After stirring at room temperature for 6 hours, the reaction mixture was concentrated. The residue was subjected to silica gel chromatography, which afforded 0.94 g of 3-ethyl-5-methyl-1-benzoyloxy-4-(4-(3-methyl-2-butenyloxy)butyloxy)benzene (yield, 79%), $n_D^{20.0}$ 1.5361.

To a solution of 0.94 g of 3-ethyl-5-methyl-1-benzoyloxy-4-(4-(3-methyl-2-butenyloxy)butyloxy)benzene dissolved in 10 ml of methanol was added a solution of 0.17 g of potassium hydroxide dissolved in 1.5 g of water. After stirring at room temperature for 1 hour, the reaction mixture was acidified by the addition of diluted hydrochloric acid and then concentrated. Water was added to the residue, which was extracted twice with ethyl acetate. The ethyl acetate layers were combined, washed with water, dried over magnesium sulfate and then concentrated. The residue was subjected to silica gel chromatography, which 0.60 g of 3-ethyl-5-methyl-4-(4-(3-methyl-2-butenyloxy)butyloxy)phenol (yield, 87%), $n_D^{24.5}$ 1.5064.

INTERMEDIATE PRODUCTION EXAMPLE 8

Production of intermediate compound 45)

To a mixture of 16.0 g of 4-(2,2-diethoxyethoxy)butanol, 18.9 g of 2,6-diethyl-4-benzoyloxyphenol, 20.2 g of triphenylphosphine and 200 ml of tetrahydrofuran was slowly added dropwise 17.0 g of dilsopropyl azodicarboxylate with stirring under ice cooling. After stirring at room temperature for 6 hours, the reaction mixture was concentrated. The residue was subjected to silica gel chromatography, which afforded 31.4 g of 3,5-diethyl-1-benzoyloxy-4-(4-(2,2-diethoxyethoxy)butyloxy)benzene (yield, 88%), $n_D^{24.8}$ 1.5129.

To a solution of 31.0 g of 3,5-diethyl-1-benzoyloxy-4-(4-(2,2-diethoxyethoxy)butyloxy)benzene dissolved in 100 ml of methanol added a solution of 5.1 g of potassium hydroxide dissolved in 25 g of water. After stirring at room temperature for 1 hour, the reaction mixture was acidified by the addition of diluted hydrochloric acid and then concentrated. Water was added to the residue, which was extracted twice with ethyl acetate. The ethyl acetate layers were combined, washed with water, dried over magnesium sulfate and then concentrated. The residue was subjected to silica gel chromatography, which afforded 0.60 g of 3,5-diethyl-4-(4-(2,2-diethoxyethoxy)butyloxy)phenol (yield, 94%), $n_D^{25.0}$ 1.4890.

The following are some specific examples of the intermediate compounds of the general formula [VII] (including compounds of the general formula [IV]) with their compound numbers and physical properties, if measured.

1) 3,5-Dichloro-4-(2-(3,3-dichloro-2-propenyloxy)ethoxy)phenol
2) 3,5-Dichloro-4-(3-(3,3-dichloro-2-propenyloxy)propyloxy)phenol
3) 3,5-Dichloro-4-(4-(3,3-dichloro-2-propenyloxy)butyloxy)phenol
4) 3,5-Dichloro-4-(5-(3,3-dichloro-2-propenyloxy)pentyloxy)phenol
5) 3,5-Dichloro-4-(6-(3,3-dichloro-2-propenyloxy)hexyloxy)phenol
6) 3,5-Dichloro-4-(3-(3-methyl-2-butenyloxy)propyloxy)phenol
7) 3,5-Dichloro-4-(4-(3-methyl-2-

-continued butenyloxy)butyloxy)phenol
8) 3,5-Dichloro-4-(4-(3-chloro-2-butenyloxy)butyloxy)phenol
9) 3,5-Dichloro-4-(4-(3-chloro-2-propenyloxy)butyloxy)phenol
10) 3-Ethyl-5-methyl-4-(4-(3,3-dichloro-2-propenyloxy)butyloxy)phenol  $n_D^{18.7}$ 1.5315
11) 3,5-Diethyl-4-(4-(3,3-dichloro-2-propenyloxy)butyloxy)phenol  $n_D^{19.0}$ 1.5308
12) 3-Ethyl-5-methyl-4-(4-(3-methyl-2-butenyloxy)butyloxy)phenol  $n_D^{24.5}$ 1.5064
13) 3,5-Diethyl-4-(4-(3-methyl-2-butenyloxy)butyloxy)phenol
14) 3,5-Dichloro-4-(5-(2-propenyloxy)pentyloxy)phenol
15) 3,5-Dichloro-4-(4-(3,3-dibromo-2-propenyloxy)butyloxy)phenol
16) 3,5-Dichloro-4-(4-(3-chloro-4,4,4-trifluoro-2-butenyloxy)butyloxy)phenol
17) 3,5-Dichloro-4-(4-(3-trifluoromethyl-2-butenyloxy)butyloxy)phenol
18) 3,5-Dichloro-4-(2-(2-ethoxyethoxy)ethoxy)phenol
19) 3,5-Dichloro-4-(4-(3-chloro-2-propynyloxy)butyloxy)phenol
20) 3,5-Dichloro-4-(4-(2-propenyloxy)butyloxy)phenol
21) 3,5-Dichloro-4-(4-(2,2-diethoxyethoxy)butyloxy)phenol
22) 3,5-Dichloro-4-(4-(2-chloro-2-propenyloxy)butyloxy)phenol
23) 3,5-Dichloro-4-(4-(3,3-dichloro-2-propenyloxy)-2-butenyloxy)phenol
24) 3,5-Diethyl-4-(5-(3,3-dichloro-2-propenyloxy)pentyloxy)phenol  $n_D^{22.5}$ 1.5230
25) 3-Ethyl-5-methyl-4-(5-(3,3-dichloro-2-propenyloxy)pentyloxy)phenol
26) 3,5-Dichloro-4-(5-(2,2-diethoxyethoxy)pentyloxy)phenol
27) 3,5-Dichloro-4-(4-(3,3-difluoro-2-propenyloxy)butyloxy)phenol
28) (Z)-3,5-dichloro-4-(4-(2,3-dichloro-2-propenyloxy)butyloxy)phenol
29) (E)-3,5-dichloro-4-(4-(2,3-dichloro-2-propenyloxy)butyloxy)phenol
30) 3,5-Dichloro-4-(4-(3,3-dichloro-4,4,4-trifluoro-2-hydroxybutyloxy)butyloxy)phenol
31) 3,5-Dichloro-4-(5-(3-chloro-4,4,4-trifluoro-2-butenyloxy)pentyloxy)phenol
32) 3,5-Dichloro-4-(4-(3,4-dichloro-4,4-difluoro-2-butenyloxy)butyloxy)phenol
33) 3,5-Dichloro-4-(5-(3,3-diethoxypropyloxy)pentyloxy)phenol
34) 3,5-Dichloro-4-(4-(3,3-diethoxypropyloxy)butyloxy)phenol
35) 3,5-Dichloro-4-(5-(4-chloro-5,5,5-trifluoro-3-pentenyloxy)pentyloxy)phenol
36) 3,5-Dichloro-4-(4-(4-chloro-5,5,5-trifluoro-3-pentenyloxy)butyloxy)phenol
37) 3,5-Dichloro-4-(5-(4,4-dichloro-5,5,5-trifluoro-3-hydroxypentyloxy)pentyloxy)phenol
38) 3,5-Dichloro-4-(4-(4,4-dichloro-5,5,5-trifluoro-3-hydroxypentyloxy)butyloxy)phenol
39) 3,5-Dichloro-4-(4-(2,2-diisopropyloxyethoxy)butyloxy)phenol
40) 3,5-Diethyl-4-(4-(2,2-diisopropyloxyethoxy)butyloxy)phenol
41) 3,5-Dichloro-4-(4-(3-chloro-3-ethoxycarbonyl-2-propenyloxy)butyloxy)phenol
42) 3,5-Dichloro-4-(4-(3-chloro-3-cyano-2-propenyloxy)butyloxy)phenol
43) 3,5-Dichloro-4-(4-(3-cyano-3,3-dichloro-2-hydroxypropyloxy)butyloxy)phenol
44) 3,5-Dichloro-4-(4-(3,3-dichloro-4,4,4-trifluoro-2-acetoxybutyloxy)butyloxy)phenol
45) 3,5-Diethyl-4-(4-(2,2-diethoxyethoxy)butyloxy)phenol  $n_D^{25.0}$ 1.4890
46) 3,5-Diethyl-4-(5-(2,2-diethoxyethoxy)pentyloxy)phenol  $n_D^{25.2}$ 1.4910
47) 3,5-Diethyl-4-(4-(3-chloro-4,4,4-trifluoro-2-butenyloxy)butyloxy)phenol
48) 3,5-Diethyl-4-(5-(3-chloro-4,4,4-trifluoro-2-butenyloxy)pentyloxy)phenol
49) 3,5-Diethyl-4-(4-(3,3-dibromo-2-propenyloxy)butyloxy)phenol
50) 3-Ethyl-5-methyl-4-(4-(3,3-dibromo-2-propenyloxy)butyloxy)phenol
51) 3,5-Dichloro-4-(5-(3,3-dibromo-2-propenyloxy)pentyloxy)phenol
52) 3,5-Diethyl-4-(5-(3,3-dibromo-2-propenyloxy)pentyloxy)phenol
53) 3-Ethyl-5-methyl-4-(5-(3,3-dibromo-2-propenyloxy)pentyloxy)phenol
54) 3-Ethyl-5-methyl-4-(4-(3-chloro-4,4,4-trifluoro-2-butenyloxy)butyloxy)phenol
55) 3-Ethyl-5-methyl-4-(5-(3-chloro-4,4,4-trifluoro-2-butenyloxy)pentyloxy)phenol
56) 3,5-Diethyl-4-(4-(4-chloro-5,5,5-trifluoro-3-pentenyloxy)butyloxy)phenol
57) 3-Ethyl-5-methyl-4-(4-(4-chloro-5,5,5-trifluoro-3-pentenyloxy)butyloxy)phenol
58) 3,5-Diethyl-4-(5-(4-chloro-5,5,5-trifluoro-3-pentenyloxy)pentyloxy)phenol
59) 3-Ethyl-5-methyl-4-(5-(4-chloro-5,5,5-trifluoro-3-pentenyloxy)pentyloxy)phenol
60) 3-Ethyl-5-methyl-4-(4-(2,2-diisopropyloxyethoxy)butyloxy)phenol
61) 3,5-Dichloro-4-(5-(2,2-diisopropyloxyethoxy)pentyloxy)phenol
62) 3,5-Diethyl-4-(5-(2,2-diisopropyloxyethoxy)pentyloxy)phenol
63) 3-Ethyl-5-methyl-4-(5-(2,2-diisopropyloxyethoxy)pentyloxy)phenol
64) 3,5-Dichloro-4-(4-(2,2-dipropyloxyethoxy)butyloxy)phenol
65) 3,5-Diethyl-4-(4-(2,2-dipropyloxyethoxy)butyloxy)phenol
66) 3-Ethyl-5-methyl-4-(4-(2,2-dipropyloxyethoxy)butyloxy)phenol
67) 3,5-Dichloro-4-(5-(2,2-dipropyloxyethoxy)pentyloxy)phenol
68) 3,5-Diethyl-4-(5-(2,2-dipropyloxyethoxy)pentyloxy)phenol
69) 3-Ethyl-5-methyl-4-(5-(2,2-dipropyloxyethoxy)pentyloxy)phenol
70) 3-Ethyl-5-methyl-4-(4-(2,2-diethoxyethoxy)butyloxy)phenol
71) 3-Ethyl-5-methyl-4-(5-(2,2-diethoxyethoxy)pentyloxy)phenol
72) 3,5-Diethyl-4-(4-(3,3-diethoxypropyloxy)butyloxy)phenol
73) 3-Ethyl-5-methyl-4-(4-(3,3-diethoxypropyloxy)butyloxy)phenol
74) 3,5-Diethyl-4-(5-(3,3-diethoxypropyloxy)pentyloxy)phenol
75) 3-Ethyl-5-methyl-4-(5-(3,3-diethoxypropyloxy)propyloxy)phenol
76) 3,5-Dichloro-4-(5-(2,2-dimethoxyethoxy)pentyloxy)phenol
77) 3,5-Diethyl-4-(5-(2,2-dimethoxyethoxy)pentyloxy)phenol
78) 3-Ethyl-5-methyl-4-(5-(2,2-dimethoxyethoxy)pentyloxy)phenol
79) 3,5-Dichloro-4-(5-(2,2-di(propylthio)ethoxy)pentyloxy)phenol
80) 3,5-Diethyl-4-(5-(2,2-di(propylthio)ethoxy)pentyloxy)phenol
81) 3-Ethyl-5-methyl-4-(5-(2,2-di(propylthio)ethoxy)pentyloxy)phenol
82) 3,5-Dichloro-4-(5-(2,2-di(2,2,2-trichloroethoxy)ethoxy)pentyloxy)phenol
83) 3,5-Diethyl-4-(5-(2,2-di(2,2,2-trifluoroethoxy)ethoxy)pentyloxy)phenol
84) 3-Ethyl-5-methyl-4-(5-(2,2-di(2,2,2-trichloroethoxy)ethoxy)pentyloxy)phenol
85) 3,5-Dichloro-4-(5-(2,2-di(ethylthio)ethoxy)pentyloxy)phenol
86) 3,5-Diethyl-4-(5-(2,2-di(ethylthio)ethoxy)pentyloxy)phenol
87) 3-Ethyl-5-methyl-4-(5-(2,2-di(ethylthio)ethoxy)pentyloxy)phenol
88) 3,5-Dichloro-4-(4-(2,2-dibutylxoyethoxy)butyloxy)phenol
89) 3,5-Diethyl-4-(4-(2,2- dibutyloxyethoxy)butyloxy)phenol
90) 3-Ethyl-5-methyl-4-(4-(2,2-dibutyloxyethoxy)butyloxy)phenol
91) 3,5-Dichloro-4-(5-(2,2-dibutyloxyethoxy)pentyloxy)phenol
92) 3,5-Diethyl-4-(5-(2,2-dibutyloxyethoxy)pentyloxy)phenol
93) 3-Ethyl-5-methyl-4-(5-(2,2-dibutyloxyethoxy)pentyloxy)phenol
94) 3,5-Dichloro-4-(4-(2,2-dimethoxyethoxy)butyloxy)phenol
95) 3,5-Diethyl-4-(4-(2,2-dimethoxyethoxy)butyloxy)phenol
96) 3-Ethyl-5-methyl-4-(4-(2,2-dimethoxyethoxy)butyloxy)phenol
97) 3,5-Dichloro-4-(4-(1,1,1,3,3,3-hexafluoro-2-propyloxy)butyloxyphenol
98) 3,5-Dichloro-4-(5-(1,1,1,3,3,3-hexafluoro-2-propyloxy)pentyloxy)phenol
99) 3,5-Dichloro-4-(4-(2,2,2-trifluoroethoxy)butyloxy)phenol
100) 3,5-Dichloro-4-(5-(2,2,2-trifluoroethoxy)pentyloxy)phenol
101) 3,5-Dichloro-4-(4-(2,2-di(propylthio)ethoxy)butyloxy)phenol
102) 3,5-Diethyl-4-(4-(2,2-di(propylthio)ethoxy)butyloxy)phenol
103) 3-Ethyl-5-methyl-4-(4-(2,2-di(propylthio)ethoxy)butyloxy)phenol
104) 3,5-Dichloro-4-(3-(3-chloro-4,4,4-trifluoro-2-butenyloxy)propyloxy)phenol
105) 3,5-Dichloro-4-(1-methyl-4-(3-chloro-4,4,4-trifluoro-2-butenyloxy)butyloxy)phenol
106) 3,5-Dichloro-4-(1-methyl-4-(3,3-dichloro-2-propenyloxy)butyloxy)phenol
107) 3,5-Dichloro-4-(4-(3-chloro-4,4,4-trifluoro-2-butenyloxy)pentyloxy)phenol
108) 3,5-Dichloro-4-(4-(3,3-dichloro-2-propenyloxy)pentyloxy)phenol
109) 3,5-Dichloro-4-(1-methyl-3-(3-chloro-4,4,4-trifluoro-2-butenyloxy)propyloxy)phenol
110) 3,5-Dichloro-4-(1-methyl-3-(3,3-dichloro-2-propenyloxy)propyloxy)phenol
111) 3,5-Dichloro-4-(3-(3-chloro-4,4,4-trifluoro-2-butenyloxy)butyloxy)phenol
112) 3,5-Dichloro-4-(3-(3,3-dichloro-2-propenyloxy)butyloxy)phenol
113) 3,5-Dichloro-4-(2,2-dimethyl-3-(3-chloro-4,4,4-trifluoro-2-butenyloxy)propyloxy)phenol
114) 3,5-Dichloro-4-(2,2-dimethyl-3-(3,3-dichloro-2-propenyloxy)propyloxy)phenol
115) 3,5-Dichloro-4-(2-ethyl-2-methyl-3-(3-chloro-4,4,4-trifluoro-2-butenyloxy)propyloxy)phenol
116) 3,5-Dichloro-4-(2-ethyl-2-methyl-3-(3,3-dichloro-2-propenyloxy)propyloxy)phenol
117) 3,5-Dichloro-4-(1-methyl-4-(3-chloro-4,4,4-trifluoro-2-butenyloxy)pentyloxy)phenol
118) 3,5-Dichloro-4-(1-methyl-4-(3,3-dichloro-2-propenyloxy)pentyloxy)phenol
119) 3,5-Dichloro-4-(1-methyl-3-(3-chloro-4,4,4-trifluoro-2-butenyloxy)butyloxy)phenol
120) 3,5-Dichloro-4-(1-methyl-3-(3,3-dichloro-2-propenyloxy)butyloxy)phenol
121) 3,5-Dichloro-4-(2-methyl-3-(3-chloro-4,4,4-trifluoro-2-butenyloxy)propyloxy)phenol
122) 3,5-Dichloro-4-(2-methyl-3-(3,3-dichloro-2-propenyloxy)propyloxy)phenol The following are production examples for the intermediate compounds (including compounds of the general formula [VI]), which are carbonyl compounds of the general formula [XXI] wherein $R^{27}$ is hydrogen.

INTERMEDIATE PRODUCTION EXAMPLE 9

Production of intermediate compound 126)

First, 1.81 g of 3,5-dichloro-1-(3,3-dichloro-2-propenyloxy)-4-(4-(2,2-diethoxyethoxy)butyloxy)benzene was added to a mixture of 10 ml of acetic acid and 1 ml of concentrated hydrochloric acid with stirring under ice cooling. After further stirring for 15 minutes, the reaction mixture was poured into water and extracted twice with diethyl ether. The diethyl ether layers were combined and washed with water, aqueous sodium hydrogencarbonate solution and then saturated sodium chloride solution. The combined diethyl ether layer was dried over magnesium sulfate, and the diethyl ether was distilled out, which afforded 1.51 g of 4-(2,6-dichloro-4-(3,3-dichloro-2-propenyloxy)phenoxy)-butyloxyacetaldehyde (yield, 94%).

$^1$H-NMR (CDCl$_3$/TMS) δ (ppm): 1.94 (4H, m), 3.65 (2H, t), 3.99 (2H, t), 4.58 (2H, d), 6.11 (1H, d), 6.84 (2H, s), 9.75 (1H, s)

The following are some specific examples of the intermediate compounds of the general formula [XXI] wherein $R^{27}$ is hydrogen (including compounds of the general formula [VI]) with their compound numbers and physical properties, if measured.

123) 3-(2,6-Dichloro-4-(3,3-dichloro-2-propenyloxy)phenoxy)propyloxyacetaldehyde
124) 3-(2,6-Diethyl-4-(3,3-dichloro-2-propenyloxy)phenoxy)propyloxyacetaldehyde
125) 3-(2-Ethyl-6-methyl-4-(3,3-dichloro-2-propenyloxy)phenoxy)propyloxyacetaldehyde
126) 4-(2,6-Dichloro-4-(3,3-dichloro-2-propenyloxy)phenoxy)butyloxyacetaldehyde $_1$H-NMR (CDCl$_3$/TMS) δ (ppm): 1.92 (4H, m), 3.65 (2H, t), 3.99 (2H, t), 4.58 (2H, d), 6.11 (1H, d), 6.48 (2H, s), 9.75 (1H, s)

127) 4-(2,6-Diethyl-4-(3,3-dichloro-2-propenyloxy)phenoxy)butyloxyacetaldehyde $^1$H-NMR (CDCl$_3$/TMS) δ (ppm): 1.22 (6H, t), 1.88 (4H, m), 2.63 (4H, q), 3.63 (2H, t), 3.74 (2H, t), 4.09 (2H, s), 4.61 (2H, d), 6.14 (1H, t), 6.57 (2H, s), 9.75 (1H, s)

128) 4-(2-Ethyl-6-methyl-4-(3,3-dichloro-2-propenyloxy)phenoxy)butyloxyacetaldehyde
129) 5-(2,6-dichloro-4-(3,3-dichloro-2-propenyloxy)phenoxy)pentyloxyacetaldehyde $^1$H-NMR (CDCl$_3$/TMS) δ (ppm): 1.59–1.77 (4H, m), 1.86 (2H, m), 3.58 (2H, t), 3.96 (2H, t), 4.07 (2H, s), 4.58 (2H, d), 6.11 (iH, t), 6.83 (2H, s), 9.74 (1H, s)

130) 5-(2,6-Diethyl-4-(3,3-dichloro-2-propenyloxy)phenoxy)pentyloxyacetaldehyde $^1$H-NMR (CDCl$_3$/TMS) δ (ppm): 1.22 (6H, t), 1.60–1.82 (6H, m), 2.63 (4H, q), 3.58 (2H, t), 3.71 (2H, t), 4.07 (2H, s), 4.61 (2H, d), 6.14 (1H, t), 6.57 (2H, s), 9.74 (1H, s)

131) 5-(2-Ethyl-6-methyl-4-(3,3-dichloro-2-propenyloxy)phenoxy)pentyloxyacetaldehyde
132) 6-(2,6-Dichloro-4-(3,3-dichloro-2-propenyloxy)phenoxy)hexyloxyacetaldehyde
133) 6-(2,6-Diethyl-4-(3,3-dichloro-2-propenyloxy)phenoxy)hexyloxyacetaldehyde
134) 6-(2-Ethyl-6-methyl-4-(3,3-dichloro-2-propenyloxy)phenoxy)hexyloxyacetaldehyde
135) 3-(4-(2,6-Dichloro-4-(3,3-dichloro-2-propenyloxy)phenoxy)butyloxy)propionaldehyde
136) 3-(4-(2,6-Diethyl-4-(3,3-dichloro-2-propenyloxy)phenoxy)butyloxy)propionaldehyde
137) 3-(4-(2-Ethyl-6-methyl-4-(3,3-dichloro-2-propenyloxy)phenoxy)butyloxy)propionaldehyde
138) 3-(5-(2,6-Dichloro-4-(3,3-dichloro-2-propenyloxy)phenoxy)pentyloxy)propionaldehyde
139) 3-(5-(2,6-Diethyl-4-(3,3-dichloro-2-propenyloxy)phenoxy)pentyloxy)propionaldehyde
140) 3-(5-(2-Ethyl-6-methyl-4-(3,3-dichloro-2-propenyloxy)phenoxy)pentyloxy)propionaldehyde The following is a production example for the intermediate compounds of the general formula [XXXIX].

INTERMEDIATE PRODUCTION EXAMPLE 10

Then, 19.54 g of 4-(2,6-dichloro-4-(3,3-dichloro-2-propenyloxy)phenoxy)butyloxyacetaldehyde was dissolved in 200 ml of N,N-dimethylformamide, to which 25.3 g of 1,1,1-trichlorotrifluoroethane, 17.6 g of zinc dust and 2.0 g of aluminum chloride were added. After stirring at room temperature for 1.5 hours, the reaction mixture was filtered. The filtrate was poured into diluted hydrochloric acid and extracted twice with diethyl ether. The diethyl ether layers were combined, washed with water, dried over magnesium sulfate and then concentrated to give a crude product. The crude product was subjected to silica gel chromatography, which afforded 8.46 g of 3,5-dichloro-1-(3,3-dichloro-2-propenyloxy)-4-(4-(3-chloro-4,4-difluoro-2-hydoxy-3-butenyloxy)butyloxy)benzene (yield, 38%), $n_D^{22.5}$ 1.5302.

The following is a production example for the intermediate compounds of the general formula [XV].

INTERMEDIATE PRODUCTION EXAMPLE 11

A reaction vessel was charged with 22.67 g of 1,4-dibromobutane, 11.06 g of potassium carbonate and 200 ml of N,N-dimethylformamide, to which a solution of 20.16 g of 2,6-dichloro-4-(3,3-dichloro-2-propenyloxy)phenol dissolved in 80 ml of N,N-dimethylformamide was slowly added dropwise. After stirring at room temperature for 24 hours, the reaction mixture was poured into water and extracted twice with 300 ml of diethyl ether. The diethyl ether layers were combined, washed with water, dried over anhydrous magnesium sulfate and then concentrated to give a crude product. The crude product was subjected to silica gel chromatography, which afforded 21.77 g of 3,5-dichloro-4-(4-bromobutyloxy)-1-(3,3-dichloro-2-propenyloxy) benzene (yield, 74%), $n_D^{25.0}$ 1.5666.

The following are formulation examples in which "parts" are by weight and the present compounds are designated by their compound numbers as described above.

FORMULATION EXAMPLE 1

Emulsifiable Concentrates

Ten parts of each of the present compounds (1) to (129) are dissolved in 35 parts of xylene and 35 parts of N,N-dimethylformamide, to which 14 parts of polyoxyethylene styrylphenyl ether and 6 parts of calcium dodecylbenzenesulfonate are added, and the mixture is well stirred to give a 10% emulsifiable concentrate of each compound.

FORMULATION EXAMPLE 2

Wettable Powders

Twenty parts of each of the present compounds (1) to (129) are added to a mixture of 4 parts of sodium lauryl sulfate, 2 parts of calcium lignin sulfonate, 20 parts of synthetic hydrated silicon oxide fine powder and 54 parts of diatomaceous earth, and the mixture is stirred with a mixer to give a 20% wettable powder of each compound.

FORMULATION EXAMPLE 3

Granules

To five parts of each of the present compounds (1) to (129) are added 5 parts of synthetic hydrated silicon oxide fine powder, 5 parts of sodium dodecylbenzenesulfonate, 30 parts of bentonite and 55 parts of clay, and the mixture is well stirred. A suitable amount of water is then added to the mixture, which is further stirred, granulated with a granulator and then air-dried to give a 5% granule of each compound.

FORMULATION EXAMPLE 4

Dusts

One part of each of the present compounds (1) to (129) is dissolved in a suitable amount of acetone, to which 5 parts of synthetic hydrated silicon oxide fine powder, 0.3 part of PAP and 93.7 parts of clay are added, and the mixture is stirred with a mixer. The removal of acetone by evaporation gives a 1% dust of each compound.

FORMULATION EXAMPLE 5

Flowables

Twenty parts of each of the present compounds (1) to (129) are mixed with 1.5 parts of sorbitan trioleate and 28.5 parts of an aqueous solution containing 2 parts of polyvinyl alcohol, and the mixture is pulverized into fine particles having a particle size of not more than 3 μm with a sand grinder, to which 40 parts of an aqueous solution containing 0.05 part of xanthan gum and 0.1 part of aluminum magnesium silicate is added and then 10 parts of propylene glycol is added. The mixture is stirred to give a 20% water-based suspension of each compound.

FORMULATION EXAMPLE 6

Oil Sprays

First, 0.1 part of each of the present compounds (1) to (129) is dissolved in 5 parts of xylene and 5 parts of trichloroethane. The solution was then mixed with 89.9 parts of deodorized kerosine to give a 0.1% oil spray of each compound.

FORMULATION EXAMPLE 7

Oil-based Aerosols

First, 0.1 part of each of the present compounds (1) to (129), 0.2 part of tetramethrin, 0.1 part of d-phenothrin, and 10 parts of trichloroethane are dissolved in 59.6 parts of deodorized kerosine, and the solution is put in an aerosol vessel. The vessel is then equipped with a valve, through which 30 parts of a propellant (liquefied petroleum gas) is charged under increased pressure to give an oil-based aerosol of each compound.

FORMULATION EXAMPLE 8

Water-based Aerosols

An aerosol vessel is filled with 50 parts of pure water and a mixture of 0.2 part of each of the present compounds (1) to (129), 0.2 part of d-allethrin, 0.2 part of d-phenothrin, 5 parts of xylene, 3.4 parts of deodorized kerosene and 1 part of an emulsifier [ATMOS 300 (registered trade name by Atlas Chemical Co.)]. The vessel is then equipped with a valve, through which 40 parts of a propellant (liquefied petroleum gas) are charged under increased pressure to give a water-based aerosol of each compound.

FORMULATION EXAMPLE 9

Mosquito-coils

First, 0.3 g of each of the present compounds (1) to (129) is mixed with 0.3 g of d-allethrin, and the mixture is dissolved in 20 ml of acetone. The solution is uniformly mixed with 99.4 g of a carrier for mosquito-coils (prepared by mixing Tabu powder, pyrethrum marc powder and wood flour in the ratio of 4:3:3) under stirring. The mixture is well kneaded with 120 ml of water, molded and dried to give a mosquito-coil of each compound.

FORMULATON EXAMPLE 10

Electric Mosquito-mats

First, 0.4 g of each of the present compounds (1) to (129), 0.3 parts of d-alletlrin and 0.4 g of pipenyl butoxide are dissolved in acetone to have a total volume of 10 ml. Then, 0.5 ml of the solution is uniformly absorbed in a substrate for electric mosquito-mats having a size of 2.5 cm×1.5 cm×0.3 cm (prepared by forming a fibrillated mixture of cotton linter and pulp into a sheet) to give an electric mosquito-mat of each compound.

FORMUALTION EXAMPLE 11

Heating Smoke Formulations

First, 100 mg of each of the present compounds (1) to (129) is dissolved in a suitable amount of acetone. The solution is absorbed in a porous ceramic plate having a size of 4.0 cm×4.0 cm×1.2 cm to give a heating smoke formulation of each compound.

FORMULATION EXAMPLE 12

Poison Baits

First, 10 mg of each of the present compounds (1) to (129) is dissolved in 0.5 ml of acetone, and the solution is uniformly mixed with 5 g of solid bait powder for animals (Breeding Solid Feed Powder CE-2, trade name by Japan Clea Co., Ltd.). The subsequent removal of acetone by air drying gives a 0.5% poison bait of each compound.

The following test examples demonstrate that the present compounds are useful as active ingredients of insecticidal/acaricidal agents. In these test examples, the present compounds are designated by their compound numbers as describe above and the compounds used for comparison are designated by their compound symbols as shown in Table 4.

TABLE 4

| Compound | Chemical structure | Remarks |
|---|---|---|
| (A) | C$_6$H$_5$—CH$_2$O—C$_6$H$_4$—OCH$_2$CH=CCl$_2$ | Compound disclosed in JP-A49-1526/1974, page 22 |

TEST EXAMPLE 1

Insecticidal Test Against *Spodoptera litura*

A 200-fold water dilution (500 ppm) of an emulsifiable concentrate of the test compound, which had been obtained according to Formulation Example 1, was absorbed at a volume of 2 ml in 13 g of an artificial diet for *Spodoptera litura*, which had been prepared in a polyethylene cup having a diameter of 11 cm. Ten fourth-instar larvae of *Spodoptera litura* were set free in the cup. After 6 days, the survival of the larvae was examined to determine the mortality. The test was conducted in duplicate.

As a result, it was found that the present compounds (1)–(4), (7)–(12), (14)–(17), (19)–(21), (23)–(45), (47)–(55), (72), (96), (102), (104) and (109) exhibited the mortality of 80% or more. In contrast, compound (A) used for comparison exhibited the mortality of 0%.

TEST EXAMLE 2

Insecticidal Test Against *Plutella xylostella*

An emulsifiable concentrate of the test compound, which had been obtained according to Formulation Example 1, was diluted with water and spreading agent RINOU (available from Nihon Noyaku K.K.) so that the concentration of active ingredient became 200 ppm and the spreading agent was 1000-fold diluted. The dilution was sprayed over potted cabbages at the five leaf stage at a volume of 25 ml per pot. After air drying, ten third-instar larvae of *Plutella xylostella* were set free on each pot. After 4 days, the mortality was determined.

As a result, it was found that the present compounds (2)–(4), (7)–(11), (14), (16), (17), (21), (23)–(33), (35), (36), (38)–(44), (47), (51), (54), (55), (72), (96), (104) and (109) exhibited the mortality of 80% or more. In contrast, compound (A) used for comparison exhibited the mortality of 0%.

TEST EXAMPLE 3

Insecticidal Test Against *Musca domestica*

In the bottom of a polyethylene cup having a diameter of 5.5 cm was placed a piece of filter paper having the same size. A water dilution (500 ppm) of an emulsifiable concentrate of the test compound, which had been obtained according to Formulation Example 1, was dropped at a volume of 0.7 ml on the filter paper, and about 30 mg of sucrose as a diet was uniformly placed thereon. Ten female adults of houseflies (Musca domestica) with a low sensitivity to pyrethroid insecticides were set free in the cup, which was kept covered. After 1 day, the survival of the adults was determined to determine the mortality.

As a result, it was found that the present compounds (10), (11), (14), (33), (40), (44), (45), (47), (52), (53), (72) and (96) exhibited the mortality of 100%. In contrast, compound (A) used for comparison exhibited the mortality of 0%.

TEST EXAMPLE 4

Insecticidal Test Against *Heliothis virescens*

A 1000-fold water dilution (100 ppm) of an emulsifiable concentrate of the test compound, which had been prepared according to Formulation Example 1, was absorbed at a volume of 0.2 ml in 3 g of an artificial diet, which had been prepared in a 30 ml plastic cup. One second-instar larva of *Heliothis virescens* was set free in the cup. Ten larvae were used for one treatment. After 6 to 7 days, the mortality of the larvae was determined.

As a result, it was found that the present compounds (3), (8)–(11), (14), (17), (26), (27), (38), (42), (43), (54) and (55) exhibited the mortality of 80%. In contrast, compound (A) used for comparison exhibited the mortality of 0%.

TEST EXAMPLE 5

Insecticidal Test Against *Adoxophyes oranafasciata*

A 500-fold water dilution (200 ppm) of an emulsifiable concentrate of the test compound, which had been prepared according to Formulation Example 1, was absorbed at a volume of 1 ml in 5 g of an artificial diet, which had been prepared in a polyethylene cup having a diameter of 6 cm. Ten forth-instar larva of *Adoxophyes oranafasciata* were set free in the cup. After 7 days, the mortality of the larvae was determined.

As a result, it was found that the present compounds (3), (4), (17), (25), (29) and (33) exhibited the mortality of 80%. In contrast, compound (A) used for comparison exhibited the mortality of 0%.

TEST EXAMPLE 6

Insecticidal Test Against *Helicoverpa armigera*

A cotton leaf fragment (diameter, 5 cm) was immersed in a 1000-fold water dilution (100 ppm) of an emulsifiable concentrate of the test compound, which had been obtained according to Formulation Example 1. This fragment was taken out from the dilution, air dried and then placed in a polyethylene cup having a diameter of 6 cm. One third-instar larva of *Helicoverpa annigera* was set free in the cup. Ten larvae were used for one treatment. After 5 days, the mortality of the larvae was determined.

As a result, it was found that the present compounds (3), (14), (38) and (53) exhibited the mortality of 80%. In contrast, compound (A) used for comparison exhibited the mortality of 0%.

TEST EXAMPLE 7

Acaricidal Test Against *Tetranychus urticae* Koch

About twenty female adults of *Tetranychus urticae* Koch were set free on brush bean (*Phaseolus vulgaris*) in the primary leaf stage, which had been potted in a plastic cup for 7 days after the seeding. After 6 days, a 200-fold water dilution (500 ppm) of an emulsifiable concentrate of the test compound, which had been obtained according to Formulation Example 1, was sprayed at a volume of 15 ml over the plant. After 8 days, the test compound was evaluated for acaricidal activity on the following criteria.

−: almost no damage and completely no surviving mites
±: slight damage and some few mites
+: rather smaller damage and a rather fewer mites than non-treatment case
++: same as non-treatment case As a result, it was found that the present compounds (25), (40), (44), (72) and (109) were evaluated at "±". In contrast, compound (A) used for comparison was evaluated at "+".

Industrial Applicability

The present compounds have excellent insecticidal/acaricidal activity, so that they are satisfactorily effective for the control of noxious insects, mites and ticks.

What is claimed is:

1. A dihalopropene compound of the general formula:

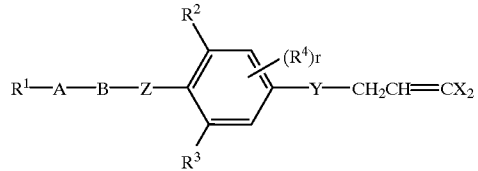

[I]

wherein $R^1$ is $C_1-C_8$ alkyl substituted with at least one atom or group selected from the class consisting of:

halogen; $C_1-C_6$ alkoxy; $C_2-C_6$ haloalkoxy; $C_3-C_6$ alkenyloxy; $C_3-C_6$ haloalkenyloxy; $C_3-C_6$ alkynyloxy; $C_3-C_6$ haloalkynyloxy; $C_1-C_6$ alkylthio; $C_2-C_6$ haloalkylthio; $C_3-C_6$ alkenylthio; $C_3-C_6$ haloalkenylthio; $C_3-C_6$ alkynylthio; $C_3-C_6$ haloalkynylthio; $C_2-C_6$ alkanoyloxy optionally substituted with halogen; $C_2-C_6$ alkanoylamino optionally substituted with halogen; ($C_1-C_6$ alkoxy)carbonyl; ($C_2-C_6$ haloalkoxy)carbonyl; ($C_3-C_6$ alkenyloxy)carbonyl; ($C_3-C_6$ haloalkenyloxy)carbonyl; ($C_3-C_6$ alkynyloxy)carbonyl; ($C_3-C_6$ haloalkynyloxy)carbonyl; cyano; nitro; hydroxyl; amino substituted with $C_1-C_6$ alkyl, $C_2-C_6$ haloalkyl, $C_3-C_6$ alkenyl, $C_3-C_6$ haloalkenyl, $C_3-C_6$ alkynyl or $C_3-C_6$ haloalkynyl; and carbamoyl substituted with $C_1-C_6$ alkyl, $C_2-C_6$ haloalkyl, $C_3-C_6$ alkenyl, $C_3-C_6$ haloalkenyl, $C_3-C_6$ alkynyl or $C_3-C_6$ haloalkynyl;

or $R^1$ is $Q^1$, $Q^2$ or $Q^3$ of the general formula:

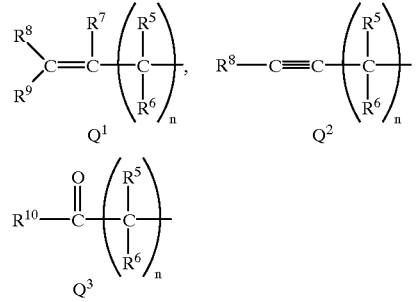

[II]

wherein $R^5$ and $R^6$ are each independently hydrogen, halogen, $C_1-C_3$ alkyl or $C_1-C_3$ haloalkyl, $R^7$ is hydrogen, halogen, $C_1-C_6$ alkyl or $C_1-C_6$ haloalkyl, $R^8$ and $R^9$ are each independently hydrogen, halogen, $C_1-C_6$ alkyl, $C_1-C_6$ haloalkyl, $C_2-C_6$ alkanoyl optionally substituted with halogen, ($C_1-C_6$ alkoxy)carbonyl, ($C_2-C_6$ haloalkoxy)carbonyl, ($C_3-C_6$ alkenyloxy)

carbonyl, ($C_3$–$C_6$ haloalkenyloxy)carbonyl, ($C_3$–$C_6$ alkynyloxy)carbonyl, ($C_3$–$C_6$ haloalkynyloxy)carbonyl, cyano, nitro, or carbamoyl substituted with $C_1$–$C_6$ alkyl, $C_2$–$C_6$ haloalkyl, $C_3$–$C_6$ alkenyl, $C_3$–$C_6$ haloalkenyl, $C_3$–$C_6$ alkynyl or $C_3$–$C_6$ haloalkynyl, $R^{10}$ is $C_1$–$C_6$ alkyl or $C_1$–$C_6$ haloalkyl, and n ia an integer of 1 to 5;

$R^2$, $R^3$ and $R^4$ are each independently halogen, $C_1$–$C_3$ alkyl, $C_1$–$C_3$ haloalkyl, $C_1$–$C_3$ alkoxy, $C_1$–$C_3$ haloalkoxy, nitro or cyano;

A is oxygen, $S(O)_t$ or $NR^{14}$ in which $R^{14}$ is hydrogen or $C_1$–$C_3$ alkyl and t is an integer of 0 to 2;

B is $B^1$, $B^2$ or $B^3$ of the general formula:

[III]

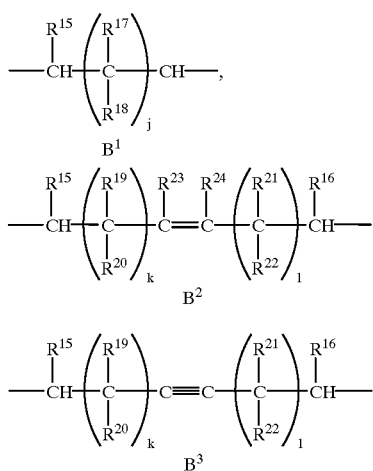

wherein $R^{15}$, $R^{16}$ $R^{17}$, $R^{18}$, $R^{19}$, $R^{20}$, $R^{21}$, $R^{22}$, $R^{23}$ and $R^{24}$ are each independently hydrogen, $C_1$–$C_3$ alkyl or trifluoromethyl, j is an integer of 0 to 5, and k and l are each independently an integer of 0 to 2;

r is an integer of 0 to 2;

X's are each independently halogen;

Y is oxygen, sulfur or NH; and

Z is oxygen, sulfur or $NR^{25}$ in which $R^{25}$ is hydrogen, acetyl or $C_1$–$C_3$ alkyl.

2. A dihalopropene compound according to claim 1, wherein Y and Z are both oxygen.

3. A dihalopropene compound according to claim 1, wherein $R^2$, $R^3$ and $R^4$ are each independently halogen, $C_1$–$C_3$ alkyl or $C_1$–$C_3$ haloalkyl.

4. A dihalopropene compound according to claim 1, wherein $R^2$ and $R^3$ are each independently halogen, $C_1$–$C_3$ alkyl or $C_1$–$C_3$ haloalkyl, and r is 0.

5. A dihalopropene compound according to claim 1, wherein $R^2$ and $R^3$ are each independently halogen or $C_1$–$C_3$ alkyl, and r is 0.

6. A dihalopropene compound according to claim 1, wherein A is oxygen.

7. A dihalopropene compound according to claim 1, wherein B is $B^1$ and X is chlorine or bromine.

8. A dihalopropene compound according to claim 7, wherein $R^{15}$, $R^{16}$, $R^{17}$ and $R^{18}$ are all hydrogen.

9. A dihalopropene compound according claim 1, wherein $R^1$ is $C_1$–$C_8$ alkyl substituted with 1 to 3 atoms or groups selected from the class consisting of:

halogen; $C_1$–$C_6$ alkoxy; $C_2$–$C_6$ haloalkoxy; $C_3$–$C_6$ alkenyloxy; $C_3$–$C_6$ haloalkenyloxy; $C_3$–$C_6$ alkynyloxy; $C_3$–$C_6$ haloalkynyloxy; $C_1$–$C_6$ alkylthio; $C_2$–$C_6$ haloalkylthio; $C_3$–$C_6$ alkenylthio; $C_3$–$C_6$ haloalkenylthio; $C_3$–$C_6$ alkynylthio; $C_3$–$C_6$ haloalkynylthio; $C_2$–$C_6$ alkanoyloxy optionally substituted with halogen; $C_2$–$C_6$ alkanoylamino optionally substituted with halogen; ($C_1$–$C_6$ alkoxy)carbonyl; ($C_2$–$C_6$ haloalkoxy)carbonyl; ($C_3$–$C_6$ alkenyloxy)carbonyl; ($C_3$–$C_6$ haloalkenyloxy)carbonyl; ($C_3$–$C_6$ alkynyloxy)carbonyl; ($C_3$–$C_6$ haloalkynyloxy)carbonyl; cyano; nitro; hydroxyl; amino substituted with $C_1$–$C_6$ alkyl, $C_2$–$C_6$ haloalkyl, $C_3$–$C_6$ alkenyl, $C_3$–$C_6$ haloalkenyl, $C_3$–$C_6$ alkynyl or $C_3$–$C_6$ haloalkynyl; and carbamoyl substituted with $C_1$–$C_6$ alkyl, $C_2$–$C_6$ haloalkyl, $C_3$–$C_6$ alkenyl, $C_3$–$C_6$ haloalkenyl, $C_3$–$C_6$ alkynyl or $C_3$–$C_6$ haloalkynyl.

10. A dihalopropene compound according to claim 9, wherein $R^1$ is $C_1$–$C_8$ alkyl substituted with 1 to 3 groups selected from the class consisting of:

$C_1$–$C_6$ alkoxy; $C_2$–$C_6$ haloalkoxy; $C_3$–$C_6$ alkenyloxy; $C_3$–$C_6$ haloalkenyloxy; $C_3$–$C_6$ alkynyloxy; $C_3$–$C_6$ haloalkynyloxy; $C_1$–$C_6$ alkylthio; $C_2$–$C_6$ haloalkylthio; $C_3$–$C_6$ alkenylthio; $C_3$–$C_6$ haloalkenylthio; $C_3$–$C_6$ alkynylthio; $C_3$–$C_6$ haloalkynylthio;

$C_2$–$C_6$ alkanoyloxy optionally substituted with halogen; $C_2$–$C_6$ alkanoylamino optionally substituted with halogen; and amino substituted with $C_1$–$C_6$ alkyl, $C_2$–$C_6$ haloalkyl, $C_3$–$C_6$ alkenyl, $C_3$–$C_6$ haloalkenyl, $C_3$–$C_6$ alkynyl or $C_3$–$C_6$ haloalkynyl.

11. A dihalopropene compound according to claim 9, wherein $R^1$ is $C_1$–$C_8$ alkyl substituted with 1 to 3 groups selected from the class consisting of $C_1$–$C_6$ alkoxy and $C_2$–$C_6$ haloalkoxy.

12. A dihalopropene compound according claim 1, wherein $R^1$ is $Q^1$.

13. A dihalopropene compound according to claim 12, wherein $R^5$ and $R^6$ are both hydrogen.

14. A dihalopropene compound according to claim 1, wherein Y and Z are both oxygen; $R^1$ is $Q^1$ in which $R^5$ and $R^6$ are both hydrogen, n is 1, and $R^7$, $R^8$ and $R^9$ are each independently hydrogen, halogen, $C_1$–$C_6$ alkyl or $C_5$–$C_3$ haloalkyl; $R^2$ and $R^3$ are each independently halogen, $C_1$–$C_3$ alkyl or $C_1$–$C_3$ haloalkyl; A is oxygen; and B is $B^1$ in which $R^{15}$, $R^{16}$, $R^{17}$ and $R^{18}$ are all hydrogen.

15. A dihalopropene compound according to claim 1, wherein $R^1$ is $Q^2$.

16. A dihalopropene compound according to claim 15, wherein $R^5$ and $R^6$ are both hydrogen.

17. A dihalopropene compound according to claim 1, wherein $R^1$ is $Q^3$.

18. A dihalopropene compound according to claim 17, wherein $R^5$ and $R^6$ are both hydrogen.

19. An insecticidal/acaricidal agent comprising, as an active ingredient, a dihalopropene compound according to claim 1.

20. A compound of the general formula:

[IV]

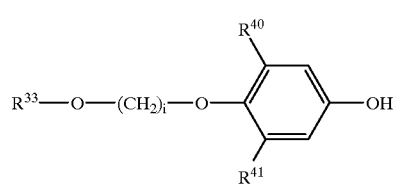

wherein $R^{33}$ is $P^1$ or $P^2$ of the general formula:

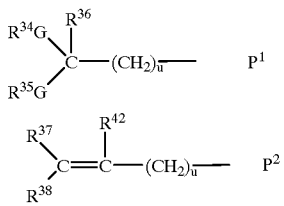
[V]

in which $R^{34}$ and $R^{35}$ are each independently $C_1$–$C_6$ alkyl or $C_2$–$C_3$ haloalkyl, $R^{37}$ and $R^{38}$ are each independently hydrogen, halogen, $C_1$–$C_6$ alkyl, $C_1$–$C_3$ haloalkyl, ($C_1$–$C_6$ alkoxy)carbonyl or cyano, $R^{36}$ is hydrogen, $C_1$–$C_6$ alkyl or $C_1$–$C_3$ haloalkyl, $R^{42}$ is hydrogen, halogen, $C_1$–$C_6$ alkyl or $C_1$–$C_3$ haloalkyl, G is oxygen or sulfur, and u is an integer of 1 to 3;

$R^{40}$ and $R^{41}$ are each independently halogen or $C_1$–$C_3$ alkyl; and i is an integer of 2 to 7.

21. A compound according to claim 20, wherein $R^{33}$ is $P^1$.
22. A compound according to claim 20, wherein $R^{33}$ is $P^2$.
23. A compound of the general formula:

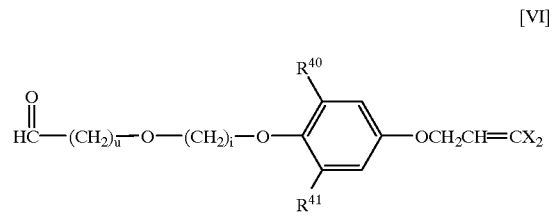
[VI]

wherein $R^{40}$ and $R^{41}$ are each independently halogen or $C_1$–$C_3$ alkyl;

X's are each halogen;

u is an integer of 1 to 3; and i is an integer of 2 to 7.

* * * * *